United States Patent
Cravatt et al.

(10) Patent No.: US 10,583,137 B2
(45) Date of Patent: Mar. 10, 2020

(54) TRIAZOLE DAGLα INHIBITORS

(71) Applicants: THE SCRIPPS RESEARCH INSTITUTE, La Jolla, CA (US); LEIDEN UNIVERSITY, Leiden (NL)

(72) Inventors: Benjamin F. Cravatt, San Diego, CA (US); Daisuke Ogasawara, San Diego, CA (US); Andreu Viader, San Diego, CA (US); Hui Deng, Leiden (NL); Tom Van Der Wel, Voorburg (NL); Marcelis Van Der Stelt, Utrecht (NL)

(73) Assignees: THE SCRIPPS RESEARCH INSTITUTE, La Jolla, CA (US); LEIDEN UNIVERSITY, Leiden (NL)

( * ) Notice: Subject to any disclaimer, the term of this patent is extended or adjusted under 35 U.S.C. 154(b) by 0 days.

(21) Appl. No.: 15/778,207

(22) PCT Filed: Dec. 2, 2016

(86) PCT No.: PCT/US2016/064844
§ 371 (c)(1),
(2) Date: May 22, 2018

(87) PCT Pub. No.: WO2017/096315
PCT Pub. Date: Jun. 8, 2017

(65) Prior Publication Data
US 2018/0344729 A1  Dec. 6, 2018

Related U.S. Application Data

(60) Provisional application No. 62/262,270, filed on Dec. 2, 2015.

(51) Int. Cl.
*A61K 31/496* (2006.01)
*A61K 31/454* (2006.01)
*A61K 31/4439* (2006.01)
*A61K 31/4192* (2006.01)
*A61K 31/506* (2006.01)
*A61P 25/28* (2006.01)

(52) U.S. Cl.
CPC ........ *A61K 31/496* (2013.01); *A61K 31/4192* (2013.01); *A61K 31/4439* (2013.01); *A61K 31/454* (2013.01); *A61K 31/506* (2013.01); *A61P 25/28* (2018.01)

(58) Field of Classification Search
CPC ................ A61K 31/496; A61K 31/454; A61K 31/4192; A61K 31/506; A61K 31/4439; A61P 25/28
See application file for complete search history.

(56) References Cited

U.S. PATENT DOCUMENTS 3,308,130 A  3/1967  Bousquet
7,772,236 B2  8/2010  Beavers et al.
2003/0013712 A1  1/2003  Tullis et al.
2011/0172230 A1  7/2011  Ishii et al.
2012/0065191 A1  3/2012  Kiss et al.
2014/0018318 A1  1/2014  Cravatt et al.
2015/0051211 A1  2/2015  Ji et al.
2017/0029390 A1  2/2017  Butler et al.
2017/0190669 A1  7/2017  Boger et al.
2018/0327410 A1  11/2018  Grice et al.
2018/0327416 A1  11/2018  Grice et al.
2018/0339970 A1  11/2018  Grice

FOREIGN PATENT DOCUMENTS

| WO | WO-2010074588 A2 | 7/2010 |
| WO | WO-2013078771 A1 | 6/2013 |
| WO | WO-2015179559 A2 | 11/2015 |
| WO | WO-2016014975 A2 | 1/2016 |
| WO | WO-2017087854 A1 | 5/2017 |
| WO | WO-2017087858 A1 | 5/2017 |
| WO | WO-2017087863 A1 | 5/2017 |
| WO | WO-2017096315 A1 | 6/2017 |
| WO | WO-2018217805 A1 | 11/2018 |
| WO | WO-2018217809 A1 | 11/2018 |

OTHER PUBLICATIONS

Hsu et al., Journal of Medicinal Chemistry, (2013), v.56, p. 8257-8269.*
Hsu et al., Journal of Medicinal Chemistry, (2013), v.56, p. 8257-8269, S1-18.*
Baggelaar et al. Development of an activity-based probe and in silico design reveal highly selective inhibitors for diacylglycerol lipase-α in brain. Angew Chem Int Ed Engl 52(46):12081-12085 (2013).
Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).

(Continued)

*Primary Examiner* — Yong L Chu
(74) *Attorney, Agent, or Firm* — Wilson Sonsini Goodrich & Rosati

(57) ABSTRACT

Provided herein are triazole compounds and pharmaceutical compositions comprising said compounds useful as modulators of DAGL(α) and DAGL(β). In some embodiments, the compounds described herein are selective DAGL(α) inhibitors. Furthermore, the subject compounds and compositions are useful for the treatment of neurodegenerative or neuroinflammatory disease.

14 Claims, 8 Drawing Sheets

(56) References Cited

OTHER PUBLICATIONS

Horig et al. From bench to clinic and back: Perspective on the 1st IQPC Translational Research conference. J Transl Med 2(1):44 (2004).
Hsu et al. Development and Optimization of Piperidyl-1,2,3-Triazole Ureas as Selective Chemical Probes of Endocannabinoid Biosynthesis. J Med Chem 56:8257-8269 (2013).
Hsu et al. Discovery and optimization of piperidyl-1,2,3-triazole ureas as potent, selective, and in vivo-active inhibitors of α/β-hydrolase domain containing 6 (ABHD6). J Med Chem 56:8270-8279 (2012).
Janssen et al. Discovery of glycine sulfonamides as dual inhibitors of sn-1-diacylglycerol lipase α and α/β-hydrolase domain 6. J Med Chem 57(15):6610-6622 (2014).
Kohnz et al. Chemical approaches to therapeutically target the metabolism and signaling of the endocannabinoid 2-AG and eicosanoids. Chem Soc Rev 43(19):6859-6869 (2014).
Long et al. Selective blockade of 2-arachidonoylglycerol hydrolysis produces cannabinoid behavioral effects. Nat Chem Biol. 5(1):37-44 (2009).
Lysenko et al. Monoacylglycerol lipase inhibitor JZL184 improves behavior and neural properties in Ts65Dn mice, a model of down syndrome. PLoS One 9(12):e114521 (2013).
Morren et al. The filaricidal derivatives of 1-methylpiperazine. Bulletin des Societes Chimiques Belges 59(3-4):228-237 (1950).
Mulvihill et al. Therapeutic potential of monoacylglycerol lipase inhibitors. Life Sci 92(8-9):492-497 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Ogasawara et al. Rapid and profound rewiring of brain lipid signaling networks by acute diacylglycerol lipase inhibition. PNAS USA 113(1):26-33 (2016).
Otrubova et al. Discovery libraries targeting the major enzyme classes: the serine hydrolases. Bioorg Med Chem Lett 24(16):3807-3813 (2014).
PCT/US2015/031834 International Preliminary Report on Patentability dated Dec. 1, 2016.
PCT/US2015/031834 International Search Report and Written Opinion dated Apr. 20, 2016.
PCT/US2016/062862 International Preliminary Report on Patentability dated May 31, 2018.
PCT/US2016/062862 International Search Report and Written Opinion dated Jan. 27, 2017.
PCT/US2016/062868 International Preliminary Report on Patentability dated May 31, 2018.
PCT/US2016/062868 International Search Report and Written Opinion dated Jan. 30, 2017.
PCT/US2016/062873 International Preliminary Report on Patentability dated May 31, 2018.
PCT/US2016/062873 International Search Report and Written Opinion dated Jan. 27, 2017.
PCT/US2016/064844 International Preliminary Report on Patentability dated Jun. 14, 2018.
PCT/US2016/064844 International Search Report and Written Opinion dated Feb. 15, 2017.
PCT/US2018/033959 International Search Report and Written Opinion dated Jul. 23, 2018.
PCT/US2018/033964 International Search Report and Written Opinion dated Sep. 13, 2018.
PCT/US2018/033964 Invitation to Pay Additional Fees dated Jul. 20, 2018.
Schafer et al. Failure is an option: learning from unsuccessful proof-of-concept trials. Drug Discov Today 13(21-22):913-916 (2008).
U.S. Appl. No. 15/315,998 Office Action dated Nov. 2, 2017.
Van Den Nieuwendijk et al. Synthesis of Eight 1-Deoxynojirimycin Isomers from a Single Chiral Cyanohydrin. Eur JOC 18:3437-3446 (2012).
Van Den Nieuwendijk et al. Synthesis of L-altro-1-deoxynojirimycin, D-allo-1-deoxynojirimycin, and D-galacto-1-deoxynojirimycin from a single chiral cyanohydrin. Org lett 12(17):3957-3959 (2010).
Van Der Wel et al. A natural substrate-based fluorescence assay for inhibitor screening on diacylglycerol lipase α. J Lipid Res 56(4):927-935 (2015).

\* cited by examiner

TRIAZOLE DAGLα INHIBITORS

CROSS-REFERENCE

This application is filed as a U.S. National Phase Application of International Application No. PCT/US2016/064844, filed Dec. 2, 2016, which claims the benefit of U.S. Provisional Application No. 62/262,270, filed on Dec. 2, 2015, which are incorporated herein by reference in its their entirety.

STATEMENT OF GOVERNMENT SUPPORT

This invention was made in part with government support under grants DA033760, DA032933, and GM109315 awarded by the National Institutes of Health (NIH). The government has certain rights in the invention.

BACKGROUND

Diacylglycerol lipases (DAGLα and DAGLβ) convert diacylglycerol (DAG) to the endocannabinoid 2-arachidonoylglycerol (2-AG). 2-AG is an arachidonic acid (AA)-derived lipid messenger that broadly modulates synaptic function, neurophysiology, and behavior through its activity on cannabinoid receptors 1 ($CB_1R$) and 2 ($CB_2R$), while also providing a source of AA precursors for eicosanoid synthesis.

BRIEF SUMMARY OF THE INVENTION

In one aspect is a compound of Formula (I):

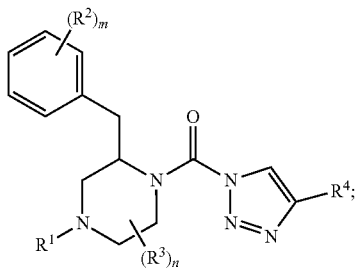

Formula (I)

wherein:
$R^1$ is H, $C_{1-6}$alkyl, —C(=O)$OR^{10}$, or —S(=O)$_2R^{10}$,
each $R^2$ is independently halogen, —CN, —$NH_2$, —NH($CH_3$), —N($CH_3$)$_2$, —OH, —C(=O)OH, —C(=O)O($C_{1-6}$ alkyl), —C(=O)$NH_2$, —C(=O)NH($C_{1-6}$ alkyl), —C(=O)N($C_{1-6}$ alkyl)$_2$, —S(=O)$_2NH_2$, —S(=O)$_2$NH($C_{1-6}$ alkyl), —S(=O)$_2$N($C_{3-6}$ alkyl)$_2$, $C_{3-6}$ alkyl, $C_{3-6}$ cycloalkyl, $C_{1-6}$haloalkyl, $C_{1-6}$ alkoxy, —O—$C_{1-6}$ alkenyl, —O—$C_{1-6}$alkynyl, $C_{1-6}$haloalkoxy, $C_{2-9}$heterocycloalkyl, $C_{6-10}$aryl, or $C_{2-9}$ heteroaryl;
each $R^3$ is independently halogen, —CN, —C(=O)OH, —C(=O)O($C_{3-6}$ alkyl), —C(=O)$NH_2$, —C(=O)NH($C_{1-6}$ alkyl), —C(=O)N($C_{1-6}$ alkyl)$_2$, —S(=O)$_2NH_2$, —S(=O)$_2$NH($C_{1-6}$ alkyl), —S(=O)$_2$N($C_{1-6}$alkyl)$_2$, $C_{1-6}$alkyl, $C_{3-6}$cycloalkyl, $C_{1-6}$haloalkyl, $C_{2-9}$heterocycloalkyl, $C_{6-10}$aryl, or $C_{2-9}$ heteroaryl;

$R^4$ is

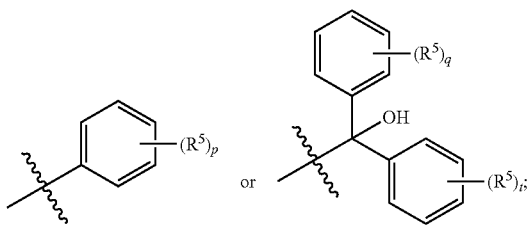

each $R^5$ is independently halogen, —CN, —$NH_2$, —NH($CH_3$), —N($CH_3$)$_2$, —OH, —C(=O)OH, —C(=O)O($C_{1-6}$ alkyl), —C(=O)$NH_2$, —C(=O)NH($C_{1-6}$ alkyl), —C(=O)N($C_{1-6}$ alkyl)$_2$, —S(=O)$_2NH_2$, —S(=O)$_2$NH($C_{1-6}$ alkyl), —S(=O)$_2$N($C_{1-6}$ alkyl)$_2$, $C_{1-6}$alkyl, $C_{1-6}$alkoxy, —O—$C_{1-6}$ alkenyl, —O—$C_{1-6}$alkynyl, or $C_{1-6}$haloalkoxy,
$R^{10}$ is $C_{1-6}$alkyl;
m is 0, 1, 2, or 3;
n is 0, 1, or 2;
p is 0, 1, 2, or 3,
q is 0, 1, 2, or 3, and
t is 0, 1, 2, or 3;
or a solvate, hydrate, tautomer, N-oxide, or pharmaceutically acceptable salt thereof.

In another aspect is a compound of Formula (II):

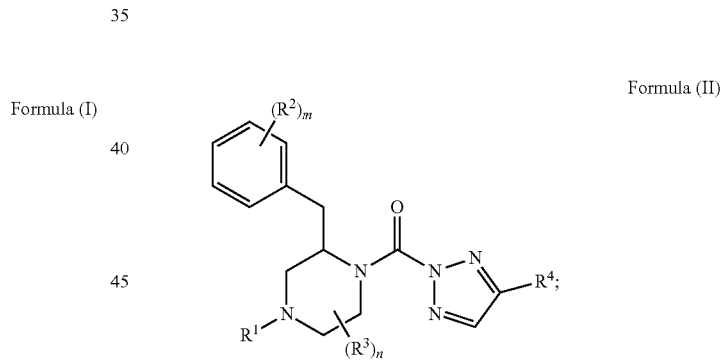

Formula (II)

wherein:
$R^1$ is H, $C_{1-6}$alkyl, —C(=O)$OR^{10}$, or —S(=O)$_2R^{10}$;
each $R^2$ is independently halogen, —CN, —$NH_2$, —NH($CH_3$), —N($CH_3$)$_2$, —OH, —C(=O)OH, —C(=O)O($C_{1-6}$ alkyl), —C(=O)$NH_2$, —C(=O)NH($C_{1-6}$ alkyl), —C(=O)N($C_{1-6}$alkyl)$_2$, —S(=O)$_2NH_2$, —S(=O)$_2$NH($C_{1-6}$ alkyl), —S(=O)$_2$N($C_{1-6}$ alkyl)$_2$, $C_{1-6}$alkyl, $C_{3-6}$cycloalkyl, $C_{1-6}$haloalkyl, $C_{1-6}$alkoxy, —O—$C_{1-6}$ alkenyl, —O—$C_{1-6}$alkynyl, $C_{1-6}$haloalkoxy, $C_{2-9}$heterocycloalkyl, $C_{6-10}$ aryl, or $C_{2-9}$ heteroaryl;
each $R^3$ is independently halogen, —CN, —C(=O)OH, —C(=O)O($C_{1-6}$ alkyl), —C(=O)$NH_2$, —C(=O)NH($C_{1-6}$alkyl), —C(=O)N($C_{1-6}$alkyl)$_2$, —S(=O)$_2NH_2$, —S(=O)$_2$NH($C_{1-6}$ alkyl), —S(=O)$_2$N($C_{1-6}$alkyl)$_2$, $C_{1-6}$alkyl, $C_{3-6}$cycloalkyl, $C_{1-6}$haloalkyl, $C_{2-9}$heterocycloalkyl, $C_{6-10}$aryl, or $C_{2-9}$ heteroaryl;

$R^4$ is

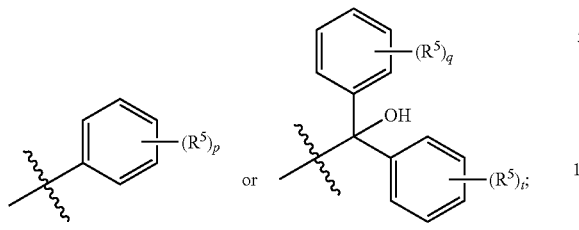

each $R^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{1-6}$alkoxy, —O—C$_{1-6}$ alkenyl, —O—C$_{1-6}$alkynyl, or C$_{1-6}$haloalkoxy, $R^{10}$ is C$_{1-6}$alkyl;

m is 0, 1, 2, or 3;

n is 0, 1, or 2;

p is 0, 1, 2, or 3, q is 0, 1, 2, or 3, and t is 0, 1, 2, or 3;

or a solvate, hydrate, tautomer, N-oxide, or pharmaceutically acceptable salt thereof.

In another aspect is a compound of Formula (V):

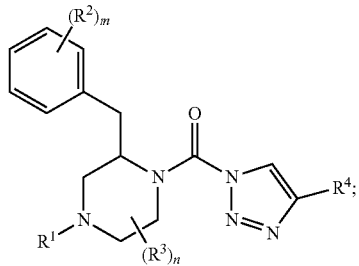

Formula (V)

wherein:

$R^1$ is H, C$_{1-6}$alkyl, —C(=O)R$^{10}$, —C(=O)OR$^{10}$, or —S(=O)$_2$R$^{10}$;

each $R^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{3-6}$cycloalkyl, C$_{1-6}$haloalkyl, C$_{1-6}$alkoxy, —O—C$_{1-6}$ alkenyl, —O—C$_{1-6}$alkynyl, C$_{1-6}$haloalkoxy, C$_{2-9}$heterocycloalkyl, C$_{6-10}$ aryl, or C$_{2-9}$ heteroaryl;

each $R^3$ is independently halogen, —CN, —C(=O)OH, —C(=O)O(C$_{1-6}$ alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$ alkyl), —S(=O)$_2$N(C$_{1-6}$alkyl)$_2$, C$_{1-6}$alkyl, C$_{3-6}$cycloalkyl, C$_{1-6}$haloalkyl, C$_{2-9}$heterocycloalkyl, C$_{6-10}$aryl, or C$_{2-9}$ heteroaryl;

$R^4$ is

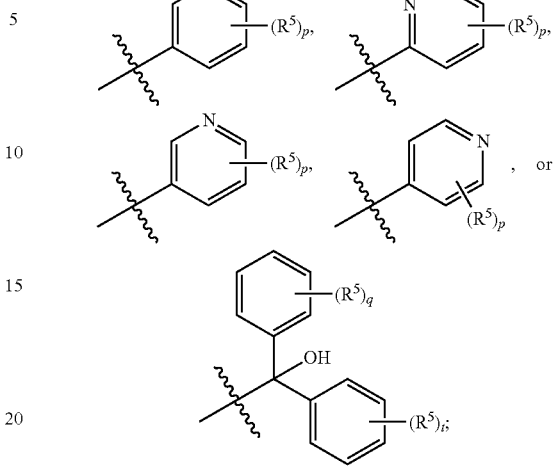

each $R^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{1-6}$haloalkyl, C$_{1-6}$alkoxy, —O—C$_{1-6}$ alkenyl, —O—C$_{1-6}$alkynyl, C$_{1-6}$haloalkoxy, optionally substituted phenyl, or optionally substituted C$_{2-9}$heteroaryl, wherein optionally substituted phenyl and optionally substituted C$_{2-9}$ heteroaryl are optionally substituted with one, two, or three groups selected from halogen, C$_{1-6}$alkyl, C$_{1-6}$haloalkyl, C$_{1-6}$alkoxy, and C$_{1-6}$haloalkoxy;

$R^{10}$ is C$_{1-6}$alkyl, C$_{1-6}$alkenyl, or C$_{1-6}$alkynyl;

m is 0, 1, 2, or 3;

n is 0, 1, or 2;

p is 0, 1, 2, or 3, q is 0, 1, 2, or 3, and t is 0, 1, 2, or 3;

or a solvate, hydrate, tautomer, N-oxide, or pharmaceutically acceptable salt thereof.

In another aspect is a compound of Formula (VI):

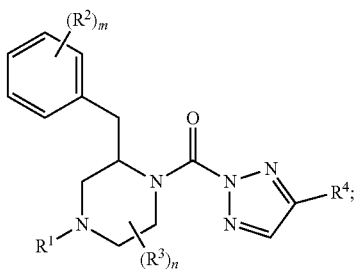

Formula (VI)

wherein:

$R^1$ is H, C$_{1-6}$alkyl, —C(=O)R$^{10}$, —C(=O)OR$^{10}$, or —S(=O)$_2$R$^{10}$;

each $R^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$ NH(C$_{1-6}$ alkyl), —S(=O)$_2$N(C$_{1-6}$ alkyl)$_2$, C$_{1-6}$alkyl, C$_{3-6}$cycloalkyl, C$_{1-6}$haloalkyl, C$_{1-6}$ alkoxy, —O—C$_{1-6}$ alkenyl, —O—C$_{1-6}$alkynyl, C$_{1-6}$haloalkoxy, C$_{2-9}$heterocycloalkyl, C$_{6-10}$aryl, or C$_{2-9}$ heteroaryl;

each R$^3$ is independently halogen, —CN, —C(=O)OH, —C(=O)O(C$_{1-6}$ alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$ alkyl), —S(=O)$_2$N(C$_{1-6}$alkyl)$_2$, C$_{1-6}$alkyl, C$_{3-6}$cycloalkyl, C$_{1-6}$haloalkyl, C$_{2-9}$heterocycloalkyl, C$_{6-10}$aryl, or C$_{2-9}$ heteroaryl;

R$^4$ is

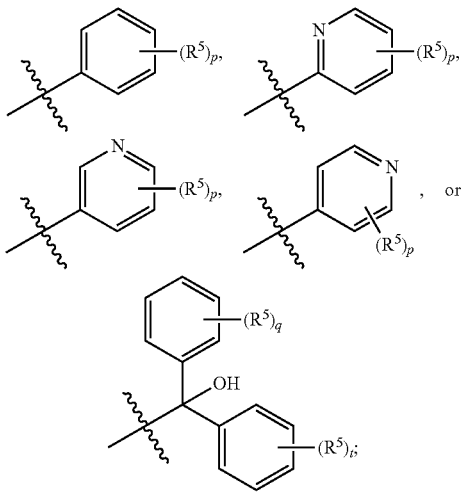

each R$^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$ alkyl, C$_{1-6}$ haloalkyl, C$_{1-6}$alkoxy, —O—C$_{1-6}$alkenyl, —O—C$_{1-6}$ alkynyl, C$_{1-6}$ haloalkoxy, optionally substituted phenyl, or optionally substituted C$_{2-9}$ heteroaryl, wherein optionally substituted phenyl and optionally substituted C$_{2-9}$ heteroaryl are optionally substituted with one, two, or three groups selected from halogen, C$_{1-6}$alkyl, C$_{1-6}$ haloalkyl, C$_{1-6}$alkoxy, and C$_{1-6}$haloalkoxy;

R$^{10}$ is C$_{1-6}$alkyl, C$_{1-6}$alkenyl, or C$_{1-6}$alkynyl;

m is 0, 1, 2, or 3;
n is 0, 1, or 2;
p is 0, 1, 2, or 3;
q is 0, 1, 2, or 3; and
t is 0, 1, 2, or 3;

or a solvate, hydrate, tautomer, N-oxide, or pharmaceutically acceptable salt thereof.

In one embodiment is a compound of Formula (I), (II), (V), or (VI), or a solvate, hydrate, tautomer, N-oxide, or pharmaceutically acceptable salt thereof, wherein R$^1$ is H. In another embodiment is a compound of Formula (I), (II), (V), or (VI), or a solvate, hydrate, tautomer, N-oxide, or pharmaceutically acceptable salt thereof, wherein R$^1$ is C$_{1-6}$alkyl. In another embodiment is a compound of Formula (I), (II), (V), or (VI), or a solvate, hydrate, tautomer, N-oxide, or pharmaceutically acceptable salt thereof, wherein R$^1$ is —C(=O)OR$^{10}$. In another embodiment is a compound of Formula (I), (II), (V), or (VI), or a solvate, hydrate, tautomer, N-oxide, or pharmaceutically acceptable salt thereof, wherein R$^1$ is —C(=O)OR$^{10}$ and R$^{10}$ is —C(CH$_3$)$_3$. In another embodiment is a compound of Formula (V) or (VI), or a solvate, hydrate, tautomer, N-oxide, or pharmaceutically acceptable salt thereof, wherein R$^1$ is —C(=O)OR$^{10}$ and R$^{10}$ is C$_{1-6}$alkynyl. In another embodiment is a compound of Formula (V) or (VI), or a solvate, hydrate, tautomer, N-oxide, or pharmaceutically acceptable salt thereof, wherein R$^1$ is —C(=O)R$^{10}$. In another embodiment is a compound of Formula (V) or (VI), or a solvate, hydrate, tautomer, N-oxide, or pharmaceutically acceptable salt thereof, wherein R$^1$ is —C(=O)R$^{10}$ and R$^{10}$ is C$_{1-6}$alkyl. In another embodiment is a compound of Formula (I), (II), (V), or (VI), or a solvate, hydrate, tautomer, N-oxide, or pharmaceutically acceptable salt thereof, wherein n is 0.

In another aspect is a compound of Formula (III):

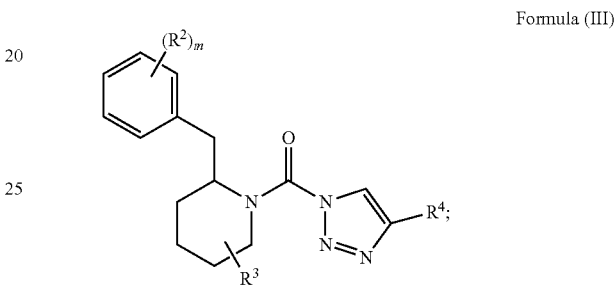

Formula (III)

wherein:
each R$^2$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{3-6}$cycloalkyl, C$_{1-6}$haloalkyl, C$_{1-6}$alkoxy, —O—C$_{1-6}$ alkenyl, —O—C$_{1-6}$alkynyl, C$_{1-6}$haloalkoxy, C$_{2-9}$heterocycloalkyl, C$_{6-10}$aryl, or C$_{2-9}$heteroaryl;

R$^3$ is C$_{1-6}$alkyl, C$_{1-6}$alkoxy, —O—C$_{1-6}$ alkenyl, or —O—C$_{1-6}$ alkynyl;

R$^4$ is

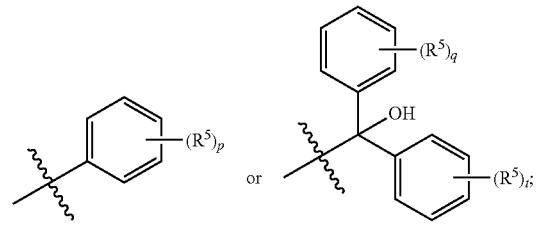

each R$^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{1-6}$haloalkyl, C$_{1-6}$alkoxy, —O—C$_{1-6}$ alkenyl, —O—C$_{1-6}$ alkynyl, or C$_{1-6}$haloalkoxy;

m is 0, 1, 2, or 3;
p is 0, 1, 2, or 3,
q is 0, 1, 2, or 3, and
t is 0, 1, 2, or 3;

or a solvate, hydrate, tautomer, N-oxide, or pharmaceutically acceptable salt thereof.

In another aspect is a compound of Formula (IV):

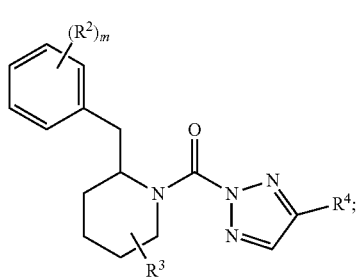

Formula (IV)

wherein:
each R² is independently halogen, —CN, —NH₂, —NH(CH₃), —N(CH₃)₂, —OH, —C(=O)OH, —C(=O)O(C₁₋₆ alkyl), —C(=O)NH₂, —C(=O)NH(C₁₋₆ alkyl), —C(=O)N(C₃₋₆ alkyl)₂, —S(=O)₂NH₂, —S(=O)₂NH(C₁₋₆ alkyl), —S(=O)₂N(C₃₋₆ alkyl)₂, C₃₋₆alkyl, C₃₋₆cycloalkyl, C₃₋₆alkoxy, —O—C₃₋₆alkenyl, —O—C₃₋₆alkynyl, C₃₋₆haloalkoxy, C₂₋₉heterocycloalkyl, C₆₋₁₀aryl, or C₂₋₉ heteroaryl;

R³ is C₁₋₆alkyl, C₁₋₆alkoxy, —O—C₁₋₆alkenyl, or —O—C₁₋₆ alkynyl;

R⁴ is

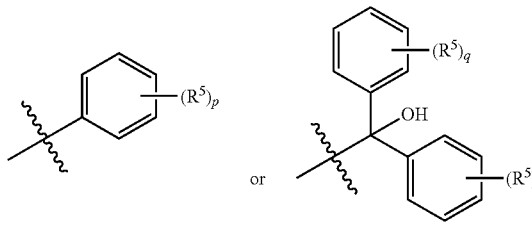

each R⁵ is independently halogen, —CN, —NH₂, —NH(CH₃), —N(CH₃)₂, —OH, —C(=O)OH, —C(=O)O(C₁₋₆ alkyl), —C(=O)NH₂, —C(=O)NH(C₁₋₆ alkyl), —C(=O)N(C₃₋₆ alkyl)₂, —S(=O)₂NH₂, —S(=O)₂NH(C₁₋₆ alkyl), —S(=O)₂N(C₃₋₆ alkyl)₂, C₃₋₆alkyl, C₁₋₆haloalkyl, C₁₋₆alkoxy, —O—C₁₋₆alkenyl, —O—C₁₋₆alkynyl, or C₃₋₆haloalkoxy, m is 0, 1, 2, or 3;
p is 0, 1, 2, or 3,
q is 0, 1, 2, or 3, and
t is 0, 1, 2, or 3;
or a solvate, hydrate, tautomer, N-oxide, or pharmaceutically acceptable salt thereof.

In another embodiment is a compound of Formula (III) or (IV), or a solvate, hydrate, tautomer, N-oxide, or pharmaceutically acceptable salt thereof, wherein R³ is —O—C₁₋₆alkynyl. In another embodiment is a compound of Formula (III) or (IV), or a solvate, hydrate, tautomer, N-oxide, or pharmaceutically acceptable salt thereof, wherein R³ is —OCH₂C≡CH.

In another aspect is a compound of Formula (VII):

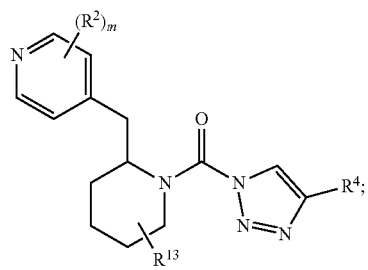

Formula (VII)

wherein:
each R² is independently halogen, —CN, —NH₂, —NH(CH₃), —N(CH₃)₂, —OH, —C(=O)OH, —C(=O)O(C₁₋₆alkyl), —C(=O)NH₂, —C(=O)NH(C₁₋₆alkyl), —C(=O)N(C₁₋₆alkyl)₂, —S(=O)₂NH₂, —S(=O)₂NH(C₁₋₆ alkyl), —S(=O)₂N(C₁₋₆ alkyl)₂, C₁₋₆alkyl, C₃₋₆cycloalkyl, C₁₋₆ alkoxy, —O—C₁₋₆ alkenyl, —O—C₁₋₆ alkynyl, C₁₋₆ haloalkoxy, C₂₋₉heterocycloalkyl, C₆₋₁₀ aryl, or C₂₋₉heteroaryl;

R¹³ is hydrogen, C₁₋₆alkyl, C₁₋₆alkoxy, —O—C₁₋₆alkenyl, —O—C₁₋₆alkynyl, or —O—CH₂C₃₋₆cycloalkyl;

R⁴ is

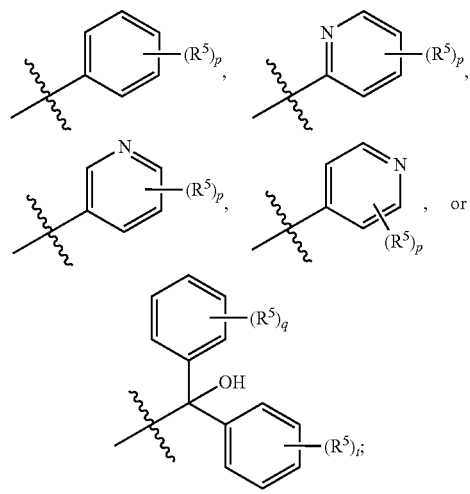

each R⁵ is independently halogen, —CN, —NH₂, —NH(CH₃), —N(CH₃)₂, —OH, —C(=O)OH, —C(=O)O(C₁₋₆ alkyl), —C(=O)NH₂, —C(=O)NH(C₁₋₆alkyl), —C(=O)N(C₁₋₆ alkyl)₂, —S(=O)₂NH₂, —S(=O)₂NH(C₁₋₆ alkyl), —S(=O)₂N(C₁₋₆ alkyl)₂, C₁₋₆ alkyl, C₁₋₆haloalkyl, C₁₋₆alkoxy, —O—C₁₋₆ alkenyl, —O—C₁₋₆alkynyl, C₁₋₆haloalkoxy, optionally substituted phenyl, or optionally substituted C₂₋₉heteroaryl, wherein optionally substituted phenyl and optionally substituted C₂₋₉heteroaryl are optionally substituted with one, two, or three groups selected from halogen, C₁₋₆ alkyl, C₁₋₆haloalkyl, C₁₋₆ alkoxy, and C₁₋₆haloalkoxy;

m is 0, 1, 2, or 3;
p is 0, 1, 2, or 3;
q is 0, 1, 2, or 3; and
t is 0, 1, 2, or 3;

or a solvate, hydrate, tautomer, N-oxide, or pharmaceutically acceptable salt thereof.

In another aspect is a compound of Formula (VIII):

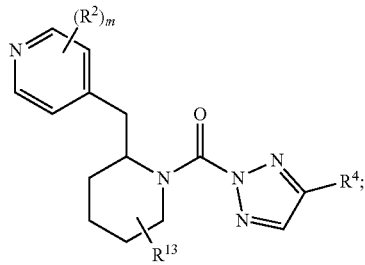

Formula (VIII)

wherein:
each $R^2$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{1-6}$alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{3-6}$cycloalkyl, C$_{1-6}$ alkoxy, —O—C$_{1-6}$ alkenyl, —O—C$_{1-6}$ alkynyl, C$_{1-6}$ haloalkoxy, C$_{2-9}$heterocycloalkyl, C$_{6-10}$ aryl, or C$_{2-9}$heteroaryl;
$R^{13}$ is hydrogen, C$_{1-6}$alkyl, C$_{1-6}$alkoxy, —O—C$_{1-6}$alkenyl, —O—C$_{1-6}$alkynyl, or —O—CH$_2$C$_{3-6}$cycloalkyl;
$R^4$ is

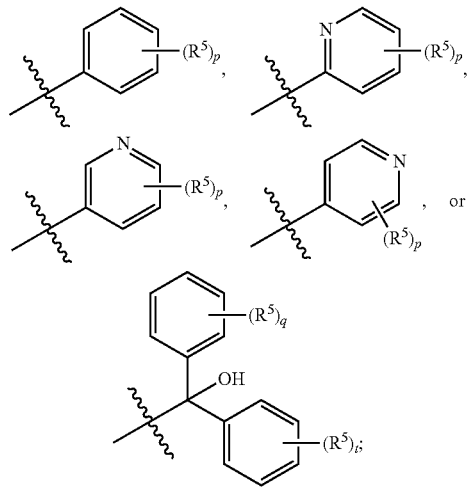

each $R^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$ alkyl, C$_{1-6}$haloalkyl, C$_{1-6}$alkoxy, —O—C$_{1-6}$ alkenyl, —O—C$_{1-6}$ alkynyl, C$_{1-6}$ haloalkoxy, optionally substituted phenyl, or optionally substituted C$_{2-9}$heteroaryl, wherein optionally substituted phenyl and optionally substituted C$_{2-9}$heteroaryl are optionally substituted with one, two, or three groups selected from halogen, C$_{1-6}$ alkyl, C$_{1-6}$haloalkyl, C$_{1-6}$ alkoxy, and C$_{1-6}$haloalkoxy;
m is 0, 1, 2, or 3;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (VII) or (VIII), or a solvate, hydrate, tautomer, N-oxide, or pharmaceutically acceptable salt thereof, wherein $R^{13}$ is hydrogen.

In another aspect is a compound of Formula (IX):

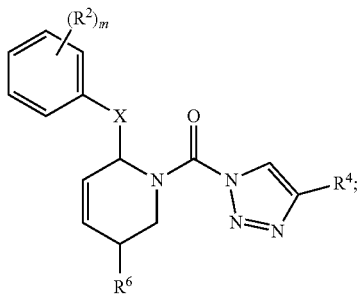

Formula (IX)

wherein:
X is —CH$_2$—, —OCH$_2$—, —CH$_2$O—, or —CH$_2$OCH$_2$—;
each $R^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{3-6}$ cycloalkyl, C$_{1-6}$haloalkyl, C$_{1-6}$alkoxy, —O—C$_{1-6}$ alkenyl, —O—C$_{1-6}$alkynyl, C$_{1-6}$haloalkoxy, C$_{2-9}$heterocycloalkyl, C$_{6-10}$ aryl, or C$_{2-9}$ heteroaryl;
$R^4$ is

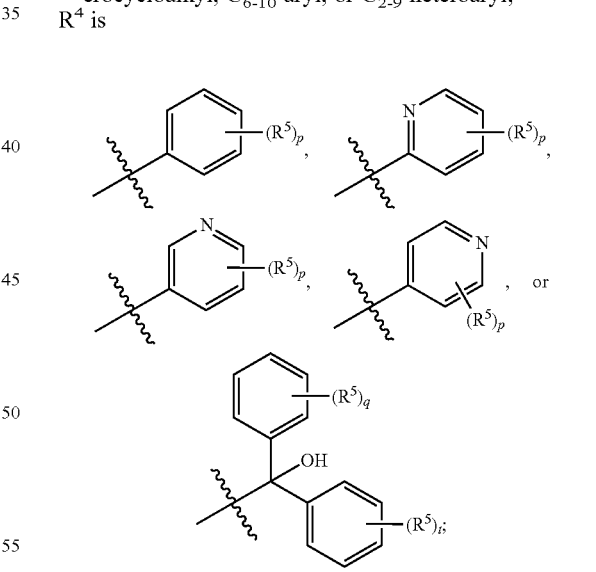

each $R^5$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{1-6}$alkyl), —C(=O)N(C$_{3-6}$ alkyl)$_2$, —S(=O)$_2$NH$_2$, —S(=O)$_2$NH(C$_{1-6}$alkyl), —S(=O)$_2$N(C$_{1-6}$ alkyl)$_2$, C$_{1-6}$alkyl, C$_{1-6}$haloalkyl, C$_{1-6}$alkoxy, —O—C$_{1-6}$ alkenyl, —O—C$_{1-6}$ alkynyl, C$_{1-6}$ haloalkoxy, optionally substituted phenyl, or optionally substituted C$_{2-9}$ heteroaryl, wherein optionally substituted phenyl and optionally substituted C$_{2-9}$heteroaryl are optionally substituted with one, two, or three groups selected from halogen, $C_{1-6}$ alkyl, $C_{1-6}$ haloalkyl, $C_{1-6}$ alkoxy, and $C_{1-6}$haloalkoxy;

$R^6$ is hydrogen, $C_{1-6}$ alkyl, —OH, $C_{1-6}$ alkoxy, —O—$C_{1-6}$ alkenyl, —O—$C_{1-6}$ alkynyl, or —O—$CH_2C_{3-6}$cycloalkyl, m is 0, 1, 2, or 3;
p is 0, 1, 2, or 3,
q is 0, 1, 2, or 3, and
t is 0, 1, 2, or 3;
or a solvate, hydrate, tautomer, N-oxide, or pharmaceutically acceptable salt thereof.

In another aspect is a compound of Formula (X):

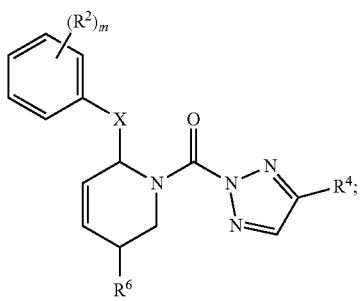

Formula (X)

wherein:

X is —$CH_2$—, —$OCH_2$—, —$CH_2O$—, or —$CH_2OCH_2$—;

each $R^2$ is independently halogen, —CN, —$NH_2$, —NH($CH_3$), —N($CH_3$)$_2$, —OH, —C(=O)OH, —C(=O)O($C_{1-6}$ alkyl), —C(=O)$NH_2$, —C(=O)NH($C_{1-6}$alkyl), —C(=O)N($C_{1-6}$ alkyl)$_2$, —S(=O)$_2NH_2$, —S(=O)$_2$NH($C_{1-6}$ alkyl), —S(=O)$_2$N($C_{1-6}$ alkyl)$_2$, $C_{1-6}$alkyl, $C_{3-6}$ cycloalkyl, $C_{1-6}$haloalkyl, $C_{1-6}$alkoxy, —O—$C_{1-6}$ alkenyl, —O—$C_{1-6}$alkynyl, $C_{1-6}$haloalkoxy, $C_{2-9}$heterocycloalkyl, $C_{6-10}$ aryl, or $C_{2-9}$ heteroaryl;

$R^4$ is

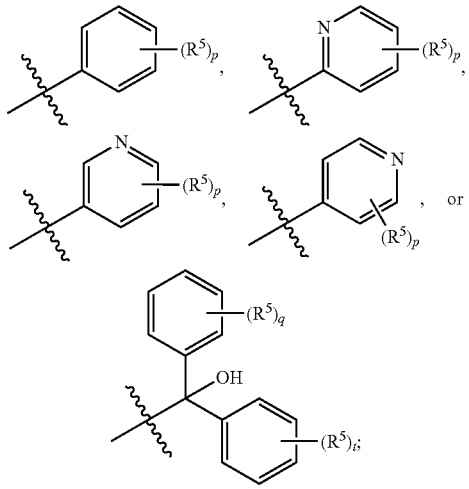

each $R^5$ is independently halogen, —CN, —$NH_2$, —NH($CH_3$), —N($CH_3$)$_2$, —OH, —C(=O)OH, —C(=O)O($C_{1-6}$alkyl), —C(=O)$NH_2$, —C(=O)NH($C_{1-6}$alkyl), —C(=O)N($C_{3-6}$ alkyl)$_2$, —S(=O)$_2NH_2$, —S(=O)$_2$NH($C_{1-6}$alkyl), —S(=O)$_2$N($C_{1-6}$ alkyl)$_2$, $C_{1-6}$alkyl, $C_{1-6}$haloalkyl, $C_{1-6}$alkoxy, —O—$C_{1-6}$ alkenyl, —O—$C_{1-6}$ alkynyl, $C_{1-6}$ haloalkoxy, optionally substituted phenyl, or optionally substituted $C_{2-9}$ heteroaryl, wherein optionally substituted phenyl and optionally substituted $C_{2-9}$heteroaryl are optionally substituted with one, two, or three groups selected from halogen, $C_{1-6}$ alkyl, $C_{1-6}$ haloalkyl, $C_{1-6}$ alkoxy, and $C_{1-6}$haloalkoxy;

$R^6$ is hydrogen, $C_{1-6}$ alkyl, —OH, $C_{1-6}$ alkoxy, —O—$C_{1-6}$ alkenyl, —O—$C_{1-6}$ alkynyl, or —O—$CH_2C_{3-6}$cycloalkyl, m is 0, 1, 2, or 3;
p is 0, 1, 2, or 3,
q is 0, 1, 2, or 3, and
t is 0, 1, 2, or 3;
or a solvate, hydrate, tautomer, N-oxide, or pharmaceutically acceptable salt thereof.

In another embodiment is a compound of Formula (IX) or (X), or a solvate, hydrate, tautomer, N-oxide, or pharmaceutically acceptable salt thereof, wherein X is —$CH_2$—. In another embodiment is a compound of Formula (IX) or (X), or a solvate, hydrate, tautomer, N-oxide, or pharmaceutically acceptable salt thereof, wherein X is —$CH_2OCH_2$—. In another embodiment is a compound of Formula (IX) or (X), or a solvate, hydrate, tautomer, N-oxide, or pharmaceutically acceptable salt thereof, wherein $R^6$ is hydrogen. In another embodiment is a compound of Formula (IX) or (X), or a solvate, hydrate, tautomer, N-oxide, or pharmaceutically acceptable salt thereof, wherein $R^6$ is —OH.

In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein $R^4$ is

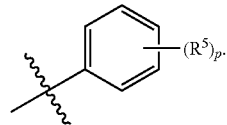

In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein each $R^5$ is independently halogen, $C_{1-6}$alkyl, $C_{1-6}$haloalkyl, $C_{1-6}$alkoxy, or $C_{1-6}$haloalkoxy. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein each $R^5$ is independently $C_{1-6}$haloalkoxy. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein each $R^5$ is —$OCF_3$. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein p is 0. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein p is 1. In another embodiment is a compound of Formula (I), (II), (III), (IV), (V), (VI), (VII), (VIII), (IX), or (X), or pharmaceutically acceptable salt thereof, wherein p is 2.

In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein $R^4$ is

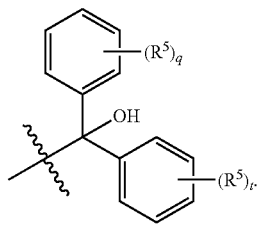

In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein each $R^5$ is independently halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein each $R^5$ is independently halogen, $C_{1-6}$alkyl, $C_{3-6}$haloalkyl, $C_{3-6}$alkoxy, or $C_{3-6}$haloalkoxy. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein q is 0 and t is 0. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein q is 1 and t is 0. In another embodiment is a compound of Formula (I), (II), (III), (IV), (V), (VI), (VII), (VIII), (IX), or (X), or a solvate, hydrate, tautomer, N-oxide, or pharmaceutically acceptable salt thereof, wherein q is 1 and t is 1.

In another aspect is a compound of Formula (XI):

Formula (XI)

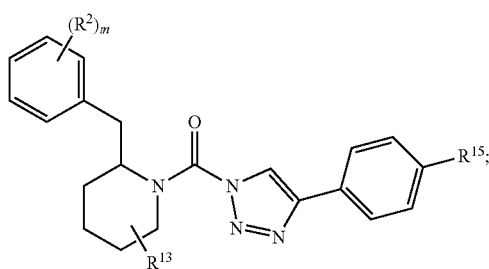

wherein:
  each $R^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{3-6}$ alkyl)$_2$, —S(=O)$_2$NH$_2$, —S(=O)$_2$NH(C$_{1-6}$ alkyl), —S(=O)$_2$N(C$_{3-6}$ alkyl)$_2$, $C_{3-6}$alkyl, $C_{3-6}$cycloalkyl, $C_{1-6}$alkoxy, —O—$C_{1-6}$ alkenyl, —O—$C_{1-6}$ alkynyl, $C_{3-6}$ haloalkoxy, $C_{2-9}$heterocycloalkyl, $C_{6-10}$ aryl, or $C_{2-9}$ heteroaryl;
  $R^{13}$ is hydrogen, $C_{1-6}$alkyl, $C_{1-6}$alkoxy, —O—$C_{1-6}$alkenyl, —O—$C_{1-6}$alkynyl, or —O—CH$_2$C$_{3-6}$cycloalkyl;
  $R^{15}$ is $C_{2-9}$ heteroaryl optionally substituted with one, two, or three groups selected from halogen, $C_{1-6}$alkyl, $C_{1-6}$haloalkyl, $C_{3-6}$ alkoxy, and $C_{3-6}$ haloalkoxy; and
  m is 0, 1, 2, or 3;
  or a solvate, hydrate, tautomer, N-oxide, or pharmaceutically acceptable salt thereof.

In another aspect is a compound of Formula (XII):

Formula (XII)

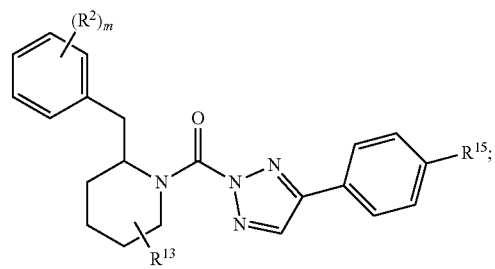

wherein:
  each $R^2$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$ alkyl), —S(=O)$_2$N(C$_{1-6}$ alkyl)$_2$, $C_{1-6}$alkyl, $C_{3-6}$cycloalkyl, $C_{1-6}$haloalkyl, $C_{1-6}$ alkoxy, —O—$C_{1-6}$ alkenyl, —O—$C_{1-6}$ alkynyl, $C_{1-6}$haloalkoxy, $C_{2-9}$heterocycloalkyl, $C_{6-10}$aryl, or $C_{2-9}$heteroaryl;
  $R^{13}$ is hydrogen, $C_{1-6}$alkyl, $C_{1-6}$alkoxy, —O—$C_{1-6}$ alkenyl, —O—$C_{1-6}$alkynyl, or —O—CH$_2$C$_{3-6}$cycloalkyl;
  $R^{15}$ is $C_{2-9}$heteroaryl optionally substituted with one, two, or three groups selected from halogen, $C_{1-6}$alkyl, $C_{1-6}$haloalkyl, $C_{1-6}$alkoxy, and $C_{1-6}$ haloalkoxy; and
  m is 0, 1, 2, or 3;
  or a solvate, hydrate, tautomer, N-oxide, or pharmaceutically acceptable salt thereof.

In another embodiment is a compound of Formula (XI) or (XII), or a solvate, hydrate, tautomer, N-oxide, or pharmaceutically acceptable salt thereof, wherein $R^{13}$ is hydrogen. In another embodiment is a compound of Formula (XI) or (XII), or a solvate, hydrate, tautomer, N-oxide, or pharmaceutically acceptable salt thereof, wherein $R^{15}$ is pyridine optionally substituted with one or two groups selected from halogen, $C_{1-6}$alkyl, $C_{1-6}$haloalkyl, $C_{1-6}$alkoxy, and $C_{1-6}$haloalkoxy. In another embodiment is a compound of Formula (XI) or (XII), or a solvate, hydrate, tautomer, N-oxide, or pharmaceutically acceptable salt thereof, wherein $R^{15}$ is pyrimidine optionally substituted with one or two groups selected from halogen, $C_{1-6}$alkyl, $C_{1-6}$haloalkyl, $C_{1-6}$alkoxy, and $C_{1-6}$haloalkoxy. In another embodiment is a compound of Formula (XI) or (XII), or a solvate, hydrate, tautomer, N-oxide, or pharmaceutically acceptable salt thereof, wherein $R^{15}$ is pyridazine optionally substituted with one or two groups selected from halogen, $C_{1-6}$alkyl, $C_{1-6}$haloalkyl, $C_{1-6}$ alkoxy, and $C_{1-6}$haloalkoxy.

In another embodiment is a compound of Formula (I), (II), (III), (IV), (V), (VI), (VII), (VIII), (IX), (X), (XI), or (XII), or a solvate, hydrate, tautomer, N-oxide, or pharmaceutically acceptable salt thereof, wherein each $R^2$ is independently halogen, $C_{1-6}$alkyl, $C_{1-6}$haloalkyl, $C_{1-6}$ alkoxy, —O—$C_{1-6}$alkenyl, —O—$C_{1-6}$alkynyl, or $C_{1-6}$haloalkoxy. In another embodiment is a compound of Formula (I), (II), (III), (IV), (V), (VI), (VII), (VIII), (IX), (X), (XI), or (XII), or a solvate, hydrate, tautomer, N-oxide, or pharmaceutically acceptable salt thereof, wherein each $R^2$ is independently halogen, $C_{1-6}$alkyl, $C_{1-6}$haloalkyl, $C_{1-6}$alkoxy, or $C_{1-6}$haloalkoxy. In another embodiment is a compound of Formula (I), (II), (III), (IV), (V), (VI), (VII), (VIII), (IX), (X), (XI), or (XII), or a solvate, hydrate, tautomer, N-oxide, or pharmaceutically acceptable salt thereof, wherein m is 0. In another embodiment is a compound of Formula (I), (II), (III), (IV), (V), (VI), (VII), (VIII), (IX), (X), (XI), or (XII), or a solvate, hydrate, tautomer, N-oxide, or pharmaceutically acceptable salt thereof, wherein m is 1. In another embodiment is a compound of Formula (I), (II), (III), (IV), (V), (VI), (VII), (VIII), (IX), (X), (XI), or (XII), or a solvate, hydrate, tautomer, N-oxide, or pharmaceutically acceptable salt thereof, wherein m is 2.

In another embodiment is a compound having the structure:

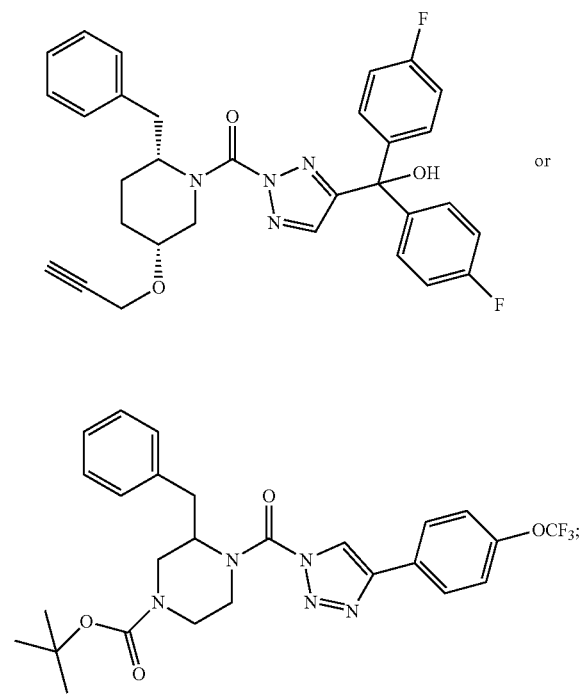 [SMILES: C#CCO[C@@H]1CC[C@H](Cc2ccccc2)N(C(=O)n2ncc(C(O)(c3ccc(F)cc3)c3ccc(F)cc3)n2)C1 ; CC(C)(C)OC(=O)N1CCN(C(=O)n2cc(-c3ccc(OC(F)(F)F)cc3)nn2)C(Cc2ccccc2)C1]

or a solvate, hydrate, tautomer, N-oxide, or a pharmaceutically acceptable salt thereof.

In another embodiment is a compound having the structure:

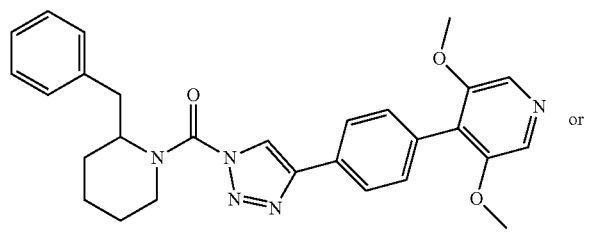

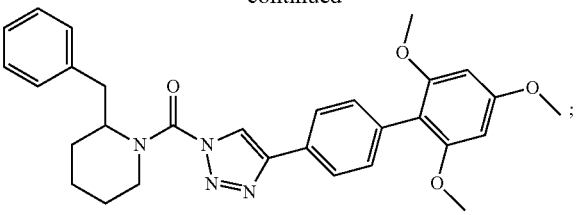

or a solvate, hydrate, tautomer, N-oxide, or a pharmaceutically acceptable salt thereof.

In another embodiment is a pharmaceutical composition comprising a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, and at least one pharmaceutically acceptable excipient.

In another embodiment is a method of treating a neurodegenerative disease or neuroinflammatory disease in a patient in need thereof, comprising administering to the patient a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof. In another embodiment is a method of treating a neurodegenerative disease or neuroinflammatory disease in a patient in need thereof, wherein the neurodegenerative disease or neuroinflammatory disease is Parkinson's Disease, Alzheimer's Disease, Huntington's Disease, or Amyotrophic Lateral Sclerosis (ALS), comprising administering to the patient a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof. In another embodiment is a method of treating hepatic fibrosis or kidney fibrosis in a patient in need thereof, comprising administering to the patient a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof.

BRIEF DESCRIPTION OF THE DRAWINGS

FIGS. 6A, C, E, G, I, & K show quantification of 2-AG (A) and related bioactive lipids (C, E, G, I, & K) in brain tissue from mice treated with vehicle or compounds 14, 17 or control compound 22. Lipid profiles from DAGLα-/- mice are shown for comparison. Data represent average values±SEM; n=5-6 mice per group. *P<0.05; P<0.01; *P<0.001 for modulator treated DAGLα+/+ mice or DAGLα-/- mice vs. vehicle treated DAGLα+/+ mice. FIGS. 6B, D, F, H, J, & L show time-dependent changes in 2-AG (B) and bioactive lipids (D, F, H, J, & L) in brain tissue from mice treated with compound 14. Data represent average values±SEM; n=4-5 mice per group. *P<0.05; P<0.01; *P<0.001 for modulator treated vs. vehicle treated mice.

FIGS. 8A-C show the quantification of 2-AG and related bioactive lipids in brain tissue from mice treated with DAGL modulators, with or without subsequent treatment with LPS. FIG. 8D shows the quantification of IL-1β cytokine from DAGL modulator treated, or DAGLα-/- mice, with or without subsequent treatment with LPS. For FIGS. 10A-D, data represent average values±SEM; n=5-8 mice per group. P<0.001; *P<0.001 for all groups vs. vehicle treated DAGLα+/+ mice and ####P<0.001 for all groups compared with LPS-treated DAGLα+/+ mice. FIGS. 8E-F show time course data of body temperature changes for mice pretreated with vehicle or DAGL modulator (E) or for DAGLα+/+ and DAGLα-/- mice (F) following LPS treatment. Data represent average values±SEM; n=5-6. For FIG. 10E, *P<0.05 Veh+Veh vs. Veh+LPS group; #P<0.05 for compound 14+LPS and compound 17+LPS vs. Veh+LPS group. For FIG. 10F, *P<0.05 for DAGLα+/++Veh vs. DAGLα+/++LPS groups; #P<0.05 for DAGLα-/-+Veh vs. DAGLα-/-+LPS groups; &P<0.05 for DAGLα-/-+LPS vs. DAGLα+/++LPS groups.

DETAILED DESCRIPTION OF THE INVENTION

Figure 1:
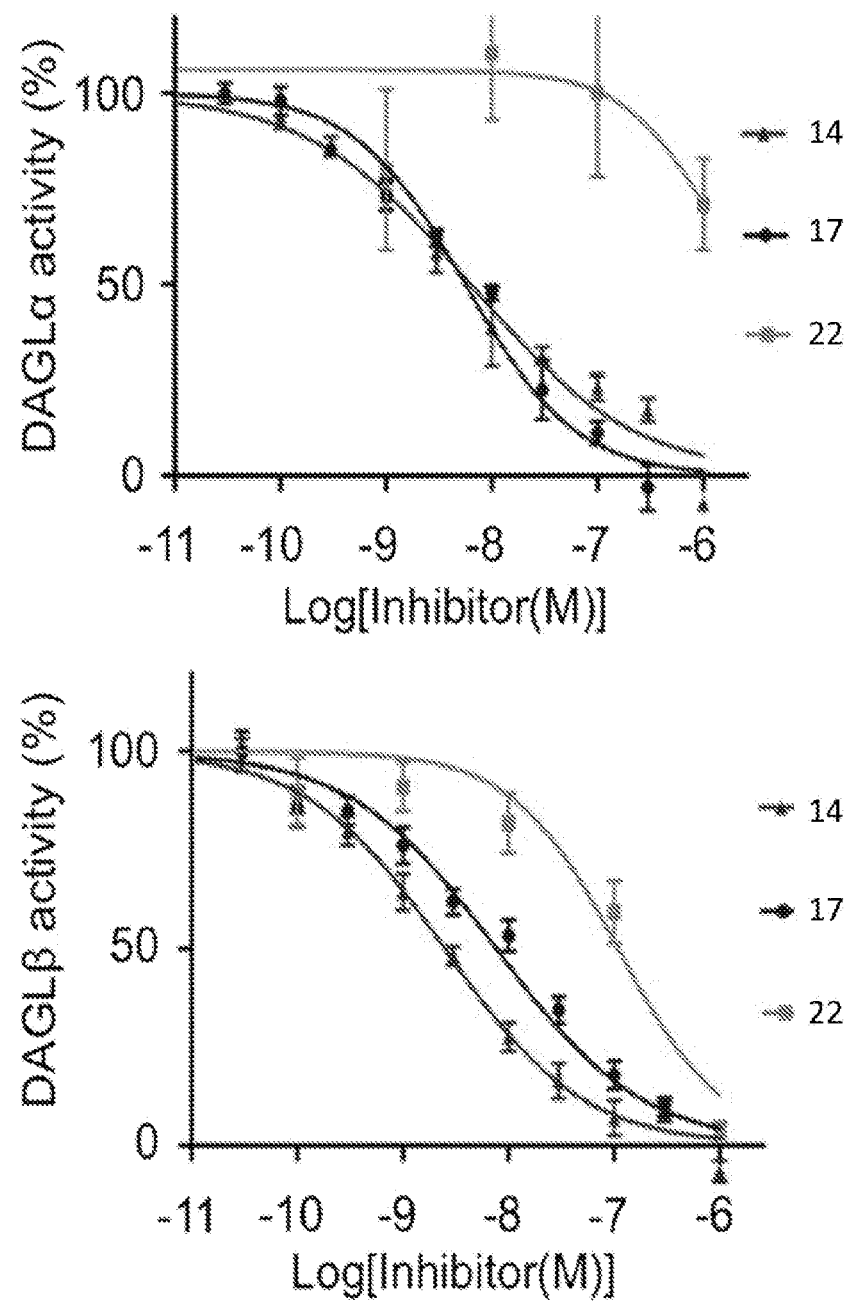
FIG. 1 provides concentration-dependent inhibition curves for DAGL modulators against DAGLα and DAGLβ as determined using a SAG assay. Data represent average values±SD; n=4 per group.

This disclosure provides, for example, compounds and compositions which are modulators of DAGL, and their use as medicinal agents, processes for their preparation, and pharmaceutical compositions that include disclosed compounds as at least one active ingredient. In some embodiments, a DAGL modulator provided herein is an inhibitor of DAGLα, DAGLβ, or both DAGLα and DAGLβ. In some cases a DAGL modulator is selective for inhibition of DAGLα over DAGLβ. In some cases a DAGL modulator is selective for inhibition of DAGLβ over DAGLα. The disclosure also provides for the use of disclosed compounds as medicaments and/or in the manufacture of medicaments for the inhibition of DAGL, and/or DAGL activity in warm-blooded animals such as humans.

In one aspect, a DAGL modulator as described herein is useful for studying the (patho) physiological role of DAGLα and DAGLβ in brain lipid signaling. In some embodiments, studying the role of DAGLα, DAGLβ, or both DAGLα and DAGLβ comprises inhibiting DAGLα, DAGLβ, or both DAGLα and DAGLβ with a DAGL modulator provided herein.

In one aspect, a DAGL modulator provided herein is useful for the treatment of a neurodegenerative disease, inflammatory pain, drug abuse, or any combination thereof.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the $NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N$(R^a)_2$, —$N(R^a)$C(O)O$R^f$, —OC(O)—NR$^a$R$^f$, —$N(R^a)$C(O)$R^f$, —$N(R^a)$S(O)$_1$$R^f$ (where t is 1 or 2), —S(O)$_t$O IV (where t is 1 or 2), —S(O)$_t$$R^f$ (where t is 1 or 2) and —S(O)$_t$N$(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(=O)—$R^f$, —$N(R^a)_2$, —C(=O)$R^a$, —C(=O)O$R^a$, —C(=O)N$(R^a)_2$, —$N(R^a)$C(=O)O$R^f$, —OC(=O)—NR$^a$R$^f$, —$N(R^a)$C(=O)$R^f$, —$N(R^a)$S(=O)$_t$$R^f$ (where t is 1 or 2), —S(=O)$_t$O$R^a$ (where t is 1 or 2), —S(=O)$_t$$R^f$ (where t is 1 or 2) and —S(=O)$_t$N$(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(=O)—$R^f$, —N$(R^a)_2$, —C(=O)$R^a$, —C(=O)O$R^a$, —C(=O)N$(R^a)_2$, —$N(R^a)$C(=O)O$R^f$, —OC(=O)—NR$^a$R$^f$, —$N(R^a)$C(=O) $R^f$, —$N(R^a)$S(=O)$_t$$R^f$ (where t is 1 or 2), —S(=O)$_t$O$R^a$ (where t is 1 or 2), —S(=O)$_t$$R^f$ (where t is 1 or 2) and —S(=O)$_t$N$(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(=O)—$R^f$, —N$(R^a)_2$, —C(=O)$R^a$, —C(=O)O$R^a$, —C(=O)N$(R^a)_2$, —$N(R^a)$C(=O)O$R^f$, —OC(=O)—NR$^a$R$^f$, —$N(R^a)$C(=O) $R^f$, —$N(R^a)$S(=O)$_t$$R^f$ (where t is 1 or 2), —S(=O)$_t$O$R^a$ (where t is 1 or 2), —S(=O)$_t$$R^f$ (where t is 1 or 2) and —S(=O)$_t$N$(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N$(R^a)_2$,—$R^b$—N$(R^a)_2$, —$R^b$—C(O)$R^a$, —$R^b$—C(O)O$R^a$, —$R^b$—C(O)N$(R^a)_2$, —$R^b$—O—$R^c$—C(O)N$(R^a)_2$, —$R^b$—N$(R^a)$C(O)O$R^a$, —$R^b$—N$(R^a)$C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula O-aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, Spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$-01V, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, $R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkyl alkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroaryl alkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

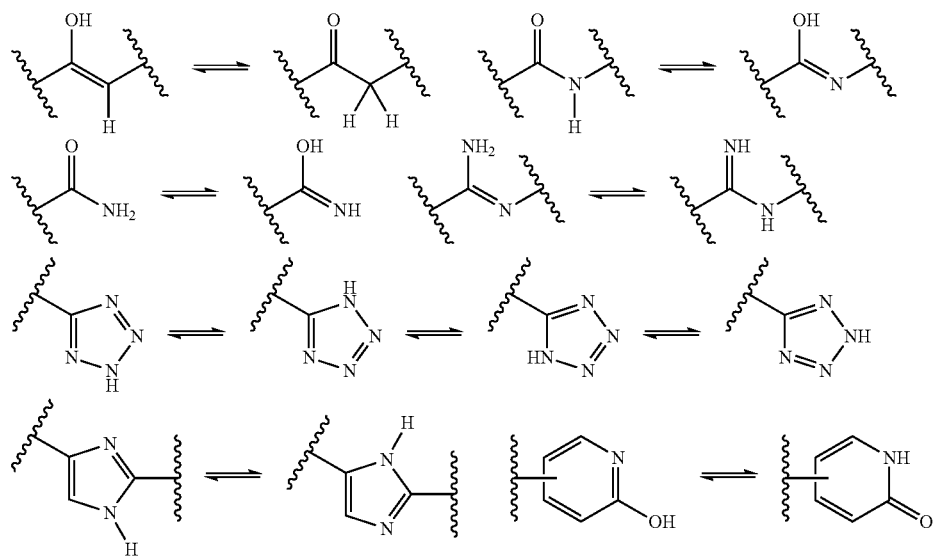

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, the prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

In some embodiments, the compounds of Formula (I), (II), (III), (IV), (V), (VI), (VII), (VIII), (IX), (X), (XI), or (XII) modulate one or more serine hydrolases (SH). In some cases, the compounds exhibit negligible cross-reactivity with other protein classes. For example, the compounds selectively inhibit enzymes from diverse branches of the SH family, including lipases (e.g., DAGL, PAFAH2), peptidases (e.g., APEH), thioesterases, amidases, and uncharacterized hydrolases (e.g, ABHD11). Non-limiting examples of peptidases include N-acylaminoacyl-peptide hydrolase (APEH), lysosomal pro-X carboxypeptidase (PRCP), and cathepsin A (CTSA). Non-limiting examples of lipases, which as used herein also encompasses phospholipases, include diacylglycerol lipases (e.g., DAGL), arylacetamide deacetylase-like 1 (AADACL1), alpha/beta-hydrolase domain 6 (ABHD6), esterase D (ESD), platelet-activating factor acetylhydrolase 2 (PAFAH2), lysosomal phospholipase A3 (LYPLA3), and alpha/beta-hydrolase domain 12 (ABHD12). Non-limiting examples of thioesterases include lysosomal phospholipase A1 (LYPLA1) and lysosomal phospholipase A2 (LYPLA2). A non-limiting example of an amidase is fatty acid amide hydrolase (FAAH). Serine hydrolase enzymes include uncharacterized serine hydrolase enzymes such as alpha/beta-hydrolase domain 11 (ABHD11), alpha/beta-hydrolase domain 13 (ABHD13), an HLA-B associated transcript 5 (BATS). In some embodiments, the compounds inhibit a single serine hydrolase enzyme. In some embodiments, the compounds inhibit multiple serine hydrolases. In some cases, the compounds have a potency of less than 1 µM, 100 nM, 10 nM, 1 nM, or 0.1 nM in cells and/or mice. In some cases, the compounds are effective at concentrations less than 10 mg/kg, 1 mg/kg, 0.1 mg/kg, or 0.01 mg/kg in cells and/or mice.

In some aspects of the disclosure, the compounds of Formula (I), (II), (III), (IV), (V), (VI), (VII), (VIII), (IX), (X), (XI), or (XII) described herein are modulators of DAGL. In some embodiments, the compounds of Formula (I), (II), (III), (IV), (V), (VI), (VII), (VIII), (IX), (X), (XI), or (XII) described herein are inhibitors of DAGL. In some embodiments, the compounds of Formula (I), (II), (III), (IV), (V), (VI), (VII), (VIII), (IX), (X), (XI), or (XII) are inhibitors of DAGLα. In some embodiments, the compounds of Formula (I), (II), (III), (IV), (V), (VI), (VII), (VIII), (IX), (X), (XI), or (XII) are inhibitors of DAGLβ. In some embodiments, the compounds of Formula (I), (II), (III), (IV), (V), (VI), (VII), (VIII), (IX), (X), (XI), or (XII) are inhibitors of DAGLα and DAGLβ. In some embodiments, the compounds of Formula (I), (II), (III), (IV), (V), (VI), (VII), (VIII), (IX), (X), (XI), or (XII) selectively inhibit DAGLα over DAGLβ. In some embodiments, the compounds of Formula (I), (II), (III), (IV), (V), (VI), (VII), (VIII), (IX), (X), (XI), or (XII) selectively inhibit DAGLβ over DAGLα.

In one embodiment is a compound of Formula (I):

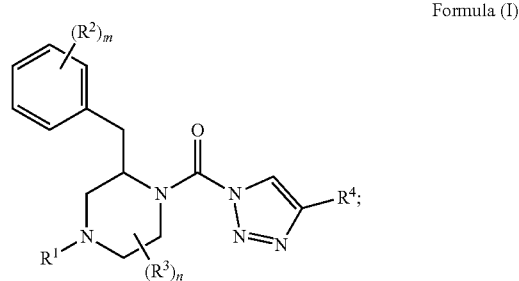

Formula (I)

wherein:
$R^1$ is H, $C_{1-6}$ alkyl, —C(=O)O$R^{10}$, or —S(=O)$_2R^{10}$,
each $R^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{3-6}$ alkyl)$_2$, $C_{3-6}$ alkyl, $C_{3-6}$ cycloalkyl, $C_{1-6}$haloalkyl, $C_{1-6}$alkoxy, —O—$C_{3-6}$ alkenyl, —O—$C_{3-6}$alkynyl, $C_{1-6}$haloalkoxy, $C_{2-9}$heterocycloalkyl, $C_{6-10}$aryl, or $C_{2-9}$ heteroaryl;
each $R^3$ is independently halogen, —CN, —C(=O)OH, —C(=O)O(C$_{3-6}$ alkyl), —C(=O)NH$_2$, —C(=O)NH(C$_{3-6}$alkyl), —C(=O)N(C$_{1-6}$alkyl)$_2$, —S(=O)$_2$NH$_2$, —S(=O)$_2$NH(C$_{1-6}$alkyl), —S(=O)$_2$N(C$_{1-6}$ alkyl)$_2$, $C_{1-6}$ alkyl, $C_{3-6}$cycloalkyl, $C_{1-6}$ haloalkyl, $C_{2-9}$ heterocycloalkyl, $C_{6-10}$aryl, or $C_{2-9}$ heteroaryl;
$R^4$ is

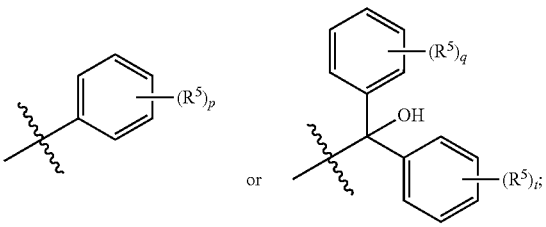

each $R^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{3-6}$ alkyl)$_2$, C$_{1-6}$alkyl, C$_{1-6}$alkoxy, —O—C$_{1-6}$alkenyl, —O—C$_{1-6}$alkynyl, or C$_{3-6}$ haloalkoxy;

$R^{10}$ is C$_{1-6}$alkyl;

m is 0, 1, 2, or 3;

n is 0, 1, or 2;

p is 0, 1, 2, or 3;

q is 0, 1, 2, or 3; and t is 0, 1, 2, or 3;

or a solvate, hydrate, tautomer, N-oxide, or pharmaceutically acceptable salt thereof.

In another embodiment is a compound of Formula (I), wherein $R^1$ is H. In another embodiment is a compound of Formula (I), wherein $R^1$ is C$_{1-6}$alkyl. In another embodiment is a compound of Formula (I), wherein $R^1$ is —C(=O)OR$^{10}$. In another embodiment is a compound of Formula (I), wherein $R^1$ is —C(=O)OR$^{10}$ and $R^{10}$ is —CH$_3$. In another embodiment is a compound of Formula (I), wherein $R^1$ is —C(=O)OR$^{10}$ and $R^{10}$ is —CH$_2$CH$_3$. In another embodiment is a compound of Formula (I), wherein $R^1$ is —C(=O)OR$^{10}$ and $R^{10}$ is —CH(CH$_3$)$_2$. In another embodiment is a compound of Formula (I), wherein $R^1$ is —C(=O)OR$^{10}$ and $R^{10}$ is —C(CH$_3$)$_3$. In another embodiment is a compound of Formula (I), wherein $R^1$ is —S(=O)$_2$R$^{10}$. In another embodiment is a compound of Formula (I), wherein $R^1$ is —S(=O)$_2$R$^{10}$ and $R^{10}$ is —CH$_3$. In another embodiment is a compound of Formula (I), wherein $R^1$ is —S(=O)$_2$R$^{10}$ and $R^{10}$ is —CH$_2$CH$_3$.

In another embodiment is a compound of Formula (I), wherein m is 0. In another embodiment is a compound of Formula (I), wherein m is 1. In another embodiment is a compound of Formula (I), wherein m is 1 and $R^2$ is halogen, C$_{1-6}$alkyl, C$_{1-6}$haloalkyl, C$_{1-6}$alkoxy, —O—C$_{1-6}$alkenyl, —O—C$_{1-6}$alkynyl, or C$_{1-6}$haloalkoxy. In another embodiment is a compound of Formula (I), wherein m is 1 and $R^2$ is halogen, C$_{1-6}$alkyl, C$_{1-6}$haloalkyl, C$_{1-6}$alkoxy, or C$_{1-6}$haloalkoxy. In another embodiment is a compound of Formula (I), wherein m is 1 and $R^2$ is halogen. In another embodiment is a compound of Formula (I), wherein m is 1 and $R^2$ is C$_{1-6}$alkyl. In another embodiment is a compound of Formula (I), wherein m is 1 and $R^2$ is C$_{1-6}$ haloalkyl. In another embodiment is a compound of Formula (I), wherein m is 1 and $R^2$ is C$_{1-6}$alkoxy. In another embodiment is a compound of Formula (I), wherein m is 1 and $R^2$ is C$_{1-6}$ haloalkoxy. In another embodiment is a compound of Formula (I), wherein m is 2. In another embodiment is a compound of Formula (I), wherein m is 2 and each $R^2$ is independently halogen, C$_{1-6}$alkyl, C$_{1-6}$haloalkyl, C$_{1-6}$alkoxy, —O—C$_{1-6}$alkenyl, —O—C$_{1-6}$alkynyl, or C$_{1-6}$haloalkoxy. In another embodiment is a compound of Formula (I), wherein m is 2 and each $R^2$ is independently halogen, C$_{1-6}$ alkyl, C$_{1-6}$haloalkyl, C$_{1-6}$alkoxy, or C$_{1-6}$haloalkoxy.

In another embodiment is a compound of Formula (I), wherein n is 0. In another embodiment is a compound of Formula (I), wherein n is 1. In another embodiment is a compound of Formula (I), wherein n is 1 and $R^3$ is halogen, C$_{1-6}$alkyl, or C$_{1-6}$haloalkyl. In another embodiment is a compound of Formula (I), wherein n is 1 and $R^3$ is halogen. In another embodiment is a compound of Formula (I), wherein n is 1 and $R^3$ is C$_{1-6}$alkyl. In another embodiment is a compound of Formula (I), wherein n is 1 and $R^3$ is C$_{1-6}$haloalkyl. In another embodiment is a compound of Formula (I), wherein n is 2. In another embodiment is a compound of Formula (I), wherein n is 2 and each $R^3$ is independently halogen, C$_{1-6}$alkyl, or C$_{1-6}$haloalkyl.

In another embodiment is a compound of Formula (I), wherein $R^4$ is

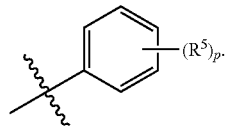

In another embodiment is a compound of Formula (I), wherein $R^4$ is

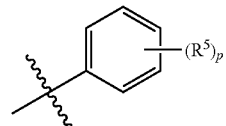

and p is 0. In another embodiment is a compound of Formula (I), wherein $R^4$ is

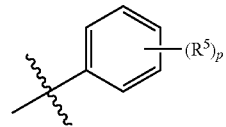

and p is 1. In another embodiment is a compound of Formula (I), wherein $R^4$ is

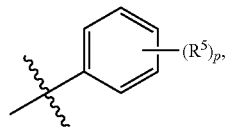

p is 1, and $R^5$ is halogen, C$_{1-6}$alkyl, C$_{1-6}$alkoxy, —O—C$_{1-6}$alkenyl, —O—C$_{1-6}$alkynyl, or C$_{1-6}$haloalkoxy. In another embodiment is a compound of Formula (I), wherein $R^4$ is

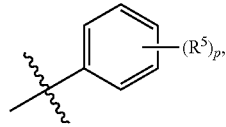

p is 1, and $R^5$ is halogen, C$_{1-6}$ alkyl, C$_{1-6}$haloalkyl, C$_{1-6}$alkoxy, or C$_{1-6}$haloalkoxy. In another embodiment is a compound of Formula (I), wherein $R^4$ is

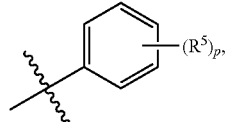

p is 1, and $R^5$ is halogen. In another embodiment is a compound of Formula (I), wherein $R^4$ is

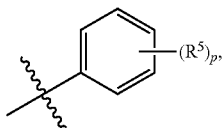

p is 1, and $R^5$ is $C_{1-6}$alkyl. In another embodiment is a compound of Formula (I), wherein $R^4$ is

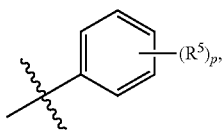

p is 1, and $R^5$ is $C_{1-6}$haloalkyl. In another embodiment is a compound of Formula (I), wherein $R^4$ is

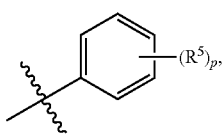

p is 1, and $R^5$ is $C_{1-6}$alkoxy. In another embodiment is a compound of Formula (I), wherein $R^4$ is

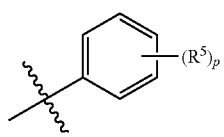

p is 1, and $R^5$ is $C_{1-6}$haloalkoxy. In another embodiment is a compound of Formula (I), wherein $R^4$ is

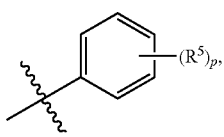

and p is 2. In another embodiment is a compound of Formula (I), wherein $R^4$ is

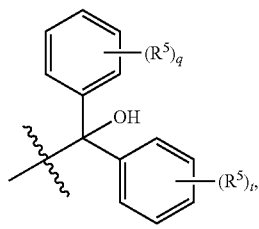

p is 2, and each $R^5$ is independently halogen, $C_{1-6}$alkyl, $C_{1-6}$haloalkyl $C_{1-6}$alkoxy, —O—$C_{1-6}$alkenyl, —O—$C_{1-6}$alkynyl, or $C_{1-6}$haloalkoxy.

In another embodiment is a compound of Formula (I), wherein $R^4$ is

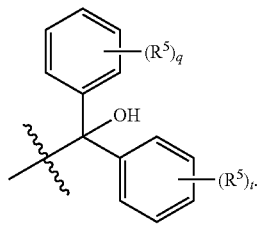

In another embodiment is a compound of Formula (I), wherein $R^4$ is

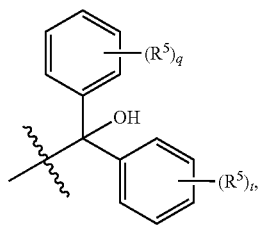

q is 0, and t is 0. In another embodiment is a compound of Formula (I), wherein $R^4$ is

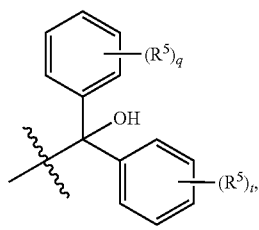

q is 1, and t is 0. In another embodiment is a compound of Formula (I), wherein $R^4$ is

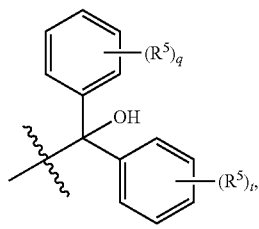

q is 1, t is 0, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (I), wherein $R^4$ is

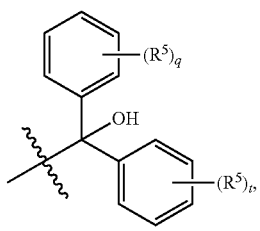

q is 1, t is 0, and R⁵ is halogen, $C_{1-6}$alkyl, $C_{1-6}$haloalkyl, $C_{1-6}$alkoxy, or $C_{1-6}$haloalkoxy. In another embodiment is a compound of Formula (I), wherein $R^4$ is

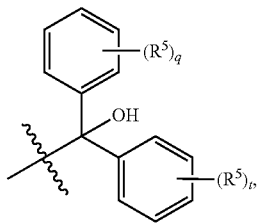

q is 1, and t is 1. In another embodiment is a compound of Formula (I), wherein $R^4$ is

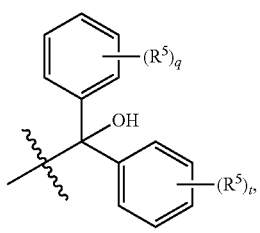

q is 1, t is 1, and each R⁵ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (I), wherein $R^4$ is

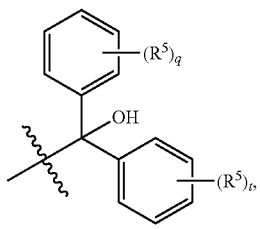

q is 1, t is 1, and each R⁵ is independently halogen, $C_{1-6}$alkyl, $C_{1-6}$alkoxy, or $C_{1-6}$haloalkoxy. In another embodiment is a compound of Formula (I), wherein $R^4$ is

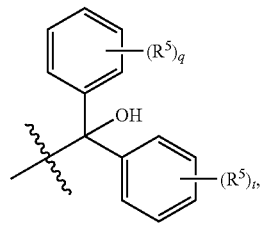

q is 1, t is 1, and each R⁵ is halogen. In another embodiment is a compound of Formula (I), wherein $R^4$ is

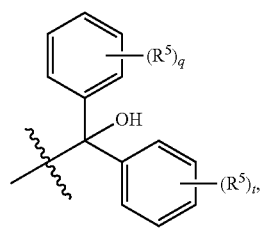

q is 1, t is 1, and each R⁵ is $C_{1-6}$alkyl. In another embodiment is a compound of Formula (I), wherein $R^4$ is

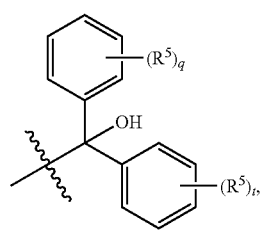

q is 1, t is 1, and each R⁵ is $C_{1-6}$ haloalkyl. In another embodiment is a compound of Formula (I), wherein $R^4$ is

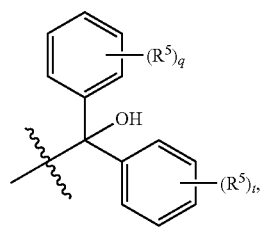

q is 1, t is 1, and each R⁵ is $C_{1-6}$alkoxy. In another embodiment is a compound of Formula (I), wherein $R^4$ is q is 1, t is 1, and each R⁵ is $C_{1-6}$haloalkoxy.

In another embodiment is a compound of Formula (II):

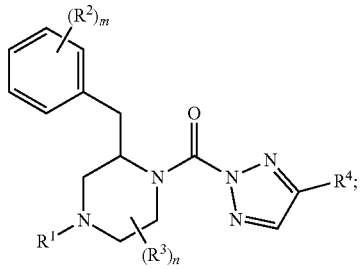

Formula (II)

wherein:
R$^1$ is H, C$_{1-6}$alkyl, —C(=O)OR$^{10}$, or —S(=O)$_2$R$^{10}$,
each R$^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{3-6}$cycloalkyl, C$_{1-6}$haloalkyl, C$_{1-6}$alkoxy, —O—C$_{1-6}$alkenyl, —O—C$_{1-6}$alkynyl, C$_{1-6}$haloalkoxy, C$_{2-9}$heterocycloalkyl, C$_{6-10}$aryl, or C$_{2-9}$ heteroaryl;
each R$^3$ is independently halogen, —CN, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$alkyl)$_2$, C$_{1-6}$ alkyl, C$_{3-6}$cycloalkyl, C$_{1-6}$haloalkyl, C$_{2-9}$ heterocycloalkyl, C$_{6-10}$aryl, or C$_{2-9}$ heteroaryl;
R$^4$ is

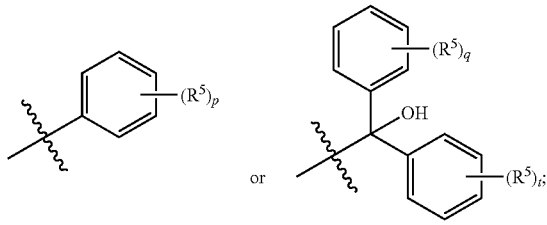

each R$^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$ alkyl, C$_{1-6}$haloalkyl, C$_{1-6}$alkoxy, —O—C$_{1-6}$alkenyl, —O—C$_{1-6}$alkynyl, or C$_{1-6}$haloalkoxy; R$^{10}$ is C$_{1-6}$alkyl;
m is 0, 1, 2, or 3;
n is 0, 1, or 2;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (II), wherein R$^1$ is H. In another embodiment is a compound of Formula (II), wherein R$^1$ is C$_{1-6}$alkyl. In another embodiment is a compound of Formula (II), wherein R$^1$ is —C(=O)OR$^{10}$. In another embodiment is a compound of Formula (II), wherein R$^1$ is —C(=O)OR$^{10}$ and R$^{10}$ is —CH$_3$. In another embodiment is a compound of Formula (II), wherein R$^1$ is —C(=O)OR$^{10}$ and R$^{10}$ is —CH$_2$CH$_3$. In another embodiment is a compound of Formula (II), wherein R$^1$ is —C(=O)OR$^{10}$ and R$^{10}$ is —CH(CH$_3$)$_2$. In another embodiment is a compound of Formula (II), wherein R$^1$ is —C(=O)OR$^{10}$ and R$^{10}$ is —C(CH$_3$)$_3$. In another embodiment is a compound of Formula (II), wherein R$^1$ is —S(=O)$_2$R$^{10}$. In another embodiment is a compound of Formula (II), wherein R$^1$ is —S(=O)$_2$R$^{10}$ and R$^{10}$ is —CH$_3$. In another embodiment is a compound of Formula (II), wherein R$^1$ is —S(=O)$_2$R$^{10}$ and R$^{10}$ is —CH$_2$CH$_3$.

In another embodiment is a compound of Formula (II), wherein m is 0. In another embodiment is a compound of Formula (II), wherein m is 1. In another embodiment is a compound of Formula (II), wherein m is 1 and R$^2$ is halogen, C$_{1-6}$alkyl, C$_{1-6}$haloalkyl, C$_{1-6}$alkoxy, —O—C$_{1-6}$alkenyl, —O—C$_{1-6}$alkynyl, or C$_{1-6}$haloalkoxy. In another embodiment is a compound of Formula (II), wherein m is 1 and R$^2$ is halogen, C$_{1-6}$alkyl, C$_{1-6}$haloalkyl, C$_{1-6}$ alkoxy, or C$_{1-6}$haloalkoxy. In another embodiment is a compound of Formula (II), wherein m is 1 and R$^2$ is halogen. In another embodiment is a compound of Formula (II), wherein m is 1 and R$^2$ is C$_{1-6}$alkyl. In another embodiment is a compound of Formula (II), wherein m is 1 and R$^2$ is C$_{1-6}$haloalkyl. In another embodiment is a compound of Formula (II), wherein m is 1 and R$^2$ is C$_{1-6}$alkoxy. In another embodiment is a compound of Formula (II), wherein m is 1 and R$^2$ is C$_{1-6}$haloalkoxy. In another embodiment is a compound of Formula (II), wherein m is 2. In another embodiment is a compound of Formula (II), wherein m is 2 and each R$^2$ is independently halogen, C$_{1-6}$alkyl, C$_{1-6}$haloalkyl, C$_{1-6}$alkoxy, —O—C$_{1-6}$alkynyl, or C$_{1-6}$haloalkoxy. In another embodiment is a compound of Formula (II), wherein m is 2 and each R$^2$ is independently halogen, C$_{1-6}$alkyl, C$_{1-6}$haloalkyl, C$_{1-6}$alkoxy, or C$_{1-6}$haloalkoxy.

In another embodiment is a compound of Formula (II), wherein n is 0. In another embodiment is a compound of Formula (II), wherein n is 1. In another embodiment is a compound of Formula (II), wherein n is 1 and R$^3$ is halogen, C$_{1-6}$alkyl, or C$_{1-6}$haloalkyl. In another embodiment is a compound of Formula (II), wherein n is 1 and R$^3$ is halogen. In another embodiment is a compound of Formula (II), wherein n is 1 and R$^3$ is C$_{1-6}$alkyl. In another embodiment is a compound of Formula (II), wherein n is 1 and R$^3$ is C$_{1-6}$haloalkyl. In another embodiment is a compound of Formula (II), wherein n is 2. In another embodiment is a compound of Formula (II), wherein n is 2 and each R$^3$ is independently halogen, C$_{1-6}$alkyl, or C$_{1-6}$haloalkyl.

In another embodiment is a compound of Formula (II), wherein R$^4$ is

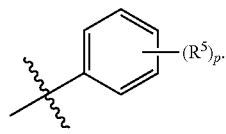

In another embodiment is a compound of Formula (II), wherein R$^4$ is

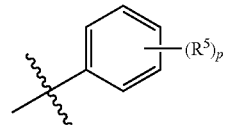

and p is 0. In another embodiment is a compound of Formula (II), wherein $R^4$ is

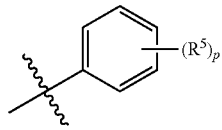

and p is 1. In another embodiment is a compound of Formula (II), wherein $R^4$ is

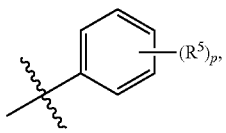

p is 1, and $R^5$ is halogen, $C_{1-6}$alkyl, $C_{1-6}$haloalkyl, $C_{1-6}$alkoxy, —O—$C_{1-6}$ alkenyl, —O—$C_{1-6}$alkynyl, or $C_{1-6}$haloalkoxy. In another embodiment is a compound of Formula (II), wherein $R^4$ is

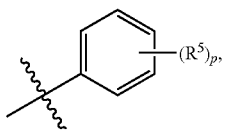

p is 1, and $R^5$ is halogen, $C_{1-6}$ alkyl, $C_{1-6}$haloalkyl, $C_{1-6}$alkoxy, or $C_{1-6}$haloalkoxy. In another embodiment is a compound of Formula (II), wherein $R^4$ is

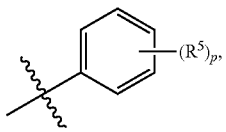

p is 1, and $R^5$ is halogen. In another embodiment is a compound of Formula (II), wherein $R^4$ is

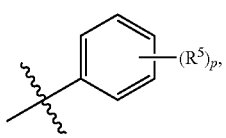

p is 1, and $R^5$ is $C_{1-6}$alkyl. In another embodiment is a compound of Formula (II), wherein $R^4$ is

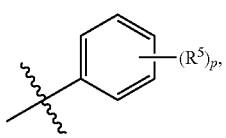

p is 1, and $R^5$ is $C_{1-6}$haloalkyl. In another embodiment is a compound of Formula (II), wherein $R^4$ is

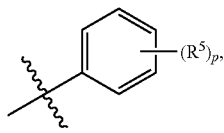

p is 1, and $R^5$ is $C_{1-6}$alkoxy. In another embodiment is a compound of Formula (II), wherein $R^4$ is

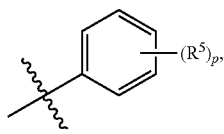

p is 1, and $R^5$ is $C_{1-6}$haloalkoxy. In another embodiment is a compound of Formula (II), wherein $R^4$ is

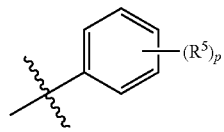

and p is 2. In another embodiment is a compound of Formula (II), wherein $R^4$ is

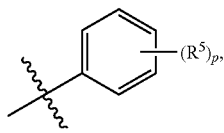

p is 2, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy.

In another embodiment is a compound of Formula (II), wherein $R^4$ is

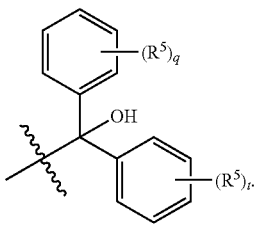

In another embodiment is a compound of Formula (II), wherein $R^4$ is

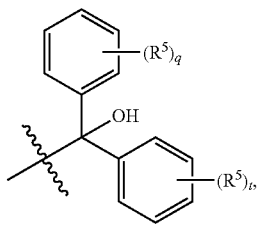

q is 0, and t is 0. In another embodiment is a compound of Formula (II), wherein $R^4$ is

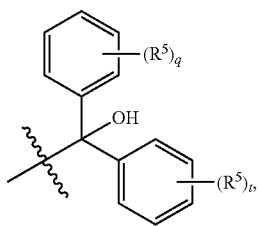

q is 1, and t is 0. In another embodiment is a compound of Formula (II), wherein $R^4$ is

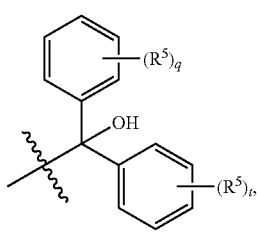

q is 1, t is 0, and $R^5$ is halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (II), wherein $R^4$ is

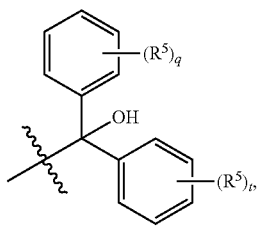

q is 1, t is 0, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (II), wherein $R^4$ is

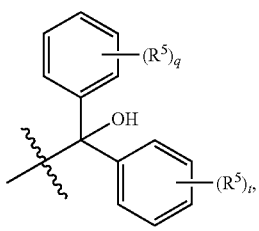

q is 1, and t is 1. In another embodiment is a compound of Formula (II), wherein $R^4$ is

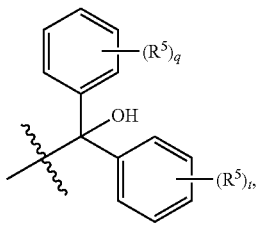

q is 1, t is 1, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (II), wherein $R^4$ is

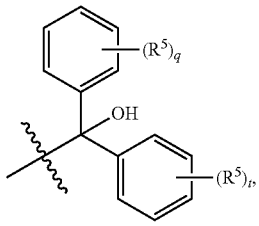

q is 1, t is 1, and each $R^5$ is independently halogen, $C_{1-6}$alkyl, $C_{1-6}$haloalkyl, $C_{1-6}$alkoxy, or $C_{1-6}$haloalkoxy. In another embodiment is a compound of Formula (II), wherein $R^4$ is

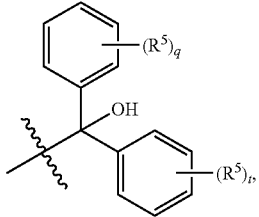

q is 1, t is 1, and each $R^5$ is halogen. In another embodiment is a compound of Formula (II), wherein $R^4$ is

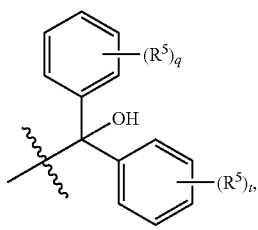

q is 1, t is 1, and each $R^5$ is $C_{1-6}$alkyl. In another embodiment is a compound of Formula (II), wherein $R^4$ is

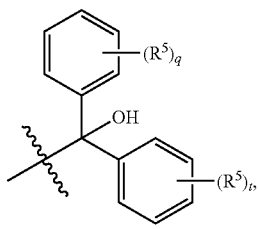

q is 1, t is 1, and each $R^5$ is $C_{1-6}$haloalkyl. In another embodiment is a compound of Formula (II), wherein $R^4$ is

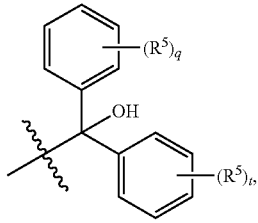

q is 1, t is 1, and each $R^5$ is $C_{1-6}$alkoxy. In another embodiment is a compound of Formula (II), wherein $R^4$ is

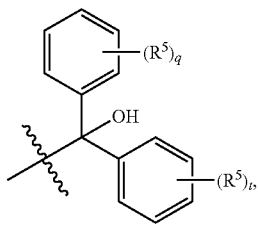

q is 1, t is 1, and each $R^5$ is $C_{1-6}$haloalkoxy.

In another embodiment is a compound of Formula (III):

Formula (III)

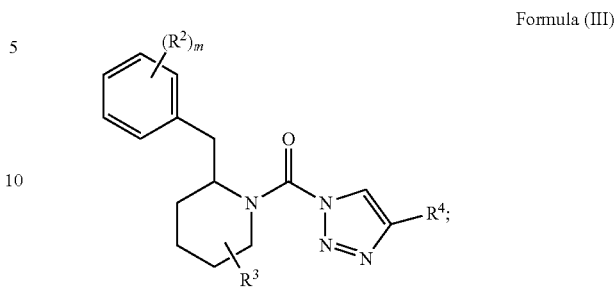

wherein:
each $R^2$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$ alkyl), —S(=O)$_2$N(C$_{1-6}$ alkyl)$_2$, $C_{1-6}$ alkyl, $C_{3-6}$cycloalkyl, $C_{1-6}$haloalkyl, $C_{1-6}$alkoxy, —O—$C_{1-6}$ alkenyl, —O—$C_{1-6}$alkynyl, $C_{1-6}$haloalkoxy, $C_{2-9}$heterocycloalkyl, $C_{6-10}$aryl, or $C_{2-9}$heteroaryl;
$R^3$ is $C_{1-6}$alkyl, $C_{1-6}$ alkoxy, —O—$C_{1-6}$ alkenyl, or —O—$C_{1-6}$ alkynyl;
$R^4$ is

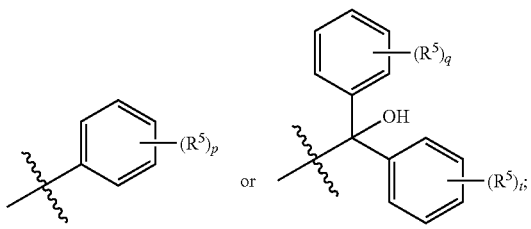

each $R^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$alkyl), —C(=O)N(C$_{1-6}$ alkyl)$_2$, —S(=O)$_2$NH$_2$, —S(=O)$_2$NH(C$_{1-6}$alkyl), —S(=O)$_2$N(C$_{1-6}$ alkyl)$_2$, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy;
m is 0, 1, 2, or 3;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (III), wherein m is 0. In another embodiment is a compound of Formula (III), wherein m is 1. In another embodiment is a compound of Formula (III), wherein m is 1 and $R^2$ is halogen, $C_{1-6}$alkyl, $C_{1-6}$haloalkyl, $C_{1-6}$alkoxy, —O—$C_{1-6}$ alkenyl, —O—$C_{1-6}$alkynyl, or $C_{1-6}$haloalkoxy. In another embodiment is a compound of Formula (III), wherein m is 1 and $R^2$ is halogen, $C_{1-6}$alkyl, $C_{1-6}$haloalkyl, $C_{1-6}$alkoxy, or $C_{1-6}$haloalkoxy. In another embodiment is a compound of Formula (III), wherein m is 1 and $R^2$ is halogen. In another embodiment is a compound of Formula (III), wherein m is 1 and $R^2$ is $C_{1-6}$alkyl. In another embodiment is a compound of Formula (III), wherein m is 1 and $R^2$ is $C_{1-6}$haloalkyl. In another embodiment is a compound of Formula (III), wherein m is 1 and $R^2$ is $C_{1-6}$alkoxy. In another embodiment is a compound of Formula (III), wherein m is 1 and $R^2$ is $C_{1-6}$haloalkoxy. In another embodiment is a compound of Formula (III), wherein m is 2. In another embodiment is a compound of Formula (III), wherein m is 2 and each $R^2$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (III), wherein m is 2 and each $R^2$ is independently halogen, $C_{1-6}$alkyl, $C_{1-6}$haloalkyl, $C_{1-6}$alkoxy, or $C_{1-6}$haloalkoxy.

In another embodiment is a compound of Formula (III), wherein $R^3$ is —O—$C_{1-6}$alkynyl. In another embodiment is a compound of Formula (III), wherein $R^3$ is —O—$C_{1-5}$alkynyl. In another embodiment is a compound of Formula (III), wherein $R^3$ is —O—$C_{1-4}$alkynyl. In another embodiment is a compound of Formula (III), wherein $R^3$ is —OCH$_2$CH$_2$C≡CH. In another embodiment is a compound of Formula (III), wherein $R^3$ is —OCH$_2$C≡CH. In another embodiment is a compound of Formula (III), wherein $R^3$ is $C_{1-6}$alkyl. In another embodiment is a compound of Formula (III), wherein $R^3$ is $C_{1-6}$alkoxy. In another embodiment is a compound of Formula (III), wherein $R^3$ is —O—$C_{1-6}$alkenyl.

In another embodiment is a compound of Formula (III), wherein $R^4$ is

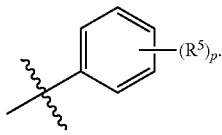

In another embodiment is a compound of Formula (III), wherein $R^4$ is

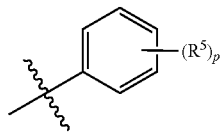

and p is 0. In another embodiment is a compound of Formula (III), wherein $R^4$ is

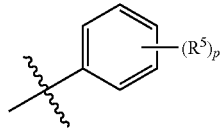

and p is 1. In another embodiment is a compound of Formula (III), wherein $R^4$ is

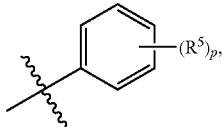

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (III), wherein $R^4$ is

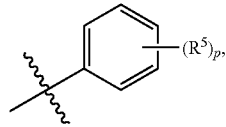

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (III), wherein $R^4$ is

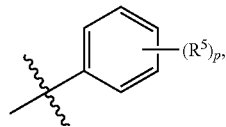

p is 1, and $R^5$ is halogen. In another embodiment is a compound of Formula (III), wherein $R^4$ is

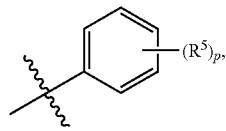

p is 1, and $R^5$ is $C_{1-6}$alkyl. In another embodiment is a compound of Formula (III), wherein $R^4$ is

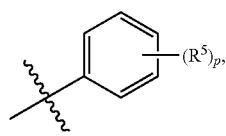

p is 1, and $R^5$ is $C_{1-6}$haloalkyl. In another embodiment is a compound of Formula (III), wherein $R^4$ is

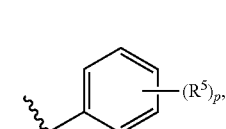

p is 1, and $R^5$ is $C_{1-6}$alkoxy. In another embodiment is a compound of Formula (III), wherein $R^4$ is

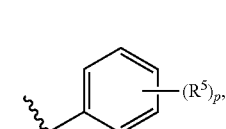

p is 1, and $R^5$ is $C_{1-6}$haloalkoxy. In another embodiment is a compound of Formula (III), wherein $R^4$ is

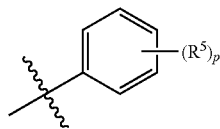

and p is 2. In another embodiment is a compound of Formula (III), wherein $R^4$ is

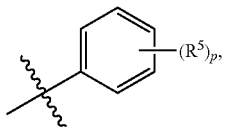

p is 2, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$ haloalkoxy.

In another embodiment is a compound of Formula (III), wherein $R^4$ is

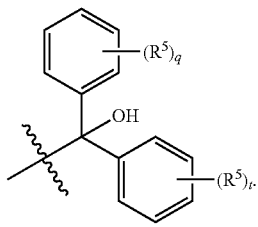

In another embodiment is a compound of Formula (III), wherein $R^4$ is

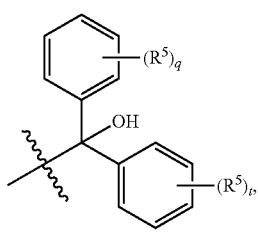

q is 0, and t is 0. In another embodiment is a compound of Formula (III), wherein $R^4$ is

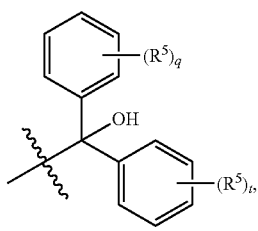

q is 1, and t is 0. In another embodiment is a compound of Formula (III), wherein $R^4$ is

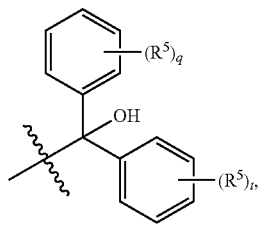

q is 1, t is 0, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (III), wherein $R^4$ is

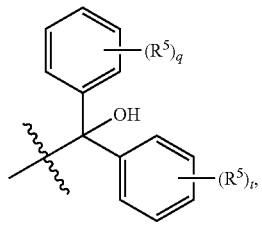

q is 1, t is 0, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (III), wherein $R^4$ is

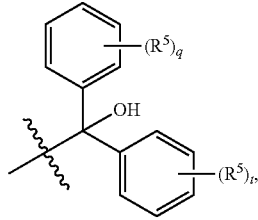

q is 1, and t is 1. In another embodiment is a compound of Formula (III), wherein $R^4$ is

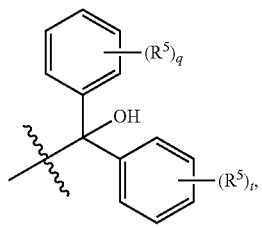

q is 1, t is 1, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (III), wherein $R^4$ is

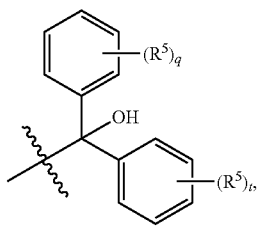

q is 1, t is 1, and each $R^5$ is independently halogen, $C_{1-6}$alkyl, $C_{1-6}$haloalkyl, $C_{1-6}$alkoxy, or $C_{1-6}$haloalkoxy. In another embodiment is a compound of Formula (III), wherein $R^4$ is

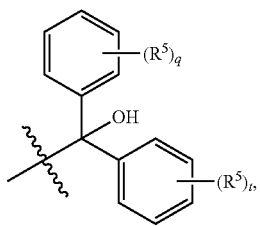

q is 1, t is 1, and each $R^5$ is halogen. In another embodiment is a compound of Formula (III), wherein $R^4$ is

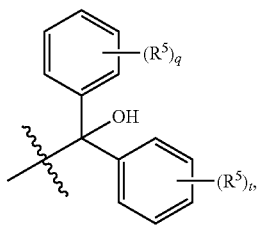

q is 1, t is 1, and each $R^5$ is $C_{1-6}$alkyl. In another embodiment is a compound of Formula (III), wherein $R^4$ is

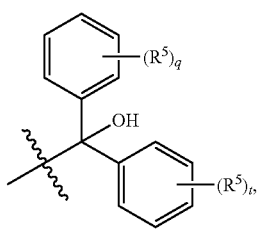

q is 1, t is 1, and each $R^5$ is $C_{1-6}$haloalkyl. In another embodiment is a compound of Formula (III), wherein $R^4$ is

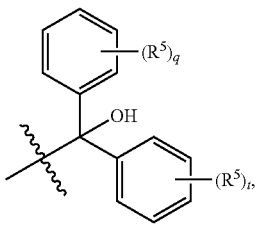

q is 1, t is 1, and each $R^5$ is $C_{1-6}$alkoxy. In another embodiment is a compound of Formula (III), wherein $R^4$ is

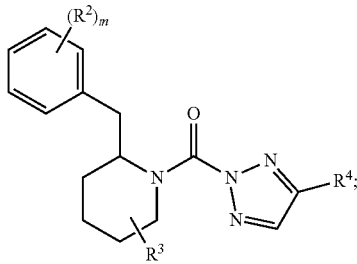

q is 1, t is 1, and each $R^5$ is $C_{1-6}$haloalkoxy.

In another embodiment is a compound of Formula (IV) having the structure:

Formula (IV)

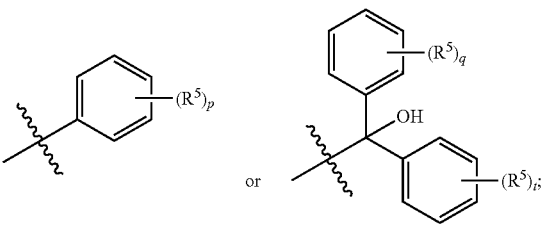

wherein:
each $R^2$ is independently halogen, —CN, —$NH_2$, —NH($CH_3$), —N($CH_3$)$_2$, —OH, —C(=O)OH, —C(=O)O($C_{1-6}$alkyl), —C(=O)$NH_2$, —C(=O)NH($C_{1-6}$alkyl), —C(=O)N($C_{1-6}$alkyl)$_2$, —S(=O)$_2NH_2$, —S(=O)$_2$NH($C_{1-6}$ alkyl), —S(=O)$_2$N($C_{1-6}$ alkyl)$_2$, $C_{1-6}$ alkyl, $C_{3-6}$cycloalkyl, $C_{1-6}$haloalkyl, $C_{1-6}$alkoxy, —O—$C_{1-6}$ alkenyl, —O—$C_{1-6}$ alkynyl, $C_{1-6}$haloalkoxy, $C_{2-9}$heterocycloalkyl, $C_{6-10}$aryl, or $C_{2-9}$ heteroaryl;

$R^3$ $C_{1-6}$ alkyl, $C_{1-6}$ alkoxy, —O—$C_{1-6}$alkenyl, or —O—$C_{1-6}$alkynyl;

$R^4$ is each R⁵ is independently halogen, —CN, —NH₂, —NH(CH₃), —N(CH₃)₂, —OH, —C(=O)OH, —C(=O)O(C₁₋₆alkyl), —C(=O)NH₂, —C(=O)NH(C₁₋₆ alkyl), —C(=O)N(C₁₋₆ alkyl)₂, —S(=O)₂NH₂, —S(=O)₂NH(C₁₋₆ alkyl), —S(=O)₂N(C₁₋₆ alkyl)₂, C₁₋₆alkyl, C₁₋₆haloalkyl, 6alkoxy, —O—C₁₋₆ alkenyl, —O—C₁₋₆ alkynyl, or C₁₋₆ haloalkoxy;

m is 0, 1, 2, or 3;

p is 0, 1, 2, or 3;

q is 0, 1, 2, or 3; and t is 0, 1, 2, or 3;

or a solvate, hydrate, tautomer, N-oxide, or pharmaceutically acceptable salt thereof.

In another embodiment is a compound of Formula (IV), wherein m is 0. In another embodiment is a compound of Formula (IV), wherein m is 1. In another embodiment is a compound of Formula (IV), wherein m is 1 and R² is halogen, C₁₋₆alkyl, C₁₋₆haloalkyl, C₁₋₆alkoxy, —O—C₁₋₆ alkenyl, —O—C₁₋₆ alkynyl, or C₁₋₆haloalkoxy. In another embodiment is a compound of Formula (IV), wherein m is 1 and R² is halogen, C₁₋₆alkyl, C₁₋₆ haloalkyl C₁₋₆alkoxy, or C₁₋₆haloalkoxy. In another embodiment is a compound of Formula (IV), wherein m is 1 and R² is halogen. In another embodiment is a compound of Formula (IV), wherein m is 1 and R² is C₁₋₆alkyl. In another embodiment is a compound of Formula (IV), wherein m is 1 and R² is C₁₋₆haloalkyl. In another embodiment is a compound of Formula (IV), wherein m is 1 and R² is C₁₋₆alkoxy. In another embodiment is a compound of Formula (IV), wherein m is 1 and R² is C₁₋₆haloalkoxy. In another embodiment is a compound of Formula (IV), wherein m is 2. In another embodiment is a compound of Formula (IV), wherein m is 2 and each R² is independently halogen, C₁₋₆ alkyl, C₁₋₆haloalkyl, C₁₋₆alkoxy, —O—C₁₋₆ alkenyl, —O—C₁₋₆ alkynyl, or C₁₋₆haloalkoxy. In another embodiment is a compound of Formula (IV), wherein m is 2 and each R² is independently halogen, C₁₋₆alkyl, C₁₋₆haloalkyl, C₁₋₆alkoxy, or C₁₋₆haloalkoxy.

In another embodiment is a compound of Formula (IV), wherein R³ is —O—C₁₋₆alkynyl. In another embodiment is a compound of Formula (IV), wherein R³ is —O—C₁₋₅alkynyl. In another embodiment is a compound of Formula (IV), wherein R³ is —O—C₁₋₄alkynyl. In another embodiment is a compound of Formula (IV), wherein R³ is —OCH₂CH₂C≡CH. In another embodiment is a compound of Formula (IV), wherein R³ is —OCH₂C≡CH. In another embodiment is a compound of Formula (IV), wherein R³ is C₁₋₆alkyl. In another embodiment is a compound of Formula (IV), wherein R³ is C₁₋₆ alkoxy. In another embodiment is a compound of Formula (IV), wherein R³ is —O—C₁₋₆ alkenyl.

In another embodiment is a compound of Formula (IV), wherein R⁴ is

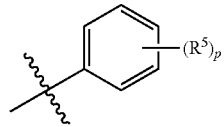

In another embodiment is a compound of Formula (IV), wherein R⁴ is

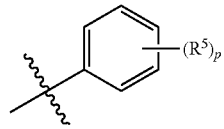

and p is 0. In another embodiment is a compound of Formula (IV), wherein R⁴ is

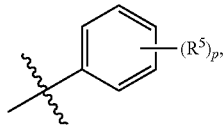

and p is 1. In another embodiment is a compound of Formula (IV), wherein R⁴ is

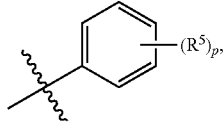

p is 1, and R⁵ is halogen, C₁₋₆alkyl, C₁₋₆haloalkyl, C₁₋₆alkoxy, —O—C₁₋₆alkenyl, —O—C₁₋₆ alkynyl, or C₁₋₆haloalkoxy. In another embodiment is a compound of Formula (IV), wherein R⁴ is

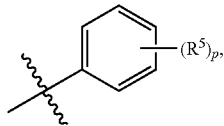

p is 1, and R⁵ is halogen, C₁₋₆ alkyl, C₁₋₆haloalkyl, C₁₋₆ alkoxy, or C₁₋₆haloalkoxy. In another embodiment is a compound of Formula (IV), wherein R⁴ is

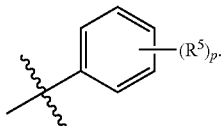

p is 1, and R⁵ is halogen. In another embodiment is a compound of Formula (IV), wherein R⁴ is

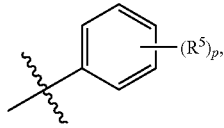

p is 1, and R⁵ is C₁₋₆alkyl. In another embodiment is a compound of Formula (IV), wherein R⁴ is

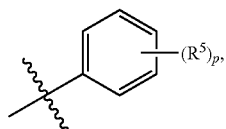

p is 1, and R⁵ is $C_{1-6}$haloalkyl. In another embodiment is a compound of Formula (IV), wherein $R^4$ is

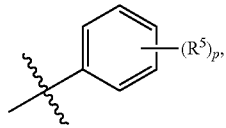

p is 1, and R⁵ is $C_{1-6}$alkoxy. In another embodiment is a compound of Formula (IV), wherein $R^4$ is

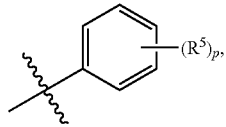

p is 1, and R⁵ is $C_{1-6}$haloalkoxy. In another embodiment is a compound of Formula (IV), wherein $R^4$ is

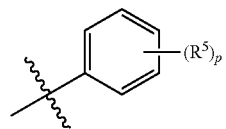

and p is 2. In another embodiment is a compound of Formula (IV), wherein $R^4$ is

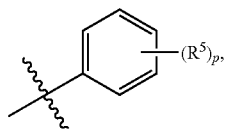

p is 2, and each R⁵ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy.

In another embodiment is a compound of Formula (IV), wherein $R^4$ is

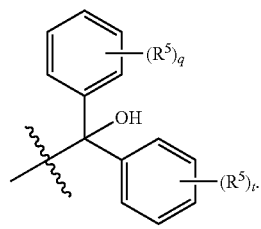

In another embodiment is a compound of Formula (IV), wherein $R^4$ is

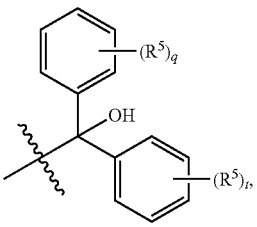

q is 0, and t is 0. In another embodiment is a compound of Formula (IV), wherein $R^4$ is

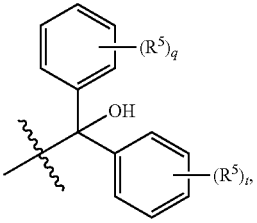

q is 1, and t is 0. In another embodiment is a compound of Formula (IV), wherein $R^4$ is

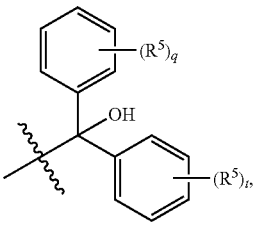

q is 1, t is 0, and R⁵ is halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (IV), wherein $R^4$ is q is 1, t is 0, and R⁵ is halogen, $C_{1-6}$alkyl, $C_{1-6}$haloalkyl, $C_{1-6}$alkoxy, or $C_{1-6}$haloalkoxy. In another embodiment is a compound of Formula (IV), wherein $R^4$ is

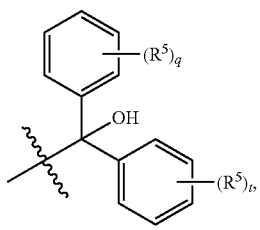

q is 1, and t is 1. In another embodiment is a compound of Formula (IV), wherein R$^4$ is

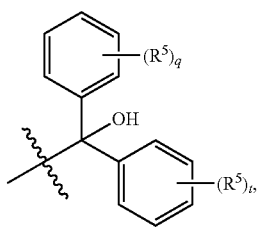

q is 1, t is 1, and each R$^5$ is independently halogen, C$_{1-6}$alkyl, C$_{1-6}$haloalkyl, C$_{1-6}$alkoxy, —O—C$_{1-6}$alkenyl, —O—C$_{1-6}$alkynyl, or C$_{1-6}$haloalkoxy. In another embodiment is a compound of Formula (IV), wherein R$^4$ is

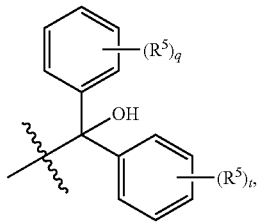

q is 1, t is 1, and each R$^5$ is independently halogen, C$_{1-6}$alkyl, C$_{1-6}$haloalkyl, C$_{1-6}$alkoxy, or C$_{1-6}$haloalkoxy. In another embodiment is a compound of Formula (IV), wherein R$^4$ is

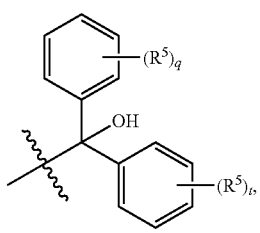

q is 1, t is 1, and each R$^5$ is halogen. In another embodiment is a compound of Formula (IV), wherein R$^4$ is

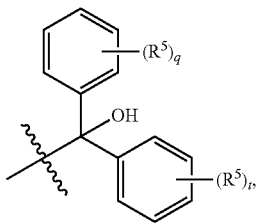

q is 1, t is 1, and each R$^5$ is C$_{1-6}$alkyl. In another embodiment is a compound of Formula (IV), wherein R$^4$ is

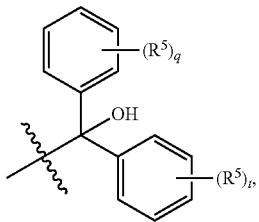

q is 1, t is 1, and each R$^5$ is C$_{1-6}$haloalkyl. In another embodiment is a compound of Formula (IV), wherein R$^4$ is

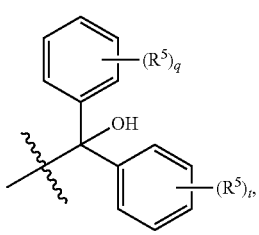

q is 1, t is 1, and each R$^5$ is C$_{1-6}$alkoxy. In another embodiment is a compound of Formula (IV), wherein R$^4$ is

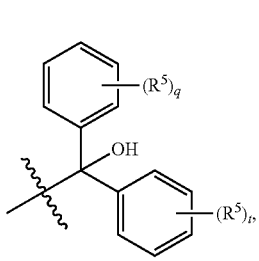

q is 1, t is 1, and each R$^5$ is C$_{1-6}$haloalkoxy.

In another embodiment is a compound of Formula (V):

Formula (V)

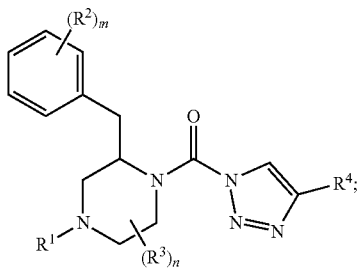

wherein:
R$^1$ is H, C$_{1-6}$alkyl, —C(=O)R$^{10}$, —C(=O)OR$^{10}$, or —S(=O)$_2$R$^{10}$,
each R$^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{3-6}$cycloalkyl, C$_{1-6}$haloalkyl, C$_{1-6}$alkoxy, —O—C$_{1-6}$alkenyl, —O—C$_{1-6}$alkynyl, C$_{1-6}$haloalkoxy, C$_{2-9}$heterocycloalkyl, C$_{6-10}$aryl, or C$_{2-9}$heteroaryl;
each R$^3$ is independently halogen, —CN, —C(=O)OH, —C(=O)O(C$_{1-6}$ alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$alkyl), —S(=O)$_2$N(C$_{1-6}$ alkyl)$_2$, C$_{1-6}$ alkyl, C$_{3-6}$cycloalkyl, C$_{1-6}$haloalkyl, C$_{2-9}$ heterocycloalkyl, C$_{6-10}$aryl, or C$_{2-9}$ heteroaryl;
R$^4$ is

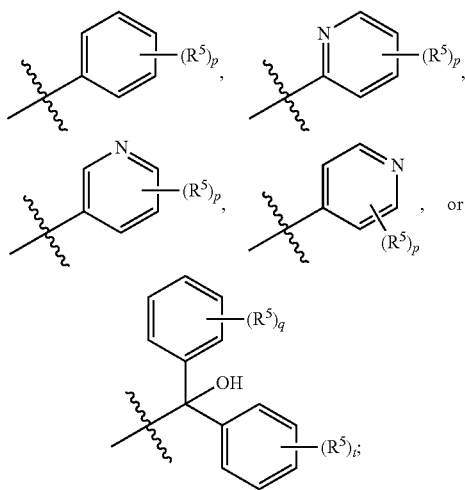

each R$^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$alkyl, C$_{1-6}$haloalkyl, C$_{1-6}$alkoxy, —O—C$_{1-6}$ alkenyl, —O—C$_{1-6}$alkynyl, C$_{1-6}$haloalkoxy, optionally substituted phenyl, or optionally substituted C$_{2-9}$ heteroaryl, wherein optionally substituted phenyl and optionally substituted C$_{2-9}$ heteroaryl are optionally substituted with one, two, or three groups selected from halogen, C$_{1-6}$alkyl, C$_{1-6}$haloalkyl, C$_{1-6}$alkoxy, and C$_{1-6}$haloalkoxy;
R$^{10}$ is C$_{1-6}$alkyl, C$_{1-6}$alkenyl, or C$_{1-6}$alkynyl;
m is 0, 1, 2, or 3;
n is 0, 1, or 2;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (V), wherein R$^1$ is H. In another embodiment is a compound of Formula (V), wherein R$^1$ is C$_{1-6}$alkyl. In another embodiment is a compound of Formula (V), wherein R$^1$ is —C(=O)OR$^{10}$. In another embodiment is a compound of Formula (V), wherein R$^1$ is —C(=O)OR$^{10}$ and R$^{10}$ is —CH$_3$. In another embodiment is a compound of Formula (V), wherein R$^1$ is —C(=O)OR$^{10}$ and R$^{10}$ is —CH$_2$CH$_3$. In another embodiment is a compound of Formula (V), wherein R$^1$ is —C(=O)OR$^{10}$ and R$^{10}$ is —CH(CH$_3$)$_2$. In another embodiment is a compound of Formula (V), wherein R$^1$ is —C(=O)OR$^{10}$ and R$^{10}$ is —C(CH$_3$)$_3$. In another embodiment is a compound of Formula (V), wherein R$^1$ is —C(=O)R$^{10}$. In another embodiment is a compound of Formula (V), wherein R$^1$ is —C(=O)R$^{10}$ and R$^{10}$ is —CH$_3$. In another embodiment is a compound of Formula (V), wherein R$^1$ is —C(=O)R$^{10}$ and R$^{10}$ is —CH$_2$CH$_3$. In another embodiment is a compound of Formula (V), wherein R$^1$ is —C(=O)R$^{10}$ and R$^{10}$ is —CH(CH$_3$)$_2$. In another embodiment is a compound of Formula (V), wherein R$^1$ is —S(=O)$_2$R$^{10}$. In another embodiment is a compound of Formula (V), wherein R$^1$ is —S(=O)$_2$R$^{10}$ and R$^{10}$ is —CH$_3$. In another embodiment is a compound of Formula (V), wherein R$^1$ is —S(=O)$_2$R$^{10}$ and R$^{10}$ is —CH$_2$CH$_3$.

In another embodiment is a compound of Formula (V), wherein m is 0. In another embodiment is a compound of Formula (V), wherein m is 1. In another embodiment is a compound of Formula (V), wherein m is 1 and R$^2$ is halogen, C$_{1-6}$alkyl, C$_{1-6}$haloalkyl C$_{1-6}$alkoxy, —O—C$_{1-6}$ alkenyl, —O—C$_{1-6}$ alkynyl, or C$_{1-6}$ haloalkoxy. In another embodiment is a compound of Formula (V), wherein m is 1 and R$^2$ is halogen, C$_{1-6}$alkyl, C$_{1-6}$ haloalkyl C$_{1-6}$alkoxy, or C$_{1-6}$haloalkoxy. In another embodiment is a compound of Formula (V), wherein m is 1 and R$^2$ is halogen. In another embodiment is a compound of Formula (V), wherein m is 1 and R$^2$ is C$_{1-6}$alkyl. In another embodiment is a compound of Formula (V), wherein m is 1 and R$^2$ is C$_{1-6}$haloalkyl. In another embodiment is a compound of Formula (V), wherein m is 1 and R$^2$ is C$_{1-6}$alkoxy. In another embodiment is a compound of Formula (V), wherein m is 1 and R$^2$ is C$_{1-6}$haloalkoxy. In another embodiment is a compound of Formula (V), wherein m is 2. In another embodiment is a compound of Formula (V), wherein m is 2 and each R$^2$ is independently halogen, C$_{1-6}$ alkyl, C$_{1-6}$alkoxy, —O—C$_{1-6}$ alkenyl, —O—C$_{1-6}$alkynyl, or C$_{1-6}$ haloalkoxy. In another embodiment is a compound of Formula (V), wherein m is 2 and each R$^2$ is independently halogen, C$_{1-6}$alkyl, C$_{1-6}$haloalkyl, C$_{1-6}$alkoxy, or C$_{1-6}$ haloalkoxy.

In another embodiment is a compound of Formula (V), wherein n is 0. In another embodiment is a compound of Formula (V), wherein n is 1. In another embodiment is a compound of Formula (V), wherein n is 1 and R$^3$ is halogen, C$_{1-6}$alkyl, or C$_{1-6}$haloalkyl. In another embodiment is a compound of Formula (V), wherein n is 1 and R$^3$ is halogen. In another embodiment is a compound of Formula (V), wherein n is 1 and R³ is C₁₋₆alkyl. In another embodiment is a compound of Formula (V), wherein n is 1 and R³ is C₁₋₆haloalkyl. In another embodiment is a compound of Formula (V), wherein n is 2. In another embodiment is a compound of Formula (V), wherein n is 2 and each R³ is independently halogen, C₁₋₆ alkyl, or C₁₋₆haloalkyl.

In another embodiment is a compound of Formula (V), wherein R⁴ is

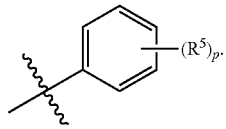

In another embodiment is a compound of Formula (V), wherein R⁴ is

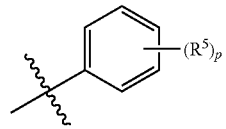

and p is 0. In another embodiment is a compound of Formula (V), wherein R⁴ is

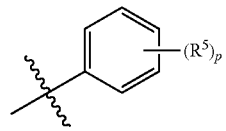

and p is 1. In another embodiment is a compound of Formula (V), wherein R⁴ is

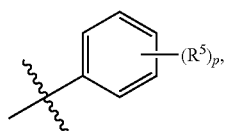

p is 1, and R⁵ is halogen, C₁₋₆alkyl, C₁₋₆haloalkyl, C₁₋₆alkoxy, —O—C₁₋₆alkenyl, —O—C₁₋₆alkynyl, or C₁₋₆haloalkoxy. In another embodiment is a compound of Formula (V), wherein R⁴ is

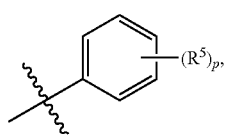

p is 1, and R⁵ is halogen, C₁₋₆alkyl, C₁₋₆haloalkyl, C₁₋₆alkoxy, or C₁₋₆haloalkoxy. In another embodiment is a compound of Formula (V), wherein R⁴ is

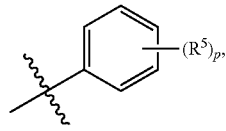

p is 1, and R⁵ is halogen. In another embodiment is a compound of Formula (V), wherein R⁴ is

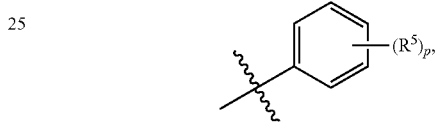

p is 1, and R⁵ is C₁₋₆alkyl. In another embodiment is a compound of Formula (V), wherein R⁴ is

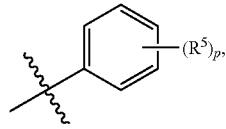

p is 1, and R⁵ is C₁₋₆haloalkyl. In another embodiment is a compound of Formula (V), wherein R⁴ is

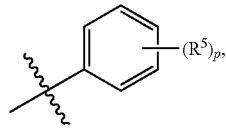

p is 1, and R⁵ is C₁₋₆alkoxy. In another embodiment is a compound of Formula (V), wherein R⁴ is p is 1, and R⁵ is C₁₋₆haloalkoxy. In another embodiment is a compound of Formula (V), wherein R⁴ is

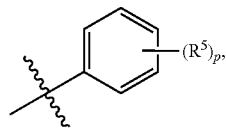

p is 1, and R⁵ is phenyl optionally substituted with one, two, or three groups selected from halogen, C₁₋₆alkyl, C₁₋₆haloalkyl, C₁₋₆alkoxy, and C₁₋₆haloalkoxy. In another embodiment is a compound of Formula (V), wherein R⁴ is

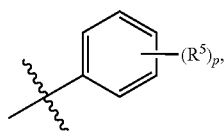

p is 1, and R⁵ is phenyl substituted with one, two, or three groups selected from halogen, $C_{1-6}$alkyl, $C_{1-6}$haloalkyl, $C_{1-6}$ alkoxy, and $C_{1-6}$ haloalkoxy. In another embodiment is a compound of Formula (V), wherein R⁴ is

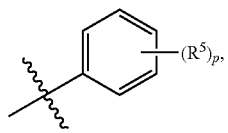

p is 1, and R⁵ is phenyl substituted with one or two groups selected from halogen, $C_{1-6}$ alkyl, and $C_{1-6}$ alkoxy. In another embodiment is a compound of Formula (V), wherein R⁴ is

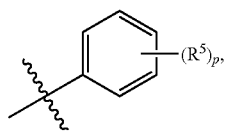

p is 1, and R⁵ is $C_{2-9}$ heteroaryl optionally substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (V), wherein R⁴ is

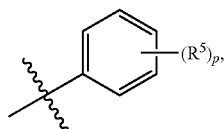

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$ haloalkoxy. In another embodiment is a compound of Formula (V), wherein R⁴ is

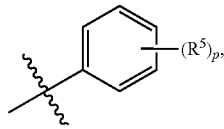

p is 1, and R⁵ is $C_{2-9}$heteroaryl substituted with one or two groups selected from halogen, $C_{1-6}$alkyl, and $C_{1-6}$alkoxy. In another embodiment is a compound of Formula (V), wherein R⁴ is

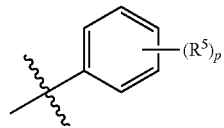

and p is 2. In another embodiment is a compound of Formula (V), wherein R⁴ is

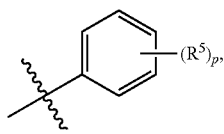

p is 2, and each R⁵ is independently halogen, $C_{1-6}$alkyl, $C_{1-6}$ haloalkyl, $C_{1-6}$alkoxy, —O—$C_{1-6}$ alkenyl, —O—$C_{1-6}$ alkynyl, or $C_{1-6}$ haloalkoxy. In another embodiment is a compound of Formula (V), wherein R⁴ is

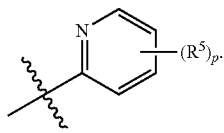

In another embodiment is a compound of Formula (V), wherein R⁴ is

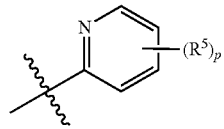

and p is 0. In another embodiment is a compound of Formula (V), wherein R⁴ is

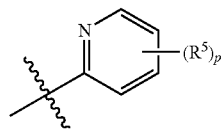

and p is 1. In another embodiment is a compound of Formula (V), wherein R⁴ is

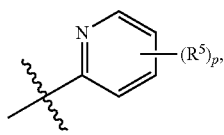

p is 1, and R⁵ is halogen, $C_{1-6}$alkyl, $C_{1-6}$ haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (V), wherein R⁴ is

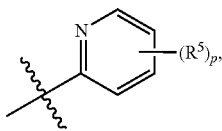

p is 1, and R$^5$ is halogen, C$_{1-6}$ alkyl, C$_{1-6}$haloalkyl, C$_{1-6}$alkoxy, or C$_{1-6}$haloalkoxy. In another embodiment is a compound of Formula (V), wherein R$^4$ is

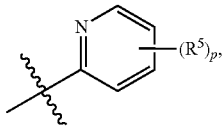

p is 1, and R$^5$ is halogen. In another embodiment is a compound of Formula (V), wherein R$^4$ is

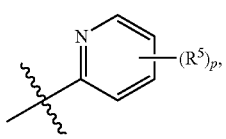

p is 1, and R$^5$ is C$_{1-6}$alkyl. In another embodiment is a compound of Formula (V), wherein R$^4$ is

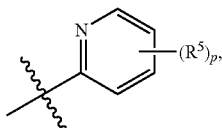

p is 1, and R$^5$ is C$_{1-6}$haloalkyl. In another embodiment is a compound of Formula (V), wherein R$^4$ is

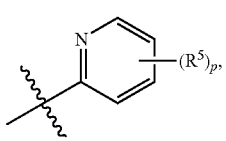

p is 1, and R$^5$ is C$_{1-6}$alkoxy. In another embodiment is a compound of Formula (V), wherein R$^4$ is

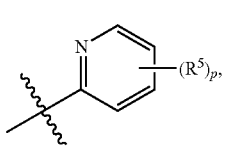

p is 1, and R$^5$ is C$_{1-6}$haloalkoxy. In another embodiment is a compound of Formula (V), wherein R$^4$ is

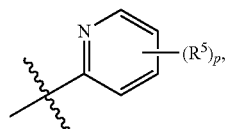

p is 1, and R$^5$ is phenyl optionally substituted with one, two, or three groups selected from halogen, C$_{1-6}$alkyl, C$_{1-6}$haloalkyl, C$_{1-6}$alkoxy, and C$_{1-6}$haloalkoxy. In another embodiment is a compound of Formula (V), wherein R$^4$ is

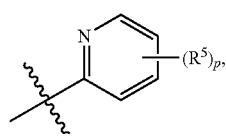

p is 1, and R$^5$ is phenyl substituted with one, two, or three groups selected from halogen, C$_{1-6}$ alkyl, C$_{1-6}$haloalkyl, C$_{1-6}$alkoxy, and C$_{1-6}$haloalkoxy. In another embodiment is a compound of Formula (V), wherein R$^4$ is

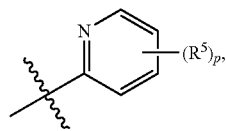

p is 1, and R$^5$ is phenyl substituted with one or two groups selected from halogen, C$_{1-6}$ alkyl, and C$_{1-6}$ alkoxy. In another embodiment is a compound of Formula (V), wherein R$^4$ is

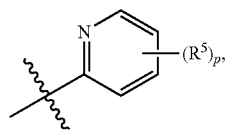

p is 1, and R$^5$ is C$_{2-9}$heteroaryl optionally substituted with one, two, or three groups selected from halogen, C$_{1-6}$ alkyl, C$_{1-6}$haloalkyl, C$_{1-6}$ alkoxy, and C$_{1-6}$haloalkoxy. In another embodiment is a compound of Formula (V), wherein R$^4$ is

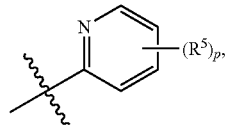

p is 1, and R$^5$ is C$_{2-9}$heteroaryl substituted with one, two, or three groups selected from halogen, C$_{1-6}$alkyl, C$_{1-6}$ haloalkyl, C$_{1-6}$alkoxy, and C$_{1-6}$haloalkoxy. In another embodiment is a compound of Formula (V), wherein R$^4$ is

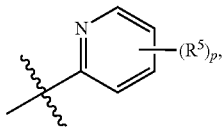

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (V), wherein $R^4$ is

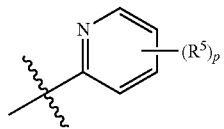

and p is 2. In another embodiment is a compound of Formula (V), wherein $R^4$ is

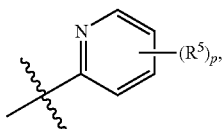

p is 2, and each $R^5$ is independently halogen, $C_{1-6}$alkyl, $C_{1-6}$haloalkyl, $C_{1-6}$ alkoxy, —O—$C_{1-6}$ alkenyl, —O—$C_{1-6}$ alkynyl, or $C_{1-6}$haloalkoxy. In another embodiment is a compound of Formula (V), wherein $R^4$ is

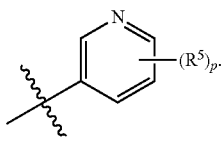

In another embodiment is a compound of Formula (V), wherein $R^4$ is

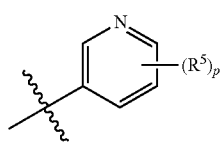

and p is 0. In another embodiment is a compound of Formula (V), wherein $R^4$ is

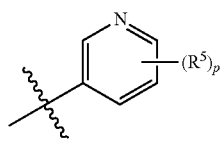

and p is 1. In another embodiment is a compound of Formula (V), wherein $R^4$ is

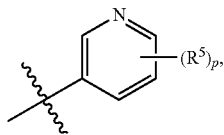

p is 1, and $R^5$ is halogen, $C_{1-6}$ alkyl, $C_{1-6}$alkoxy, —O—$C_{1-6}$ alkenyl, —O—$C_{1-6}$ alkynyl, or $C_{1-6}$ haloalkoxy. In another embodiment is a compound of Formula (V), wherein $R^4$ is

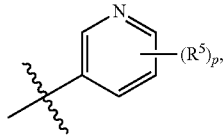

p is 1, and $R^5$ is halogen, $C_{1-6}$alkyl, $C_{1-6}$alkoxy, or $C_{1-6}$haloalkoxy. In another embodiment is a compound of Formula (V), wherein $R^4$ is

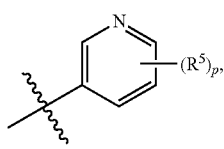

p is 1, and $R^5$ is halogen. In another embodiment is a compound of Formula (V), wherein $R^4$ is

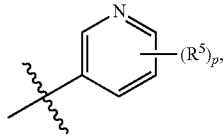

p is 1, and $R^5$ is $C_{1-6}$alkyl. In another embodiment is a compound of Formula (V), wherein $R^4$ is

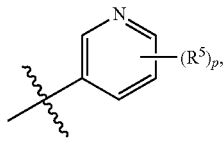

p is 1, and $R^5$ is $C_{1-6}$haloalkyl. In another embodiment is a compound of Formula (V), wherein $R^4$ is p is 1, and $R^5$ is $C_{1-6}$alkoxy. In another embodiment is a compound of Formula (V), wherein $R^4$ is

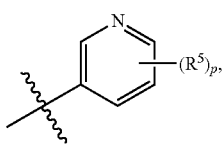

p is 1, and $R^5$ is $C_{1-6}$haloalkoxy. In another embodiment is a compound of Formula (V), wherein $R^4$ is

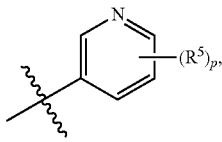

p is 1 and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (V), wherein $R^4$ is

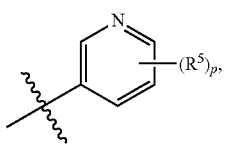

p is 1, and $R^5$ is phenyl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (V), wherein $R^4$ is

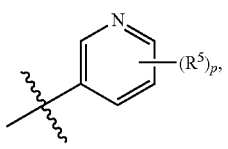

p is 1, and $R^5$ is phenyl substituted with one or two groups selected from halogen, $C_{1-6}$alkyl, and $C_{1-6}$alkoxy. In another embodiment is a compound of Formula (V), wherein $R^4$ is

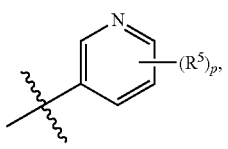

p is 1, and $R^5$ is $C_{2-9}$ heteroaryl optionally substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (V), wherein $R^4$ is

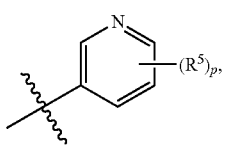

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (V), wherein $R^4$ is

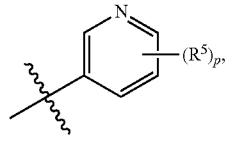

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (V), wherein $R^4$ is

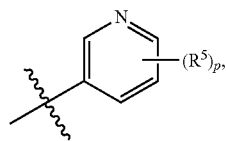

and p is 2. In another embodiment is a compound of Formula (V), wherein $R^4$ is

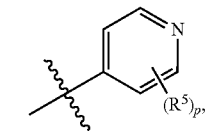

p is 2, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (V), wherein $R^4$ is

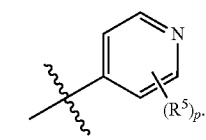

In another embodiment is a compound of Formula (V), wherein $R^4$ is

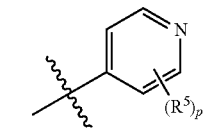

and p is 0. In another embodiment is a compound of Formula (V), wherein $R^4$ is

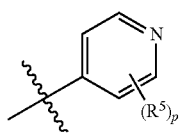

and p is 1. In another embodiment is a compound of Formula (V), wherein $R^4$ is

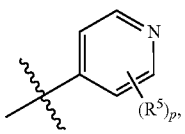

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (V), wherein $R^4$ is

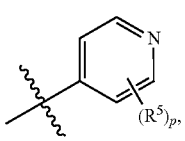

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (V), wherein $R^4$ is

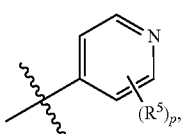

p is 1, and $R^5$ is halogen. In another embodiment is a compound of Formula (V), wherein $R^4$ is

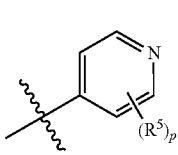

p is 1, and $R^5$ is $C_{1-6}$alkyl. In another embodiment is a compound of Formula (V), wherein $R^4$ is

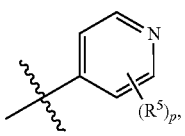

p is 1, and $R^5$ is $C_{1-6}$haloalkyl. In another embodiment is a compound of Formula (V), wherein $R^4$ is

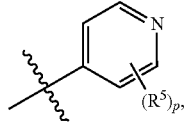

p is 1, and $R^5$ is $C_{1-6}$alkoxy. In another embodiment is a compound of Formula (V), wherein $R^4$ is

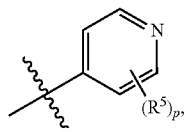

p is 1, and $R^5$ is $C_{1-6}$haloalkoxy. In another embodiment is a compound of Formula (V), wherein $R^4$ is

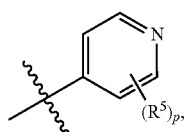

p is 1, and $R^5$ is phenyl optionally substituted with one, two, or three groups selected from halogen, $C_{1-6}$ alkyl, $C_{1-6}$ haloalkyl, $C_{1-6}$ alkoxy, and $C_{1-6}$haloalkoxy. In another embodiment is a compound of Formula (V), wherein $R^4$ is

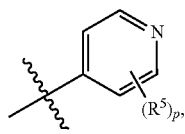

p is 1, and $R^5$ is phenyl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (V), wherein $R^4$ is

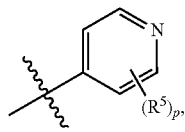

p is 1, and $R^5$ is phenyl substituted with one or two groups selected from halogen, $C_{1-6}$ alkyl, and $C_{1-6}$ alkoxy. In another embodiment is a compound of Formula (V), wherein $R^4$ is

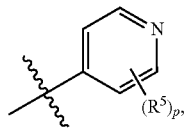

p is 1, and $R^5$ is $C_{2-9}$ heteroaryl optionally substituted with one, two, or three groups selected from halogen, $C_{1-6}$alkyl, C$_{1-6}$haloalkyl, C$_{1-6}$alkoxy, and C$_{1-6}$haloalkoxy. In another embodiment is a compound of Formula (V), wherein R$^4$ is

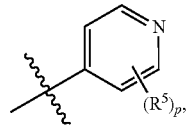

p is 1, and R$^5$ is C$_{2-9}$heteroaryl substituted with one, two, or three groups selected from halogen, C$_{1-6}$alkyl, C$_{1-6}$haloalkyl, C$_{1-6}$alkoxy, and C$_{1-6}$haloalkoxy. In another embodiment is a compound of Formula (V), wherein R$^4$ is

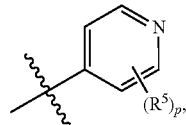

p is 1, and R$^5$ is C$_{2-9}$ heteroaryl substituted with one or two groups selected from halogen, C$_{1-6}$alkyl, and C$_{1-6}$alkoxy. In another embodiment is a compound of Formula (V), wherein R$^4$ is

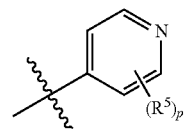

and p is 2. In another embodiment is a compound of Formula (V), wherein R$^4$ is

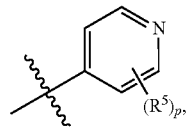

p is 2, and each R$^5$ is independently halogen, C$_{1-6}$alkyl, C$_{1-6}$haloalkyl, C$_{1-6}$ alkoxy, —O—C$_{1-6}$ alkenyl, —O—C$_{1-6}$ alkynyl, or C$_{1-6}$haloalkoxy. In another embodiment is a compound of Formula (V), wherein R$^4$ is

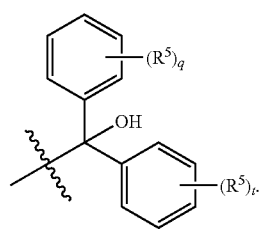

In another embodiment is a compound of Formula (V), wherein R$^4$ is

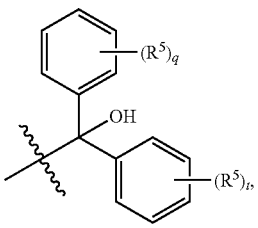

q is 0, and t is 0. In another embodiment is a compound of Formula (V), wherein R$^4$ is

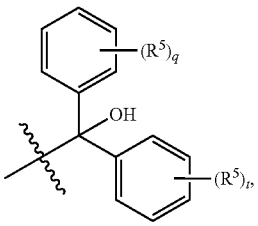

q is 1, and t is 0. In another embodiment is a compound of Formula (V), wherein R$^4$ is q is 1, t is 0, and R$^5$ is halogen, C$_{1-6}$alkyl, C$_{1-6}$haloalkyl, C$_{1-6}$ alkoxy, —O—C$_{1-6}$ alkenyl, —O—C$_{1-6}$ alkynyl, or C$_{1-6}$haloalkoxy. In another embodiment is a compound of Formula (V), wherein R$^4$ is q is 1, t is 0, and R$^5$ is halogen, C$_{1-6}$alkyl, C$_{1-6}$haloalkyl, C$_{1-6}$alkoxy, or C$_{1-6}$haloalkoxy. In another embodiment is a compound of Formula (V), wherein R$^4$ is

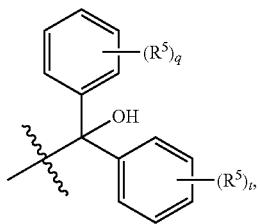

q is 1, and t is 1. In another embodiment is a compound of Formula (V), wherein $R^4$ is

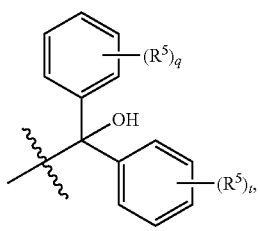

q is 1, t is 1, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (V), wherein $R^4$ is

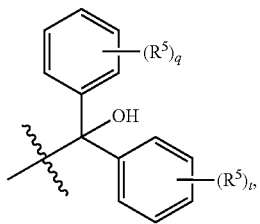

q is 1, t is 1, and each $R^5$ is independently halogen, $C_{1-6}$alkyl, $C_{1-6}$haloalkyl, $C_{1-6}$alkoxy, or $C_{1-6}$haloalkoxy. In another embodiment is a compound of Formula (V), wherein $R^4$ is

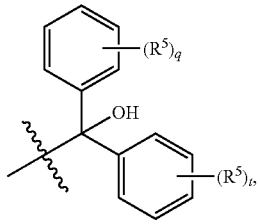

q is 1, t is 1, and each $R^5$ is halogen. In another embodiment is a compound of Formula (V), wherein $R^4$ is

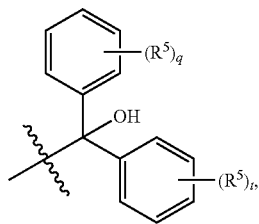

q is 1, t is 1, and each $R^5$ is $C_{1-6}$alkyl. In another embodiment is a compound of Formula (V), wherein $R^4$ is

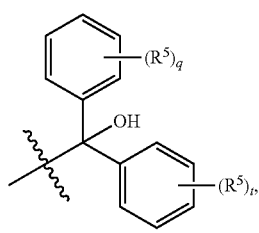

q is 1, t is 1, and each $R^5$ is $C_{3-6}$ haloalkyl. In another embodiment is a compound of Formula (V), wherein $R^4$ is

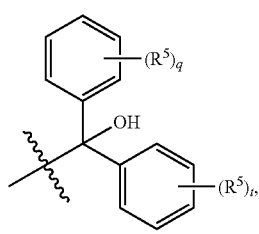

q is 1, t is 1, and each $R^5$ is $C_{3-6}$alkoxy. In another embodiment is a compound of Formula (V), wherein $R^4$ is

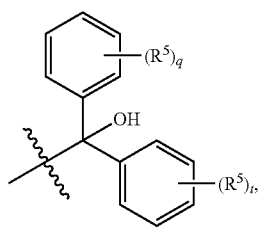

q is 1, t is 1, and each $R^5$ is $C_{1-6}$haloalkoxy.

In another embodiment is a compound of Formula (VI):

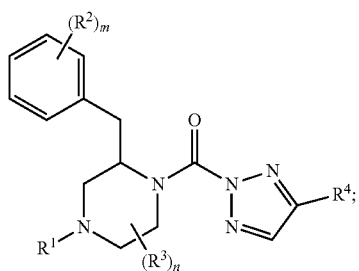

Formula (VI)

wherein:
R$^1$ is H, C$_{1-6}$alkyl, —C(=O)R$^{10}$, —C(=O)OR$^{10}$, or —S(=O)$_2$R$^{10}$;
each R$^2$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{3-6}$alkyl), —C(=O)N(C$_{3-6}$ alkyl)$_2$, —S(=O)$_2$NH$_2$, —S(=O)$_2$NH(C$_{1-6}$ alkyl), —S(=O)$_2$N(C$_{3-6}$ alkyl)$_2$, C$_{3-6}$ alkyl, C$_{3-6}$ cycloalkyl, C$_{1-6}$haloalkyl, C$_{1-6}$alkoxy, —O—C$_{1-6}$ alkenyl, —O—C$_{1-6}$ alkynyl, C$_{3-6}$ haloalkoxy, C$_{2-9}$heterocycloalkyl, C$_{6-10}$ aryl, or C$_{2-9}$heteroaryl;
each R$^3$ is independently halogen, —CN, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$alkyl)$_2$, C$_{1-6}$alkyl, C$_{3-6}$cycloalkyl, C$_{1-6}$haloalkyl, C$_{2-9}$heterocycloalkyl, C$_{6-10}$aryl, or C$_{2-9}$ heteroaryl;
R$^4$ is

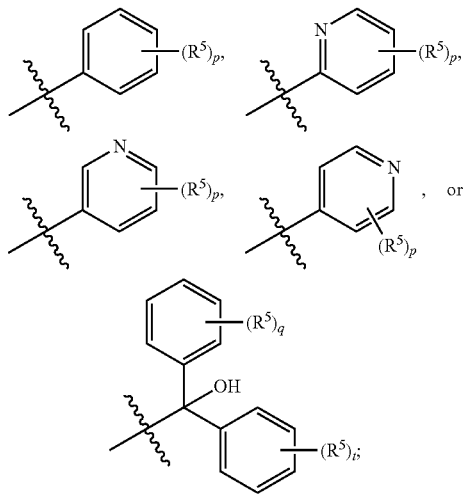

each R$^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$alkyl), —C(=O)N(C$_{1-6}$ alkyl)$_2$, —S(=O)$_2$NH$_2$, —S(=O)$_2$NH(C$_{1-6}$alkyl), —S(=O)$_2$N(C$_{1-6}$ alkyl)$_2$, C$_{1-6}$alkyl, C$_{1-6}$haloalkyl, C$_{1-6}$alkoxy, —O—C$_{1-6}$alkenyl, —O—C$_{1-6}$alkynyl, C$_{1-6}$haloalkoxy, optionally substituted phenyl, or optionally substituted C$_{2-9}$ heteroaryl, wherein optionally substituted phenyl and optionally substituted C$_{2-9}$ heteroaryl are optionally substituted with one, two, or three groups selected from halogen, C$_{1-6}$alkyl, C$_{1-6}$haloalkyl, C$_{1-6}$alkoxy, and C$_{1-6}$haloalkoxy;

R$^{10}$ is C$_{1-6}$alkyl, C$_{1-6}$alkenyl, or C$_{1-6}$alkynyl;
m is 0, 1, 2, or 3;
n is 0, 1, or 2;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (VI), wherein R$^1$ is H. In another embodiment is a compound of Formula (VI), wherein R$^1$ is C$_{1-6}$alkyl. In another embodiment is a compound of Formula (VI), wherein R$^1$ is —C(=O)OR$^{10}$. In another embodiment is a compound of Formula (VI), wherein R$^1$ is —C(=O)OR$^{10}$ and R$^{10}$ is —CH$_3$. In another embodiment is a compound of Formula (VI), wherein R$^1$ is —C(=O)OR$^{10}$ and R$^{10}$ is —CH$_2$CH$_3$. In another embodiment is a compound of Formula (VI), wherein R$^1$ is —C(=O)OR$^{10}$ and R$^{10}$ is —CH(CH$_3$)$_2$. In another embodiment is a compound of Formula (VI), wherein R$^1$ is —C(=O)OR$^{10}$ and R$^{10}$ is —C(CH$_3$)$_3$. In another embodiment is a compound of Formula (VI), wherein R$^1$ is —C(=O)R$^{10}$. In another embodiment is a compound of Formula (VI), wherein R$^1$ is —C(=O)R$^{10}$ and R$^{10}$ is —CH$_3$. In another embodiment is a compound of Formula (VI), wherein R$^1$ is —C(=O)R$^{10}$ and R$^{10}$ is —CH$_2$CH$_3$. In another embodiment is a compound of Formula (VI), wherein R$^1$ is —C(=O)R$^{10}$ and R$^{10}$ is —CH(CH$_3$)$_2$. In another embodiment is a compound of Formula (VI), wherein R$^1$ is —S(=O)$_2$R$^{10}$. In another embodiment is a compound of Formula (VI), wherein R$^1$ is —S(=O)$_2$R$^{10}$ and R$^{10}$ is —CH$_3$. In another embodiment is a compound of Formula (VI), wherein R$^1$ is —S(=O)$_2$R$^{10}$ and R$^{10}$ is —CH$_2$CH$_3$.

In another embodiment is a compound of Formula (VI), wherein m is 0. In another embodiment is a compound of Formula (VI), wherein m is 1. In another embodiment is a compound of Formula (VI), wherein m is 1 and R$^2$ is halogen, C$_{1-6}$alkyl, C$_{1-6}$haloalkyl, C$_{1-6}$alkoxy, —O—C$_{1-6}$alkenyl, —O—C$_{1-6}$ alkynyl, or C$_{1-6}$haloalkoxy. In another embodiment is a compound of Formula (VI), wherein m is 1 and R$^2$ is halogen, C$_{1-6}$alkyl, C$_{1-6}$haloalkyl, C$_{1-6}$alkoxy, or C$_{1-6}$haloalkoxy. In another embodiment is a compound of Formula (VI), wherein m is 1 and R$^2$ is halogen. In another embodiment is a compound of Formula (VI), wherein m is 1 and R$^2$ is C$_{1-6}$alkyl. In another embodiment is a compound of Formula (VI), wherein m is 1 and R$^2$ is C$_{1-6}$haloalkyl. In another embodiment is a compound of Formula (VI), wherein m is 1 and R$^2$ is C$_{1-6}$alkoxy. In another embodiment is a compound of Formula (VI), wherein m is 1 and R$^2$ is C$_{1-6}$haloalkoxy. In another embodiment is a compound of Formula (VI), wherein m is 2. In another embodiment is a compound of Formula (VI), wherein m is 2 and each R$^2$ is independently halogen, C$_{1-6}$alkyl, C$_{1-6}$haloalkyl, C$_{1-6}$alkoxy, —O—C$_{1-6}$alkenyl, —O—C$_{1-6}$alkynyl, or C$_{1-6}$haloalkoxy. In another embodiment is a compound of Formula (VI), wherein m is 2 and each R$^2$ is independently halogen, C$_{1-6}$alkyl, C$_{1-6}$haloalkyl, C$_{1-6}$alkoxy, or C$_{1-6}$haloalkoxy.

In another embodiment is a compound of Formula (VI), wherein n is 0. In another embodiment is a compound of Formula (VI), wherein n is 1. In another embodiment is a compound of Formula (VI), wherein n is 1 and R$^3$ is halogen, C$_{1-6}$alkyl, or C$_{1-6}$haloalkyl. In another embodiment is a compound of Formula (VI), wherein n is 1 and R$^3$ is halogen. In another embodiment is a compound of Formula (VI), wherein n is 1 and R$^3$ is C$_{1-6}$alkyl. In another embodiment is a compound of Formula (VI), wherein n is 1 and R$^3$ is $C_{1-6}$haloalkyl. In another embodiment is a compound of Formula (VI), wherein n is 2. In another embodiment is a compound of Formula (VI), wherein n is 2 and each $R^3$ is independently halogen, $C_{1-6}$alkyl, or $C_{1-6}$haloalkyl.

In another embodiment is a compound of Formula (VI), wherein $R^4$ is

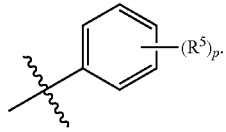

In another embodiment is a compound of Formula (VI), wherein $R^4$ is

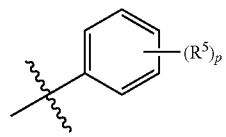

and p is 0. In another embodiment is a compound of Formula (VI), wherein $R^4$ is

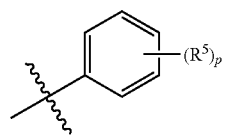

and p is 1. In another embodiment is a compound of Formula (VI), wherein $R^4$ is

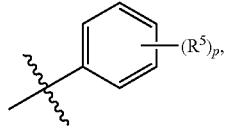

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VI), wherein $R^4$ is

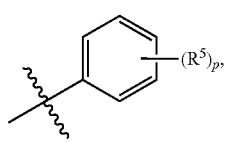

p is 1, and $R^5$ is halogen, $C_{1-6}$ alkyl, $C_{1-6}$haloalkyl, $C_{1-6}$alkoxy, or $C_{1-6}$haloalkoxy. In another embodiment is a compound of Formula (VI), wherein $R^4$ is

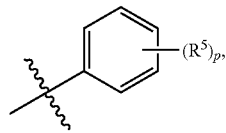

p is 1, and $R^5$ is halogen. In another embodiment is a compound of Formula (VI), wherein $R^4$ is

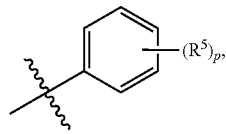

p is 1, and $R^5$ is $C_{1-6}$alkyl. In another embodiment is a compound of Formula (VI), wherein $R^4$ is

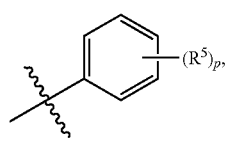

p is 1, and $R^5$ is $C_{1-6}$haloalkyl. In another embodiment is a compound of Formula (VI), wherein $R^4$ is

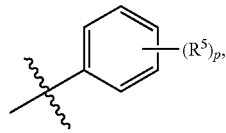

p is 1, and $R^5$ is $C_{1-6}$alkoxy. In another embodiment is a compound of Formula (VI), wherein $R^4$ is

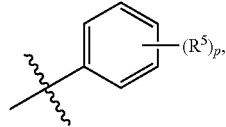

p is 1, and $R^5$ is $C_{1-6}$haloalkoxy. In another embodiment is a compound of Formula (VI), wherein $R^4$ is

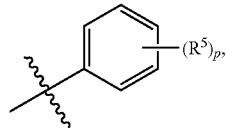

p is 1, and $R^5$ is phenyl optionally substituted with one, two, or three groups selected from halogen, $C_{1-6}$ alkyl, $C_{1-6}$ haloalkyl, $C_{1-6}$ alkoxy, and $C_{1-6}$haloalkoxy. In another embodiment is a compound of Formula (VI), wherein $R^4$ is

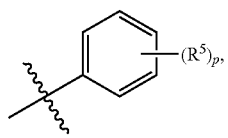

p is 1, and $R^5$ is phenyl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

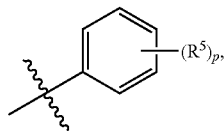

p is 1, and $R^5$ is phenyl substituted with one or two groups selected from halogen, $C_{1-6}$alkyl, and $C_{1-6}$alkoxy. In another embodiment is a compound of Formula (VI), wherein $R^4$ is

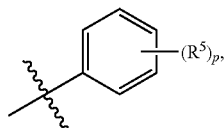

p is 1, and $R^5$ is $C_{2-9}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

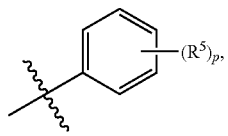

p is 1, and $R^5$ is $C_{2-9}$heteroaryl substituted with one, two, or three groups selected from halogen, $C_{1-6}$ alkyl, $C_{1-6}$ haloalkyl, $C_{1-6}$ alkoxy, and $C_{1-6}$haloalkoxy. In another embodiment is a compound of Formula (VI), wherein $R^4$ is

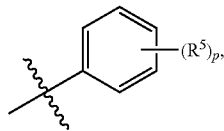

p is 1, and $R^5$ is $C_{2-9}$heteroaryl substituted with one or two groups selected from halogen, $C_{1-6}$alkyl, and $C_{1-6}$alkoxy. In another embodiment is a compound of Formula (VI), wherein $R^4$ is

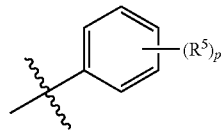

and p is 2. In another embodiment is a compound of Formula (VI), wherein $R^4$ is

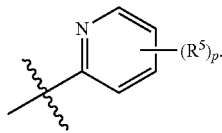

p is 2, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (VI), wherein $R^4$ is

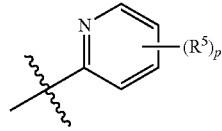

In another embodiment is a compound of Formula (VI), wherein $R^4$ is

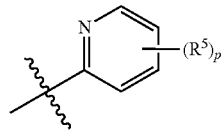

and p is 0. In another embodiment is a compound of Formula (VI), wherein $R^4$ is

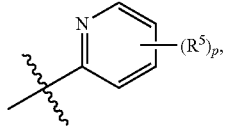

and p is 1. In another embodiment is a compound of Formula (VI), wherein $R^4$ is p is 1, and $R^5$ is halogen, $C_{1-6}$ alkyl, $C_{1-6}$haloalkyl, $C_{1-6}$alkoxy, —O—$C_{1-6}$alkenyl, —O—$C_{1-6}$alkynyl, or $C_{1-6}$ haloalkoxy. In another embodiment is a compound of Formula (VI), wherein $R^4$ is

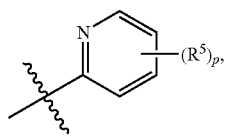

p is 1, and R⁵ is halogen, $C_{1-6}$alkyl, $C_{1-6}$ haloalkyl, $C_{1-6}$alkoxy, or $C_{1-6}$haloalkoxy. In another embodiment is a compound of Formula (VI), wherein $R^4$ is

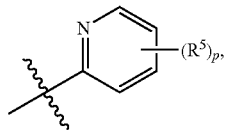

p is 1, and R⁵ is halogen. In another embodiment is a compound of Formula (VI), wherein $R^4$ is

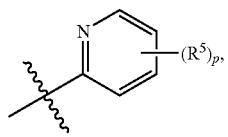

p is 1, and R⁵ is $C_{1-6}$alkyl. In another embodiment is a compound of Formula (VI), wherein $R^4$ is

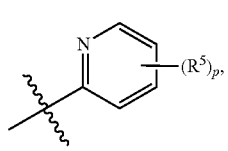

p is 1, and R⁵ is $C_{1-6}$haloalkyl. In another embodiment is a compound of Formula (VI), wherein $R^4$ is

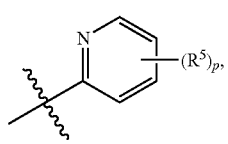

p is 1, and R⁵ is $C_{1-6}$alkoxy. In another embodiment is a compound of Formula (VI), wherein $R^4$ is

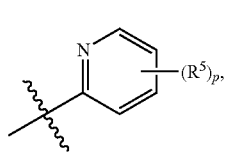

p is 1, and R⁵ is $C_{1-6}$haloalkoxy. In another embodiment is a compound of Formula (VI), wherein $R^4$ is

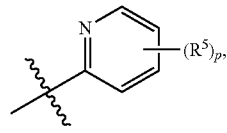

p is 1, and R⁵ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

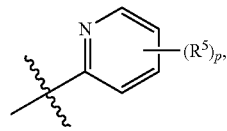

p is 1, and R⁵ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VI), wherein $R^4$ is

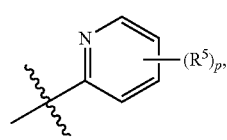

p is 1, and R⁵ is phenyl substituted with one or two groups selected from halogen, $C_{1-6}$alkyl, and $C_{1-6}$alkoxy. In another embodiment is a compound of Formula (VI), wherein $R^4$ is

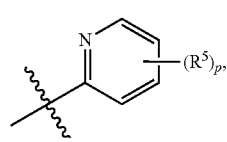

p is 1, and R⁵ is $C_{2-9}$heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

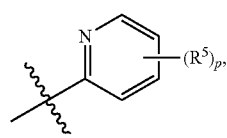

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

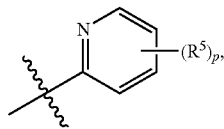

p is 1, and R⁵ is $C_{2-9}$ heteroaryl substituted with one or two groups selected from halogen, $C_{1-6}$alkyl, and $C_{1-6}$alkoxy. In another embodiment is a compound of Formula (VI), wherein $R^4$ is

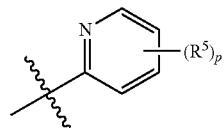

and p is 2. In another embodiment is a compound of Formula (VI), wherein $R^4$ is

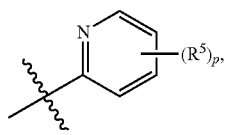

p is 2, and each R⁵ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$ haloalkoxy. In another embodiment is a compound of Formula (VI), wherein $R^4$ is

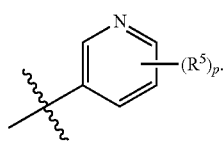

In another embodiment is a compound of Formula (VI), wherein $R^4$ is

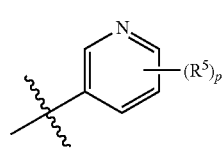

and p is 0. In another embodiment is a compound of Formula (VI), wherein $R^4$ is

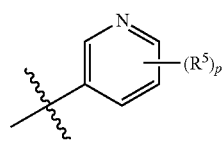

and p is 1. In another embodiment is a compound of Formula (VI), wherein $R^4$ is

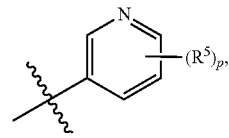

p is 1, and R⁵ is halogen, $C_{1-6}$alkyl, $C_{1-6}$haloalkyl, $C_{1-6}$alkoxy, —O—$C_{1-6}$ alkenyl, —O—$C_{1-6}$alkynyl, or $C_{1-6}$haloalkoxy. In another embodiment is a compound of Formula (VI), wherein $R^4$ is p is 1, and R⁵ is halogen, $C_{1-6}$alkyl, $C_{1-6}$alkoxy, or $C_{1-6}$haloalkoxy. In another embodiment is a compound of Formula (VI), wherein $R^4$ is p is 1, and R⁵ is halogen. In another embodiment is a compound of Formula (VI), wherein $R^4$ is p is 1, and R⁵ is $C_{1-6}$ alkyl. In another embodiment is a compound of Formula (VI), wherein $R^4$ is p is 1, and R⁵ is $C_{1-6}$haloalkyl. In another embodiment is a compound of Formula (VI), wherein $R^4$ is p is 1, and R⁵ is $C_{1-6}$alkoxy. In another embodiment is a compound of Formula (VI), wherein $R^4$ is

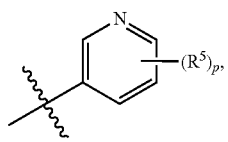

p is 1, and $R^5$ is $C_{1-6}$haloalkoxy. In another embodiment is a compound of Formula (VI), wherein $R^4$ is

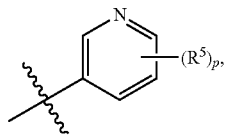

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

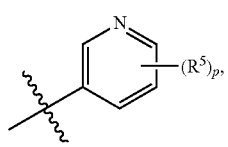

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VI), wherein $R^4$ is

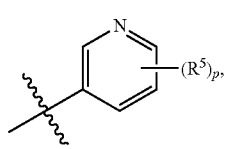

p is 1, and $R^5$ is phenyl substituted with one or two groups selected from halogen, $C_{1-6}$alkyl, and $C_{1-6}$alkoxy. In another embodiment is a compound of Formula (VI), wherein $R^4$ is

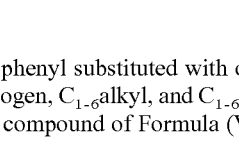

p is 1, and $R^5$ is $C_{2-9}$heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VI), wherein $R^4$ is

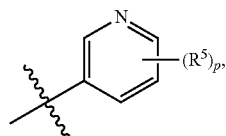

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

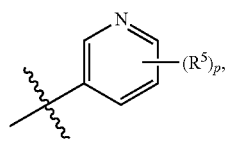

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (VI), wherein $R^4$ is

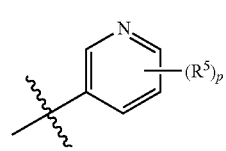

and p is 2. In another embodiment is a compound of Formula (VI), wherein $R^4$ is

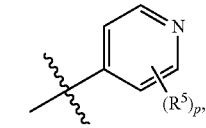

p is 2, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VI), wherein $R^4$ is

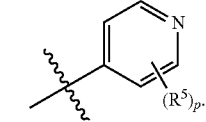

In another embodiment is a compound of Formula (VI), wherein $R^4$ is

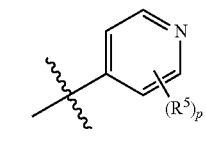

and p is 0. In another embodiment is a compound of Formula (VI), wherein $R^4$ is

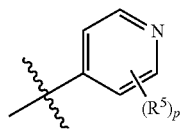

and p is 1 In another embodiment is a compound of Formula (VI), wherein $R^4$ is

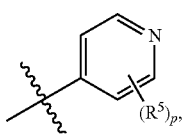

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VI), wherein $R^4$ is

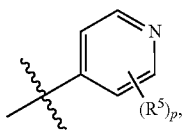

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (VI), wherein $R^4$ is

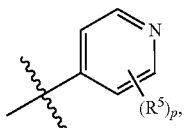

p is 1, and $R^5$ is halogen. In another embodiment is a compound of Formula (VI), wherein $R^4$ is

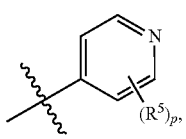

p is 1, and $R^5$ is $C_{1-6}$alkyl. In another embodiment is a compound of Formula (VI), wherein $R^4$ is

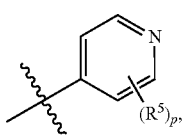

p is 1, and $R^5$ is $C_{1-6}$haloalkyl. In another embodiment is a compound of Formula (VI), wherein $R^4$ is

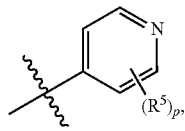

p is 1, and $R^5$ is $C_{1-6}$alkoxy. In another embodiment is a compound of Formula (VI), wherein $R^4$ is

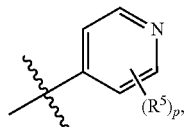

p is 1, and $R^5$ is $C_{1-6}$haloalkoxy. In another embodiment is a compound of Formula (VI), wherein $R^4$ is

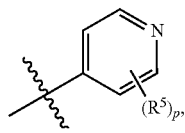

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

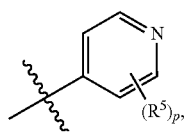

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VI), wherein $R^4$ is

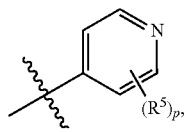

p is 1, and $R^5$ is phenyl substituted with one or two groups selected from halogen, $C_{1-6}$ alkyl, and $C_{1-6}$alkoxy. In another embodiment is a compound of Formula (VI), wherein $R^4$ is

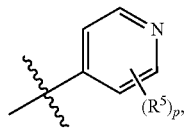

p is 1, and $R^5$ is $C_{2-6}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VI), wherein $R^4$ is

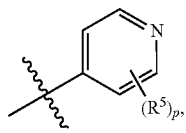

p is 1, and R⁵ is $C_{2-9}$ heteroaryl substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (VI), wherein R⁴ is

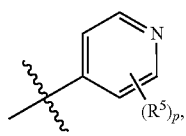

p is 1, and R⁵ is $C_{2-9}$heteroaryl substituted with one or two groups selected from halogen, $C_{1-6}$alkyl, and $C_{1-6}$alkoxy. In another embodiment is a compound of Formula (VI), wherein R⁴ is

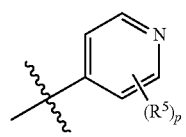

and p is 2. In another embodiment is a compound of Formula (VI), wherein R⁴ is

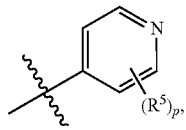

p is 2, and each R⁵ is independently halogen, $C_{1-6}$ alkyl, $C_{1-6}$ haloalkyl, $C_{1-6}$alkoxy, —O—$C_{1-6}$ alkenyl, —O—$C_{1-6}$alkynyl, or $C_{1-6}$haloalkoxy.

In another embodiment is a compound of Formula (VI), wherein R⁴ is

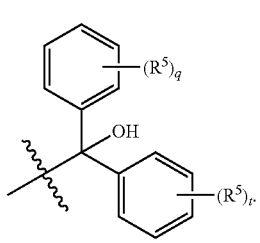

In another embodiment is a compound of Formula (VI), wherein R⁴ is

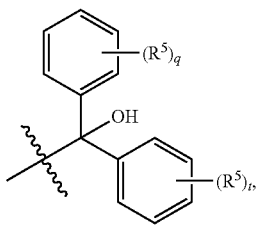

q is 0, and t is 0. In another embodiment is a compound of Formula (VI), wherein R⁴ is

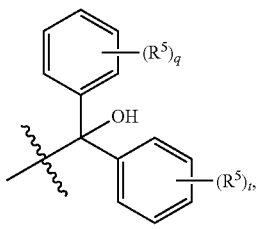

q is 1, and t is 0. In another embodiment is a compound of Formula (VI), wherein R⁴ is

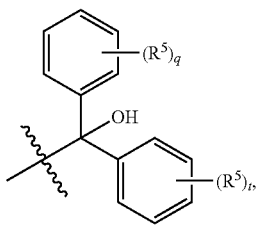

q is 1, t is 0, and R⁵ is halogen, $C_{1-6}$alkyl, $C_{1-6}$ haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VI), wherein R⁴ is

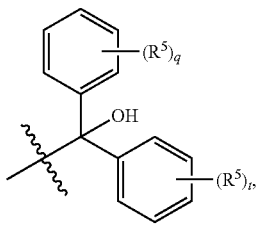

q is 1, t is 0, and R⁵ is halogen, $C_{1-6}$alkyl, $C_{1-6}$haloalkyl, $C_{1-6}$alkoxy, or $C_{1-6}$haloalkoxy. In another embodiment is a compound of Formula (VI), wherein R⁴ is

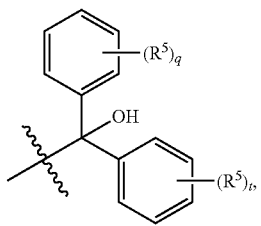

q is 1, and t is 1. In another embodiment is a compound of Formula (VI), wherein R⁴ is

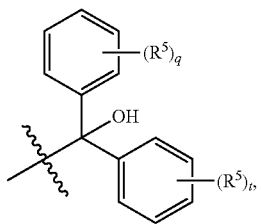

q is 1, t is 1, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VI), wherein R⁴ is

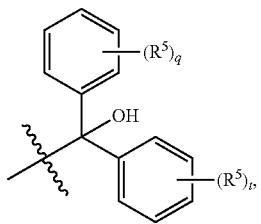

q is 1, t is 1, and each $R^5$ is independently halogen, $C_{1-6}$alkyl, $C_{1-6}$ haloalkyl, $C_{1-6}$alkoxy, or $C_{1-6}$ haloalkoxy. In another embodiment is a compound of Formula (VI), wherein R⁴ is

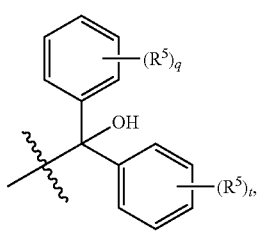

q is 1, t is 1, and each $R^5$ is halogen. In another embodiment is a compound of Formula (VI), wherein R⁴ is

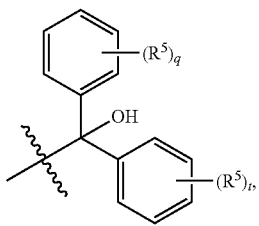

q is 1, t is 1, and each $R^5$ is $C_{1-6}$alkyl. In another embodiment is a compound of Formula (VI), wherein R⁴ is

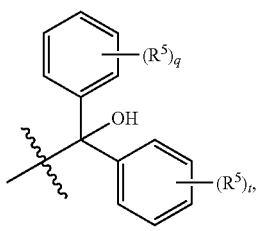

q is 1, t is 1, and each $R^5$ is $C_{1-6}$haloalkyl. In another embodiment is a compound of Formula (VI), wherein R⁴ is

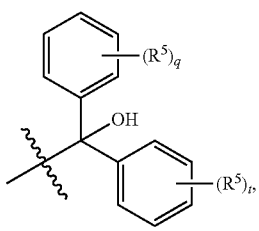

q is 1, t is 1, and each $R^5$ is $C_{1-6}$alkoxy. In another embodiment is a compound of Formula (VI), wherein R⁴ is

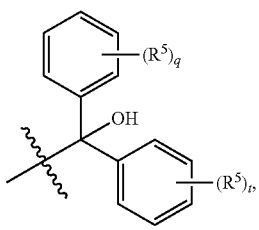

q is 1, t is 1, and each $R^5$ is $C_{1-6}$haloalkoxy.

In another embodiment is a compound of Formula (VII):

Formula (VII)

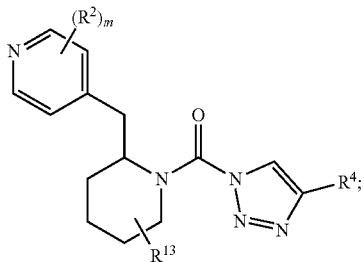

wherein:
each R² is independently halogen, —CN, —NH₂, —NH(CH₃), —N(CH₃)₂, —OH, —C(=O)OH, —C(=O)O(C₁₋₆ alkyl), —C(=O)NH₂, —C(=O)NH(C₁₋₆ alkyl), —C(=O)N(C₁₋₆ alkyl)₂, —S(=O)₂NH₂, —S(=O)₂NH(C₁₋₆alkyl), —S(=O)₂N(C₁₋₆alkyl)₂, C₁₋₆alkyl, C₃₋₆cycloalkyl, C₁₋₆haloalkyl, C₁₋₆ alkoxy, —O—C₁₋₆ alkenyl, —O—C₁₋₆ alkynyl, C₁₋₆ haloalkoxy, C₂₋₉heterocycloalkyl, C₆₋₁₀ aryl, or C₂₋₉ heteroaryl;

R¹³ is hydrogen, C₁₋₆alkyl, C₁₋₆alkoxy, —O—C₁₋₆ alkenyl, —O—C₁₋₆ alkynyl, or —O—CH₂C₃₋₆cycloalkyl;

R⁴ is

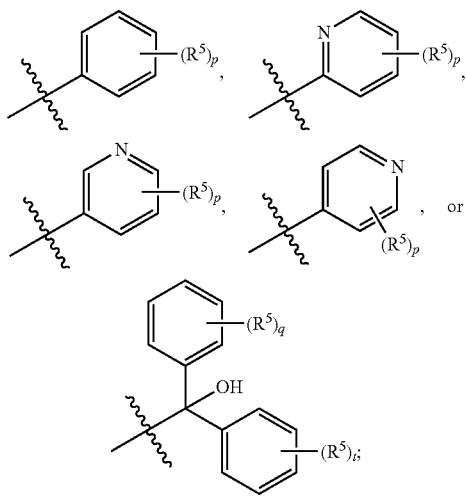

each R⁵ is independently halogen, —CN, —NH₂, —NH(CH₃), —N(CH₃)₂, —OH, —C(=O)OH, —C(=O)O(C₁₋₆alkyl), —C(=O)NH₂, —C(=O)NH(C₁₋₆ alkyl), —C(=O)N(C₁₋₆ alkyl)₂, —S(=O)₂NH₂, —S(=O)₂NH(C₁₋₆ alkyl), —S(=O)₂N(C₁₋₆ alkyl)₂, C₁₋₆ alkyl, C₁₋₆haloalkyl, C₁₋₆alkoxy, —O—C₁₋₆ alkenyl, —O—C₁₋₆ alkynyl, C₁₋₆ haloalkoxy, optionally substituted phenyl, or optionally substituted C₂₋₉ heteroaryl, wherein optionally substituted phenyl and optionally substituted C₂₋₉ heteroaryl are optionally substituted with one, two, or three groups selected from halogen, C₁₋₆ alkyl, C₁₋₆ haloalkyl, C₁₋₆ alkoxy, and C₁₋₆haloalkoxy;
m is 0, 1, 2, or 3;
p is 0, 1, 2, or 3,
q is 0, 1, 2, or 3, and
t is 0, 1, 2, or 3;

or a solvate, hydrate, tautomer, N-oxide, or pharmaceutically acceptable salt thereof.

In another embodiment is a compound of Formula (VII), wherein m is 0. In another embodiment is a compound of Formula (VII), wherein m is 1. In another embodiment is a compound of Formula (VII), wherein m is 1 and R² is halogen, C₁₋₆alkyl, C₁₋₆haloalkyl, C₁₋₆alkoxy, —O—C₁₋₆ alkenyl, —O—C₁₋₆alkynyl, or C₁₋₆haloalkoxy. In another embodiment is a compound of Formula (VII), wherein m is 1 and R² is halogen, C₁₋₆alkyl, C₁₋₆haloalkyl, C₁₋₆alkoxy, or C₁₋₆haloalkoxy. In another embodiment is a compound of Formula (VII), wherein m is 1 and R² is halogen. In another embodiment is a compound of Formula (VII), wherein m is 1 and R² is C₁₋₆alkyl. In another embodiment is a compound of Formula (VII), wherein m is 1 and R² is C₁₋₆haloalkyl. In another embodiment is a compound of Formula (VII), wherein m is 1 and R² is C₁₋₆alkoxy. In another embodiment is a compound of Formula (VII), wherein m is 1 and R² is C₁₋₆haloalkoxy. In another embodiment is a compound of Formula (VII), wherein m is 2. In another embodiment is a compound of Formula (VII), wherein m is 2 and each R² is independently halogen, C₁₋₆alkyl, C₁₋₆haloalkyl, C₁₋₆alkoxy, —O—C₁₋₆alkenyl, —O—C₁₋₆alkynyl, or C₁₋₆haloalkoxy. In another embodiment is a compound of Formula (VII), wherein m is 2 and each R² is independently halogen, C₁₋₆alkyl, C₁₋₆haloalkyl, C₁₋₆alkoxy, or C₁₋₆haloalkoxy.

In another embodiment is a compound of Formula (VII), wherein R¹³ is hydrogen. In another embodiment is a compound of Formula (VII), wherein R¹³ is —O—C₁₋₆alkynyl. In another embodiment is a compound of Formula (VII), wherein R¹³ is —O—C₁₋₅alkynyl. In another embodiment is a compound of Formula (VII), wherein R¹³ is —O—C₁₋₄ alkynyl. In another embodiment is a compound of Formula (VII), wherein R¹³ is —OCH₂CH₂C≡CH. In another embodiment is a compound of Formula (VII), wherein R¹³ is —OCH₂C≡CH. In another embodiment is a compound of Formula (VII), wherein R¹³ is C₁₋₆alkyl. In another embodiment is a compound of Formula (VII), wherein R¹³ is C₁₋₆alkoxy. In another embodiment is a compound of Formula (VII), wherein R¹³ is —O—C₁₋₆alkenyl. In another embodiment is a compound of Formula (VII), wherein R¹³ is —O—CH₂C₃₋₆cycloalkyl. In another embodiment is a compound of Formula (VII), wherein R¹³ is —O—CH₂cyclopropyl.

In another embodiment is a compound of Formula (VII), wherein R⁴ is

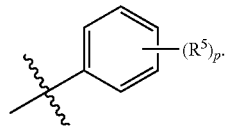

In another embodiment is a compound of Formula (VII), wherein R⁴ is

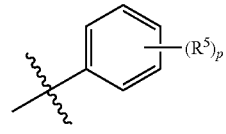

and p is 0. In another embodiment is a compound of Formula (VII), wherein $R^4$ is

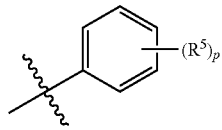

and p is 1. In another embodiment is a compound of Formula (VII), wherein $R^4$ is

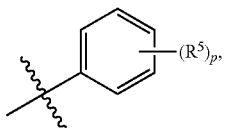

p is 1, and $R^5$ is halogen, $C_{1-6}$alkyl, $C_{1-6}$haloalkyl, $C_{1-6}$ alkoxy, —O—$C_{1-6}$ alkenyl, —O—$C_{1-6}$alkynyl, or $C_{1-6}$haloalkoxy. In another embodiment is a compound of Formula (VII), wherein $R^4$ is

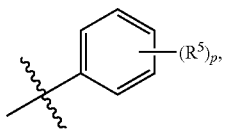

p is 1, and $R^5$ is halogen, $C_{1-6}$ alkyl, $C_{1-6}$ haloalkyl, $C_{1-6}$alkoxy, or $C_{1-6}$ haloalkoxy. In another embodiment is a compound of Formula (VII), wherein $R^4$ is

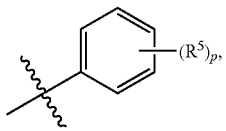

p is 1, and $R^5$ is halogen. In another embodiment is a compound of Formula (VII), wherein $R^4$ is

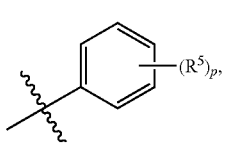

p is 1, and $R^5$ is $C_{1-6}$ alkyl. In another embodiment is a compound of Formula (VII), wherein $R^4$ is

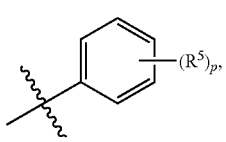

p is 1, and $R^5$ is $C_{1-6}$ haloalkyl. In another embodiment is a compound of Formula (VII), wherein $R^4$ is

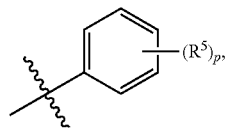

p is 1, and $R^5$ is $C_{1-6}$alkoxy. In another embodiment is a compound of Formula (VII), wherein $R^4$ is

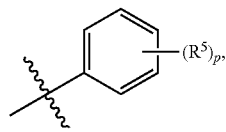

p is 1, and $R^5$ is $C_{1-6}$ haloalkoxy. In another embodiment is a compound of Formula (VII), wherein $R^4$ is

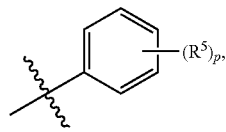

p is 1, and $R^5$ is phenyl optionally substituted with one, two, or three groups selected from halogen, $C_{1-6}$ alkyl, $C_{1-6}$ haloalkyl, $C_{1-6}$ alkoxy, and $C_{1-6}$ haloalkoxy. In another embodiment is a compound of Formula (VII), wherein $R^4$ is

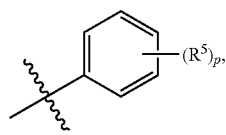

p is 1, and $R^5$ is phenyl substituted with one, two, or three groups selected from halogen, $C_{1-6}$ alkyl, $C_{1-6}$ haloalkyl, $C_{1-6}$ alkoxy, and $C_{1-6}$ haloalkoxy. In another embodiment is a compound of Formula (VII), wherein $R^4$ is

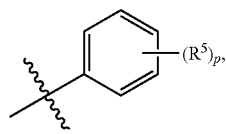

p is 1, and $R^5$ is phenyl substituted with one or two groups selected from halogen, $C_{1-6}$ alkyl, and $C_{1-6}$alkoxy. In another embodiment is a compound of Formula (VII), wherein $R^4$ is

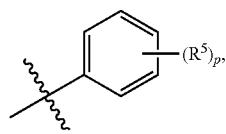

p is 1, and $R^5$ is $C_{2-9}$heteroaryl optionally substituted with one, two, or three groups selected from halogen, $C_{1-6}$ alkyl, $C_{1-6}$ haloalkyl, $C_{1-6}$alkoxy, and $C_{1-6}$ haloalkoxy. In another embodiment is a compound of Formula (VII), wherein $R^4$ is

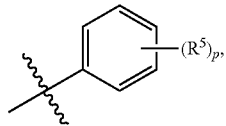

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein $R^4$ is

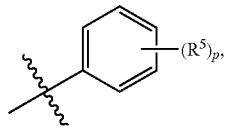

p is 1, and $R^5$ is $C_{2-9}$heteroaryl substituted with one or two groups selected from halogen, $C_{1-6}$ alkyl, and $C_{1-6}$alkoxy. In another embodiment is a compound of Formula (VII), wherein $R^4$ is

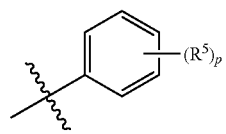

and p is 2. In another embodiment is a compound of Formula (VII), wherein $R^4$ is

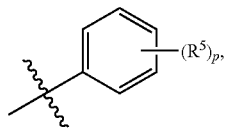

p is 2, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VII), wherein $R^4$ is

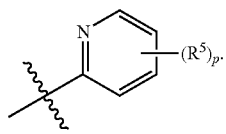

In another embodiment is a compound of Formula (VII), wherein $R^4$ is

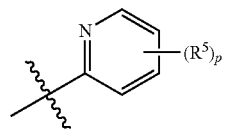

and p is 0. In another embodiment is a compound of Formula (VII), wherein $R^4$ is

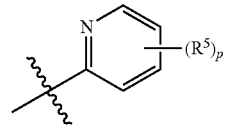

and p is 1. In another embodiment is a compound of Formula (VII), wherein $R^4$ is

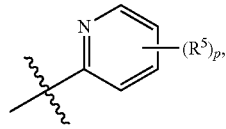

p is 1, and $R^5$ is halogen, $C_{1-6}$ alkyl, $C_{1-6}$haloalkyl, $C_{1-6}$ alkoxy, —O—$C_{1-6}$alkenyl, —O—$C_{1-6}$alkynyl, or $C_{1-6}$haloalkoxy. In another embodiment is a compound of Formula (VII), wherein $R^4$ is

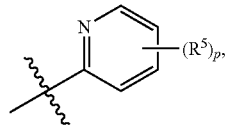

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (VII), wherein $R^4$ is

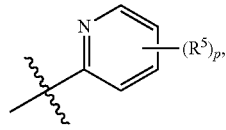

p is 1, and $R^5$ is halogen. In another embodiment is a compound of Formula (VII), wherein $R^4$ is

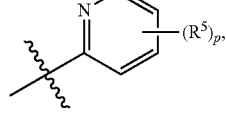

p is 1, and $R^5$ is $C_{1-6}$ alkyl. In another embodiment is a compound of Formula (VII), wherein $R^4$ is

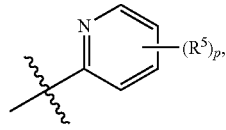

p is 1, and $R^5$ is $C_{1-6}$haloalkyl. In another embodiment is a compound of Formula (VII), wherein $R^4$ is

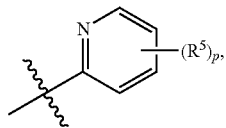

p is 1, and R⁵ is $C_{1-6}$alkoxy. In another embodiment is a compound of Formula (VII), wherein R⁴ is

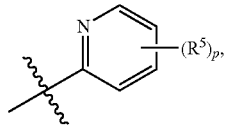

p is 1, and R⁵ is $C_{1-6}$haloalkoxy. In another embodiment is a compound of Formula (VII), wherein R⁴ is

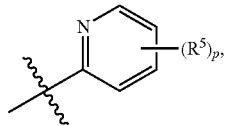

p is 1, and R⁵ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein R⁴ is

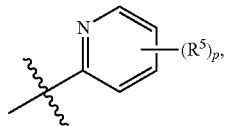

p is 1, and R⁵ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VII), wherein R⁴ is

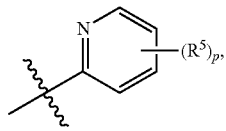

p is 1, and R⁵ is phenyl substituted with one or two groups selected from halogen, $C_{1-6}$alkyl, and $C_{1-6}$alkoxy. In another embodiment is a compound of Formula (VII), wherein R⁴ is

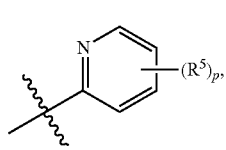

p is 1, and R⁵ is $C_{2-9}$heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VII), wherein R⁴ is

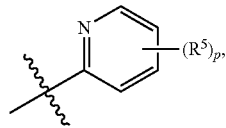

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein R⁴ is

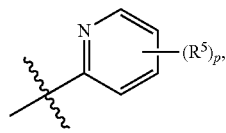

p is 1, and R⁵ is $C_{2-9}$ heteroaryl substituted with one or two groups selected from halogen, $C_{1-6}$alkyl, and $C_{1-6}$alkoxy. In another embodiment is a compound of Formula (VII), wherein R⁴ is

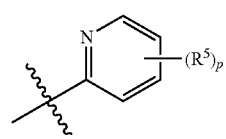

and p is 2. In another embodiment is a compound of Formula (VII), wherein R⁴ is

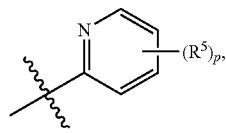

p is 2, and each R⁵ is independently halogen, $C_{1-6}$alkyl, $C_{1-6}$haloalkyl, $C_{1-6}$ alkoxy, —O—$C_{1-6}$ alkenyl, —O—$C_{1-6}$ alkynyl, or $C_{1-6}$ haloalkoxy. In another embodiment is a compound of Formula (VII), wherein R⁴ is

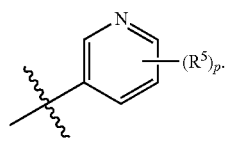

In another embodiment is a compound of Formula (VII), wherein R⁴ is

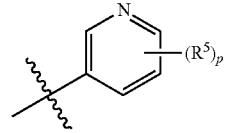

and p is 0. In another embodiment is a compound of Formula (VII), wherein R⁴ is

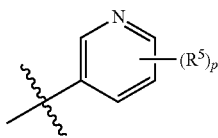

and p is 1. In another embodiment is a compound of Formula (VII), wherein $R^4$ is

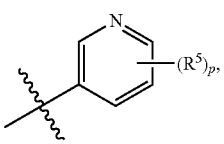

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VII), wherein $R^4$ is

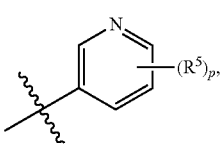

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (VII), wherein $R^4$ is

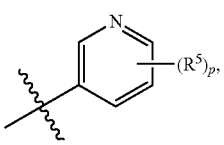

p is 1, and $R^5$ is halogen. In another embodiment is a compound of Formula (VII), wherein $R^4$ is

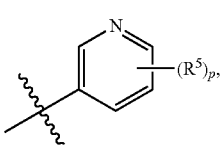

p is 1, and $R^5$ is $C_{1-6}$alkyl. In another embodiment is a compound of Formula (VII), wherein $R^4$ is

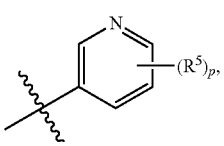

p is 1, and $R^5$ is $C_{1-6}$haloalkyl. In another embodiment is a compound of Formula (VII), wherein $R^4$ is

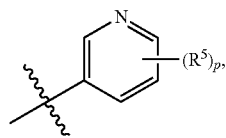

p is 1, and $R^5$ is $C_{1-6}$alkoxy. In another embodiment is a compound of Formula (VII), wherein $R^4$ is

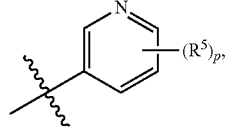

p is 1, and $R^5$ is $C_{1-6}$haloalkoxy. In another embodiment is a compound of Formula (VII), wherein $R^4$ is

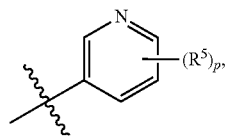

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein $R^4$ is

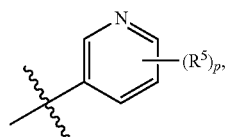

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VII), wherein $R^4$ is

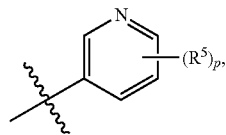

p is 1, and $R^5$ is phenyl substituted with one or two groups selected from halogen, $C_{1-6}$alkyl, and $C_{1-6}$alkoxy. In another embodiment is a compound of Formula (VII), wherein $R^4$ is

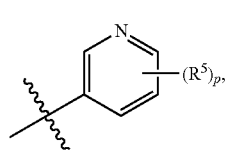

p is 1, and $R^5$ is $C_{2-9}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein $R^4$ is

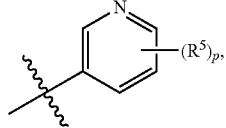

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein $R^4$ is

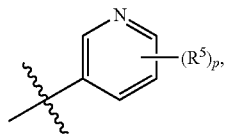

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (VII), wherein $R^4$ is

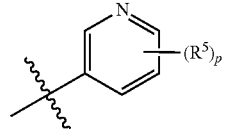

and p is 2. In another embodiment is a compound of Formula (VII), wherein $R^4$ is

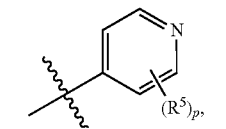

p is 2, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VII), wherein $R^4$ is

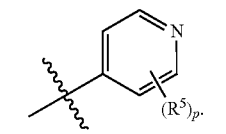

In another embodiment is a compound of Formula (VII), wherein $R^4$ is

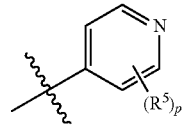

and p is 0. In another embodiment is a compound of Formula (VII), wherein $R^4$ is

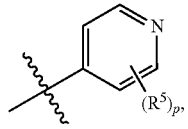

and p is 1. In another embodiment is a compound of Formula (VII), wherein $R^4$ is

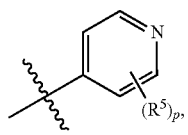

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VII), wherein $R^4$ is

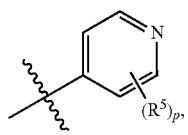

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (VII), wherein $R^4$ is p is 1, and $R^5$ is halogen. In another embodiment is a compound of Formula (VII), wherein $R^4$ is p is 1, and $R^5$ is $C_{1-6}$alkyl. In another embodiment is a compound of Formula (VII), wherein $R^4$ is

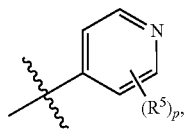

p is 1, and $R^5$ is $C_{1-6}$haloalkyl. In another embodiment is a compound of Formula (VII), wherein $R^4$ is

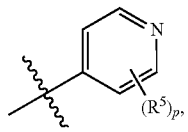

p is 1, and $R^5$ is $C_{1-6}$alkoxy. In another embodiment is a compound of Formula (VII), wherein $R^4$ is

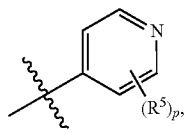

p is 1, and $R^5$ is $C_{1-6}$haloalkoxy. In another embodiment is a compound of Formula (VII), wherein $R^4$ is

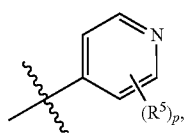

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein $R^4$ is

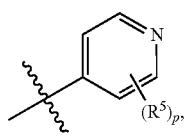

p is 1, and $R^5$ is phenyl substituted with one, two, or three groups selected from halogen, $C_{1-6}$alkyl, $C_{1-6}$haloalkyl, $C_{1-6}$alkoxy, and $C_{1-6}$ haloalkoxy. In another embodiment is a compound of Formula (VII), wherein $R^4$ is

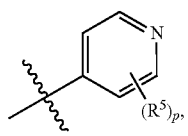

p is 1, and $R^5$ is phenyl substituted with one or two groups selected from halogen, $C_{1-6}$alkyl, and $C_{1-6}$alkoxy. In another embodiment is a compound of Formula (VII), wherein $R^4$ is

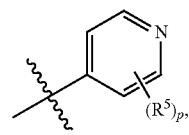

p is 1, and $R^5$ is $C_{2-9}$ heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VII), wherein $R^4$ is

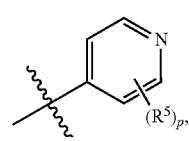

p is 1, and $R^5$ is $C_{2-6}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VII), wherein $R^4$ is

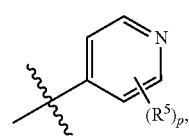

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (VII), wherein $R^4$ is

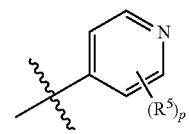

and p is 2. In another embodiment is a compound of Formula (VII), wherein $R^4$ is

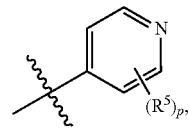

p is 2, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VII), wherein $R^4$ is

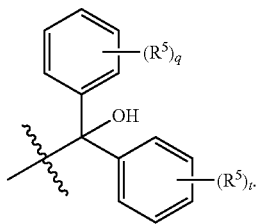

In another embodiment is a compound of Formula (VII), wherein $R^4$ is

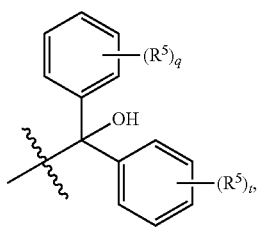

q is 0, and t is 0. In another embodiment is a compound of Formula (VII), wherein $R^4$ is

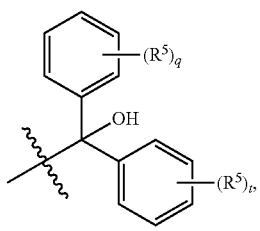

q is 1, and t is 0. In another embodiment is a compound of Formula (VII), wherein $R^4$ is

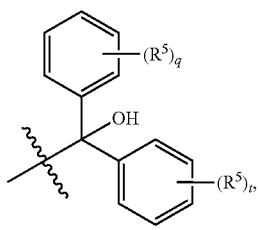

q is 1, t is 0, and $R^5$ is halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VII), wherein $R^4$ is

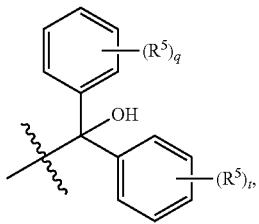

q is 1, t is 0, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (VII), wherein $R^4$ is

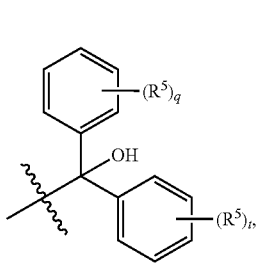

q is 1, and t is 1. In another embodiment is a compound of Formula (VII), wherein $R^4$ is

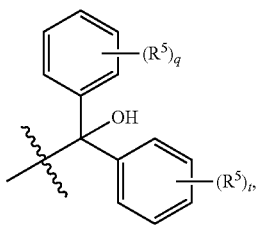

q is 1, t is 1, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VII), wherein $R^4$ is

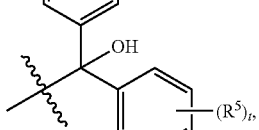

q is 1, t is 1, and each $R^5$ is independently halogen, $C_{1-6}$alkyl, $C_{1-6}$haloalkyl, $C_{1-6}$alkoxy, or $C_{1-6}$haloalkoxy. In another embodiment is a compound of Formula (VII), wherein $R^4$ is

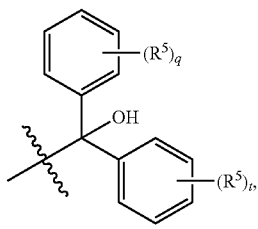

q is 1, t is 1, and each $R^5$ is halogen. In another embodiment is a compound of Formula (VII), wherein $R^4$ is

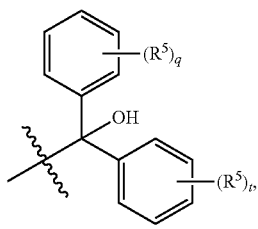

q is 1, t is 1, and each $R^5$ is $C_{1-6}$alkyl. In another embodiment is a compound of Formula (VII), wherein $R^4$ is

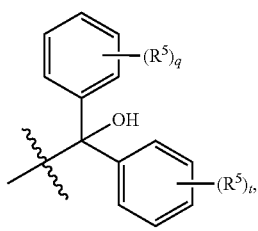

q is 1, t is 1, and each $R^5$ is $C_{1-6}$haloalkyl. In another embodiment is a compound of Formula (VII), wherein $R^4$ is

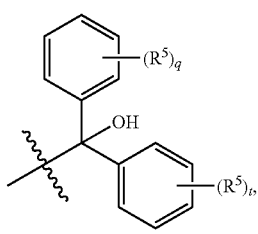

q is 1, t is 1, and each $R^5$ is $C_{1-6}$alkoxy. In another embodiment is a compound of Formula (VII), wherein $R^4$ is

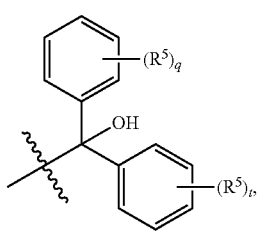

q is 1, t is 1, and each $R^5$ is $C_{1-6}$haloalkoxy.

In another embodiment is a compound of Formula (VIII):

Formula (VIII)

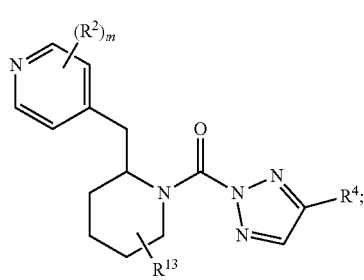

wherein:
each $R^2$ is independently halogen, —CN, —$NH_2$, —NH($CH_3$), —N($CH_3$)$_2$, —OH, —C(=O)OH, —C(=O)O($C_{1-6}$ alkyl), —C(=O)$NH_2$, —C(=O)NH($C_{1-6}$ alkyl), —C(=O)N($C_{1-6}$ alkyl)$_2$, —S(=O)$_2$$NH_2$, —S(=O)$_2$NH($C_{1-6}$ alkyl), —S(=O)$_2$N($C_{1-6}$ alkyl)$_2$, $C_{1-6}$alkyl, $C_{3-6}$cycloalkyl, $C_{1-6}$haloalkyl, $C_{1-6}$alkoxy, —O—$C_{1-6}$ alkenyl, —O—$C_{1-6}$alkynyl, $C_{1-6}$haloalkoxy, $C_{2-9}$heterocycloalkyl, $C_{6-10}$aryl, or $C_{2-9}$ heteroaryl;

$R^{13}$ is hydrogen, $C_{1-6}$alkyl, $C_{1-6}$alkoxy, —O—$C_{1-6}$alkenyl, —O—$C_{1-6}$alkynyl, or —O—$CH_2$$C_{3-6}$cycloalkyl;

$R^4$ is

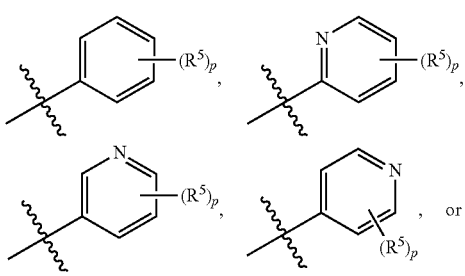

, or

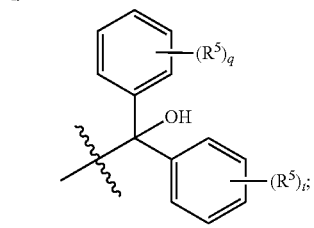

each $R^5$ is independently halogen, —CN, —$NH_2$, —NH($CH_3$), —N($CH_3$)$_2$, —OH, —C(=O)OH, —C(=O)O($C_{1-6}$alkyl), —C(=O)$NH_2$, —C(=O)NH($C_{1-6}$ alkyl), —C(=O)N($C_{1-6}$ alkyl)$_2$, —S(=O)$_2$$NH_2$, —S(=O)$_2$NH($C_{1-6}$alkyl), —S(=O)$_2$N($C_{1-6}$alkyl)$_2$, $C_{1-6}$alkyl, $C_{1-6}$haloalkyl, $C_{1-6}$alkoxy, —O—$C_{1-6}$ alkenyl, —O—$C_{1-6}$ alkynyl, $C_{1-6}$haloalkoxy, optionally substituted phenyl, or optionally substituted $C_{2-9}$heteroaryl, wherein optionally substituted phenyl and optionally substituted $C_{2-6}$ heteroaryl are optionally substituted with one, two, or three groups selected from halogen, $C_{1-6}$ alkyl, $C_{1-6}$haloalkyl, $C_{1-6}$ alkoxy, and $C_{1-6}$haloalkoxy;

m is 0, 1, 2, or 3;
p is 0, 1, 2, or 3;
q is 0, 1, 2, or 3; and
t is 0, 1, 2, or 3;

or a solvate, hydrate, tautomer, N-oxide, or pharmaceutically acceptable salt thereof.

In another embodiment is a compound of Formula (VIII), wherein m is 0. In another embodiment is a compound of Formula (VIII), wherein m is 1. In another embodiment is a compound of Formula (VIII), wherein m is 1 and $R^2$ is halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VIII), wherein m is 1 and $R^2$ is halogen, $C_{1-6}$alkyl, $C_{1-6}$haloalkyl, $C_{1-6}$ alkoxy, or $C_{1-6}$haloalkoxy. In another embodiment is a compound of Formula (VIII), wherein m is 1 and $R^2$ is halogen. In another embodiment is a compound of Formula (VIII), wherein m is 1 and $R^2$ is $C_{1-6}$alkyl. In another embodiment is a compound of Formula (VIII), wherein m is 1 and $R^2$ is $C_{1-6}$haloalkyl. In another embodiment is a compound of Formula (VIII), wherein m is 1 and $R^2$ is $C_{1-6}$alkoxy. In another embodiment is a compound of Formula (VIII), wherein m is 1 and $R^2$ is $C_{1-6}$haloalkoxy. In another embodiment is a compound of Formula (VIII), wherein m is 2. In another embodiment is a compound of Formula (VIII), wherein m is 2 and each $R^2$ is independently halogen, $C_{1-6}$ alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VIII), wherein m is 2 and each $R^2$ is independently halogen, $C_{1-6}$alkyl, $C_{1-6}$haloalkyl, $C_{1-6}$alkoxy, or $C_{1-6}$haloalkoxy.

In another embodiment is a compound of Formula (VIII), wherein $R^{13}$ is hydrogen. In another embodiment is a compound of Formula (VIII), wherein $R^{13}$ is —O—$C_{1-6}$ alkynyl. In another embodiment is a compound of Formula (VIII), wherein $R^{13}$ is —O—$C_{1-5}$ alkynyl. In another embodiment is a compound of Formula (VIII), wherein $R^{13}$ is —O—$C_{1-4}$ alkynyl. In another embodiment is a compound of Formula (VIII), wherein $R^{13}$ is —OCH$_2$CH$_2$C≡CH. In another embodiment is a compound of Formula (VIII), wherein $R^{13}$ is —OCH$_2$C≡CH. In another embodiment is a compound of Formula (VIII), wherein $R^{13}$ is $C_{1-6}$alkyl. In another embodiment is a compound of Formula (VIII), wherein $R^{13}$ is $C_{1-6}$alkoxy. In another embodiment is a compound of Formula (VIII), wherein $R^{13}$ is —O—$C_{1-6}$alkenyl. In another embodiment is a compound of Formula (VIII), wherein $R^{13}$ is —O—CH$_2$C$_{3-6}$ cycloalkyl. In another embodiment is a compound of Formula (VIII), wherein $R^{13}$ is —O—CH$_2$cyclopropyl.

In another embodiment is a compound of Formula (VIII), wherein $R^4$ is

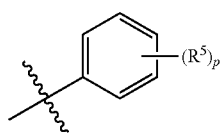

In another embodiment is a compound of Formula (VIII), wherein $R^4$ is

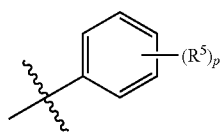

and p is 0. In another embodiment is a compound of Formula (VIII), wherein $R^4$ is

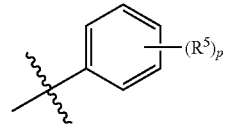

and p is 1. In another embodiment is a compound of Formula (VIII), wherein $R^4$ is

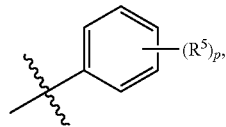

p is 1, and $R^5$ is halogen, $C_{1-6}$ alkyl, $C_{1-6}$haloalkyl, $C_{1-6}$alkoxy, —O—$C_{1-6}$ alkenyl, —O—$C_{1-6}$alkynyl, or $C_{1-6}$haloalkoxy. In another embodiment is a compound of Formula (VIII), wherein $R^4$ is

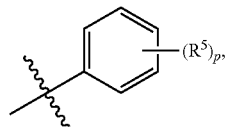

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (VIII), wherein $R^4$ is

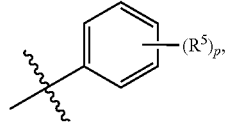

p is 1, and $R^5$ is halogen. In another embodiment is a compound of Formula (VIII), wherein $R^4$ is

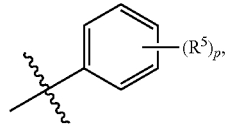

p is 1, and $R^5$ is $C_{1-6}$alkyl. In another embodiment is a compound of Formula (VIII), wherein $R^4$ is

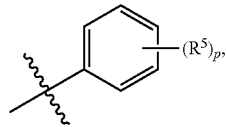

p is 1, and $R^5$ is $C_{1-6}$haloalkyl. In another embodiment is a compound of Formula (VIII), wherein $R^4$ is

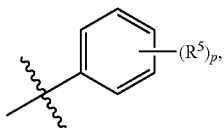

p is 1, and $R^5$ is $C_{1-6}$alkoxy. In another embodiment is a compound of Formula (VIII), wherein $R^4$ is

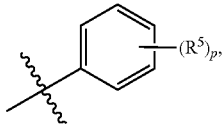

p is 1, and $R^5$ is $C_{1-6}$haloalkoxy. In another embodiment is a compound of Formula (VIII), wherein $R^4$ is

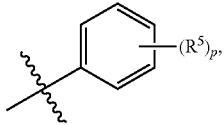

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

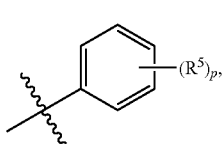

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VIII), wherein $R^4$ is

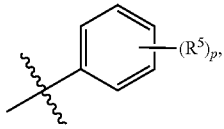

p is 1, and $R^5$ is phenyl substituted with one or two groups selected from halogen, $C_{1-6}$alkyl, and $C_{1-6}$alkoxy. In another embodiment is a compound of Formula (VIII), wherein $R^4$ is

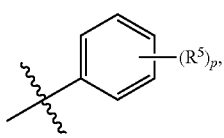

p is 1, and $R^5$ is $C_{2-9}$ heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VIII), wherein $R^4$ is

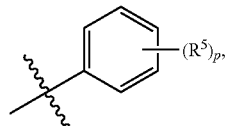

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

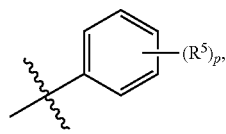

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (VIII), wherein $R^4$ is

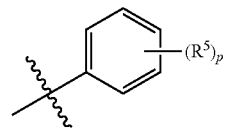

and p is 2. In another embodiment is a compound of Formula (VIII), wherein $R^4$ is

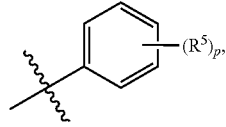

p is 2, and each $R^5$ is independently halogen, $C_{1-6}$alkyl, $C_{1-6}$haloalkyl, $C_{1-6}$ alkoxy, —O—$C_{1-6}$ alkenyl, —O—$C_{1-6}$ alkynyl, or $C_{1-6}$haloalkoxy. In another embodiment is a compound of Formula (VIII), wherein $R^4$ is

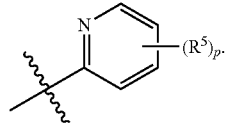

In another embodiment is a compound of Formula (VIII), wherein $R^4$ is

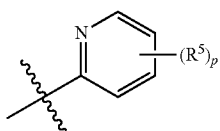

and p is 0. In another embodiment is a compound of Formula (VIII), wherein $R^4$ is

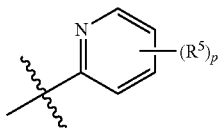

and p is 1. In another embodiment is a compound of Formula (VIII), wherein $R^4$ is

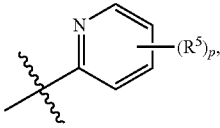

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (VIII), wherein $R^4$ is

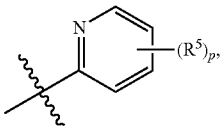

p is 1, and $R^5$ is halogen, $C_{1-6}$alkyl, $C_{1-6}$ haloalkyl, $C_{1-6}$alkoxy, or $C_{1-6}$ haloalkoxy. In another embodiment is a compound of Formula (VIII), wherein $R^4$ is

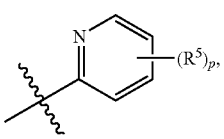

p is 1, and $R^5$ is halogen. In another embodiment is a compound of Formula (VIII), wherein $R^4$ is

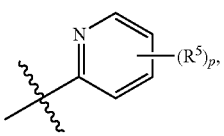

p is 1, and $R^5$ is $C_{1-6}$alkyl. In another embodiment is a compound of Formula (VIII), wherein $R^4$ is

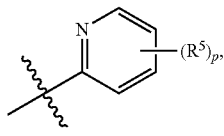

p is 1, and $R^5$ is $C_{1-6}$haloalkyl. In another embodiment is a compound of Formula (VIII), wherein $R^4$ is

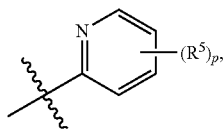

p is 1, and $R^5$ is $C_{1-6}$alkoxy. In another embodiment is a compound of Formula (VIII), wherein $R^4$ is

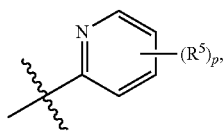

p is 1, and $R^5$ is $C_{1-6}$haloalkoxy. In another embodiment is a compound of Formula (VIII), wherein $R^4$ is

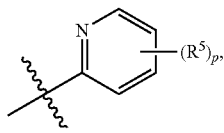

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

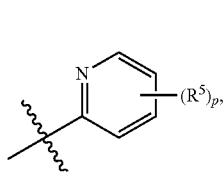

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VIII), wherein $R^4$ is p is 1, and $R^5$ is phenyl substituted with one or two groups selected from halogen, $C_{1-6}$alkyl, and $C_{1-6}$ alkoxy. In another embodiment is a compound of Formula (VIII), wherein $R^4$ is

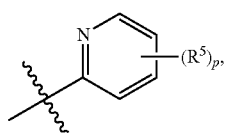

p is 1, and R⁵ is $C_{2-9}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein R⁴ is

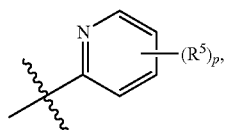

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein R⁴ is

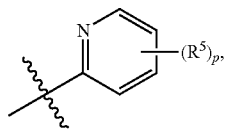

p is 1, and R⁵ is $C_{2-9}$ heteroaryl substituted with one or two groups selected from halogen, $C_{1-6}$alkyl, and $C_{1-6}$alkoxy. In another embodiment is a compound of Formula (VIII), wherein R⁴ is

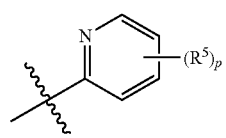

and p is 2. In another embodiment is a compound of Formula (VIII), wherein R⁴ is

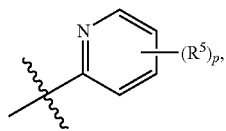

p is 2, and each R⁵ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VIII), wherein R⁴ is In another embodiment is a compound of Formula (VIII), wherein R⁴ is

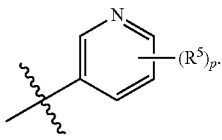

and p is 0. In another embodiment is a compound of Formula (VIII), wherein R⁴ is

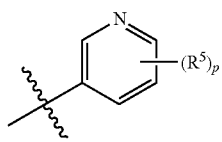

and p is 1. In another embodiment is a compound of Formula (VIII), wherein R⁴ is

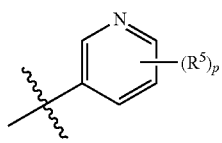

p is 1, and R⁵ is halogen, $C_{1-6}$alkyl, $C_{1-6}$ haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VIII), wherein R⁴ is

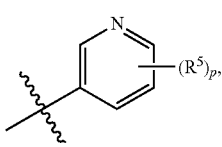

p is 1, and R⁵ is halogen, $C_{1-6}$alkyl, $C_{1-6}$alkoxy, or $C_{1-6}$haloalkoxy. In another embodiment is a compound of Formula (VIII), wherein R⁴ is

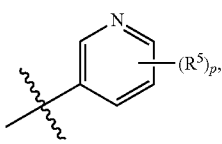

p is 1, and R⁵ is halogen. In another embodiment is a compound of Formula (VIII), wherein R⁴ is

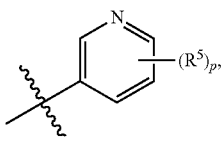

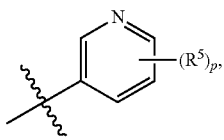

p is 1, and $R^5$ is $C_{1-6}$alkyl. In another embodiment is a compound of Formula (VIII), wherein $R^4$ is

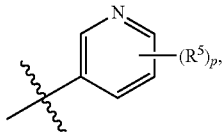

p is 1, and $R^5$ is $C_{1-6}$haloalkyl. In another embodiment is a compound of Formula (VIII), wherein $R^4$ is

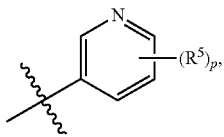

p is 1, and $R^5$ is $C_{1-6}$alkoxy. In another embodiment is a compound of Formula (VIII), wherein $R^4$ is

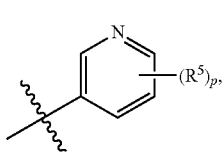

p is 1, and $R^5$ is $C_{1-6}$haloalkoxy. In another embodiment is a compound of Formula (VIII), wherein $R^4$ is

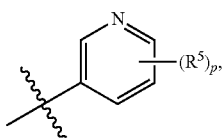

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

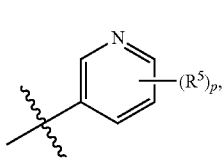

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VIII), wherein $R^4$ is

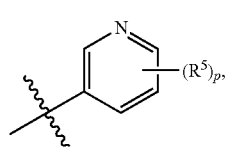

p is 1, and $R^5$ is phenyl substituted with one or two groups selected from halogen, $C_{1-6}$alkyl, and $C_{1-6}$alkoxy. In another embodiment is a compound of Formula (VIII), wherein $R^4$ is

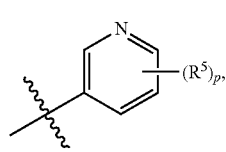

p is 1, and $R^5$ is $C_{2-6}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

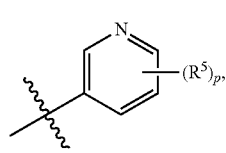

p is 1, and $R^5$ is $C_{2-6}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

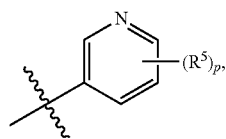

p is 1, and $R^5$ is $C_{2-9}$ heteroaryl substituted with one or two groups selected from halogen, $C_{1-6}$alkyl, and $C_{1-6}$ alkoxy. In another embodiment is a compound of Formula (VIII), wherein $R^4$ is

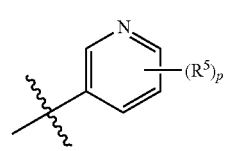

and p is 2. In another embodiment is a compound of Formula (VIII), wherein $R^4$ is

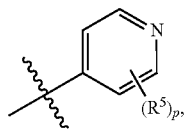

p is 2, and each R⁵ is independently halogen, $C_{1-6}$ alkyl, $C_{1-6}$haloalkyl, $C_{1-6}$ alkoxy, —O—$C_{1-6}$ alkenyl, —O—$C_{1-6}$ alkynyl, or $C_{1-6}$haloalkoxy. In another embodiment is a compound of Formula (VIII), wherein R⁴ is

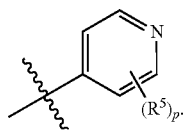

In another embodiment is a compound of Formula (VIII), wherein R⁴ is

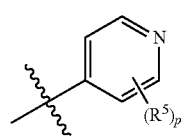

and p is 0. In another embodiment is a compound of Formula (VIII), wherein R⁴ is

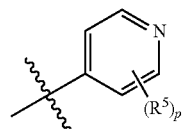

and p is 1. In another embodiment is a compound of Formula (VIII), wherein R⁴ is

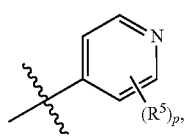

p is 1, and R⁵ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VIII), wherein R⁴ is

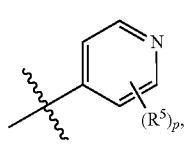

p is 1, and R⁵ is halogen, $C_{1-6}$alkyl, $C_{1-6}$haloalkyl, $C_{1-6}$alkoxy, or $C_{1-6}$haloalkoxy. In another embodiment is a compound of Formula (VIII), wherein R⁴ is

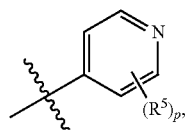

p is 1, and R⁵ is halogen. In another embodiment is a compound of Formula (VIII), wherein R⁴ is

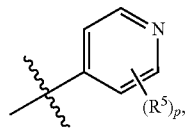

p is 1, and R⁵ is $C_{1-6}$alkyl. In another embodiment is a compound of Formula (VIII), wherein R⁴ is

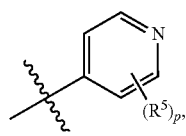

p is 1, and R⁵ is $C_{1-6}$haloalkyl. In another embodiment is a compound of Formula (VIII), wherein R⁴ is

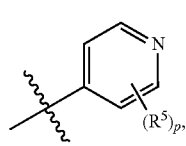

p is 1, and R⁵ is $C_{1-6}$alkoxy. In another embodiment is a compound of Formula (VIII), wherein R⁴ is

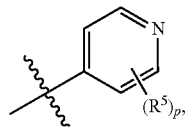

p is 1, and R⁵ is $C_{1-6}$haloalkoxy. In another embodiment is a compound of Formula (VIII), wherein R⁴ is

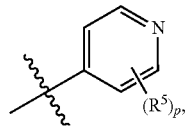

p is 1, and R⁵ is phenyl optionally substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (VIII), wherein R⁴ is

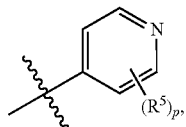

p is 1, and R⁵ is phenyl substituted with one, two, or three groups selected from halogen, $C_{1-6}$ alkyl, $C_{1-6}$haloalkyl, $C_{1-6}$ alkoxy, and $C_{1-6}$ haloalkoxy. In another embodiment is a compound of Formula (VIII), wherein $R^4$ is

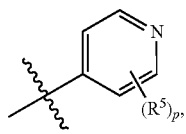

p is 1, and R⁵ is phenyl substituted with one or two groups selected from halogen, $C_{1-6}$alkyl, and $C_{1-6}$alkoxy. In another embodiment is a compound of Formula (VIII), wherein $R^4$ is

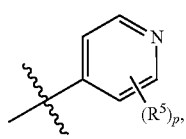

p is 1, and R⁵ is $C_{2-9}$heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (VIII), wherein $R^4$ is

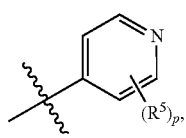

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (VIII), wherein $R^4$ is

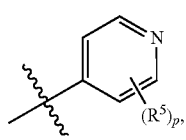

p is 1, and R⁵ is $C_{2-9}$ heteroaryl substituted with one or two groups selected from halogen, $C_{1-6}$alkyl, and $C_{1-6}$ alkoxy. In another embodiment is a compound of Formula (VIII), wherein $R^4$ is

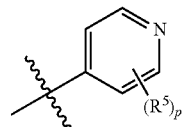

and p is 2. In another embodiment is a compound of Formula (VIII), wherein $R^4$ is

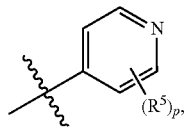

p is 2, and each R⁵ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (VIII), wherein $R^4$ is

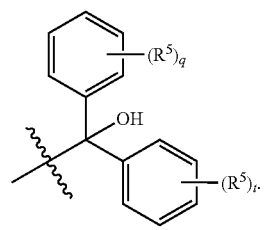

In another embodiment is a compound of Formula (VIII), wherein $R^4$ is

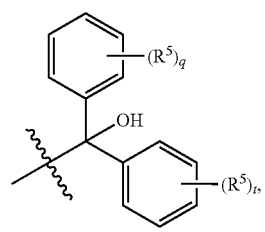

q is 0, and t is 0. In another embodiment is a compound of Formula (VIII), wherein $R^4$ is

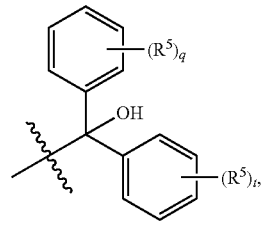

q is 1, and t is 0. In another embodiment is a compound of Formula (VIII), wherein $R^4$ is

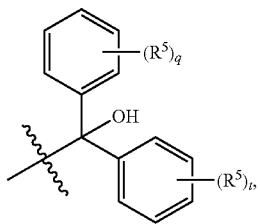

q is 1, t is 0, and R⁵ is halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (VIII), wherein R⁴ is

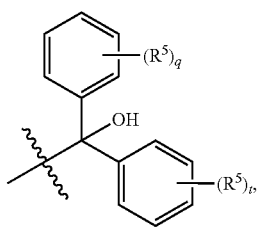

q is 1, t is 0, and R⁵ is halogen, $C_{1-6}$alkyl, $C_{1-6}$haloalkyl, $C_{1-6}$alkoxy, or $C_{1-6}$haloalkoxy. In another embodiment is a compound of Formula (VIII), wherein R⁴ is

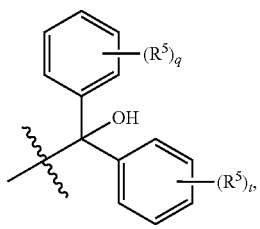

q is 1, and t is 1. In another embodiment is a compound of Formula (VIII), wherein R⁴ is

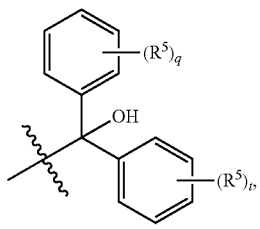

q is 1, t is 1, and each R⁵ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$ haloalkoxy. In another embodiment is a compound of Formula (VIII), wherein R⁴ is

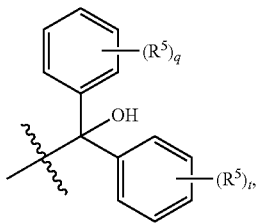

q is 1, t is 1, and each R⁵ is independently halogen, $C_{1-6}$alkyl, $C_{1-6}$haloalkyl, $C_{1-6}$alkoxy, or $C_{1-6}$haloalkoxy. In another embodiment is a compound of Formula (VIII), wherein R⁴ is

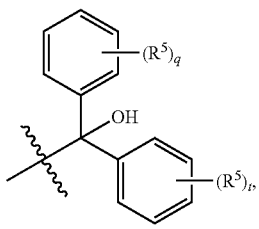

q is 1, t is 1, and each R⁵ is halogen. In another embodiment is a compound of Formula (VIII), wherein R⁴ is

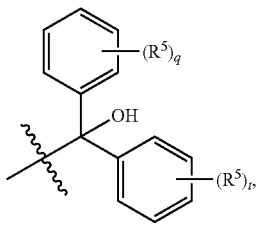

q is 1, t is 1, and each R⁵ is $C_{1-6}$alkyl. In another embodiment is a compound of Formula (VIII), wherein R⁴ is

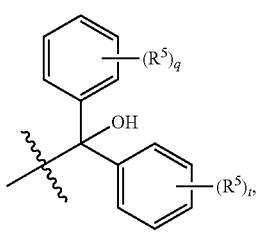

q is 1, t is 1, and each R⁵ is $C_{1-6}$haloalkyl. In another embodiment is a compound of Formula (VIII), wherein R⁴ is

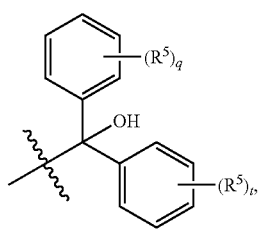

q is 1, t is 1, and each $R^5$ is $C_{1-6}$alkoxy. In another embodiment is a compound of Formula (VIII), wherein $R^4$ is

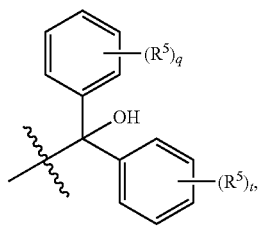

q is 1, t is 1, and each $R^5$ is $C_{1-6}$haloalkoxy.

In another embodiment is a compound of Formula (IX):

Formula (IX)

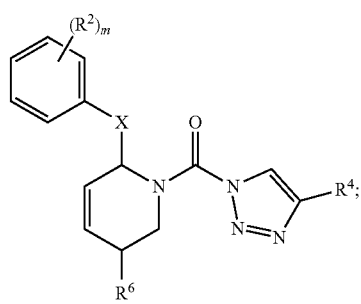

wherein:
X is —$CH_2$—, —$OCH_2$—, —$CH_2O$—, or —$CH_2OCH_2$—;
each $R^2$ is independently halogen, —CN, —$NH_2$, —NH($CH_3$), —N($CH_3$)$_2$, —OH, —C(=O)OH, —C(=O)O($C_{1-6}$alkyl), —C(=O)$NH_2$, —C(=O)NH($C_{1-6}$ alkyl), —C(=O)N($C_{1-6}$ alkyl)$_2$, —S(=O)$_2NH_2$, —S(=O)$_2$NH($C_{1-6}$alkyl), —S(=O)$_2$N($C_{1-6}$alkyl)$_2$, $C_{1-6}$alkyl, $C_{3-6}$cycloalkyl, $C_{1-6}$alkoxy, —O—$C_{1-6}$alkenyl, —O—$C_{1-6}$alkynyl, $C_{1-6}$haloalkoxy, $C_{2-9}$heterocycloalkyl, $C_{6-10}$aryl, or $C_{2-9}$ heteroaryl;
$R^4$ is

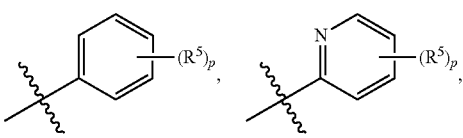

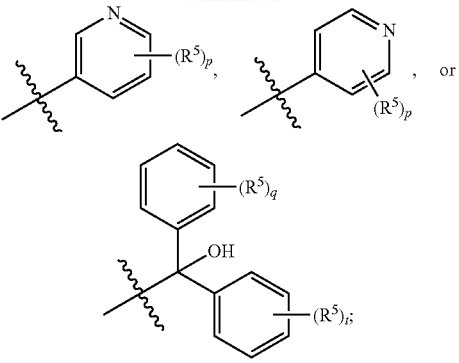

each $R^5$ is independently halogen, —CN, —$NH_2$, —NH($CH_3$), —N($CH_3$)$_2$, —OH, —C(=O)OH, —C(=O)O($C_{1-6}$ alkyl), —C(=O)$NH_2$, —C(=O)NH($C_{1-6}$ alkyl), —C(=O)N($C_{1-6}$ alkyl)$_2$, —S(=O)$_2NH_2$, —S(=O)$_2$NH($C_{1-6}$ alkyl), —S(=O)$_2$N($C_{1-6}$ alkyl)$_2$, $C_{1-6}$alkyl, $C_{1-6}$haloalkyl, $C_{1-6}$ alkoxy, —O—$C_{1-6}$ alkenyl, —O—$C_{1-6}$ alkynyl, $C_{1-6}$haloalkoxy, optionally substituted phenyl, or optionally substituted $C_{2-9}$heteroaryl, wherein optionally substituted phenyl and optionally substituted $C_{2-9}$ heteroaryl are optionally substituted with one, two, or three groups selected from halogen, $C_{1-6}$alkyl, $C_{1-6}$haloalkyl, $C_{1-6}$alkoxy, and $C_{1-6}$haloalkoxy;
$R^6$ is hydrogen, $C_{1-6}$ alkyl, —OH, $C_{1-6}$ alkoxy, —O—$C_{1-6}$ alkenyl, —O—$C_{1-6}$ alkynyl, or —O—$CH_2C_{3-6}$cycloalkyl;
m is 0, 1, 2, or 3;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (IX), wherein X is —$CH_2$—. In another embodiment is a compound of Formula (IX), wherein X is —$OCH_2$—. In another embodiment is a compound of Formula (IX), wherein X is —$CH_2O$—. In another embodiment is a compound of Formula (IX), wherein X is —$CH_2OCH_2$—.

In another embodiment is a compound of Formula (IX), wherein m is 0. In another embodiment is a compound of Formula (IX), wherein m is 1. In another embodiment is a compound of Formula (IX), wherein m is 1 and $R^2$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein m is 1 and $R^2$ is halogen, $C_{1-6}$alkyl, $C_{1-6}$haloalkyl, $C_{1-6}$ alkoxy, or $C_{1-6}$haloalkoxy. In another embodiment is a compound of Formula (IX), wherein m is 1 and $R^2$ is halogen. In another embodiment is a compound of Formula (IX), wherein m is 1 and $R^2$ is $C_{1-6}$alkyl. In another embodiment is a compound of Formula (IX), wherein m is 1 and $R^2$ is $C_{1-6}$haloalkyl. In another embodiment is a compound of Formula (IX), wherein m is 1 and $R^2$ is $C_{1-6}$alkoxy. In another embodiment is a compound of Formula (IX), wherein m is 1 and $R^2$ is $C_{1-6}$haloalkoxy. In another embodiment is a compound of Formula (IX), wherein m is 2. In another embodiment is a compound of Formula (IX), wherein m is 2 and each $R^2$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein m is 2 and each $R^2$ is independently halogen, $C_{1-6}$alkyl, $C_{1-6}$haloalkyl, $C_{1-6}$alkoxy, or $C_{1-6}$haloalkoxy.

In another embodiment is a compound of Formula (IX), wherein $R^6$ is hydrogen. In another embodiment is a compound of Formula (IX), wherein $R^6$ is —OH. In another embodiment is a compound of Formula (IX), wherein $R^6$ is —O—$C_{1-6}$ alkynyl. In another embodiment is a compound of Formula (IX), wherein $R^6$ is —O—$C_{1-5}$ alkynyl. In another embodiment is a compound of Formula (IX), wherein $R^6$ is —O—$C_{1-4}$ alkynyl. In another embodiment is a compound of Formula (IX), wherein $R^6$ is —OCH$_2$CH$_2$C≡CH. In another embodiment is a compound of Formula (IX), wherein $R^6$ is —OCH$_2$C≡CH. In another embodiment is a compound of Formula (IX), wherein $R^6$ is $C_{1-6}$alkyl. In another embodiment is a compound of Formula (IX), wherein $R^6$ is $C_{1-6}$ alkoxy. In another embodiment is a compound of Formula (IX), wherein $R^6$ is —O—$C_{1-6}$alkenyl. In another embodiment is a compound of Formula (IX), wherein $R^6$ is —O—CH$_2$C$_{3-6}$cycloalkyl. In another embodiment is a compound of Formula (IX), wherein $R^6$ is —O—CH$_2$cyclopropyl.

In another embodiment is a compound of Formula (IX), wherein $R^4$ is

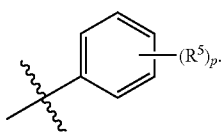

In another embodiment is a compound of Formula (IX), wherein $R^4$ is

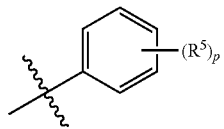

and p is 0. In another embodiment is a compound of Formula (IX), wherein $R^4$ is

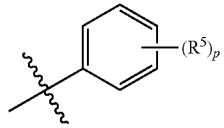

and p is 1. In another embodiment is a compound of Formula (IX), wherein $R^4$ is

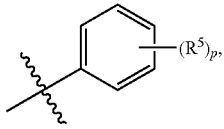

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (IX), wherein $R^4$ is

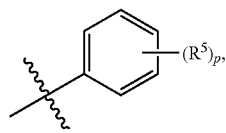

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (IX), wherein $R^4$ is

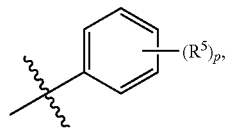

p is 1, and $R^5$ is halogen. In another embodiment is a compound of Formula (IX), wherein $R^4$ is

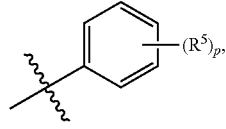

p is 1, and $R^5$ is $C_{1-6}$alkyl. In another embodiment is a compound of Formula (IX), wherein $R^4$ is

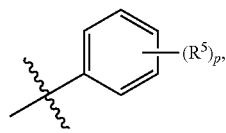

p is 1, and $R^5$ is $C_{1-6}$haloalkyl. In another embodiment is a compound of Formula (IX), wherein $R^4$ is

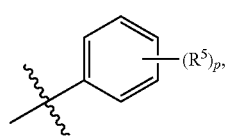

p is 1, and $R^5$ is $C_{1-6}$alkoxy. In another embodiment is a compound of Formula (IX), wherein $R^4$ is p is 1, and $R^5$ is $C_{1-6}$haloalkoxy. In another embodiment is a compound of Formula (IX), wherein $R^4$ is

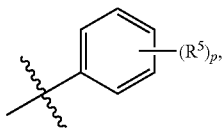

p is 1, and $R^5$ is phenyl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (IX), wherein $R^4$ is

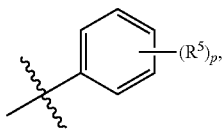

p is 1, and $R^5$ is phenyl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein $R^4$ is

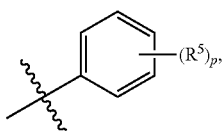

p is 1, and $R^5$ is phenyl substituted with one or two groups selected from halogen, $C_{1-6}$alkyl, and $C_{1-6}$ alkoxy. In another embodiment is a compound of Formula (IX), wherein $R^4$ is

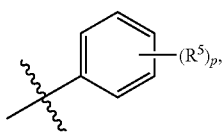

p is 1, and $R^5$ is $C_{2-9}$ heteroaryl optionally substituted with one, two, or three groups selected from halogen, $C_{1-6}$alkyl, $C_{1-6}$haloalkyl, $C_{1-6}$ alkoxy, and $C_{1-6}$haloalkoxy. In another embodiment is a compound of Formula (IX), wherein $R^4$ is

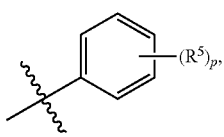

p is 1, and $R^5$ is $C_{2-9}$ heteroaryl substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (IX), wherein $R^4$ is

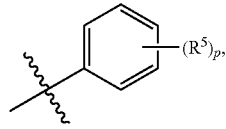

p is 1, and $R^5$ is $C_{2-9}$heteroaryl substituted with one or two groups selected from halogen, $C_{1-6}$alkyl, and $C_{1-6}$alkoxy. In another embodiment is a compound of Formula (IX), wherein $R^4$ is

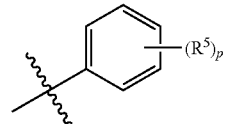

and p is 2. In another embodiment is a compound of Formula (IX), wherein $R^4$ is

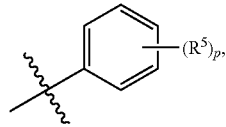

p is 2, and each $R^5$ is independently halogen, $C_{1-6}$ alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (IX), wherein $R^4$ is

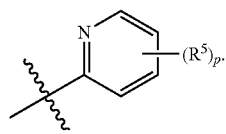

In another embodiment is a compound of Formula (IX), wherein $R^4$ is

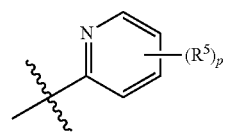

and p is 0. In another embodiment is a compound of Formula (IX), wherein $R^4$ is

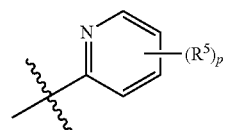

and p is 1. In another embodiment is a compound of Formula (IX), wherein $R^4$ is

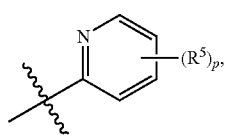

p is 1, and R⁵ is halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (IX), wherein R⁴ is

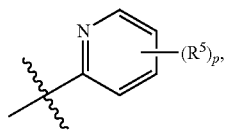

p is 1, and R⁵ is halogen, $C_{1-6}$alkyl, $C_{1-6}$haloalkyl, $C_{1-6}$alkoxy, or $C_{1-6}$ haloalkoxy. In another embodiment is a compound of Formula (IX), wherein R⁴ is

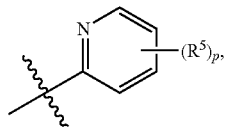

p is 1, and R⁵ is halogen. In another embodiment is a compound of Formula (IX), wherein R⁴ is

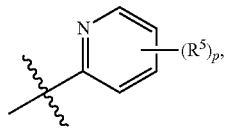

p is 1, and R⁵ is $C_{1-6}$ alkyl. In another embodiment is a compound of Formula (IX), wherein R⁴ is

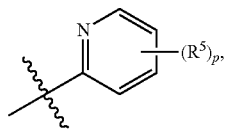

p is 1, and R⁵ is $C_{1-6}$haloalkyl. In another embodiment is a compound of Formula (IX), wherein R⁴ is

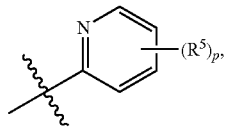

p is 1, and R⁵ is $C_{1-6}$ alkoxy. In another embodiment is a compound of Formula (IX), wherein R⁴ is

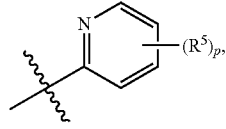

p is 1, and R⁵ is $C_{1-6}$ haloalkoxy. In another embodiment is a compound of Formula (IX), wherein R⁴ is

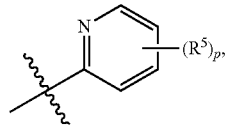

p is 1, and R⁵ is phenyl optionally substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (IX), wherein R⁴ is

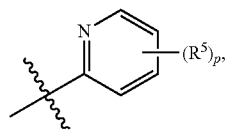

p is 1, and R⁵ is phenyl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein R⁴ is

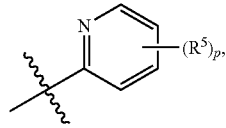

p is 1, and R⁵ is phenyl substituted with one or two groups selected from halogen, $C_{1-6}$alkyl, and $C_{1-6}$alkoxy. In another embodiment is a compound of Formula (IX), wherein R⁴ is

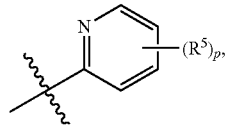

p is 1, and R⁵ is $C_{2-9}$heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein R⁴ is

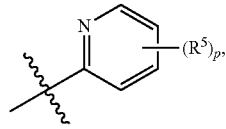

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein $R^4$ is

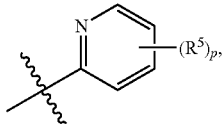

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (IX), wherein $R^4$ is

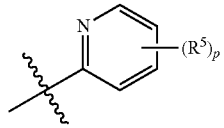

and p is 2. In another embodiment is a compound of Formula (IX), wherein $R^4$ is

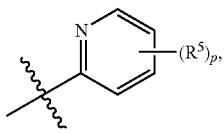

p is 2, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein $R^4$ is

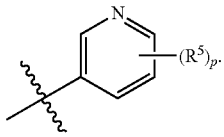

In another embodiment is a compound of Formula (IX), wherein $R^4$ is

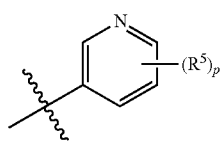

and p is 0. In another embodiment is a compound of Formula (IX), wherein $R^4$ is

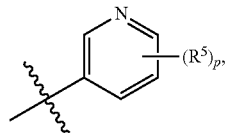

and p is 1. In another embodiment is a compound of Formula (IX), wherein $R^4$ is

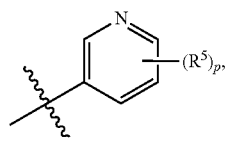

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein $R^4$ is

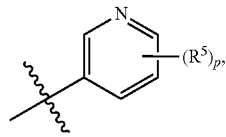

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (IX), wherein $R^4$ is

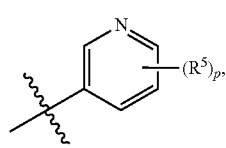

p is 1, and $R^5$ is halogen. In another embodiment is a compound of Formula (IX), wherein $R^4$ is p is 1, and $R^5$ is $C_{1-6}$alkyl. In another embodiment is a compound of Formula (IX), wherein $R^4$ is p is 1, and $R^5$ is $C_{1-6}$haloalkyl. In another embodiment is a compound of Formula (IX), wherein $R^4$ is

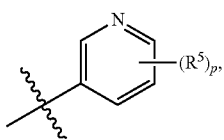

p is 1, and
R⁵ is $C_{1-6}$alkoxy. In another embodiment is a compound of Formula (IX), wherein R⁴ is

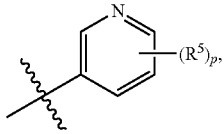

p is 1, and R⁵ is $C_{1-6}$haloalkoxy. In another embodiment is a compound of Formula (IX), wherein R⁴ is

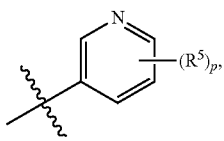

p is 1, and R⁵ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein R⁴ is

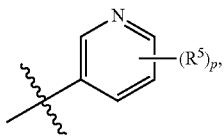

p is 1, and R⁵ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (IX), wherein R⁴ is

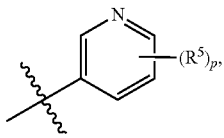

p is 1, and R⁵ is phenyl substituted with one or two groups selected from halogen, $C_{1-6}$alkyl, and $C_{1-6}$alkoxy. In another embodiment is a compound of Formula (IX), wherein R⁴ is

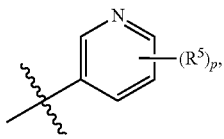

p is 1, and R⁵ is $C_{2-9}$heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (IX), wherein R⁴ is

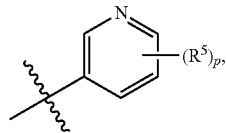

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein R⁴ is

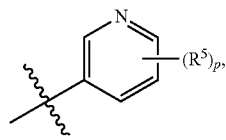

p is 1, and R⁵ is $C_{2-9}$ heteroaryl substituted with one or two groups selected from halogen, $C_{1-6}$alkyl, and $C_{1-6}$alkoxy. In another embodiment is a compound of Formula (IX), wherein R⁴ is

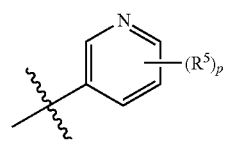

and p is 2. In another embodiment is a compound of Formula (IX), wherein R⁴ is

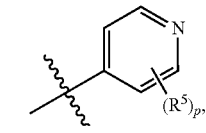

p is 2, and each R⁵ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$ haloalkoxy. In another embodiment is a compound of Formula (IX), wherein R⁴ is

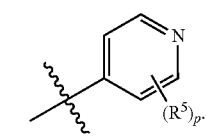

In another embodiment is a compound of Formula (IX), wherein R⁴ is

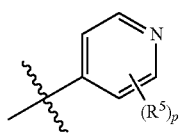

and p is 0. In another embodiment is a compound of Formula (IX), wherein $R^4$ is

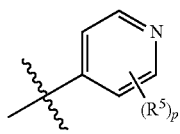

and p is 1. In another embodiment is a compound of Formula (IX), wherein $R^4$ is

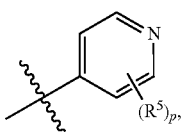

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein $R^4$ is

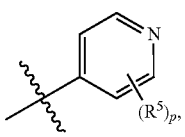

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (IX), wherein $R^4$ is

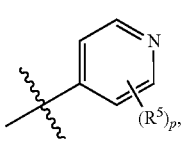

p is 1, and $R^5$ is halogen. In another embodiment is a compound of Formula (IX), wherein $R^4$ is

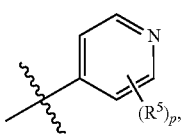

p is 1, and $R^5$ is $C_{1-6}$alkyl. In another embodiment is a compound of Formula (IX), wherein $R^4$ is

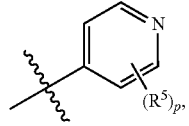

p is 1, and $R^5$ is $C_{1-6}$haloalkyl. In another embodiment is a compound of Formula (IX), wherein $R^4$ is

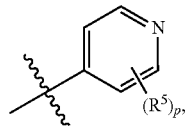

p is 1, and $R^5$ is $C_{1-6}$alkoxy. In another embodiment is a compound of Formula (IX), wherein $R^4$ is

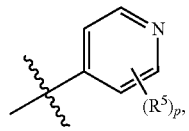

p is 1, and $R^5$ is $C_{1-6}$ haloalkoxy. In another embodiment is a compound of Formula (IX), wherein $R^4$ is

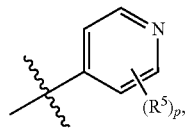

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein $R^4$ is

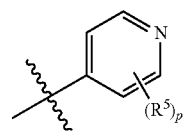

p is 1, and $R^5$ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (IX), wherein $R^4$ is

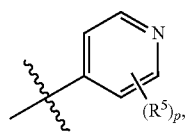

p is 1, and $R^5$ is phenyl substituted with one or two groups selected from halogen, $C_{1-6}$alkyl, and $C_{1-6}$ alkoxy. In another embodiment is a compound of Formula (IX), wherein $R^4$ is

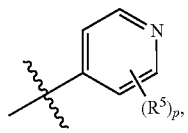

p is 1, and $R^5$ is $C_{2-9}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (IX), wherein $R^4$ is

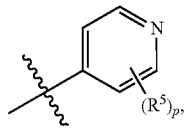

p is 1, and $R^5$ is $C_{2-9}$ heteroaryl substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (IX), wherein $R^4$ is

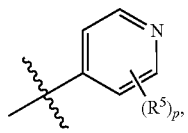

p is 1, and $R^5$ is $C_{2-9}$heteroaryl substituted with one or two groups selected from halogen, $C_{1-6}$ alkyl, and $C_{1-6}$alkoxy. In another embodiment is a compound of Formula (IX), wherein $R^4$ is

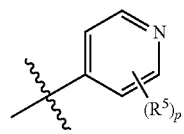

and p is 2. In another embodiment is a compound of Formula (IX), wherein $R^4$ is

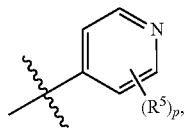

p is 2, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$ haloalkoxy.

In another embodiment is a compound of Formula (IX), wherein $R^4$ is

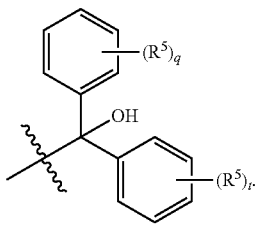

In another embodiment is a compound of Formula (IX), wherein $R^4$ is

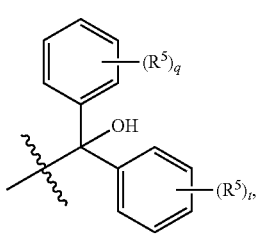

q is 0, and t is 0. In another embodiment is a compound of Formula (IX), wherein $R^4$ is

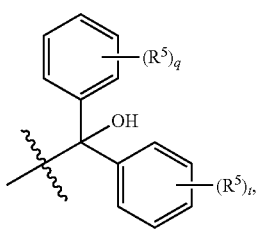

q is 1, and t is 0. In another embodiment is a compound of Formula (IX), wherein $R^4$ is

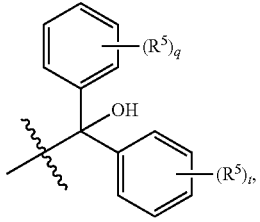

q is 1, t is 0, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein $R^4$ is

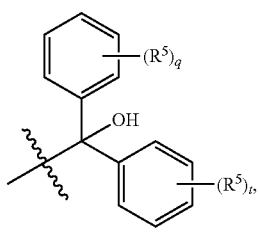

q is 1, t is 0, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (IX), wherein $R^4$ is

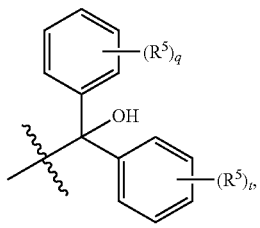

q is 1, and t is 1. In another embodiment is a compound of Formula (IX), wherein $R^4$ is

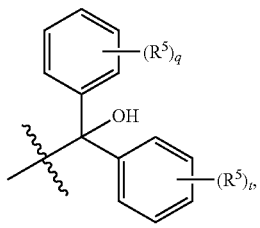

q is 1, t is 1, and each $R^5$ is independently halogen, $C_{1-6}$ alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (IX), wherein $R^4$ is

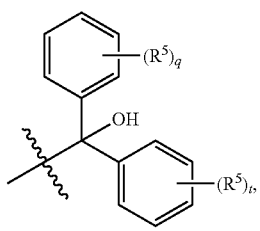

q is 1, t is 1, and each $R^5$ is independently halogen, $C_{1-6}$ alkyl, $C_{1-6}$haloalkyl, $C_{1-6}$alkoxy, or $C_{1-6}$haloalkoxy. In another embodiment is a compound of Formula (IX), wherein $R^4$ is

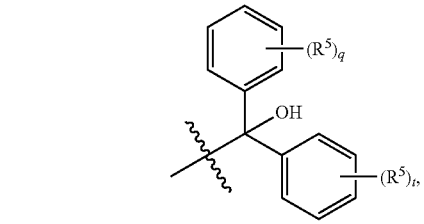

q is 1, t is 1, and each $R^5$ is halogen. In another embodiment is a compound of Formula (IX), wherein $R^4$ is

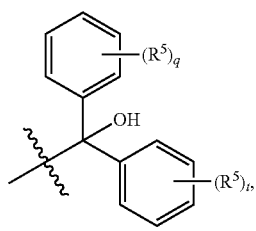

q is 1, t is 1, and each $R^5$ is $C_{1-6}$alkyl. In another embodiment is a compound of Formula (IX), wherein $R^4$ is

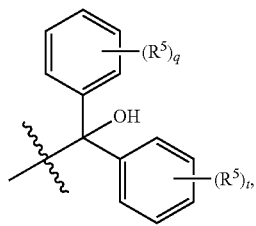

q is 1, t is 1, and each $R^5$ is $C_{1-6}$haloalkyl. In another embodiment is a compound of Formula (IX), wherein $R^4$ is

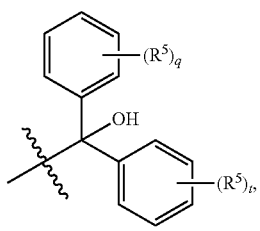

q is 1, t is 1, and each $R^5$ is $C_{1-6}$alkoxy. In another embodiment is a compound of Formula (IX), wherein $R^4$ is

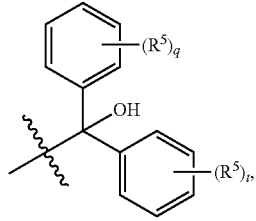

q is 1, t is 1, and each $R^5$ is $C_{1-6}$haloalkoxy.

In another embodiment is a compound of Formula (X):

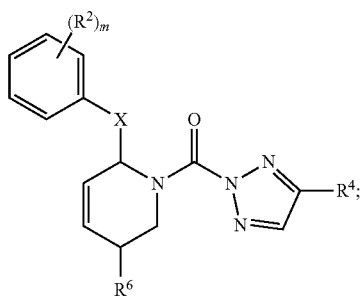

Formula (X)

wherein:
X is —CH$_2$—, —OCH$_2$—, —CH$_2$O—, or —CH$_2$OCH$_2$—;
each R$^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{3-6}$ alkyl)$_2$, —S(=O)$_2$NH$_2$, —S(=O)$_2$NH(C$_{1-6}$ alkyl), —S(=O)$_2$N(C$_{3-6}$ alkyl)$_2$, C$_{3-6}$alkyl, C$_{3-6}$cycloalkyl, C$_{1-6}$haloalkyl, C$_{3-6}$ alkoxy, —O—C$_{3-6}$ alkenyl, —O—C$_{3-6}$alkynyl, C$_{3-6}$haloalkoxy, C$_{2-9}$heterocycloalkyl, C$_{6-10}$ aryl, or C$_{2-9}$ heteroaryl;
R$^4$ is

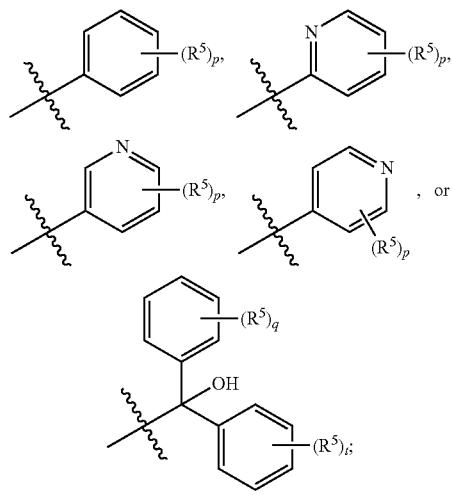

each R$^5$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{3-6}$ alkyl)$_2$, —S(=O)$_2$NH$_2$, —S(=O)$_2$NH(C$_{1-6}$ alkyl), —S(=O)$_2$N(C$_{3-6}$ alkyl)$_2$, C$_{3-6}$alkyl, C$_{1-6}$haloalkyl, C$_{1-6}$alkoxy, —O—C$_{1-6}$alkenyl, —O—C$_{1-6}$ alkynyl, C$_{1-6}$haloalkoxy, optionally substituted phenyl, or optionally substituted C$_{2-9}$heteroaryl, wherein optionally substituted phenyl and optionally substituted C$_{2-9}$ heteroaryl are optionally substituted with one, two, or three groups selected from halogen, C$_{1-6}$ C$_{1-6}$haloalkyl, C$_{1-6}$ alkoxy, and C$_{3-6}$haloalkoxy;
R$^6$ is hydrogen, C$_{1-6}$ alkyl, —OH, C$_{1-6}$ alkoxy, —O—C$_{1-6}$ alkenyl, —O—C$_{1-6}$ alkynyl, or —O—CH$_2$C$_{3-6}$cycloalkyl;
m is 0, 1, 2, or 3;
p is 0, 1, 2, or 3;
q is 0, 1, 2, or 3; and
t is 0, 1, 2, or 3;
or a solvate, hydrate, tautomer, N-oxide, or pharmaceutically acceptable salt thereof.

In another embodiment is a compound of Formula (X), wherein X is —CH$_2$—. In another embodiment is a compound of Formula (X), wherein X is —OCH$_2$—. In another embodiment is a compound of Formula (X), wherein X is —CH$_2$O—. In another embodiment is a compound of Formula (X), wherein X is —CH$_2$OCH$_2$—.

In another embodiment is a compound of Formula (X), wherein m is 0. In another embodiment is a compound of Formula (X), wherein m is 1. In another embodiment is a compound of Formula (X), wherein m is 1 and R$^2$ is halogen, C$_{3-6}$alkyl, C$_{3-6}$haloalkyl, C$_{1-6}$ alkoxy, —O—C$_{3-6}$alkenyl, —O—C$_{3-6}$alkynyl, or C$_{3-6}$ haloalkoxy. In another embodiment is a compound of Formula (X), wherein m is 1 and R$^2$ is halogen, C$_{3-6}$alkyl, C$_{3-6}$haloalkyl, C$_{1-6}$alkoxy, or C$_{1-6}$haloalkoxy. In another embodiment is a compound of Formula (X), wherein m is 1 and R$^2$ is halogen. In another embodiment is a compound of Formula (X), wherein m is 1 and R$^2$ is C$_{1-6}$alkyl. In another embodiment is a compound of Formula (X), wherein m is 1 and R$^2$ is C$_{1-6}$haloalkyl. In another embodiment is a compound of Formula (X), wherein m is 1 and R$^2$ is C$_{1-6}$alkoxy. In another embodiment is a compound of Formula (X), wherein m is 1 and R$^2$ is C$_{1-6}$haloalkoxy. In another embodiment is a compound of Formula (X), wherein m is 2. In another embodiment is a compound of Formula (X), wherein m is 2 and each R$^2$ is independently halogen, C$_{1-6}$ alkyl, C$_{1-6}$haloalkyl, C$_{1-6}$ alkoxy, —O—C$_{1-6}$alkenyl, —O—C$_{1-6}$alkynyl, or C$_{1-6}$haloalkoxy. In another embodiment is a compound of Formula (X), wherein m is 2 and each R$^2$ is independently halogen, C$_{1-6}$alkyl, C$_{1-6}$haloalkyl, C$_{1-6}$alkoxy, or C$_{1-6}$haloalkoxy.

In another embodiment is a compound of Formula (X), wherein R$^6$ is hydrogen. In another embodiment is a compound of Formula (X), wherein R$^6$ is —OH. In another embodiment is a compound of Formula (X), wherein R$^6$ is —O—C$_{1-6}$alkynyl. In another embodiment is a compound of Formula (X), wherein R$^6$ is —O—C$_{1-5}$alkynyl. In another embodiment is a compound of Formula (X), wherein R$^6$ is —O—C$_{1-4}$ alkynyl. In another embodiment is a compound of Formula (X), wherein R$^6$ is —OCH$_2$CH$_2$C≡CH. In another embodiment is a compound of Formula (X), wherein R$^6$ is —OCH$_2$C≡CH. In another embodiment is a compound of Formula (X), wherein R$^6$ is C$_{1-6}$ alkyl. In another embodiment is a compound of Formula (X), wherein R$^6$ is C$_{1-6}$alkoxy. In another embodiment is a compound of Formula (X), wherein R$^6$ is —O—C$_{1-6}$alkenyl. In another embodiment is a compound of Formula (X), wherein R$^6$ is —O—CH$_2$C$_{3-6}$cycloalkyl. In another embodiment is a compound of Formula (X), wherein R$^6$ is —O—CH$_2$cyclopropyl.

In another embodiment is a compound of Formula (X), wherein R$^4$ is

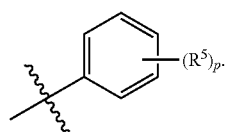

In another embodiment is a compound of Formula (X), wherein R$^4$ is

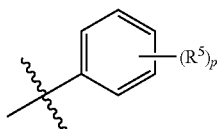

and p is 0. In another embodiment is a compound of Formula (X), wherein $R^4$ is

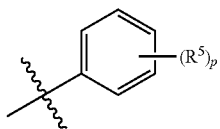

and p is 1. In another embodiment is a compound of Formula (X), wherein $R^4$ is

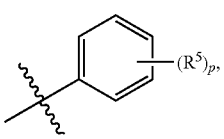

p is 1, and $R^5$ is halogen, $C_{1-6}$alkyl, $C_{1-6}$ haloalkyl, $C_{1-6}$alkoxy, —O—$C_{1-6}$ alkenyl, —O—$C_{1-6}$alkynyl, or $C_{1-6}$haloalkoxy. In another embodiment is a compound of Formula (X), wherein $R^4$ is

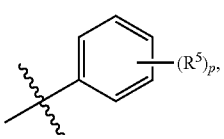

p is 1, and $R^5$ is halogen, $C_{1-6}$ alkyl, $C_{1-6}$haloalkyl, $C_{1-6}$alkoxy, or $C_{1-6}$ haloalkoxy. In another embodiment is a compound of Formula (X), wherein $R^4$ is

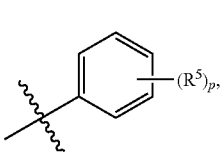

p is 1, and $R^5$ is halogen. In another embodiment is a compound of Formula (X), wherein $R^4$ is

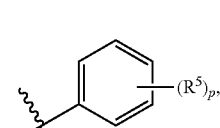

p is 1, and $R^5$ is $C_{1-6}$alkyl. In another embodiment is a compound of Formula (X), wherein $R^4$ is

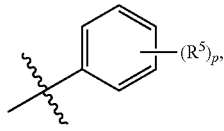

p is 1, and $R^5$ is $C_{1-6}$haloalkyl. In another embodiment is a compound of Formula (X), wherein $R^4$ is

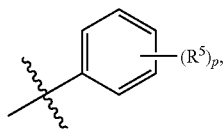

p is 1, and $R^5$ is $C_{1-6}$alkoxy. In another embodiment is a compound of Formula (X), wherein $R^4$ is

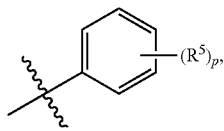

p is 1, and $R^5$ is $C_{1-6}$haloalkoxy. In another embodiment is a compound of Formula (X), wherein $R^4$ is

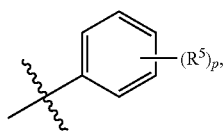

p is 1, and $R^5$ is phenyl optionally substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (X), wherein $R^4$ is

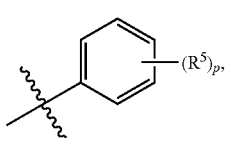

p is 1, and $R^5$ is phenyl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein $R^4$ is p is 1, and $R^5$ is phenyl substituted with one or two groups selected from halogen, $C_{1-6}$alkyl, and $C_{1-6}$alkoxy. In another embodiment is a compound of Formula (X), wherein $R^4$ is

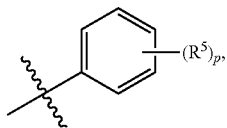

p is 1, and $R^5$ is $C_m$heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein $R^4$ is

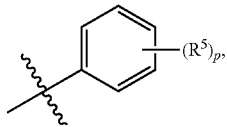

p is 1, and $R^5$ is $C_{2-9}$ heteroaryl substituted with one, two, or three groups selected from halogen, $C_{1-6}$ alkyl, $C_{1-6}$haloalkyl, $C_{1-6}$ alkoxy, and $C_{1-6}$haloalkoxy. In another embodiment is a compound of Formula (X), wherein $R^4$ is

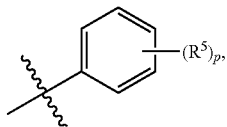

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (X), wherein $R^4$ is

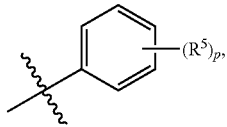

and p is 2. In another embodiment is a compound of Formula (X), wherein $R^4$ is

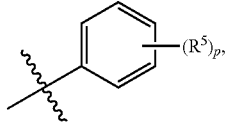

p is 2, and each $R^5$ is independently halogen, $C_{1-6}$alkyl, $C_{1-6}$haloalkyl, $C_{1-6}$alkoxy, —O—$C_{1-6}$alkenyl, —O—$C_{1-6}$ alkynyl, or $C_{1-6}$haloalkoxy. In another embodiment is a compound of Formula (X), wherein $R^4$ is

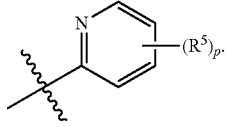

In another embodiment is a compound of Formula (X), wherein $R^4$ is

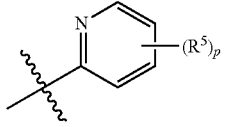

and p is 0. In another embodiment is a compound of Formula (X), wherein $R^4$ is

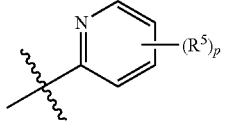

and p is 1. In another embodiment is a compound of Formula (X), wherein $R^4$ is

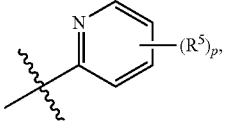

p is 1, and $R^5$ is halogen, $C_{1-6}$alkyl, $C_{1-6}$haloalkyl, $C_{1-6}$alkoxy, —O—$C_{1-6}$ alkenyl, —O—$C_{1-6}$alkynyl, or $C_{1-6}$haloalkoxy. In another embodiment is a compound of Formula (X), wherein $R^4$ is

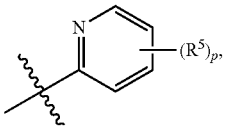

p is 1, and $R^5$ is halogen, $C_{1-6}$alkyl, $C_{1-6}$ haloalkyl, $C_{1-6}$alkoxy, or $C_{1-6}$haloalkoxy. In another embodiment is a compound of Formula (X), wherein $R^4$ is

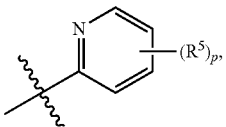

p is 1, and $R^5$ is halogen. In another embodiment is a compound of Formula (X), wherein $R^4$ is

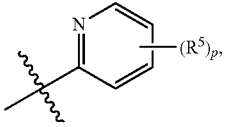

p is 1, and $R^5$ is $C_{1-6}$alkyl. In another embodiment is a compound of Formula (X), wherein $R^4$ is

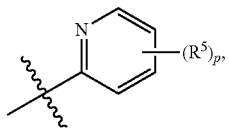

p is 1, and R⁵ is $C_{1-6}$haloalkyl. In another embodiment is a compound of Formula (X), wherein R⁴ is

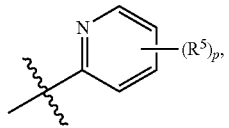

p is 1, and R⁵ is $C_{1-6}$alkoxy. In another embodiment is a compound of Formula (X), wherein R⁴ is

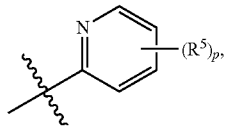

p is 1, and R⁵ is $C_{1-6}$haloalkoxy. In another embodiment is a compound of Formula (X), wherein R⁴ is

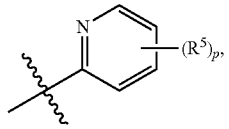

p is 1, and R⁵ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein R⁴ is

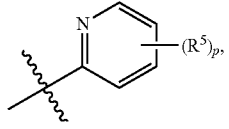

p is 1, and R⁵ is phenyl substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (X), wherein R⁴ is

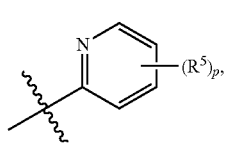

p is 1, and R⁵ is phenyl substituted with one or two groups selected from halogen, $C_{1-6}$alkyl, and $C_{1-6}$alkoxy. In another embodiment is a compound of Formula (X), wherein R⁴ is

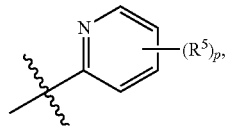

p is 1, and R⁵ is $C_{2-9}$ heteroaryl optionally substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (X), wherein R⁴ is

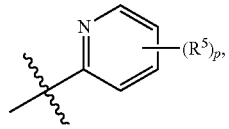

p is 1, and R⁵ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein R⁴ is

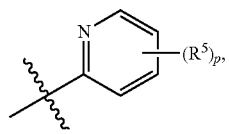

p is 1, and R⁵ is $C_{2-9}$heteroaryl substituted with one or two groups selected from halogen, $C_{1-6}$alkyl, and $C_{1-6}$ alkoxy. In another embodiment is a compound of Formula (X), wherein R⁴ is

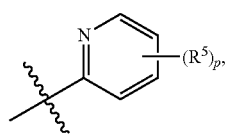

and p is 2. In another embodiment is a compound of Formula (X), wherein R⁴ is

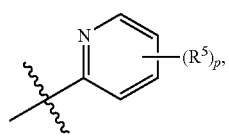

p is 2, and each R⁵ is independently halogen, $C_{1-6}$alkyl, $C_{1-6}$haloalkyl, $C_{1-6}$ alkoxy, —O—$C_{1-6}$ alkenyl, —O—$C_{1-6}$ alkynyl, or $C_{1-6}$ haloalkoxy. In another embodiment is a compound of Formula (X), wherein R⁴ is

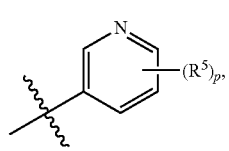

In another embodiment is a compound of Formula (X), wherein $R^4$ is

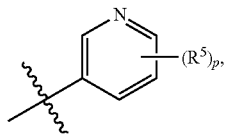

and p is 0. In another embodiment is a compound of Formula (X), wherein $R^4$ is

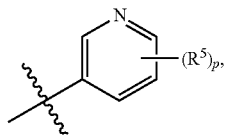

and p is 1. In another embodiment is a compound of Formula (X), wherein $R^4$ is

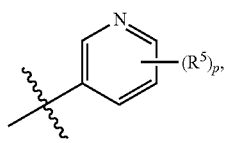

p is 1, and $R^5$ is halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (X), wherein $R^4$ is

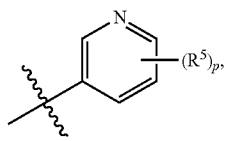

p is 1, and $R^5$ is halogen, $C_{1-6}$alkyl, $C_{1-6}$ haloalkyl, $C_{1-6}$alkoxy, or $C_{1-6}$haloalkoxy. In another embodiment is a compound of Formula (X), wherein $R^4$ is

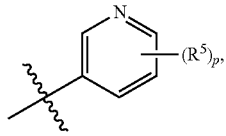

p is 1, and $R^5$ is halogen. In another embodiment is a compound of Formula (X), wherein $R^4$ is

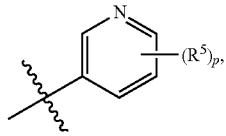

p is 1, and $R^5$ is $C_{1-6}$alkyl. In another embodiment is a compound of Formula (X), wherein $R^4$ is

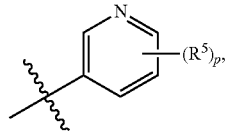

p is 1, and $R^5$ is $C_{1-6}$haloalkyl. In another embodiment is a compound of Formula (X), wherein $R^4$ is

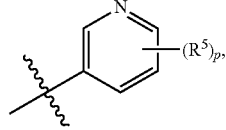

p is 1, and $R^5$ is $C_{1-6}$alkoxy. In another embodiment is a compound of Formula (X), wherein $R^4$ is

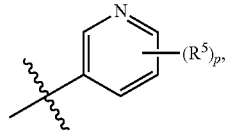

p is 1, and $R^5$ is $C_{1-6}$haloalkoxy. In another embodiment is a compound of Formula (X), wherein $R^4$ is

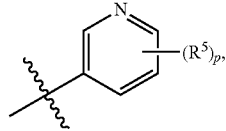

p is 1, and $R^5$ is phenyl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein $R^4$ is

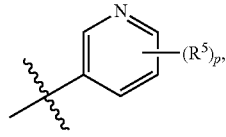

p is 1, and $R^5$ is phenyl substituted with one, two, or three groups selected from halogen, $C_{1-6}$alkyl, $C_{1-6}$ haloalkyl, $C_{1-6}$alkoxy, and $C_{1-6}$ haloalkoxy. In another embodiment is a compound of Formula (X), wherein $R^4$ is

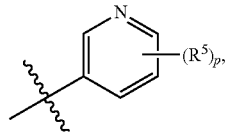

p is 1, and $R^5$ is phenyl substituted with one or two groups selected from halogen, $C_{1-6}$ alkyl, and $C_{1-6}$alkoxy. In another embodiment is a compound of Formula (X), wherein $R^4$ is

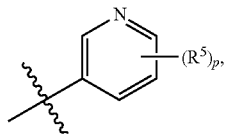

p is 1, and $R^5$ is $C_{2-6}$ heteroaryl optionally substituted with one, two, or three groups selected from halogen, $C_{1-6}$alkyl, $C_{1-6}$haloalkyl, $C_{1-6}$alkoxy, and $C_{1-6}$ haloalkoxy. In another embodiment is a compound of Formula (X), wherein $R^4$ is

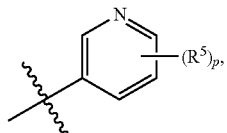

p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein $R^4$ is

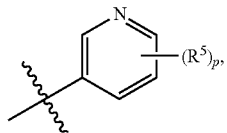

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (X), wherein $R^4$ is

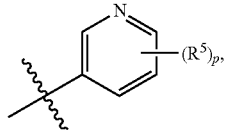

and p is 2. In another embodiment is a compound of Formula (X), wherein $R^4$ is

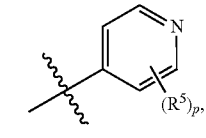

p is 2, and each $R^5$ is independently halogen, $C_{1-6}$alkyl, $C_{1-6}$haloalkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (X), wherein $R^4$ is

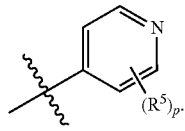

In another embodiment is a compound of Formula (X), wherein $R^4$ is

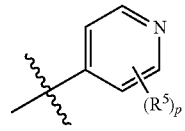

and p is 0. In another embodiment is a compound of Formula (X), wherein $R^4$ is

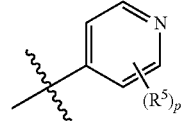

and p is 1. In another embodiment is a compound of Formula (X), wherein $R^4$ is

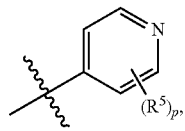

p is 1, and $R^5$ is halogen, $C_{1-6}$alkyl, $C_{1-6}$haloalkyl, $C_{1-6}$alkoxy, —O—$C_{1-6}$alkenyl, —O—$C_{1-6}$alkynyl, or $C_{1-6}$haloalkoxy. In another embodiment is a compound of Formula (X), wherein $R^4$ is

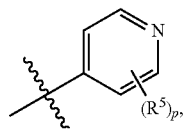

p is 1, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (X), wherein $R^4$ is

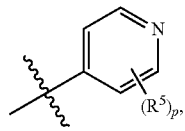

p is 1, and $R^5$ is halogen. In another embodiment is a compound of Formula (X), wherein $R^4$ is

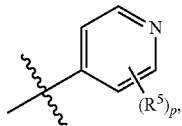

p is 1, and $R^5$ is $C_{1-6}$alkyl. In another embodiment is a compound of Formula (X), wherein $R^4$ is

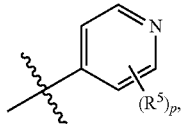

p is 1, and $R^5$ is $C_{1-6}$haloalkyl. In another embodiment is a compound of Formula (X), wherein $R^4$ is

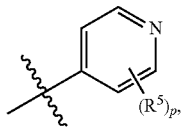

p is 1, and $R^5$ is $C_{1-6}$alkoxy. In another embodiment is a compound of Formula (X), wherein $R^4$ is

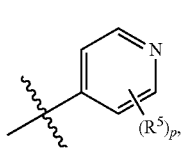

is 1, and $R^5$ is $C_{1-6}$haloalkoxy. In another embodiment is a compound of Formula (X), wherein $R^4$ is

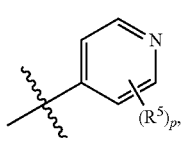

p is 1, and $R^5$ is phenyl optionally substituted with one, two, or three groups selected from halogen, $C_{1-6}$ alkyl, $C_{1-6}$ haloalkyl, $C_{1-6}$ alkoxy, and $C_{1-6}$haloalkoxy. In another embodiment is a compound of Formula (X), wherein $R^4$ is

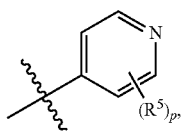

p is 1, and $R^5$ is phenyl substituted with one, two, or three groups selected from halogen, $C_{1-6}$alkyl, $C_{1-6}$haloalkyl, $C_{1-6}$ alkoxy, and $C_{1-6}$haloalkoxy. In another embodiment is a compound of Formula (X), wherein $R^4$ is

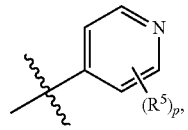

p is 1, and $R^5$ is phenyl substituted with one or two groups selected from halogen, $C_{1-6}$alkyl, and $C_{1-6}$alkoxy. In another embodiment is a compound of Formula (X), wherein $R^4$ is p is 1, and $R^5$ is $C_{2-9}$heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein $R^4$ is p is 1, and $R^5$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (X), wherein $R^4$ is

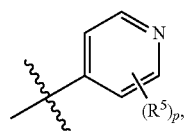

p is 1, and $R^5$ is $C_{2-9}$ heteroaryl substituted with one or two groups selected from halogen, $C_{1-6}$alkyl, and $C_{1-6}$alkoxy. In another embodiment is a compound of Formula (X), wherein $R^4$ is and p is 2. In another embodiment is a compound of Formula (X), wherein $R^4$ is

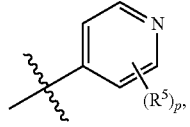

p is 2, and each $R^5$ is independently halogen, $C_{1-6}$alkyl, $C_{1-6}$alkoxy, —O—$C_{1-6}$ alkenyl, —O—$C_{1-6}$alkynyl, or $C_{1-6}$haloalkoxy. In another embodiment is a compound of Formula (X), wherein $R^4$ is

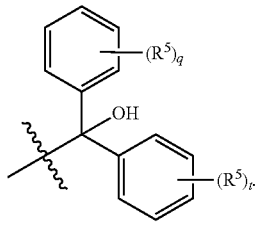

In another embodiment is a compound of Formula (X), wherein $R^4$ is

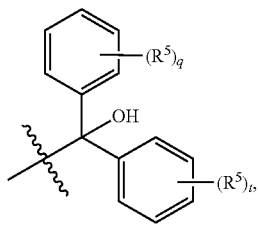

q is 0, and t is 0. In another embodiment is a compound of Formula (X), wherein $R^4$ is

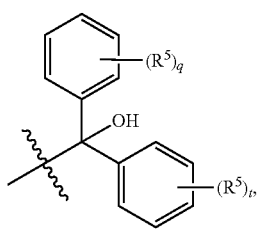

q is 1, and t is 0. In another embodiment is a compound of Formula (X), wherein $R^4$ is

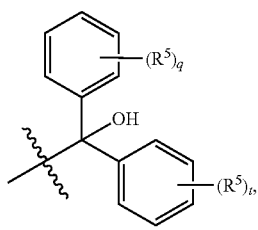

q is 1, t is 0, and $R^5$ is halogen, $C_{1-6}$alkyl, $C_{1-6}$alkoxy, —O—$C_{1-6}$ alkenyl, —O—$C_{1-6}$ alkynyl, or $C_{1-6}$haloalkoxy. In another embodiment is a compound of Formula (X), wherein $R^4$ is

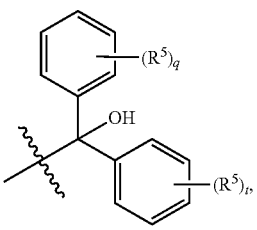

q is 1, t is 0, and $R^5$ is halogen, $C_{1-6}$alkyl, $C_{1-6}$haloalkyl, $C_{1-6}$alkoxy, or $C_{1-6}$haloalkoxy. In another embodiment is a compound of Formula (X), wherein $R^4$ is

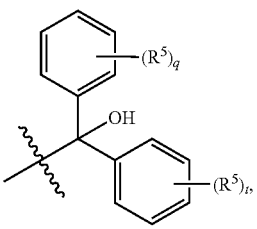

q is 1, and t is 1. In another embodiment is a compound of Formula (X), wherein $R^4$ is

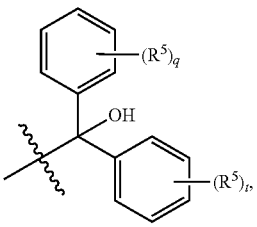

q is 1, t is 1, and each $R^5$ is independently halogen, $C_{1-6}$alkyl, $C_{1-6}$haloalkyl, $C_{1-6}$ alkoxy, —O—$C_{1-6}$ alkenyl, —O—$C_{1-6}$ alkynyl, or $C_{1-6}$haloalkoxy. In another embodiment is a compound of Formula (X), wherein $R^4$ is

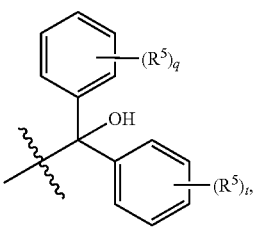

q is 1, t is 1, and each $R^5$ is independently halogen, $C_{1-6}$alkyl, $C_{1-6}$ haloalkyl, $C_{1-6}$alkoxy, or $C_{1-6}$haloalkoxy. In another embodiment is a compound of Formula (X), wherein $R^4$ is

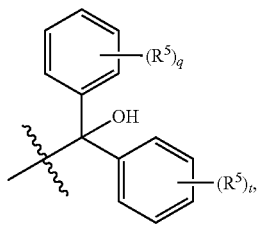

q is 1, t is 1, and each $R^5$ is halogen. In another embodiment is a compound of Formula (X), wherein $R^4$ is

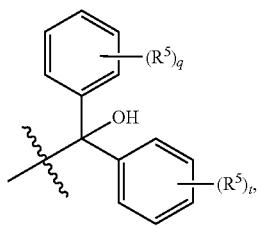

q is 1, t is 1, and each $R^5$ is $C_{1-6}$alkyl. In another embodiment is a compound of Formula (X), wherein $R^4$ is

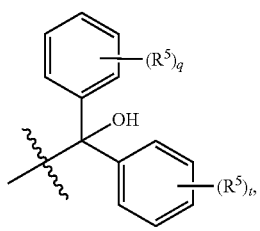

q is 1, t is 1, and each $R^5$ is $C_{1-6}$haloalkyl. In another embodiment is a compound of Formula (X), wherein $R^4$ is

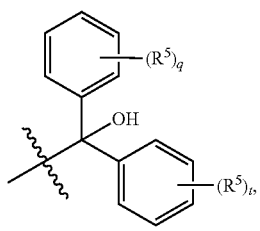

q is 1, t is 1, and each $R^5$ is $C_{1-6}$alkoxy. In another embodiment is a compound of Formula (X), wherein $R^4$ is

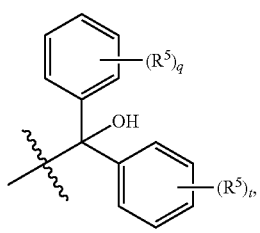

q is 1, t is 1, and each $R^5$ is $C_{1-6}$haloalkoxy.

In another embodiment is a compound of Formula (XI):

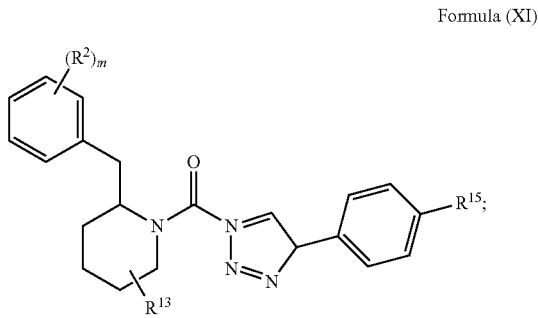

Formula (XI)

wherein:
each $R^2$ is independently halogen, —CN, —NH$_2$, —NH(CH$_3$), —N(CH$_3$)$_2$, —OH, —C(═O)OH, —C(═O)O(C$_{1-6}$ alkyl), —C(═O)NH$_2$, —C(═O)NH(C$_{1-6}$alkyl), —C(═O)N(C$_{1-6}$ alkyl)$_2$, —S(═O)$_2$NH$_2$, —S(═O)$_2$NH(C$_{1-6}$alkyl), —S(═O)$_2$N(C$_{1-6}$ alkyl)$_2$, $C_{1-6}$alkyl, $C_{3-6}$cycloalkyl, $C_{1-6}$haloalkyl, $C_{1-6}$alkoxy, —O—C$_{1-6}$alkenyl, —O—C$_{1-6}$alkynyl, $C_{1-6}$haloalkoxy, $C_{2-9}$heterocycloalkyl, $C_{6-10}$ aryl, or $C_{2-9}$ heteroaryl;
$R^{13}$ is hydrogen, $C_{1-6}$alkyl, $C_{1-6}$alkoxy, —O—C$_{1-6}$alkenyl, —O—C$_{1-6}$alkynyl, or —O—CH$_2$C$_{3-6}$cycloalkyl;
$R^{15}$ is $C_{2-9}$ heteroaryl optionally substituted with one, two, or three groups selected from halogen, $C_{1-6}$alkyl, $C_{1-6}$haloalkyl, $C_{1-6}$alkoxy, and $C_{1-6}$haloalkoxy; and
m is 0, 1, 2, or 3;
or a solvate, hydrate, tautomer, N-oxide, or pharmaceutically acceptable salt thereof.

In another embodiment is a compound of Formula (XI), wherein m is 0. In another embodiment is a compound of Formula (XI), wherein m is 1. In another embodiment is a compound of Formula (XI), wherein m is 1 and $R^2$ is halogen, $C_{1-6}$alkyl, $C_{1-6}$haloalkyl, $C_{1-6}$alkoxy, —O—C$_{1-6}$alkenyl, —O—C$_{1-6}$alkynyl, or $C_{1-6}$haloalkoxy. In another embodiment is a compound of Formula (XI), wherein m is 1 and $R^2$ is halogen, $C_{1-6}$alkyl, $C_{1-6}$haloalkyl, $C_{1-6}$alkoxy, or $C_{1-6}$haloalkoxy. In another embodiment is a compound of Formula (XI), wherein m is 1 and $R^2$ is halogen. In another embodiment is a compound of Formula (XI), wherein m is 1 and $R^2$ is $C_{1-6}$alkyl. In another embodiment is a compound of Formula (XI), wherein m is 1 and $R^2$ is $C_{1-6}$haloalkyl. In another embodiment is a compound of Formula (XI), wherein m is 1 and $R^2$ is $C_{1-6}$alkoxy. In another embodiment is a compound of Formula (XI), wherein m is 1 and $R^2$ is $C_{1-6}$haloalkoxy. In another embodiment is a compound of Formula (XI), wherein m is 2. In another embodiment is a compound of Formula (XI), wherein m is 2 and each $R^2$ is independently halogen, $C_{1-6}$alkyl, $C_{1-6}$haloalkyl, $C_{1-6}$alkoxy, —O—C$_{1-6}$alkenyl, —O—C$_{1-6}$alkynyl, or $C_{1-6}$haloalkoxy. In another embodiment is a compound of Formula (XI), wherein m is 2 and each $R^2$ is independently halogen, $C_{1-6}$alkyl, $C_{1-6}$haloalkyl, $C_{1-6}$alkoxy, or $C_{1-6}$haloalkoxy.

In another embodiment is a compound of Formula (XI), wherein $R^{13}$ is hydrogen. In another embodiment is a compound of Formula (XI), wherein 11'$^{3}$ is —O—C$_{1-6}$alkynyl. In another embodiment is a compound of Formula (XI), wherein $R^{13}$ is —O—C$_{1-5}$alkynyl. In another embodiment is a compound of Formula (XI), wherein $R^{13}$ is —O—C$_{1-4}$alkynyl. In another embodiment is a compound of Formula (XI), wherein $R^{13}$ is —OCH$_2$CH$_2$C≡CH. In another embodiment is a compound of Formula (XI), wherein $R^{13}$ is —OCH$_2$C≡CH. In another embodiment is a compound of Formula (XI), wherein $R^{13}$ is C$_{1-6}$alkyl. In another embodiment is a compound of Formula (XI), wherein $R^{13}$ is C$_{1-6}$alkoxy. In another embodiment is a compound of Formula (XI), wherein $R^{13}$ is —O—C$_{1-6}$alkenyl. In another embodiment is a compound of Formula (XI), wherein $R^{13}$ is —O—CH$_2$C$_{3-6}$cycloalkyl. In another embodiment is a compound of Formula (XI), wherein $R^{13}$ is —O—CH$_2$cyclopropyl.

In another embodiment is a compound of Formula (XI), wherein $R^{15}$ is an unsubstituted C$_{2-9}$ heteroaryl. In another embodiment is a compound of Formula (XI), wherein $R^{15}$ is an unsubstituted pyridine. In another embodiment is a compound of Formula (XI), wherein $R^{15}$ is an unsubstituted pyrimidine. In another embodiment is a compound of Formula (XI), wherein $R^{1'}$ is an unsubstituted pyridazine. In another embodiment is a compound of Formula (XI), wherein $R^{15}$ is an unsubstituted pyrazine. In another embodiment is a compound of Formula (XI), wherein $R^{15}$ is C$_{2-9}$ heteroaryl substituted with one, two, or three groups selected from halogen, C$_{1-6}$alkyl, C$_{1-6}$haloalkyl, C$_{1-6}$alkoxy, and C$_{1-6}$haloalkoxy. In another embodiment is a compound of Formula (XI), wherein $R^{15}$ is C$_{2-9}$ heteroaryl substituted with one or two groups selected from halogen, C$_{1-6}$alkyl, C$_{1-6}$haloalkyl, C$_{1-6}$alkoxy, and C$_{1-6}$haloalkoxy. In another embodiment is a compound of Formula (XI), wherein $R^{1'}$ is C$_{2-9}$ heteroaryl substituted with one or two groups selected from halogen, C$_{1-6}$alkyl, and C$_{1-6}$alkoxy. In another embodiment is a compound of Formula (XI), wherein $R^{15}$ is C$_{2-9}$ heteroaryl substituted with one or two halogens. In another embodiment is a compound of Formula (XI), wherein $R^{1'}$ is C$_{2-9}$heteroaryl substituted with one or two groups C$_{1-6}$alkoxy groups. In another embodiment is a compound of Formula (XI), wherein $R^{15}$ is pyridine substituted with one, two, or three groups selected from halogen, C$_{1-6}$alkyl, C$_{1-6}$haloalkyl, C$_{1-6}$alkoxy, and C$_{1-6}$haloalkoxy. In another embodiment is a compound of Formula (XI), wherein $R^{15}$ is pyridine substituted with one or two groups selected from halogen, C$_{1-6}$alkyl, C$_{1-6}$haloalkyl, C$_{1-6}$alkoxy, and C$_{1-6}$haloalkoxy. In another embodiment is a compound of Formula (XI), wherein $R^{15}$ is pyridine substituted with one or two groups selected from halogen, C$_{1-6}$alkyl, and C$_{1-6}$alkoxy. In another embodiment is a compound of Formula (XI), wherein $R^{15}$ is pyridine substituted with one or two halogens. In another embodiment is a compound of Formula (XI), wherein $R^{15}$ is pyridine substituted with one or two groups C$_{1-6}$ alkoxy groups. In another embodiment is a compound of Formula (XI), wherein $R^{15}$ is pyrimidine substituted with one, two, or three groups selected from halogen, C$_{1-6}$alkyl, C$_{1-6}$ haloalkyl, C$_{3-6}$ alkoxy, and C$_{1-6}$ haloalkoxy. In another embodiment is a compound of Formula (XI), wherein $R^{15}$ is pyrimidine substituted with one or two groups selected from halogen, C$_{1-6}$ alkyl, C$_{1-6}$ haloalkyl, C$_{1-6}$alkoxy, and C$_{1-6}$ haloalkoxy. In another embodiment is a compound of Formula (XI), wherein $R^{15}$ is pyrimidine substituted with one or two groups selected from halogen, C$_{1-6}$ alkyl, and C$_{1-6}$alkoxy. In another embodiment is a compound of Formula (XI), wherein $R^{15}$ is pyrimidine substituted with one or two halogens. In another embodiment is a compound of Formula (XI), wherein $R^{15}$ is pyrimidine substituted with one or two groups C$_{1-6}$alkoxy groups. In another embodiment is a compound of Formula (XI), wherein $R^{15}$ is pyridazine substituted with one, two, or three groups selected from halogen, C$_{1-6}$ alkyl, C$_{1-6}$haloalkyl, C$_{1-6}$ alkoxy, and C$_{1-6}$ haloalkoxy. In another embodiment is a compound of Formula (XI), wherein $R^{15}$ is pyridazine substituted with one or two groups selected from halogen, C$_{1-6}$alkyl, C$_{1-6}$ haloalkyl, C$_{3-6}$alkoxy pyridazine substituted with one or two groups selected from halogen, C$_{1-6}$ alkyl, and C$_{1-6}$alkoxy. In another embodiment is a compound of Formula (XI), wherein $R^{15}$ is pyridazine substituted with one or two halogens. In another embodiment is a compound of Formula (XI), wherein $R^{1'}$ is pyridazine substituted with one or two groups C$_{1-6}$alkoxy groups.

In another embodiment is a compound of Formula (XII):

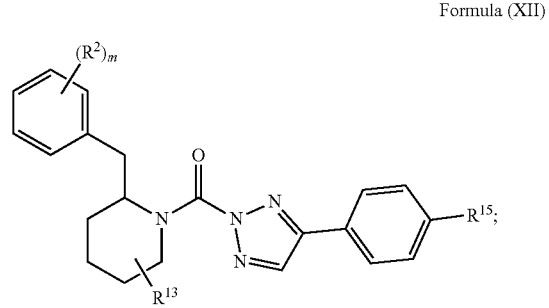

Formula (XII)

wherein:
each $R^2$ is independently halogen, —CN, —NH$_2$, —NH(CH$_3$), —N(CH$_3$)$_2$, —OH, —C(=O)OH, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —S(=O)$_2$NH$_2$, —S(=O)$_2$NH(C$_{1-6}$ alkyl), —S(=O)$_2$N(C$_{1-6}$ alkyl)$_2$, C$_{1-6}$ alkyl, C$_{3-6}$ cycloalkyl, C$_{1-6}$haloalkyl, C$_{1-6}$alkoxy, —O—C$_{1-6}$ alkenyl, —O—C$_{1-6}$alkynyl, C$_{1-6}$ haloalkoxy, C$_{2-9}$heterocycloalkyl, C$_{6-10}$aryl, or C$_{2-9}$ heteroaryl;
$R^{13}$ is hydrogen, C$_{1-6}$alkyl, C$_{1-6}$alkoxy, —O—C$_{3-6}$ alkenyl, —O—C$_{1-6}$ alkynyl, or —O—CH$_2$C$_{3-6}$cycloalkyl;
$R^{15}$ is C$_{2-9}$ heteroaryl optionally substituted with one, two, or three groups selected from halogen, C$_{1-6}$alkyl, C$_{1-6}$ haloalkyl C$_{1-6}$ alkoxy, and C$_{1-6}$haloalkoxy; and
m is 0, 1, 2, or 3;
or a solvate, hydrate, tautomer, N-oxide, or pharmaceutically acceptable salt thereof.

In another embodiment is a compound of Formula (XII), wherein m is 0. In another embodiment is a compound of Formula (XII), wherein m is 1. In another embodiment is a compound of Formula (XII), wherein m is 1 and $R^2$ is halogen, C$_{1-6}$alkyl, C$_{1-6}$haloalkyl, C$_{1-6}$alkoxy, —O—C$_{1-6}$ alkenyl, —O—C$_{1-6}$alkynyl, or C$_{1-6}$haloalkoxy. In another embodiment is a compound of Formula (XII), wherein m is 1 and $R^2$ is halogen, C$_{1-6}$alkyl, C$_{1-6}$haloalkyl, C$_{1-6}$alkoxy, or C$_{1-6}$haloalkoxy. In another embodiment is a compound of Formula (XII), wherein m is 1 and $R^2$ is halogen. In another embodiment is a compound of Formula (XII), wherein m is 1 and $R^2$ is C$_{1-6}$alkyl. In another embodiment is a compound of Formula (XII), wherein m is 1 and $R^2$ is C$_{1-6}$haloalkyl. In another embodiment is a compound of Formula (XII), wherein m is 1 and $R^2$ is C$_{1-6}$alkoxy. In another embodiment is a compound of Formula (XII), wherein m is 1 and $R^2$ is C$_{1-6}$haloalkoxy. In another embodiment is a compound of Formula (XII), wherein m is 2. In another embodiment is a compound of Formula (XII), wherein m is 2 and each $R^2$ is independently halogen, C$_{1-6}$alkyl, C$_{1-6}$haloalkyl, C$_{1-6}$alkoxy, —O—C$_{1-6}$alkenyl, —O—C$_{1-6}$alkynyl, or C$_{1-6}$haloalkoxy. In another embodiment is a compound of Formula (XII), wherein m is 2 and each $R^2$ is independently halogen, C$_{1-6}$alkyl, C$_{1-6}$haloalkyl, C$_{1-6}$alkoxy, or C$_{1-6}$haloalkoxy.

In another embodiment is a compound of Formula (XII), wherein $R^{13}$ is hydrogen. In another embodiment is a compound of Formula (XII), wherein $R^{13}$ is —O—$C_{1-6}$alkynyl. In another embodiment is a compound of Formula (XII), wherein $R^{13}$ is —O—$C_{1-5}$alkynyl. In another embodiment is a compound of Formula (XII), wherein $R^{13}$ is —O—$C_{1-4}$alkynyl. In another embodiment is a compound of Formula (XII), wherein $R^{13}$ is —OCH$_2$CH$_2$C≡CH. In another embodiment is a compound of Formula (XII), wherein $R^{13}$ is —OCH$_2$C≡CH. In another embodiment is a compound of Formula (XII), wherein $R^{13}$ is $C_{1-6}$alkyl. In another embodiment is a compound of Formula (XII), wherein $R^{13}$ is $C_{1-6}$alkoxy. In another embodiment is a compound of Formula (XII), wherein $R^{13}$ is —O—$C_{1-6}$alkenyl. In another embodiment is a compound of Formula (XII), wherein $R^{13}$ is —O—CH$_2$C$_{3-6}$cycloalkyl. In another embodiment is a compound of Formula (XII), wherein $R^{13}$ is —O—CH$_2$cyclopropyl.

In another embodiment is a compound of Formula (XII), wherein $R^{15}$ is an unsubstituted $C_{2-9}$ heteroaryl. In another embodiment is a compound of Formula (XII), wherein $R^{15}$ is an unsubstituted pyridine. In another embodiment is a compound of Formula (XII), wherein $R^{15}$ is an unsubstituted pyrimidine. In another embodiment is a compound of Formula (XII), wherein $R^{15}$ is an unsubstituted pyridazine. In another embodiment is a compound of Formula (XII), wherein $R^{15}$ is an unsubstituted pyrazine. In another embodiment is a compound of Formula (XII), wherein $R^{15}$ is $C_{2-9}$ heteroaryl substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (XII), wherein $R^5$ is $C_{2-9}$ heteroaryl substituted with one or two groups selected from halogen, $C_{1-6}$alkyl, $C_{1-6}$haloalkyl, $C_{1-6}$alkoxy, and $C_{1-6}$haloalkoxy. In another embodiment is a compound of Formula (XII), wherein $R^{15}$ is $C_{2-9}$ heteroaryl substituted with one or two groups selected from halogen, $C_{1-6}$alkyl, and $C_{1-6}$alkoxy. In another embodiment is a compound of Formula (XII), wherein $R^{15}$ is $C_{2-9}$ heteroaryl substituted with one or two halogens. In another embodiment is a compound of Formula (XII), wherein $R^{15}$ is $C_{2-9}$heteroaryl substituted with one or two groups $C_{1-6}$alkoxy groups. In another embodiment is a compound of Formula (XII), wherein $R^{15}$ is pyridine substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (XII), wherein $R^5$ is pyridine substituted with one or two groups selected from halogen, $C_{1-6}$alkyl, $C_{1-6}$haloalkyl, $C_{1-6}$alkoxy, and $C_{1-6}$haloalkoxy. In another embodiment is a compound of Formula (XII), wherein $R^{15}$ is pyridine substituted with one or two groups selected from halogen, $C_{1-6}$alkyl, and $C_{1-6}$alkoxy. In another embodiment is a compound of Formula (XII), wherein $R^{15}$ is pyridine substituted with one or two halogens. In another embodiment is a compound of Formula (XII), wherein $R^{1'}$ is pyridine substituted with one or two groups $C_{1-6}$alkoxy groups. In another embodiment is a compound of Formula (XII), wherein $R^{15}$ is pyrimidine substituted with one, two, or three groups selected from halogen, $C_{1-6}$ alkyl, $C_{1-6}$haloalkyl, $C_{1-6}$alkoxy, and $C_{1-6}$haloalkoxy. In another embodiment is a compound of Formula (XII), wherein $R^{15}$ is pyrimidine substituted with one or two groups selected from halogen, $C_{1-6}$alkyl, $C_{1-6}$haloalkyl, $C_{1-6}$alkoxy, and $C_{1-6}$haloalkoxy. In another embodiment is a compound of Formula (XII), wherein $R^{1'}$ is pyrimidine substituted with one or two groups selected from halogen, $C_{1-6}$alkyl, and $C_{1-6}$ alkoxy. In another embodiment is a compound of Formula (XII), wherein $R^{15}$ is pyrimidine substituted with one or two halogens. In another embodiment is a compound of Formula (XII), wherein $R^{1'}$ is pyrimidine substituted with one or two groups $C_{1-6}$alkoxy groups. In another embodiment is a compound of Formula (XII), wherein $R^{15}$ is pyridazine substituted with one, two, or three groups selected from halogen, $C_{1-6}$alkyl, $C_{1-6}$haloalkyl, $C_{1-6}$alkoxy, and $C_{1-6}$haloalkoxy. In another embodiment is a compound of Formula (XII), wherein $R^{15}$ is pyridazine substituted with one or two groups selected from halogen, $C_{1-6}$alkyl, $C_{1-6}$haloalkyl, $C_{1-6}$alkoxy pyridazine substituted with one or two groups selected from halogen, $C_{1-6}$alkyl, and $C_{1-6}$ alkoxy. In another embodiment is a compound of Formula (XII), wherein $R^{15}$ is pyridazine substituted with one or two halogens. In another embodiment is a compound of Formula (XII), wherein $R^{15}$ is pyridazine substituted with one or two groups $C_{1-6}$ alkoxy groups.

Further embodiments provided herein include combinations of one or more of the particular embodiments set forth above.

In some embodiments, the compound disclosed herein has the structure provided in Table 1.

TABLE 1

| Ex. | Structure | Name |
|---|---|---|
| 1 | 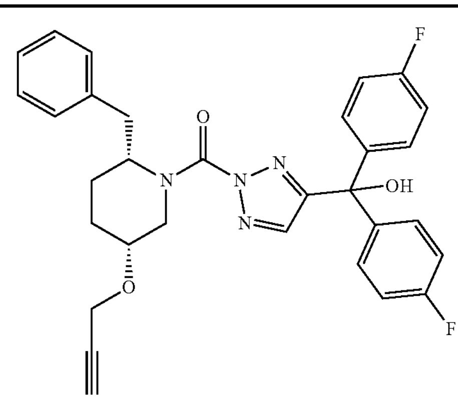 | ((2R,5R)-2-benzyl-5-(prop-2-ynyloxy)piperidin-1-yl)(4-(bis(4-fluorophenyl)(hydroxy)methyl)-2H-1,2,3-triazol-2-yl)methanone |

TABLE 1-continued
| Ex. | Structure | Name |
|---|---|---|
| 2 | 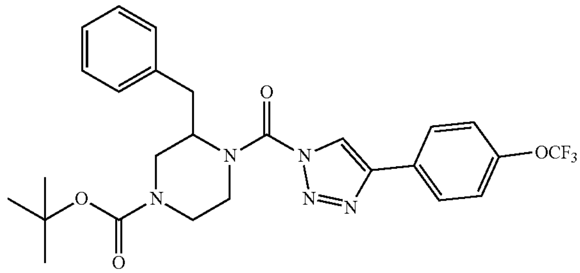 [SMILES: CC(C)(C)OC(=O)N1CCN(C(=O)n2cc(-c3ccc(OC(F)(F)F)cc3)nn2)C(Cc2ccccc2)C1] | tert-Butyl 3-benzyl-4-(4-(4-(trifluoromethoxy)phenyl)-1H-1,2,3-triazole-1-carbonyl)piperazine-1-carboxylate |
| 3 | 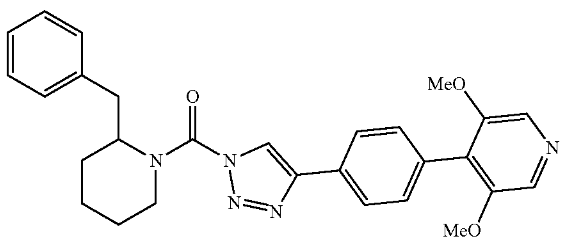 [SMILES: COc1cncc(OC)c1-c1ccc(-c2cn(C(=O)N3CCCCC3Cc3ccccc3)nn2)cc1] | (2-Benzylpiperidin-1-yl)(4-(4-(3,5-dimethoxypyridin-4-yl)phenyl)-1H-1,2,3-triazol-1-yl)methanone |
| 4 | 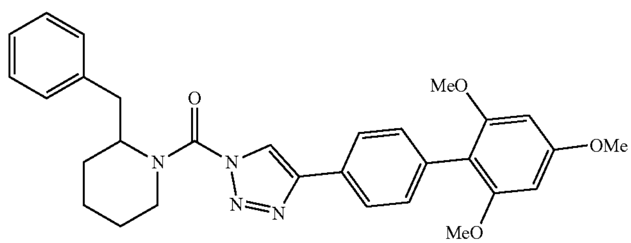 [SMILES: COc1cc(OC)c(-c2ccc(-c3cn(C(=O)N4CCCCC4Cc4ccccc4)nn3)cc2)c(OC)c1] | ((2-Benzylpiperidin-1-yl)(4-(2',4',6'-trimethoxybiphenyl-4-yl)-1H-1,2,3-triazol-1-yl)methanone |
In another embodiment is a compound having the structure:
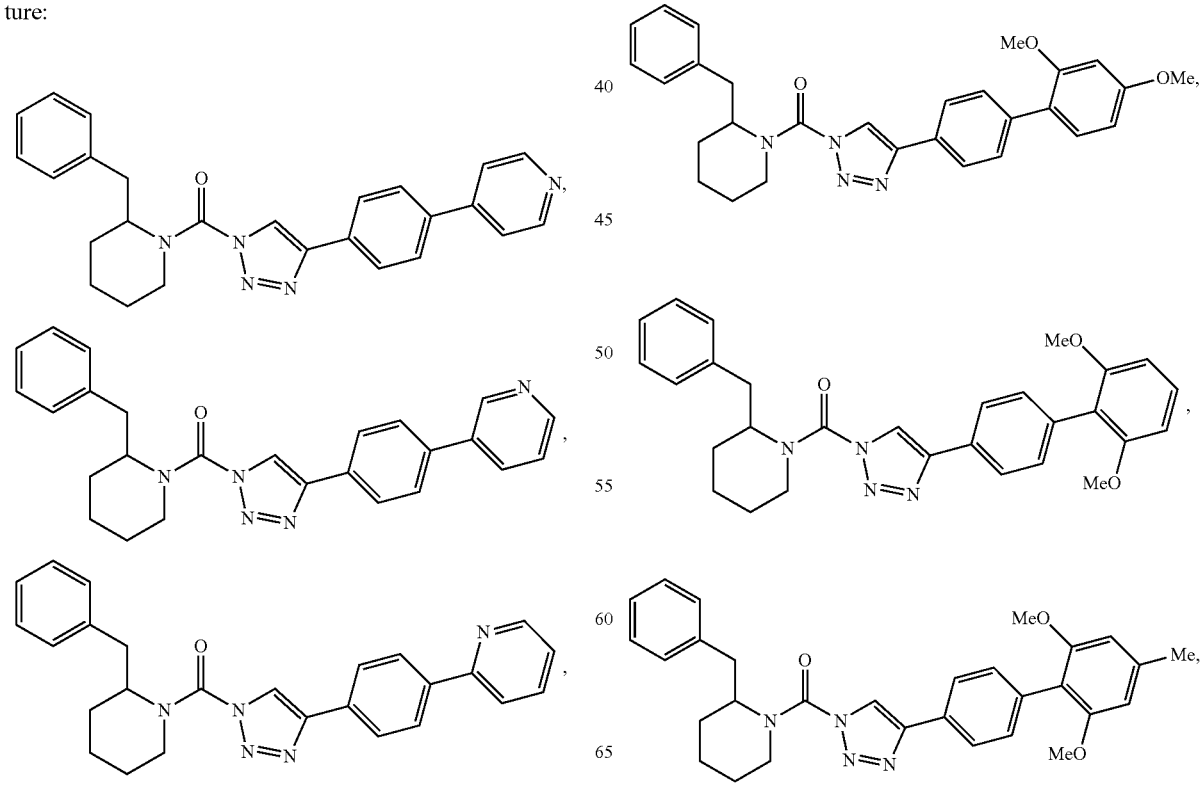

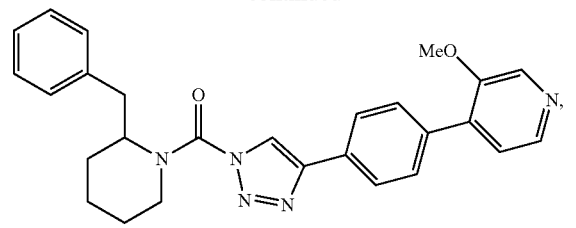
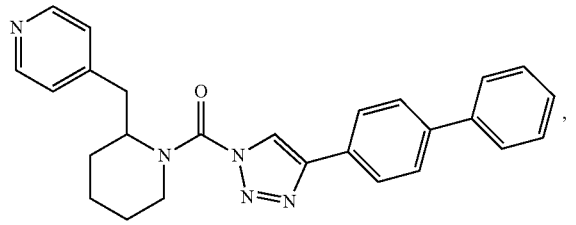
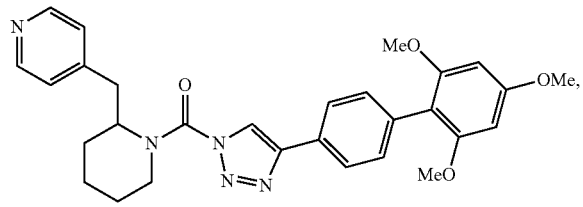
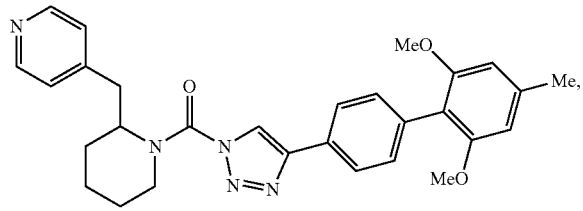
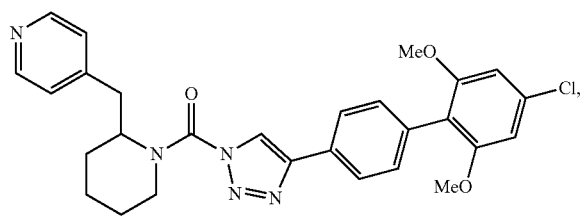
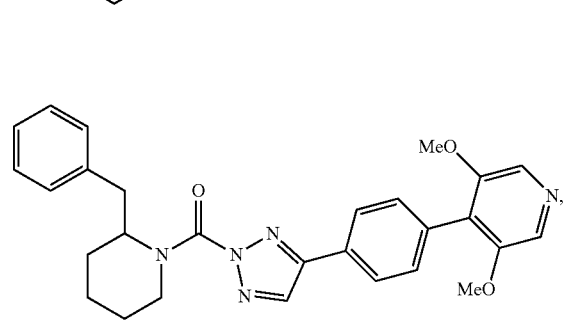
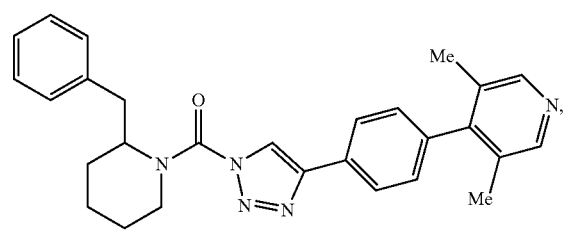
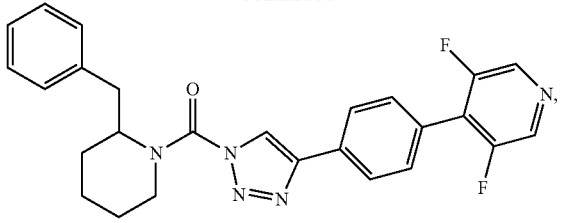
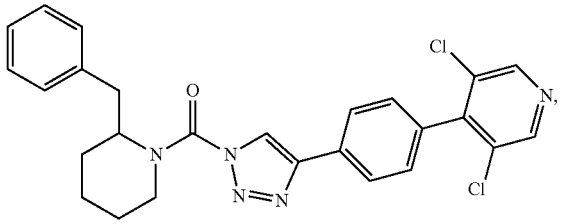
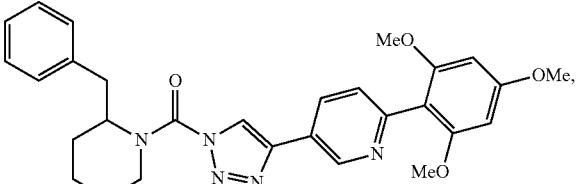
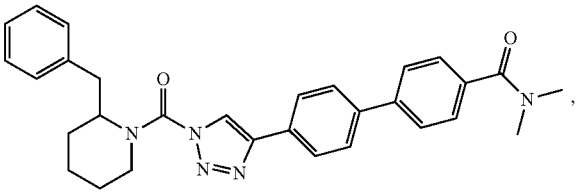
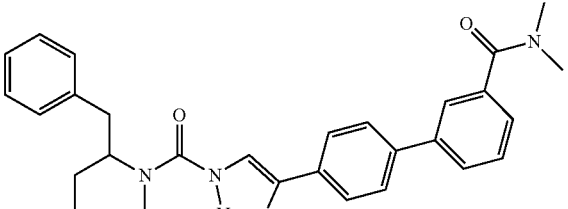
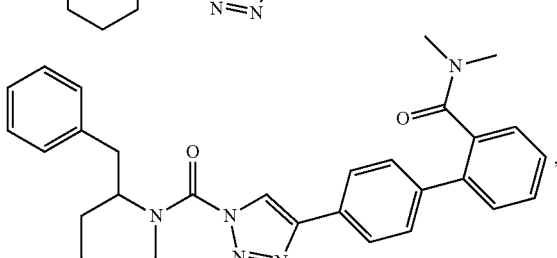
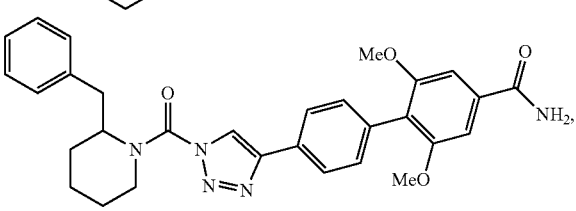
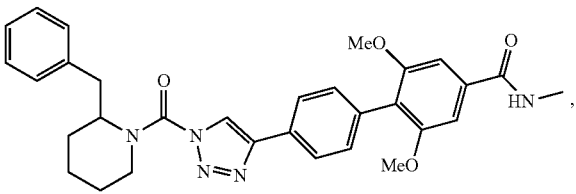

169
-continued
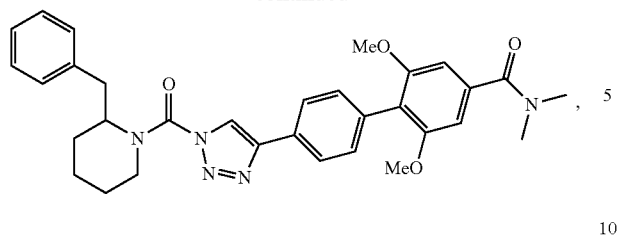
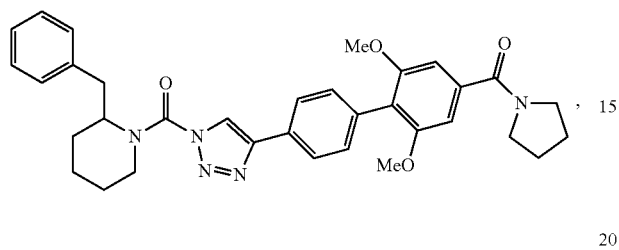
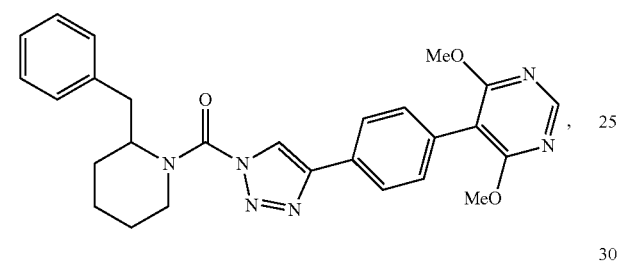
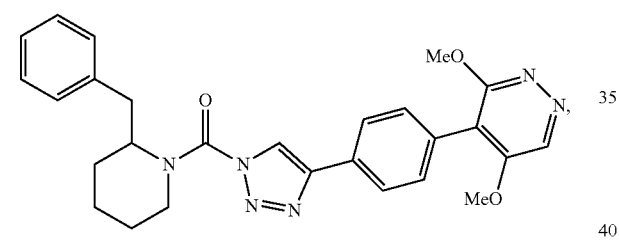
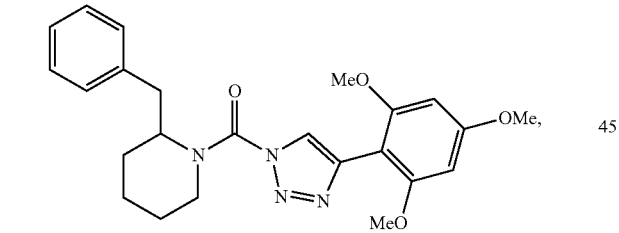
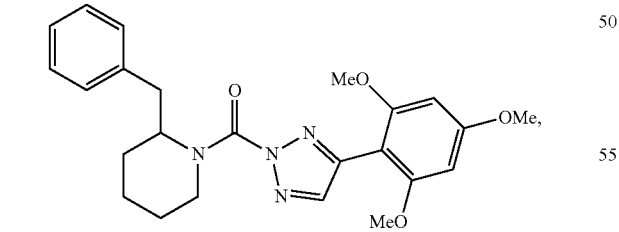
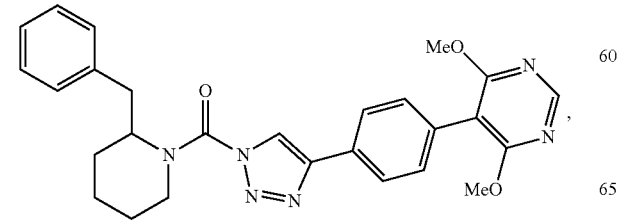
170
-continued
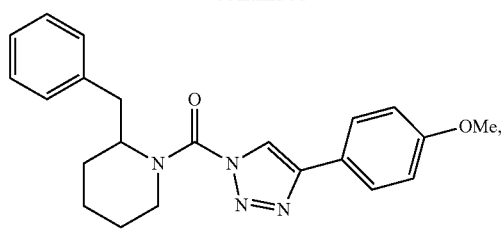
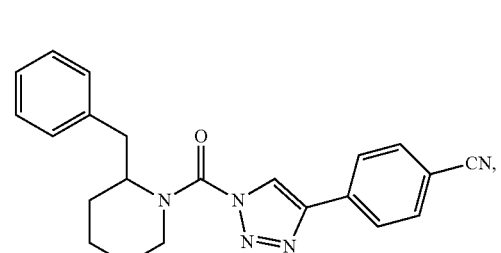
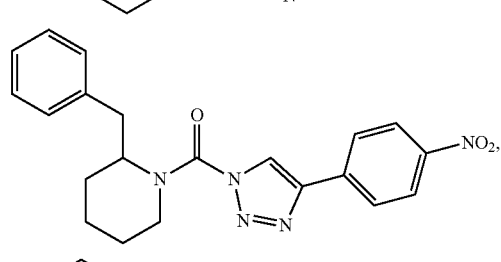
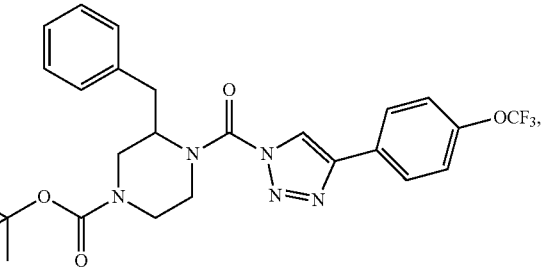
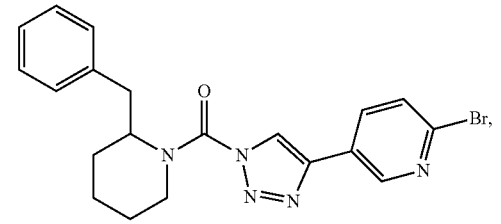
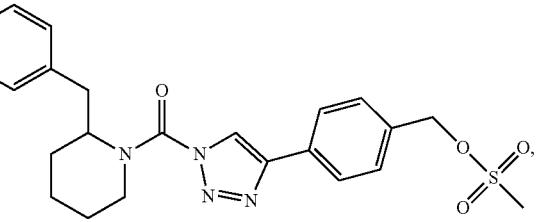
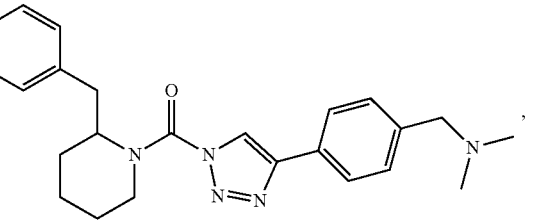

171
-continued
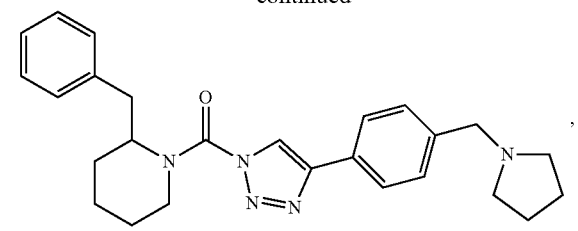
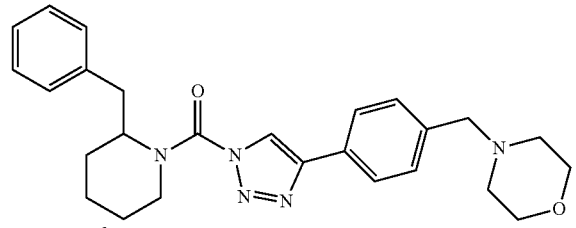
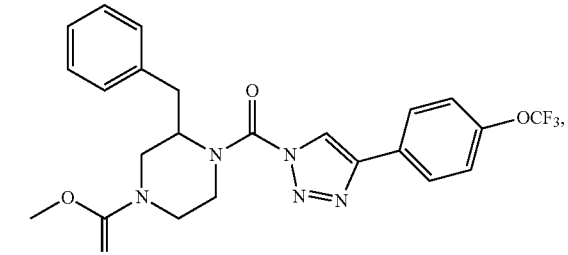
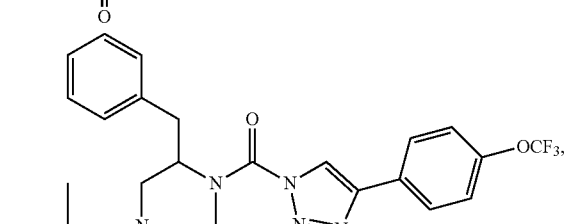
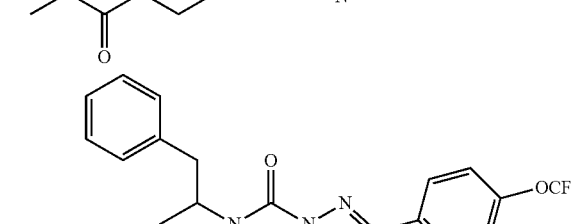
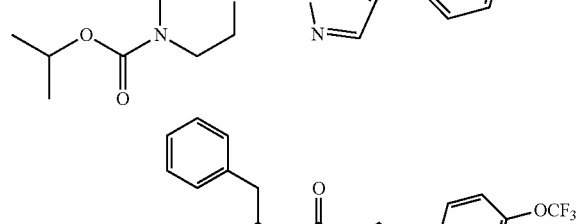
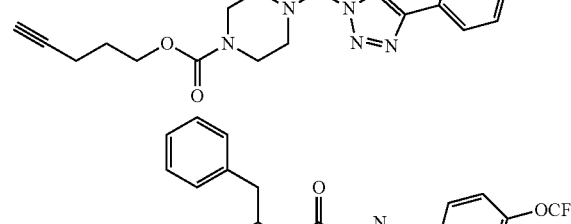
172
-continued
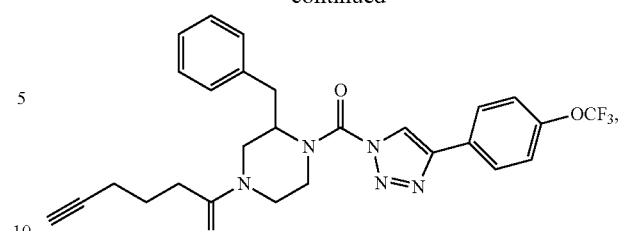
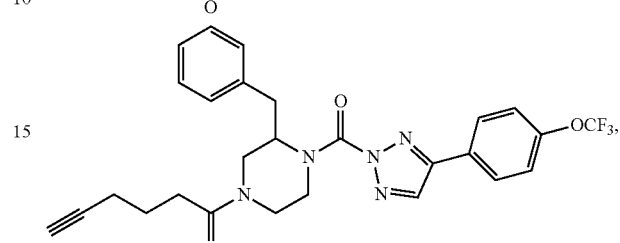
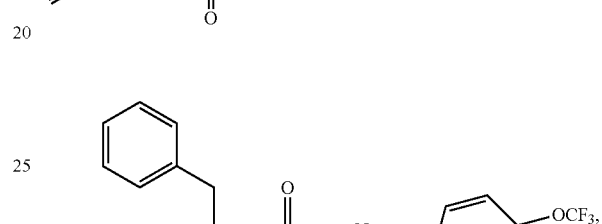
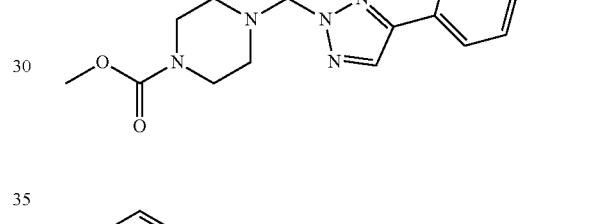
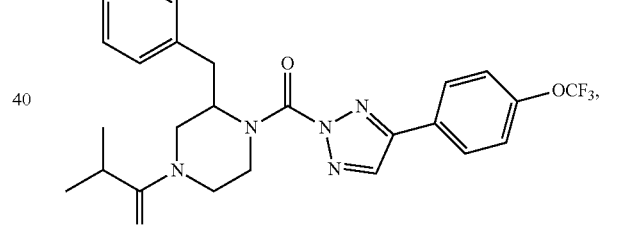
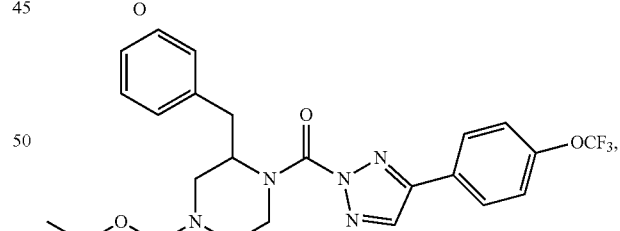
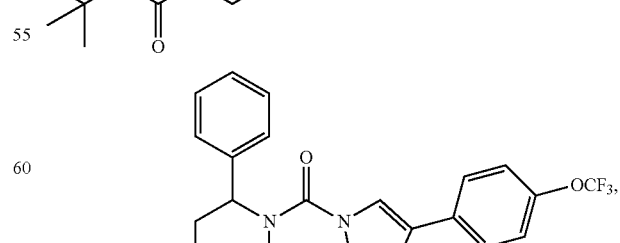

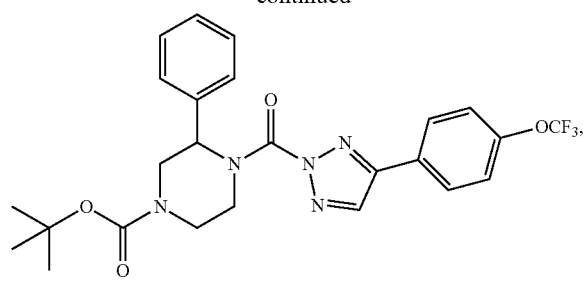
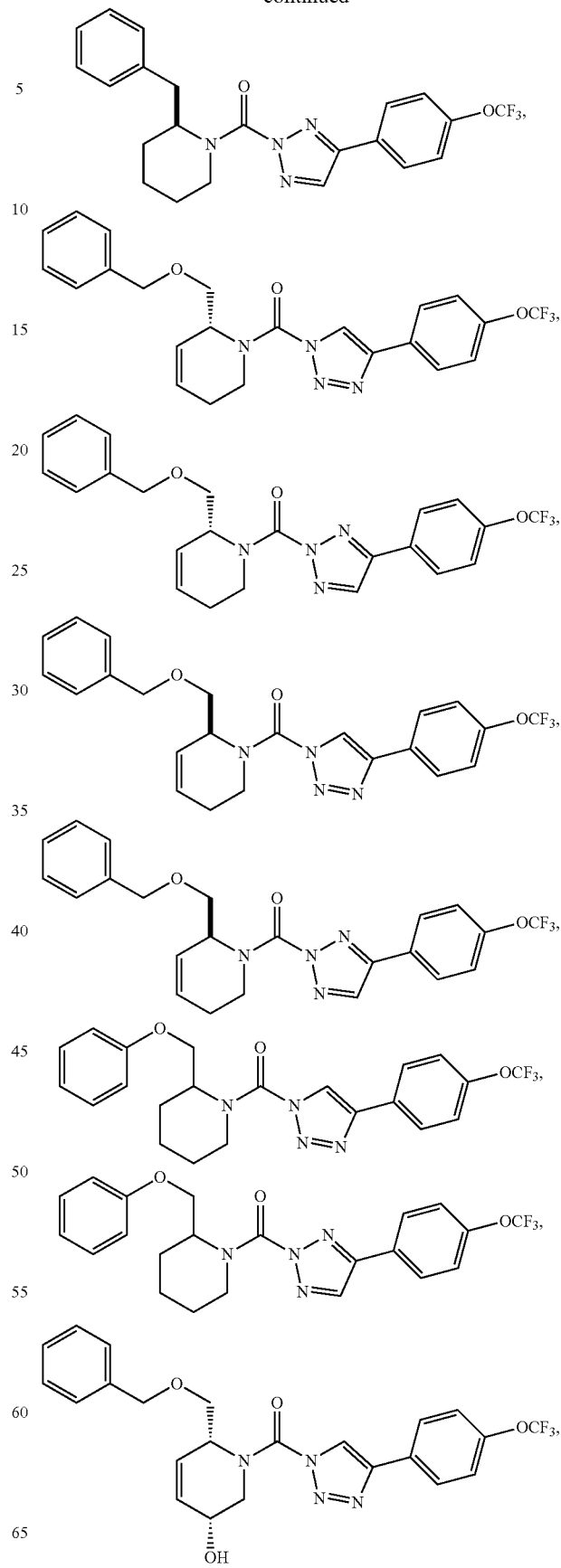

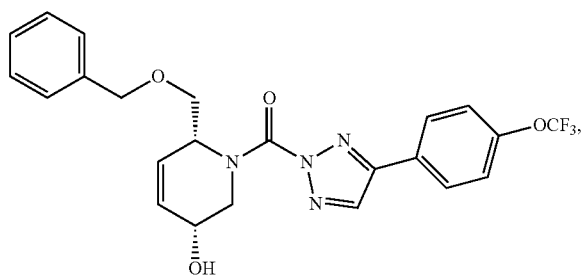
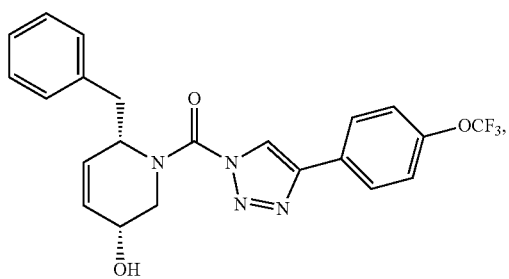
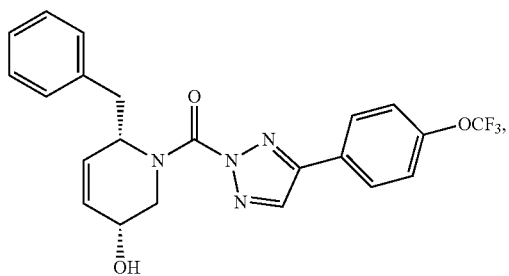
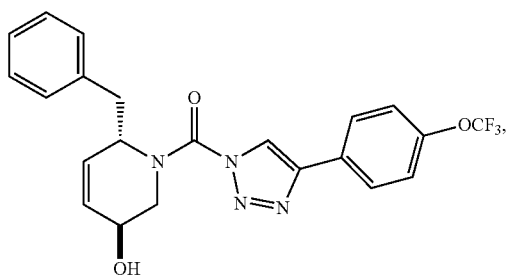
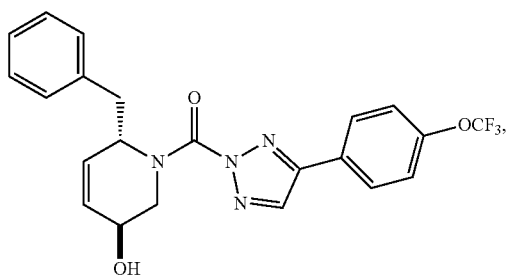
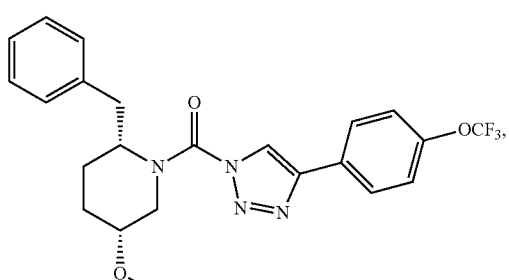
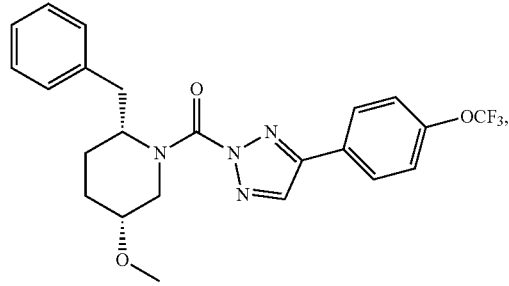
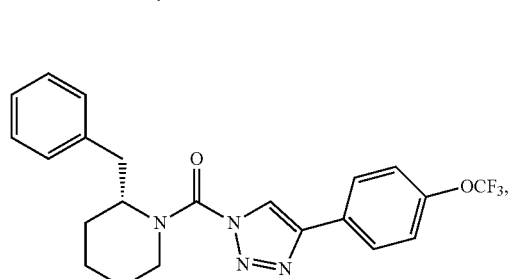
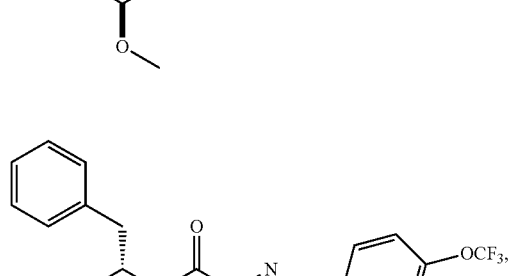
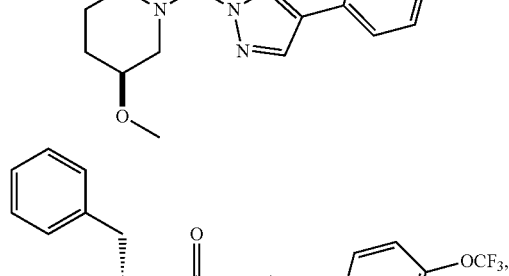
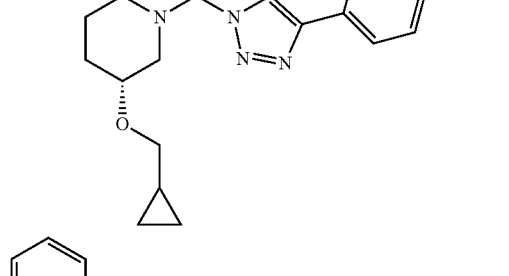
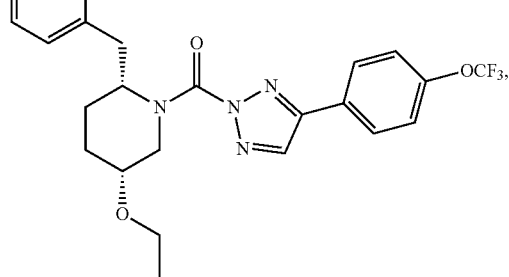

177
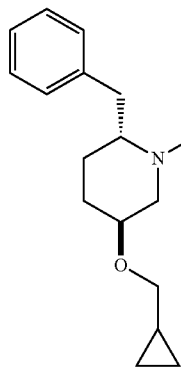
, or
178
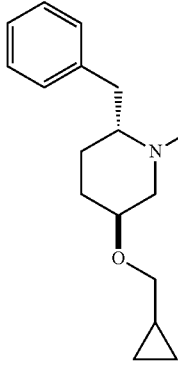
or a solvate, hydrate, N-oxide, or a pharmaceutically acceptable salt thereof.
In another embodiment is a compound having the structure:
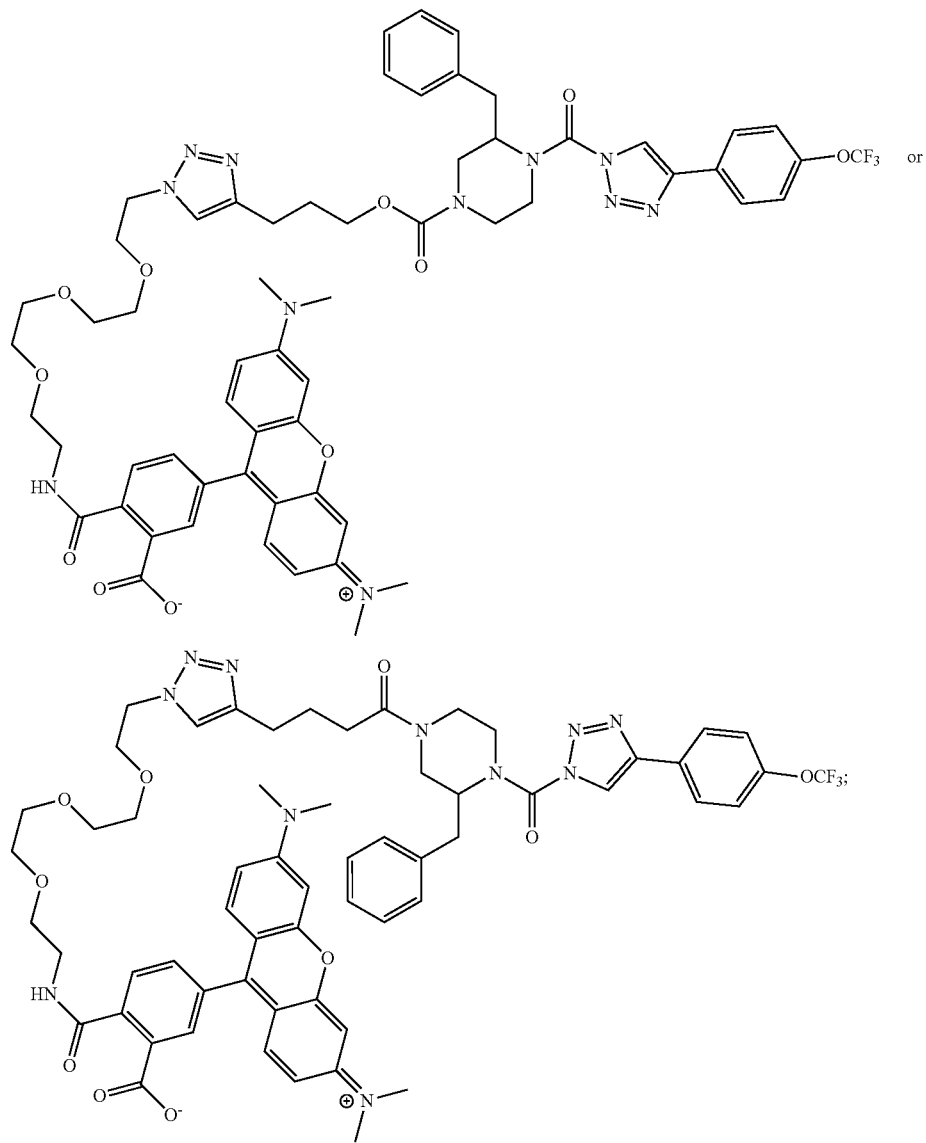
or or a solvate, hydrate, N-oxide, or a pharmaceutically acceptable salt thereof.
In another embodiment is a compound having the structure:
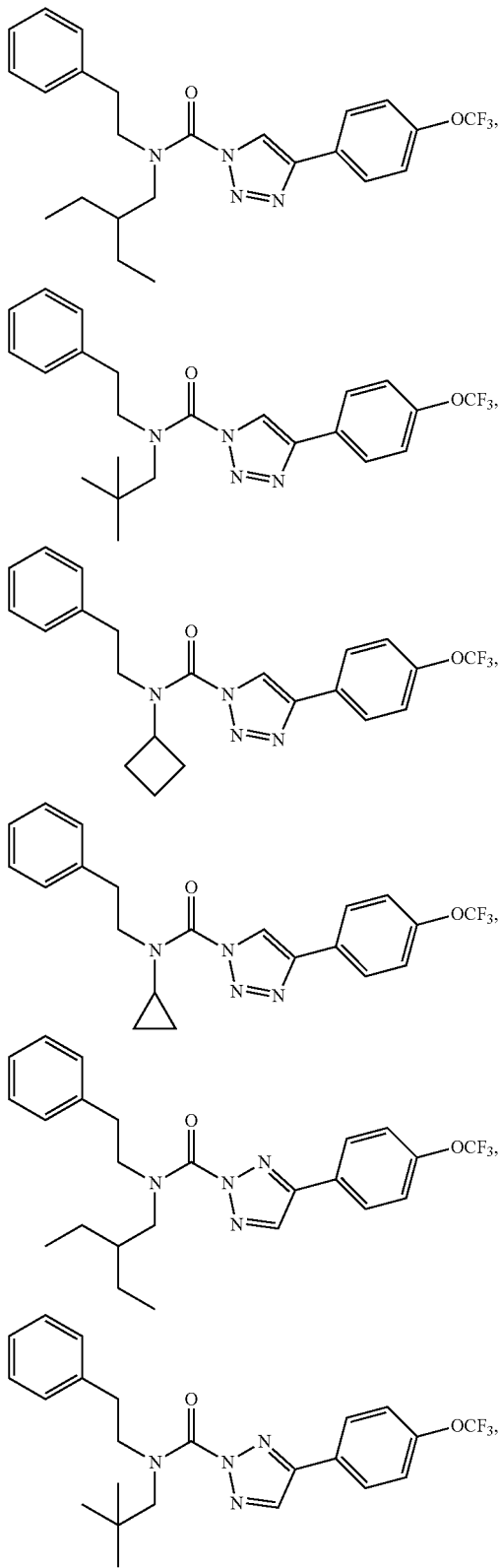
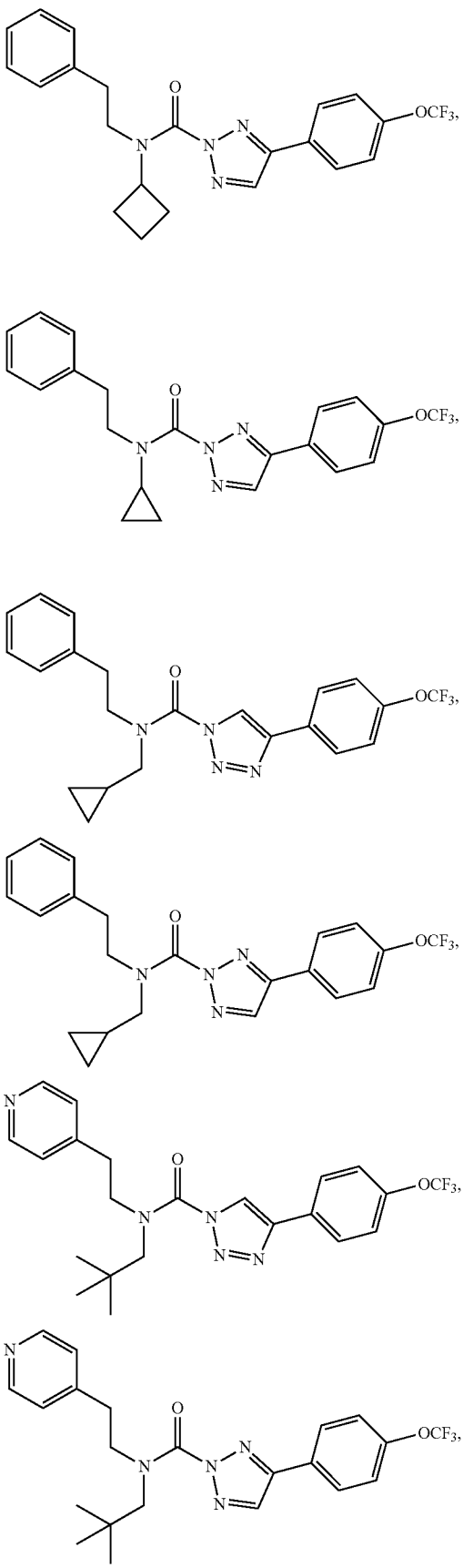

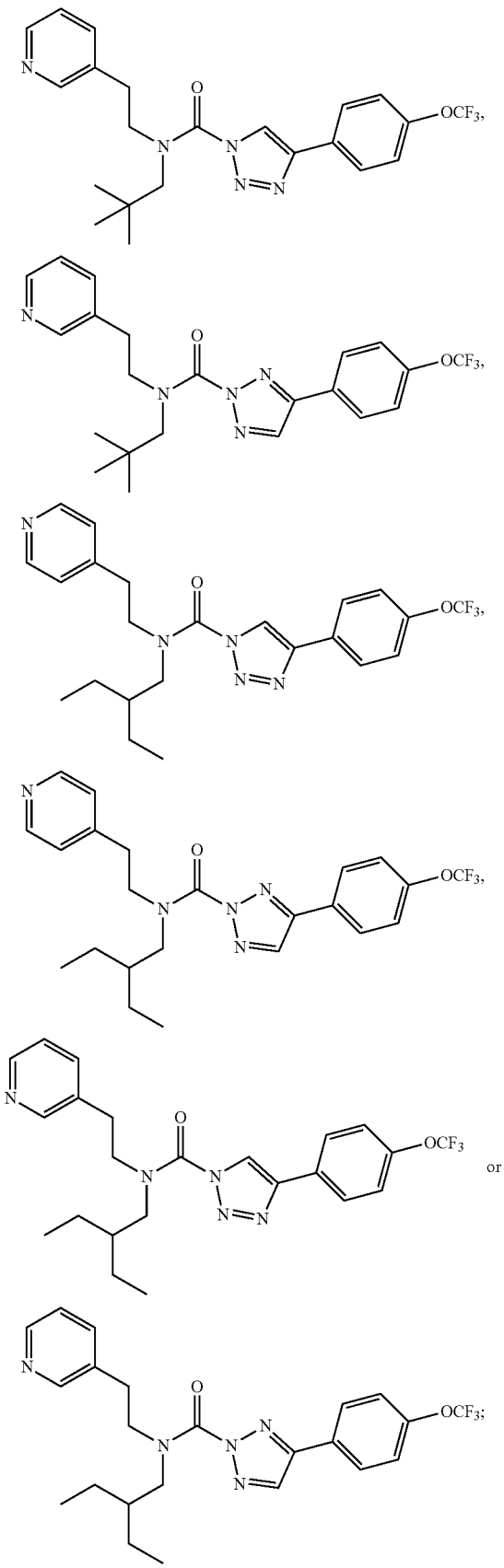

or a solvate, hydrate, N-oxide, or a pharmaceutically acceptable salt thereof.

Preparation of the Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemi succinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

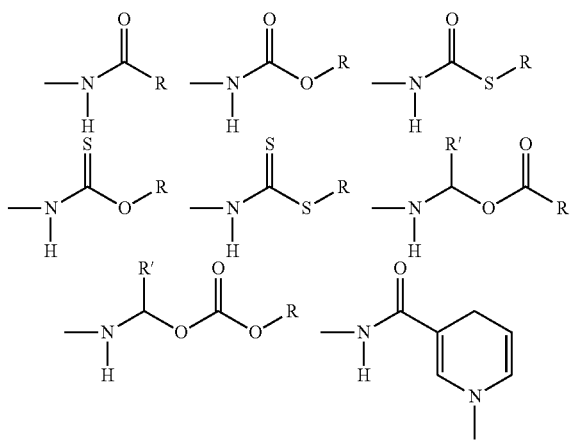
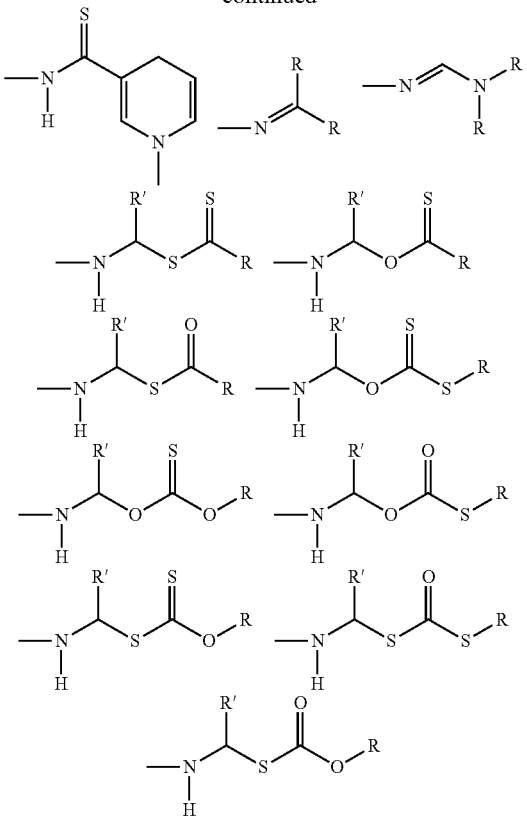

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Metabolites

In some embodiments, the compounds of Formula (I), (II), (III), (IV), (V), (VI), (VII), (VIII), (IX), (X), (XI), or (XII) described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, compounds of Formula (I), (II), (III), (IV), (V), (VI), (VII), (VIII), (IX), (X), (XI), or (XII) described herein are metabolized upon administration to an organism in need to produce a metabolite that is then used to produce a desired effect, including a desired therapeutic effect.

Pharmaceutical Compositions

In certain embodiments, the compound of Formula (I), (II), (III), (IV), (V), (VI), (VII), (VIII), (IX), (X), (XI), or (XII) as described herein is administered as a pure chemical. In some embodiments, the compound of Formula (I), (II), (III), (IV), (V), (VI), (VII), (VIII), (IX), (X), (XI), or (XII) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (II), (III), (IV), (V), (VI), (VII), (VIII), (IX), (X), (XI), or (XII) described herein, or a pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (II), or a pharmaceutically acceptable salt thereof.

One embodiment provides a pharmaceutical composition comprising a pharmaceutically acceptable excipient and a compound of Formula (III), or a pharmaceutically acceptable salt thereof.

One embodiment provides a pharmaceutical composition comprising a pharmaceutically acceptable excipient and a compound of Formula (IV), or a pharmaceutically acceptable salt thereof.

One embodiment provides a pharmaceutical composition comprising a pharmaceutically acceptable excipient and a compound of Formula (V), or a pharmaceutically acceptable salt thereof.

One embodiment provides a pharmaceutical composition comprising a pharmaceutically acceptable excipient and a compound of Formula (VI), or a pharmaceutically acceptable salt thereof.

One embodiment provides a pharmaceutical composition comprising a pharmaceutically acceptable excipient and a compound of Formula (VII), or a pharmaceutically acceptable salt thereof.

One embodiment provides a pharmaceutical composition comprising a pharmaceutically acceptable excipient and a compound of Formula (VIII), or a pharmaceutically acceptable salt thereof.

One embodiment provides a pharmaceutical composition comprising a pharmaceutically acceptable excipient and a compound of Formula (IX), or a pharmaceutically acceptable salt thereof.

One embodiment provides a pharmaceutical composition comprising a pharmaceutically acceptable excipient and a compound of Formula X), or a pharmaceutically acceptable salt thereof.

One embodiment provides a pharmaceutical composition comprising a pharmaceutically acceptable excipient and a compound of Formula (XI), or a pharmaceutically acceptable salt thereof.

One embodiment provides a pharmaceutical composition comprising a pharmaceutically acceptable excipient and a compound of Formula (XII), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (II), or a pharmaceutically acceptable salt thereof. Another embodiment provides a pharmaceutical composition consisting essentially of a pharmaceutically acceptable excipient and a compound of Formula (III), or a pharmaceutically acceptable salt thereof. Another embodiment provides a pharmaceutical composition consisting essentially of a pharmaceutically acceptable excipient and a compound of Formula (IV), or a pharmaceutically acceptable salt thereof. Another embodiment provides a pharmaceutical composition consisting essentially of a pharmaceutically acceptable excipient and a compound of Formula (V), or a pharmaceutically acceptable salt thereof. Another embodiment provides a pharmaceutical composition consisting essentially of a pharmaceutically acceptable excipient and a compound of Formula (VI), or a pharmaceutically acceptable salt thereof. Another embodiment provides a pharmaceutical composition consisting essentially of a pharmaceutically acceptable excipient and a compound of Formula (VII), or a pharmaceutically acceptable salt thereof. Another embodiment provides a pharmaceutical composition consisting essentially of a pharmaceutically acceptable excipient and a compound of Formula (VIII), or a pharmaceutically acceptable salt thereof. Another embodiment provides a pharmaceutical composition consisting essentially of a pharmaceutically acceptable excipient and a compound of Formula (IX), or a pharmaceutically acceptable salt thereof. Another embodiment provides a pharmaceutical composition consisting essentially of a pharmaceutically acceptable excipient and a compound of Formula (X), or a pharmaceutically acceptable salt thereof. Another embodiment provides a pharmaceutical composition consisting essentially of a pharmaceutically acceptable excipient and a compound of Formula (XI), or a pharmaceutically acceptable salt thereof. Another embodiment provides a pharmaceutical composition consisting essentially of a pharmaceutically acceptable excipient and a compound of Formula (XII), or a pharmaceutically acceptable salt thereof.

In certain embodiments, the compound of Formula (I), (II), (III), (IV), (V), (VI), (VII), (VIII), (IX), (X), (XI), or (XII) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HP-MCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit 5100, Kollicoat EMM30D, Estacryl 30D, Coateric, and Aquateric). The solubility of each of the above materials is either known or is readily determinable in vitro.

The dose of the composition comprising at least one compound of Formula (I), (II), (III), (IV), (V), (VI), (VII), (VIII), (IX), (X), (XI), or (XII) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of DAGL, e.g., DAGLα and/or DAGLβ. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (II), (III), (IV), (V), (VI), (VII), (VIII), (IX), (X), (XI), or (XII). The ability of compounds described herein to modulate or inhibit DAGL is evaluated by procedures known in the art and/or described herein. Another aspect of this disclosure provides methods of treating a disease associated with expression or activity of DAGL in a patient. For example, provided herein are compounds that are selective in inhibiting DAGLα and/or DAGLβ, as compared to inhibition of other serine hydrolases e.g., 10, 100, 1000 or more fold inhibition of DAGLα and/or DAGLβ over another serin hydrolase.

In another embodiment is a method of treating a neurodegenerative disease or neuroinflammatory disease, comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof.

In another embodiment is a method of treating a neurodegenerative disease, comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof.

In another embodiment is a method of treating a neuroinflammatory disease, comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof.

In another embodiment is a method of treating a neurodegenerative disease or neuroinflammatory disease, wherein the neurodegenerative disease or neuroinflammatory disease is Parkinson's Disease, Alzheimer's Disease, Huntington's Disease, or Amyotrophic Lateral Sclerosis (ALS), comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof. In another embodiment is a method of treating Parkinson's Disease comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof. In another embodiment is a method of treating Alzheimer's Disease comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof. In another embodiment is a method of treating Huntington's Disease comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof. In another embodiment is a method of treating Amyotrophic Lateral Sclerosis (ALS) comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof.

In another embodiment is a method of treating hepatic fibrosis or kidney fibrosis, comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof. In another embodiment is a method of treating hepatic fibrosis comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof. In another embodiment is a method of treating kidney fibrosis comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof.

In another embodiment is a method of treating obesity, comprising administering a therapeutically effective amount of a compound of Formula (I), (II), (III), (IV), (V), (VI), (VII), (VIII), (IX), (X), (XI), or (XII) described herein, or a solvate, hydrate, tautomer, N-oxide, or a pharmaceutically acceptable salt thereof, to a patient in need thereof.

In certain embodiments, a disclosed compound utilized by one or more of the foregoing methods is one of the generic, subgeneric, or specific compounds described herein, such as a compound of Formula (I), (II), (III), (IV), (V), (VI), (VII), (VIII), (IX), (X), (XI), or (XII).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In some embodiments, a disclosed compound is co-administered with a therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxic.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:
ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
equiv or eq equivalent(s)
Et ethyl
$Et_2O$ diethyl ether
EtOH ethanol
EtOAc ethyl acetate
HPLC high performance liquid chromatography
LAH lithium aluminum anhydride
Me methyl
MeOH methanol
MS mass spectroscopy
NMM N-methyl-morpholine
NMP N-methyl-pyrrolidin-2-one
NMR nuclear magnetic resonance
PyBOP benzotriazol-1-yl-oxytripyrrolidinophosphonium hexafluorophosphate
RP-HPLC reverse phase-high pressure liquid chromatography
TFA trifluoroacetic acid
THF tetrahydrofuran
TLC thin layer chromatography I. Chemical Synthesis Unless otherwise noted, chemicals were obtained from commercial suppliers and were used without further purification. Merck silica gel TLC plates (0.25 mm, 60 F254) were used to monitor reactions. Flash chromatography was performed using SiliaFlash F60 silica gel (40-63 μm, 60 Å). NMR spectra were recorded at room temperature or at high temperature (60° C. or 100° C.) on Broker AV 400 MHz spectrometer at 400 ($^1$H) and 101 ($^{13}$C) MHz, or on Broker DRX-600 spectrometer at 600 ($^1$H) and 150 ($^{13}$C) MHz using $CDCl_3$, $CD_3OD$ or $(CD_3)_2SO$ as solvent, unless stated otherwise. Chemical shifts are recorded in ppm relative to tetramethylsilane (TMS) with peaks being reported as follows: chemical shift, multiplicity (s=singlet, br s=broad singlet, d=doublet, t=triplet, q=quartet, m=multiplet), coupling constant (Hz). High-resolution mass spectra (HRMS) were obtained on an Agilent LC/MSD TOF mass spectrometer by electrospray ionizationtime-of-flight (ESI-TOF) or on a Thermo Scientific LTQ Orbitrap XL. HPLC purification was performed on a preparative LC-MS system (Agilent 1200 series) with an Agilent 6130 Quadruple MS detector. Optical rotations were measured on a Propol automatic polarimeter (Sodium D-line, =589 nm).

Example 1: ((2R,5R)-2-Benzyl-5-(prop-2-ynyloxy)piperidin-1-yl)(4-(bis(4-fluorophenyl)(hydroxy)methyl)-2H-1,2,3-triazol-2-yl)methanone (14)

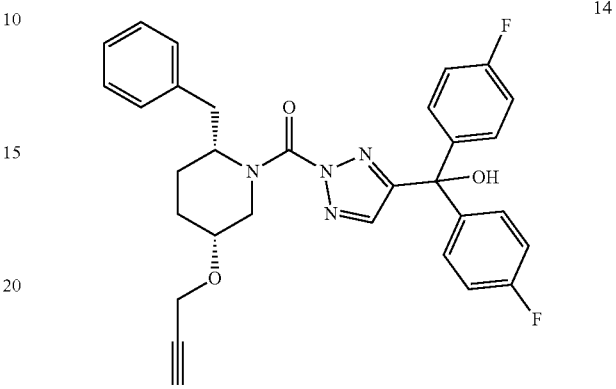

Synthesis of bis(4-fluorophenyl)(1H-1,2,3-triazol-5-yl)methanol (3)

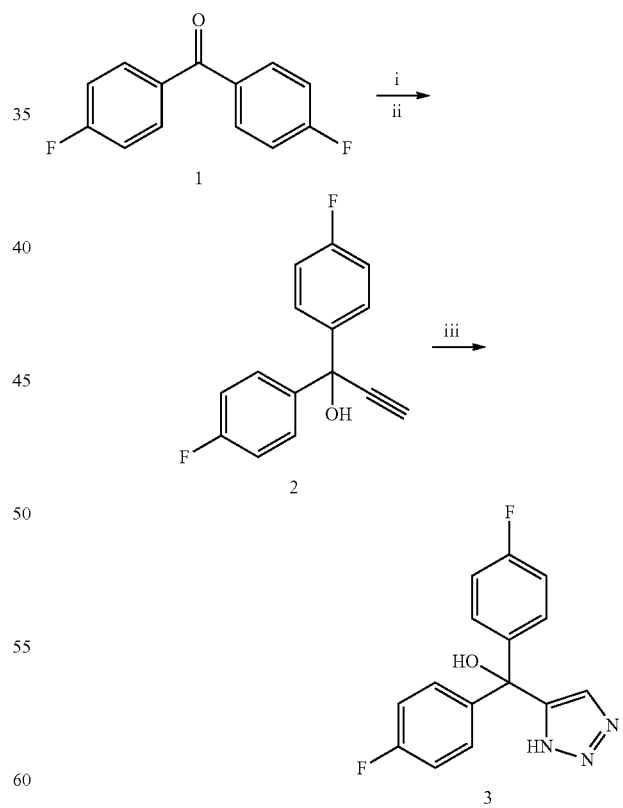

Reagents and conditions: i) ethynyltrimethylsilane, n-BuLi, THF, -10° C. ii) NaOH, MeOH iii) azidotrimethylsilane, CuI, DMF/MeOH (5:1), 100° C.

To a solution of ethynyltrimethylsilane (0.712 mL, 5.04 mmol) in anhydrous THF (20 mL) under a nitrogen atmosphere was slowly added n-butyllithium (3.15 mL, 5.04 mmol) (1.6 M in hexane) at −10° C. After stirring for one hour at −10° C., a solution of bis(4-fluorophenyl)methanone (1) (1.00 g, 4.58 mmol) in dry THF (10 mL) was added. After stirring for three hours at −10° C., the temperature was raised to 0° C. and a solution of NaOH (238 mg, 5.95 mmol) in MeOH (4.60 mL) was added. The solution was warmed to room temperature, neutralized to pH 7 with acetic acid and poured into water. Subsequent extraction with ethyl acetate (3×10 mL), drying over MgSO$_4$, filtering and concentration in vacuo afforded a crude product that was purified by flash chromatography over silica gel using pentane/ethyl acetate, yielding 1,1-bis(4-fluorophenyl)prop-2-yn-1-ol (2) (1.08 g, 4.42 mmol, 96%) as a yellow oil. $^1$H NMR (400 MHz, CDCl$_3$) δ 7.57-7.51 (m, 4H), 7.03-6.98 (m, 4H), 2.89 (s, 2H); $^{13}$C NMR (101 MHz, CDCl$_3$) δ 162.50 (d, J=248 Hz), 140.24 (d, J=3.1 Hz), 127.98 (d, J=9.1 Hz), 115.32 (d, J=21 Hz), 86.08, 76.09, 73.52; HRMS (m/z): [M+H]$^+$ calcd. for C$_{15}$H$_{10}$F$_2$O, 245.07782; found: 245.07735.

To 1,1-bis(4-fluorophenyl)prop-2-yn-1-ol (2) (1.00 g, 4.09 mmol) and CuI (0.153 g, 0.819 mmol) were dissolved in DMF/MeOH (5:1, 36 mL). Azidotrimethylsilane (0.815 mL, 6.14 mmol) was added and the mixture was stirred at 100° C. over the weekend. The reaction mixture was quenched with H$_2$O (90 mL), the organic layer extracted with DCM (3×100 mL). The combined organic layers were washed with H$_2$O and brine and dried on MgSO$_4$. Filtering and concentration under reduced pressure gave a residue that was purified by flash chromatography over silica gel using pentane/ethyl acetate with 1% Et$_3$N (30-100% pentane/ethyl acetate) yielding bis(4-fluorophenyl)(1H-1,2,3-triazol-5-yl)methanol (3) (0.694 g, 2.42 mmol, 59%) as a white solid. $^1$H NMR (400 MHz, MeOD) δ 7.58 (s, 1H), 7.38-7.31 (m, 4H), 7.06-7.01 (m, 4H); $^{13}$C NMR (101 MHz, MeOD) δ 163.45 (d, J=246 Hz), 143.57 (d, J=2.0 Hz), 130.62, 128.59, 130.31 (d, J=9.1 Hz), 115.52 (d, J=22 Hz), 76.99; HRMS (m/z): [M+H]$^+$ calcd. for C$_{15}$H$_{11}$F$_2$N$_3$O, 288.09429; found 288.09473.

Synthesis of (S)-1-phenylbut-3-en-2-amine (7)

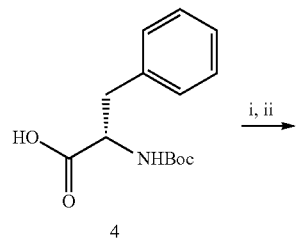

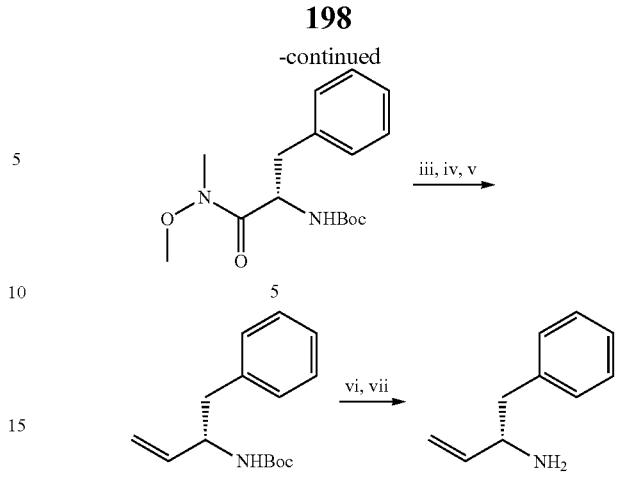

Reagents and conditions: i) Me(OMe)NH·HCl ii) EDCI, NMM iii) LiAlH$_4$ iv) H$_3$O$^+$ v) (Ph)$_3$P═CH$_2$ vi) MeOH/6M HCl vii) NaOH.

Compound 6 was prepared according the route reported for the (R)-enantiomer (J. Med. Chem, 54(6):1655-1666) on 120 mmol scale, affording 25.4 g of compound 6 (86%, [α]$_D^{20}$=+35.0 (c=1.00, CHCl$_3$). The Boc-protected amine 6 was dissolved in a mixture of MeOH (200 mL) and aqueous 6M HCl (50 mL). After TLC confirmed total conversion of compound 6 evaporation of the solvents afforded a white solid that was dissolved in water (200 mL). After addition of aqueous 8M NaOH (30 mL), extraction with chloroform (4×75 mL), drying (MgSO$_4$), filtering and evaporation of the solvent, amine 7 was obtained as a brown oil that was used without further purification. [α]$_D^{20}$=+14.1 (c=1.00, CHCl$_3$); $^1$H NMR (400 MHz, CDCl$_3$) δ 7.31-7.19 (m, 5H), 5.88 (ddd, J=17.2, 10.3, 6.3 Hz, 1H), 5.13 (d, J=17.2 Hz, 1H), 5.03 (d, J=10.3 Hz, 1H), 3.59 (q, J=6.3 Hz, 1H), 2.82 (dd, J=13.3, 5.3 Hz, 1H), 2.61 (dd, J=13.3, 8.3 Hz, 1H), 1.28 (br s, 2H); $^{13}$C NMR (101 MHz, CDCl$_3$) δ 142.30, 138.65, 129.29, 128.28, 126.22, 113.52, 55.36, 44.23; HRMS (m/z): [M+H]$^+$ calcd. for C$_{10}$H$_{E}$N, 148.11208; found 148.11199. For chiral HPLC analysis amine 7 was derivatized as its benzoate followed by analysis on a Daicel Chiralpak AD column (250×4.5 mm, 10 μm particle size). Eluent hexane/2-propanol=90/10, 1.0 mL/min., detection UV 254 nm. (R)-Enantiomer, R$_t$=12.2 min (not observed); (S)-enantiomer, R$_t$=14.4 min (100%).

Synthesis of ((2R,5R)-2-benzyl-5-(prop-2-ynyloxy)piperidin-1-yl)(4-(bis(4-fluorophenyl)(hydroxy)methyl)-2H-1,2,3-triazol-2-yl)methanone (14)

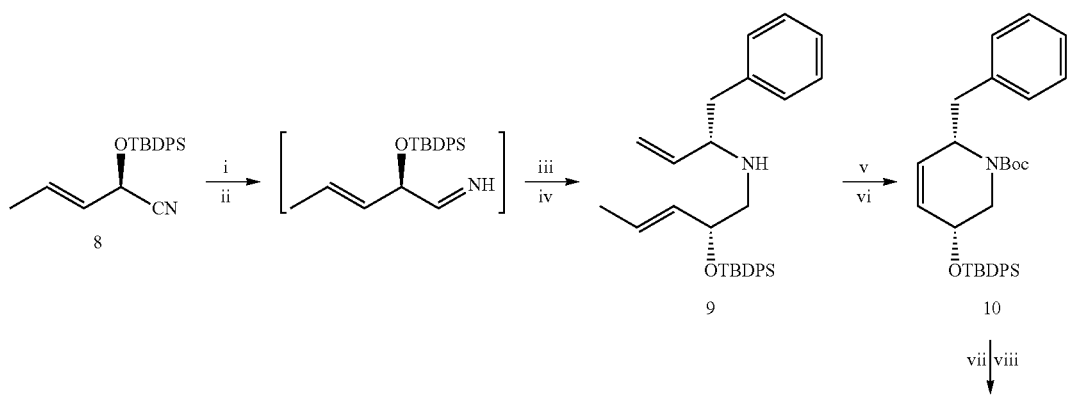

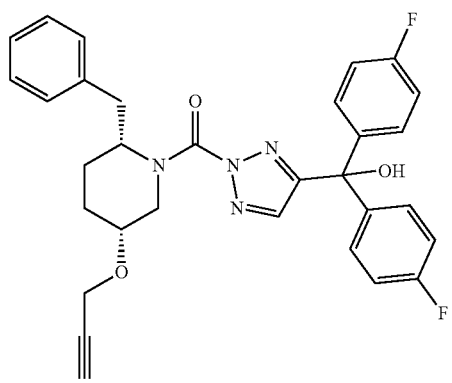

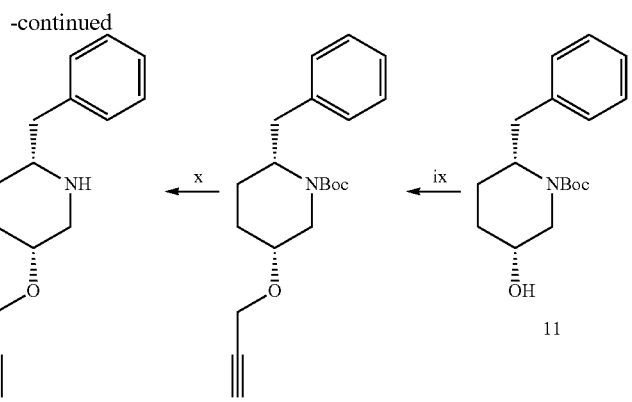

Reagents and conditions: i) Dibal-H, Diethyl ether, -78° C. → . ii) MeOH, -90° C. iii) Compound 7 (3 eq.), MeOH iv) NaBH$_4$. v) Boc$_2$O, Et$_3$N, THF, 50° C. vi) Grubbs 2$^{nd}$ generation, DCM, 45° C. vii) TBAF, THF. viii) Hydrazine, CuSO$_4$, EtOH, 70° C. ix) 3-bromoprop-1-yne, NaH, DMF. x) 20% TFa, DCM. xi) DIPEA, triphosgene, THF, 0° C. xii) DIPEA, DMAP, Compound 3, THF, 60° C.

Under an argon atmosphere, a flame dried three necked reaction flask was charged with a solution of (R,E)-2-((tert-butyldiphenylsilyl)oxy)pent-3-enenitrile (8) (2.60 g, 7.76 mmol) in dry diethyl ether. At -78° C. a 1.0 M solution of Dibal-H (12.0 mL, 12.0 mmol) in toluene was added dropwise. The reaction was warmed slowly on the cooling bath until 5° C. in circa two hours. After re-cooling to -90° C., dry MeOH (12 mL) was added at once. After five minutes followed by a solution of (S)-1-phenylbut-3-en-2-amine (7) (2.99 g, 20.3 mmol, e.e. =99%) in MeOH (10 mL). The cooling bath was removed and the mixture stirred at room temperature for 16 hours. Subsequently, an excess of NaBH$_4$ (870 mg, 22.9 mmol) was added at 0° C. in two portions with a five minute interval. The reaction was left stirring on the ice bath and slowly warmed up to room temperature overnight. The reaction mixture was poured into an 0.8 M aqueous NaOH solution (150 mL) and extracted with diethyl ether (3×80 mL). The ether layers were combined and washed twice with an aqueous 1 M HCl solution (2×30 mL) to recover the excess (S)-1-phenylbut-3-en-2-amine. The ether layers were subsequently washed with an aqueous 0.8 M NaOH-solution (50 mL) and brine (20 mL), dried (MgSO$_4$), filtered and concentrated in vacuo to afford the crude product (9) as a yellow oil (3.74 g, quant.) that was used crude in the next reaction. $[\alpha]_D^{22}$=-18.0 (c=1.00, CHCl$_3$); $^1$H NMR (400 MHz, CDCl$_3$) δ 7.64-7.57 (m, 4H), 7.42-7.27 (m, 6H), 7.23 (app. t, J=7.2 Hz, 2H), 7.18-7.10 (m, 3H), 5.58 (ddd, J=17.8, 10.3, 7.9 Hz, 1H), 5.35-5.26 (m, 1H), 5.23-5.09 (m, 1H), 5.05-4.90 (m, 2H), 4.16 (app. q, J=5.9 Hz, 1H), 3.17 (app. q, J=7.5 Hz, 1H), 2.78-2.62 (m, 3H), 2.38 (dd, J=11.5, 5.7 Hz, 1H), 1.52 (br s, 1H), 1.42 (d, J=6.4 Hz, 3H), 0.99 (s, 9H); $^{13}$C NMR (101 MHz, CDCl$_3$) δ 140.75, 138.53, 135.94, 135.79, 134.24, 134.11, 132.21, 129.44, 129.32, 128.20, 127.39, 127.21, 126.16, 115.76, 74.00, 63.04, 53.64, 42.54, 26.98, 19.20, 17.45; IR (film) 3071, 2930, 2857, 1472, 1105, 1078, 1030, 964 cm$^{-1}$; HRMS (m/z): [M+H]$^+$ calcd. for C$_{31}$H$_{39}$NOSi, 470.28737; found 470.28682.

Compound 9 (3.74 g, max 7.76 mmol) was dissolved in a mixture of THF (50 mL) and TEA (2 mL). Boc$_2$O (4.01 g, 18.3 mmol) was added and the reaction was heated at reflux overnight. The reaction mixture was cooled and concentrated. The residue was purified by silica gel column chromatography using pentane:ethyl acetate=98:2 as the eluent to afford 4.40 g of the Boc-protected amine in circa 80% purity (contaminated with 20% Boc$_2$O). $[\alpha]_D^{20}$=-39.6 (c=1.00, CHCl$_3$); $^1$H NMR (400 MHz, CDCl$_3$) mixture of rotamers (1:2) δ 7.72-7.57 (m, 4H), 7.44-7.33 (m, 6H), 7.27-7.10 (m, 3H), 7.02 (d, J=7.0 Hz, 2H), 5.99-5.63 (m, 1H), 5.34-5.28 (m, 1H), 5.11-5.04 (m, 1H), 4.94 (d, J=10.2 Hz, 1H), 4.75 (d, J=17.3 Hz, 1H), 4.10 (br s, 1H), 4.01-3.78 (m, 1H), 3.55-3.09 (m, 1H), 3.03-2.79 (m, 1H), 2.70-2.65 (m, 2H), 1.52 (s, 3H), 1.41&1.34 (2×s, 9H), 1.03 (s, 9H); $^{13}$C NMR (101 MHz, CDCl$_3$) mixture of rotamers, major peaks: δ 154.85, 146.68, 138.58, 137.70, 137.38, 135.97, 135.81, 134.23, 133.92, 132.02, 129.61, 129.48, 129.17, 128.01, 127.52, 127.31, 125.99, 115.71, 79.14, 72.96, 62.28, 52.83, 38.41, 28.32, 27.35, 19.16, 17.73; IR (film) 3066, 2932, 2859, 1809, 1767, 1694, 1427, 1366, 1173, 1113, 1069 cm$^{-1}$; HRMS (m/z): [M+H]$^+$ calcd. for C$_{36}$H$_{47}$NO$_3$Si, 570.33980; found 570.33994.

The Boc-protected diene from above (5.40 g, max 7.59 mmol) was dissolved in DCM (50 mL) and purged with argon. After the addition of Grubb's 2$^{nd}$ generation catalyst (190 mg, 0.224 mmol) and refluxing overnight TLC analysis confirmed complete conversion. The solvent was evaporated and the crude product purified by silica gel column chromatography using pentane:ethyl acetate=99:1→97:3 as the eluent, to afford (3R,6S)-6-benzyl-3-((tert-butyldiphenylsilyl)oxy)-3,6-dihydropy-ridine-1(2H)-carboxylate (10) as a colorless oil (2.93 g, 72% based on nitrile 8). $[\alpha]_D^{20}$=+47.8 (c=1.00, CHCl$_3$); $^1$H NMR (400 MHz CDCl$_3$) mixture of rotamers (1:1) δ 7.72-7.65 (m, 4H), 7.41-7.34 (m, 6H), 7.30-7.09 (m, 5H), 5.72-5.64 (m, 1H), 5.52-5.42 (m, 1H), 4.57-4.38 (m, 1H), 4.38-3.94 (m, 2H), 2.95-2.84 (m, 1H), 2.80-2.67 (m, 2H), 1.31&1.29 (2×s, 9H), 1.09 (s, 9H); $^{13}$C NMR (101 MHz, CDCl$_3$) mixture of rotamers (1:1) δ 153.86, 153.77, 138.15, 137.88, 135.69, 135.60, 133.92, 133.73, 133.65, 133.54, 131.23, 131.13, 129.69, 129.61, 129.34, 129.27, 128.31, 128.16, 127.75, 127.60, 127.55, 126.28, 126.18, 79.55, 79.47, 65.35, 53.68, 52.66, 44.40, 42.69, 39.44, 39.09, 28.22, 28.13, 26.87, 19.11; IR (film): 3069, 3030, 2961, 2930, 2859, 1694, 1454, 1414, 1157, 1111, 1086, 1018 cm$^{-1}$; HRMS (m/z): [M+H]$^+$ calcd. for C$_{33}$H$_{41}$NO$_3$Si, 528.29285; found 528.29227.

A 1M solution of TBAF (2.84 mL, 2.84 mmol) in THF was added to an ice cold solution of Compound 10 (1.01 g, 1.90 mmol) in THF (15 mL). After 15 minutes the cooling bath was removed and the mixture was stirred at room temperature for 2.5 h. After being diluted with water (25 mL), the mixture was extracted with ethyl acetate (3×20 mL), the combined organic layer was washed with water and brine, dried over MgSO$_4$ and concentrated under reduced pressure. A suspension of the above crude product (600 mg, 2.07 mmol) and CuSO$_4$ (3.31 g, 20.7 mmol) in EtOH (15 mL) was cooled on an ice bath. Hydrazine monohydrate (6.51 ml, 207 mmol) was added drop wise, the mixture was subsequently stirred for 15 minutes at room temperature and then at 70° C. overnight. The reaction mixture was filtered over celite and concentrated under reduced pressure. The residue was purified by flash silica gel chromatography (10-50% ethyl acetate/pentane) to furnish tert-butyl (2R, 5R)-2-benzyl-5-hydroxypiperidine-1-carboxylate (11) (435 mg, 1.49 mmol, 72%) as a yellow oil. $[\alpha]_D^{22}$=−45.7 (c=0.70, CHCl$_3$). $^1$H NMR (400 MHz, CDCl$_3$) δ 7.30-7.23 (m, 2H), 7.21-7.13 (m, 3H), 4.35 (br s, 1H), 4.25 (br s, 1H), 3.97 (br s, 1H), 3.63-3.57 (m, 1H), 2.91 (dd, J=12.7, 8.2 Hz, 1H), 2.78-2.72 (m, 2H), 1.95-1.85 (m, 1H), 1.68-1.54 (m, 3H), 1.30 (s, 9H); $^{13}$C NMR (101 MHz, CDCl$_3$) δ 154.56, 138.79, 128.98, 128.21, 126.03, 79.48, 66.76, 51.71, 45.12, 35.62, 28.24, 28.04, 26.22; HRMS (m/z): [M+H]$^+$ calcd. for C$_{17}$H$_{25}$NO$_3$, 292.19072; found 292.19080.

To a solution of compound 11 (130 mg, 0.446 mmol) in DMF (3 mL) at 0° C., was added NaH (44.6 mg, 1.12 mmol). After 5 minutes followed by drop wise addition of 3-bromoprop-1-yne (0.144 mL, 1.34 mmol). The reaction was allowed to warm to room temperature and stirred for 24 hours. The mixture was diluted with water (10 mL), and extracted with ethyl acetate (3×20 mL). The organic layer was washed with water, brine, dried over MgSO$_4$, filtered, and concentrated under reduced pressure. The residue was purified by flash chromatography (5-20% ethyl acetate/pentane) to furnish tert-butyl (2R,5R)-2-benzyl-5-(prop-2-yn-1-yloxy)piperidine-1-carboxylate (12) (128 mg, 0.389 mmol, 87%) as a yellow oil. $[\alpha]_D^{22}$=−24.9 (c=1.00, CHCl$_3$); $^1$H NMR (400 MHz, CDCl$_3$) δ 7.29-7.25 (m, 2H), 7.20-7.16 (m, 3H), 4.42 (br s, 1H), 4.32 (br s, 1H), 4.22 (s, 2H), 3.50-3.45 (m, 1H), 2.88 (dd, J=13.5, 7.9 Hz, 1H), 2.76-2.70 (m, 2H), 2.46 (t, J=4.0 Hz, 1H), 2.00-1.93 (m, 1H), 1.66-1.57 (m, 3H), 1.28 (s, 9H). $^{13}$C NMR (101 MHz, CDCl$_3$) δ 154.71, 138.96, 129.24, 128.51, 126.34, 80.03, 79.71, 74.43, 74.07, 56.02, 52.14, 42.15, 35.90, 28.31, 25.85; HRMS (m/z): [M+H]$^+$ calcd. for C$_{20}$H$_{27}$NO$_3$, 330.20637; found 330.20643.

To a solution of compound 12 (140 mg, 0.425 mmol) in DCM (2 mL) was added 20% TFA/DCM (5 mL). The reaction mixture was stirred at room temperature for 2.5 hours, after which TLC showed complete conversion of the starting material. Toluene (20 mL) was added and the mixture concentrated. The mixture was dissolved in toluene (2×20 mL) two times more and concentrated in vacuo. The residue was diluted with ethyl acetate and washed subsequently with aqueous 10% Na$_2$CO$_3$ solution, water, brine and dried over MgSO$_4$. Filtering and concentration under reduced pressure afforded (2R,5R)-2-benzyl-5-(prop-2-yn-1-yloxy)piperidine (13) that was used without further purification. $^1$H NMR (400 MHz, CDCl$_3$) δ 7.31-7.26 (m, 2H), 7.23 (d, J=6.9 Hz, 1H), 7.18 (d, J=6.9 Hz, 2H), 4.21 (s, 2H), 4.03 (s, 1H), 3.45 (d, J=12.7 Hz, 1H), 3.29 (br s, 1H), 3.17 (dd, J=12.9, 4.1 Hz, 2H), 3.06 (d, J=11.5 Hz, 1H), 2.85 (dd, J=12.9, 9.7 Hz, 1H), 2.41 (t, J=2.1 Hz, 1H), 2.05 (d, J=13.3 Hz, 1H), 1.92-1.77 (m, 1H), 1.62 (d, J=11.9 Hz, 1H), 1.51 (t, J=13.3 Hz, 1H), 1.26 (br s, 1H). $^{13}$C NMR (101 MHz, CDCl$_3$) δ135.40, 129.45, 128.87, 127.28, 78.87, 75.31, 66.94, 57.89, 55.32, 47.04, 39.54, 25.91, 22.66. LC-MS (m/z): [1\4+H]$^+$ calcd. for C$_{15}$H$_{19}$NO, 230.32; found 230.10.

An ice cold solution of compound 13 (80 mg, 0.349 mmol) in THF (4 mL) was treated with DIPEA (0.305 mL, 1.74 mmol) and triphosgene (51.8 mg, 0.174 mmol) and the reaction mixture was stirred for 30 min at 0° C. The mixture was poured into water and extracted with ethyl acetate (3×20 mL). The organic layer was washed with water, brine, dried over MgSO$_4$, filtered and concentrated under reduced pressure. The intermediate was dissolved in a mixture of THF (8 mL) and DIPEA (0.305 mL, 1.74 mmol). Subsequently DMAP (42.6 mg, 0.349 mmol) and compound 3 (100 mg, 0.349 mmol) were added to the solution. The mixture was stirred for two hours at 60° C. and poured into a saturated aqueous NH$_4$Cl solution. The mixture was extracted with ethyl acetate (3×20 mL), washed with water, brine, dried over MgSO$_4$, filtered. The solvents were removed under reduced pressure to yield the crude triazole urea 14 as a mixture of N2- and N1-carbamoylated regioisomers. Regioisomers were easily distinguishable by $^1$H-NMR shift of the triazole ring proton by comparison to NMRs for urea triazoles of known regiochemistry based on solved crystal structures. The N2-carbamoyl triazole was isolated by silica gel chromatography (2-20% ethyl acetate/pentane) to afford 2,4-triazole urea (14) (47.3 mg, 0.087 mmol, 25%) as lower TLC spot. $[\alpha]_D^{22}$=−5.16 (c=1.00, CHCl$_3$); $^1$H NMR (400 MHz, (CD$_3$)$_2$SO, 110° C.) δ 7.90 (s, 1H), 7.39-7.35 (m, 4H), 7.23-7.16 (m, 3H), 7.13-7.07 (m, 5H), 6.64 (br d, J=4.0 Hz, 1H), 4.38 (br s, 1H), 4.16 (d, J=2.4 Hz, 2H), 4.05 (br d, J=12.0 Hz, 1H), 3.62-3.55 (m, 1H), 3.15 (br d, J=4.0 Hz, 1H), 3.08-2.97 (m, 3H), 2.01-1.96 (m, 1H), 1.76-1.63 (m, 3H); $^{13}$C NMR (101 MHz, CDCl$_3$, 60° C.) δ 162.57 (d, J=247 Hz), 155.76, 149.37, 140.95 (d, J=3.0 Hz), 137.67, 135.22, 129.96, 129.20 (d, J=8.1 Hz), 128.83, 126.94, 115.28 (d, J=22 Hz), 79.88, 76.69, 74.77, 73.61, 56.26, 55.17, 45.94, 36.10, 25.99, 25.88; IR (film) 3425, 2925, 1709, 1602, 1506, 1429, 1225, 1159, 1093 cm$^{-1}$; HRMS (m/z): [M+H]$^+$ calcd. for C$_{31}$H$_{28}$F$_2$N$_4$O$_3$, 543.21575; found 543.21552.

Example 2: tert-Butyl 3-benzyl-4-(4-(4-(trifluoromethoxy)phenyl)-1H-1,2,3-triazole-1-carbonyl)piperazine-1-carboxylate (17)

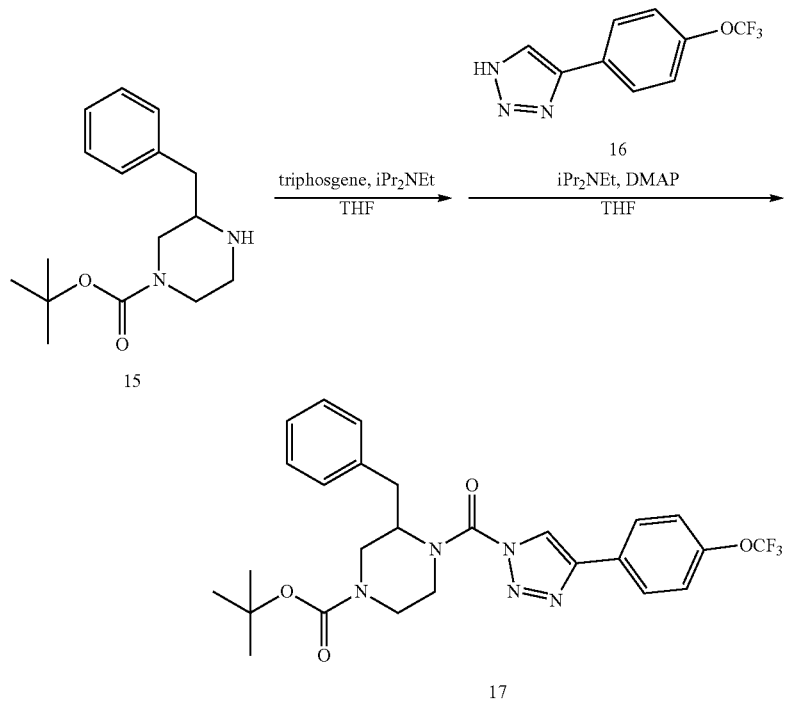

A solution of 1-Boc-3-benzylpiperazine (350 mg, 1.3 mmol) (15) in dry THF (9.5 mL) was treated with iPr$_2$NEt (670 μL, 3.7 mmol) and triphosgene (190 mg, 0.63 mmol), and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The residue was dissolved in THF (20 mL), and iPr$_2$NEt (670 μL, 3.7 mmol), DMAP (150 mg, 1.3 mmol) and 4-(4-trifluoromethoxyphenyl)-1H-1,2,3-triazole (16) (J. Med. Chem, (21):8257-8269) (290 mg, 1.3 mmol) were added to the solution. The mixture was stirred for 1.5 h at 50° C. and poured into saturated aqueous NH$_4$Cl solution. The mixture was extracted with ethyl acetate. The organic layer was washed with H$_2$O and brine, dried over Na$_2$SO$_4$ and concentrated under reduced pressure. The residue was purified by flash column chromatography (ethyl acetate:hexane=1:8 to 1:3) to afford tert-butyl 3-benzyl-4-(4-(4-(trifluoromethoxy)phenyl)-1H-1,2,3-triazole-1-carbonyl)piperazine-1-carboxylate (17) (230 mg, 34%). $^1$H NMR (CDCl$_3$, 600 MHz) δ 7.87-7.79 (m, 2H), 7.57 (s, 1H), 7.32-7.17 (m, 5H), 7.01 (s, 1H), 4.94-4.05 (m, 4H), 3.58-3.49 (m, 1H), 3.23-2.80 (m, 4H), 1.50 (s, 9H). $^{13}$C NMR (CDCl$_3$, 150 MHz) 154.89, 149.45, 145.37, 137.10, 129.39, 128.87, 128.34, 127.35, 126.92, 121.57, 120.57 (q, J=256.0 Hz, OCF$_3$), 80.81, 57.38, 46.73, 43.63, 42.53, 40.60, 36.08, 28.48, 14.28. HRMS calculated for C$_{26}$H$_{28}$F$_3$N$_5$O$_4$ [M+H]$^+$ 532.2166, found 532.2167.

Example 3: (2-Benzylpiperidin-1-yl)(4-(4-(3,5-dimethoxypyridin-4-yl)phenyl)-1H-1,2,3-triazol-1-yl)methanone (19)

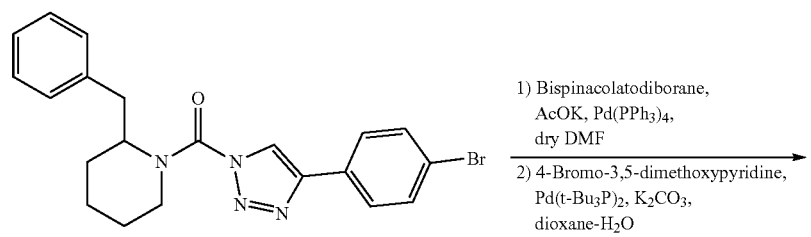

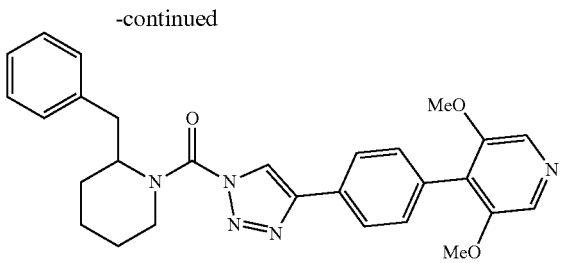

19

A solution of compound 18 (J. Med. Chem, (21):8257-8269) (55 mg, 0.13 mmol), bispinacolatodiborane (85 mg, 0.33 mmol), AcOK (39 mg, 0.40 mmol) and Pd(PPh$_3$)$_4$ (40 mg, 0.036 mmol) in dry DMF (1.7 mL) was sealed in a vessel and heated in the microwave at 100° C. for 1 h. The mixture was diluted with AcOEt, washed with sat. NH$_4$Cl and brine, dried over Na$_2$SO$_4$ and concentrated under reduced pressure. The residue was passed through a short column (ethyl acetate:hexane=1:5) to give the crude pinacolatoborane. Resulting crude, 4-bromo-3,5-dimethoxypyridine (32 mg, 0.15 mmol), K$_2$CO$_3$ (27 mg, 0.19 mmol) and Pd(t-Bu$_3$P)$_2$ (15 mg, 0.029 mmol) in dioxane-H$_2$O was sealed in a vessel and heated in the microwave at 100° C. for 1 h. The mixture was diluted with AcOEt, washed with sat. NH$_4$Cl, H$_2$O and brine, dried over Na$_2$SO$_4$ and concentrated under reduced pressure. The residue was purified by flash column chromatography (ethyl acetate:hexane=1:1 to 3:1) to afford (2-benzylpiperidin-1-yl)(4-(4-(3,5-dimethoxypyridin-4-yl)phenyl)-1H-1,2,3-triazol-1-yl)methanone (19) (24 mg, 38%). $^1$H NMR (CDCl$_3$, 600 MHz) δ 8.12 (s, 2H), 7.84 (br s, 2H), 7.45 (d, 2H, J=8.4 Hz), 7.20 (br s, 3H), 6.99 (br s, 1H), 4.85 (br s, 1H), 4.34 (d, 1H, J=13.2 Hz), 3.85 (s, 6H), 3.34-2.22 (m, 2H), 2.69 8 (br s, 1H), 2.10-1.60 (m, 6H). $^{13}$C NMR (CDCl$_3$, 150 MHz) 152.53, 148.81, 145.77, 137.48, 131.13, 130.52, 128.72, 128.27, 127.57, 126.17, 125.51, 125.20, 120.18, 56.88, 56.29, 43.33, 40.72, 36.18, 35.57, 28.18, 25.04, 18.35. HRMS calculated for C$_{28}$H$_{29}$N$_5$O$_3$ [M+H]$^+$ 484.2343, found 484.2344.

Example 4: (2-Benzylpiperidin-1-yl)(4-(2',4',6'-trimethoxybiphenyl-4-yl)-1H-1,2,3-triazol-1-yl)methanone (20)

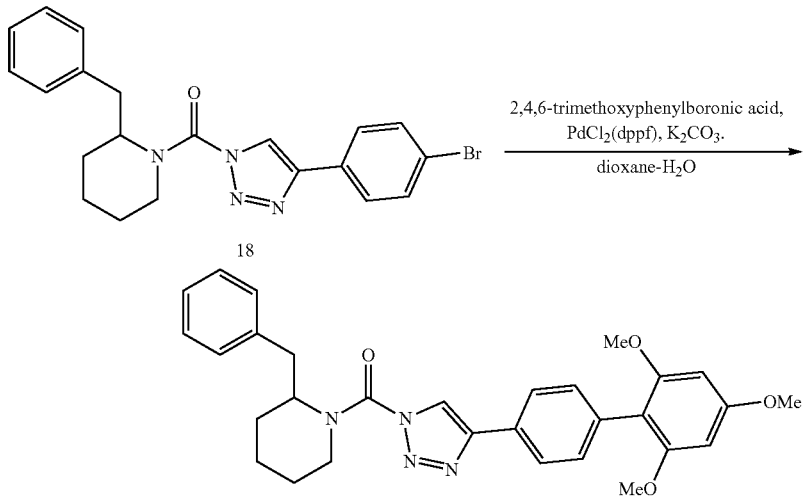

A solution of compound 18 (20 mg, 0.047 mmol), 2,4,6-trimethoxyphenylboronic acid (28 mg, 0.13 mmol), K$_2$CO$_3$ (20 mg, 0.15 mmol) and PdCl$_2$(dppf) (12 mg, 0.014 mmol) in dioxane (1 mL) and H$_2$O (0.1 mL) was sealed in a vessel and heated in the microwave at 100° C. for 1 h. The mixture was poured into H$_2$O and extracted with ethyl acetate. The organic layer was washed with H$_2$O and brine, dried over Na$_2$SO$_4$ and concentrated under reduced pressure. The residue was purified by pTLC (ethylacetate:hexane=1:2) to afford (2-benzylpiperidin-1-yl)(4-(2',4',6'-trimethoxybiphenyl-4-yl)-1H-1,2,3-triazol-1-yl)methanone (20) (14 mg, 59%). $^1$H NMR (CDCl$_3$, 600 MHz) δ 7.84 (s, 2H), 7.51 (s, 1H), 7.45 (d, 2H, J=7.8 Hz), 7.25 (br s, 3H), 7.04 (br s, 1H), 6.28 (s, 2H), 4.91 (s, 1H), 4.39 (1H, d, J=6.3 Hz), 3.90 (s, 3H), 3.78 (s, 6H), 3.38-3.26 (m, 2H), 2.74 (br s, 1H), 2.07-1.66 (m, 6H). $^{13}$C NMR (CDCl$_3$, 150 MHz) 160.89, 158.56, 149.56, 146.89, 138.13, 134.73, 131.99, 129.35, 128.92, 127.92, 126.83, 125.34, 120.53, 112.03, 91.14, 57.58, 56.11, 55.60, 43.88, 41.07, 36.76, 28.99, 25.63, 19.08. HRMS calculated for C$_{30}$H$_{32}$N$_4$O$_4$ [M+H]$^+$ 513.2496, found 513.2495.

Example 5: tert-Butyl 3-phenyl-4-(4-(4-(trifluoromethoxy)phenyl)-1H-1,2,3-triazole-1-carbonyl)piperazine-1-carboxylate (22) and tert-butyl 3-phenyl-4-(4-(4-(trifluoromethoxy)phenyl)-2H-1,2,3-triazole-2-carbonyl)piperazine-1-carboxylate (23)

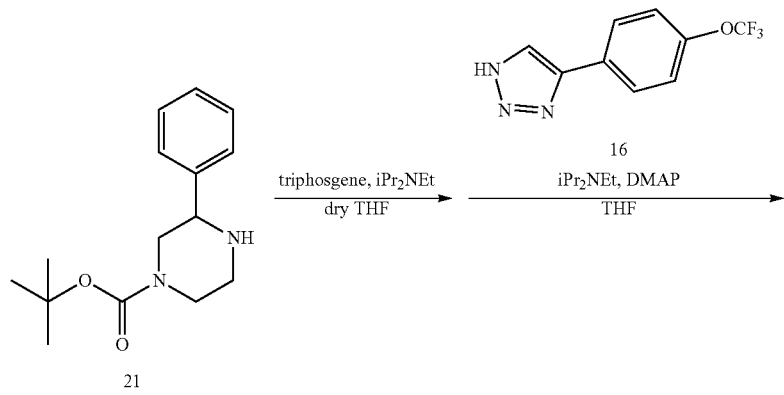

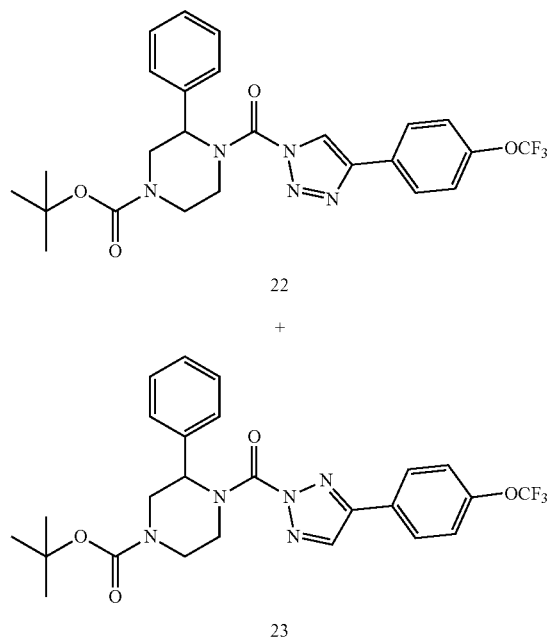

A solution of 1-Boc-3-phenylpiperazine (350 mg, 1.3 mmol) (21) in dry THF (9.5 mL) was treated with iPr₂NEt (720 μL, 4.0 mmol) and triphosgene (200 mg, 0.67 mmol), and the reaction mixture was stirred for 30 min at 4° C. The mixture was poured into H₂O and extracted with ethyl acetate. The organic layer was washed with H₂O and brine, dried over Na₂SO₄ and concentrated under reduced pressure. The residue was dissolved in THF (20 mL), and iPr₂NEt (720 μL, 4.0 mmol), DMAP (160 mg, 1.3 mmol) and 4-(4-trifluoromethoxyphenyl)-1H-1,2,3-triazole (16) (300 mg, 1.3 mmol) were added to the solution. The mixture was stirred for 1.5 h at 50° C. and poured into saturated aqueous NH₄Cl solution. The mixture was extracted with ethyl acetate. The organic layer was washed with H₂O and brine, dried over Na₂SO₄ and concentrated under reduced pressure. The residue was purified by flash column chromatography (ethyl acetate:hexane=1:3) to afford tert-butyl 3-phenyl-4-(4-(4-(trifluoromethoxy)phenyl)-1H-1,2,3-triazole-1-carbonyl)piperazine-1-carboxylate (22) (240 mg, 35%) and tert-butyl 3-phenyl-4-(4-(4-(trifluoromethoxy)phenyl)-2H-1,2,3-triazole-2-carbonyl)piperazine-1-carboxylate (23) (263 mg, 38%). Compound 22: $^1$H NMR (CDCl₃, 600 MHz) δ 8.40 (s, 1H), 7.88 (d, 2H, J=8.6 Hz), 7.41-7.24 (m, 7H), 5.84 (s, 1H), 4.68 (s, 1H), 4.41 (s, 1H), 4.13 (s, 0.5H), 3.94 (s, 0.5H), 3.52-3.17 (m, 3H), 1.45 (s, 9H). $^{13}$C NMR (CDCl₃, 150 MHz) 154.74, 154.37, 149.69, 149.05, 146.01, 136.78, 129.14, 128.29, 128.20, 127.63, 127.13, 121.50, 120.65 (q, J=256.2 Hz, OCF₃), 80.97, 58.68, 45.96, 44.33, 43.09, 28.56, 18.65. HRMS calculated for $C_{25}H_{26}F_3N_5O_4$ [M+H]⁺ 518.2010, found 518.2009. Compound 23: ESI-MS [M+Na]⁺ 540.2.

Example 6: 1-(3-Benzyl-4-(4-(4-(trifluoromethoxy)phenyl)-1H-1,2,3-triazole-1-carbonyl)piperazin-1-yl)-2-methylpropan-1-one (26) and 1-(3-Benzyl-4-(4-(4-(trifluoromethoxy)phenyl)-2H-1,2,3-triazole-2-carbonyl)piperazin-1-yl)-2-methylpropan-1-one (27)

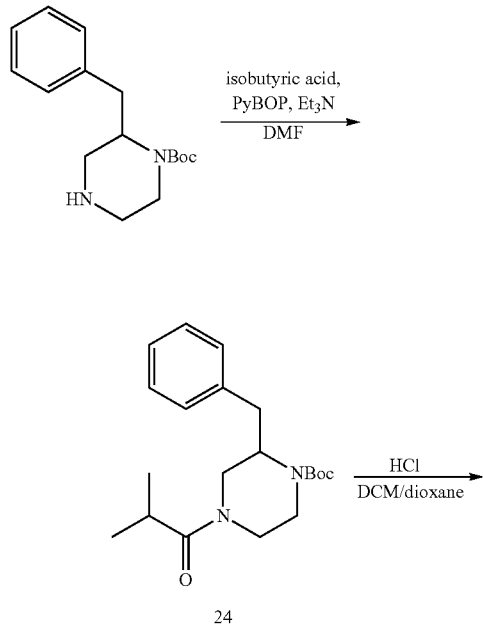

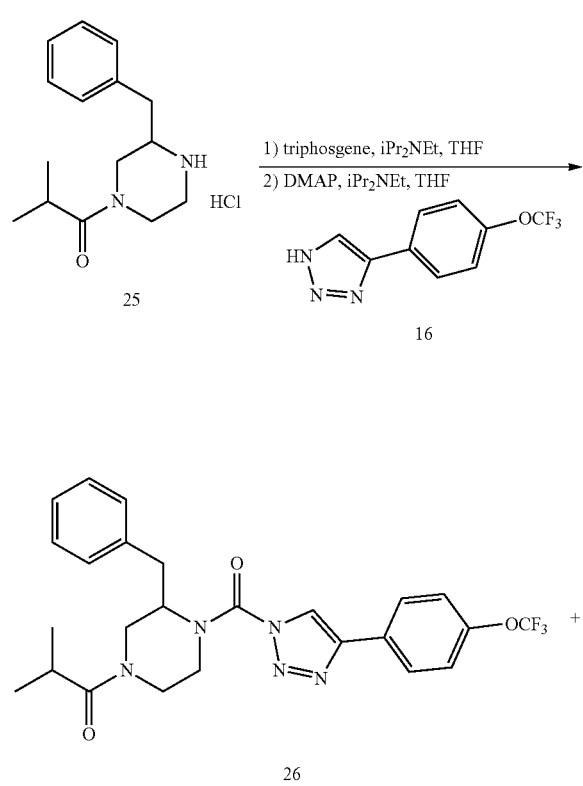

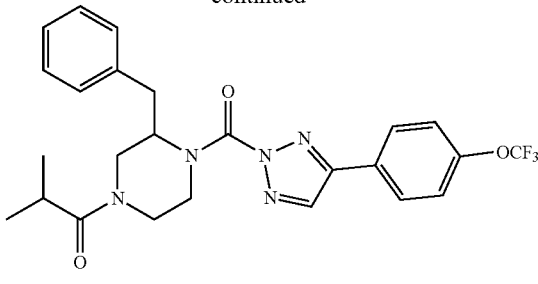

27

A solution of 1-Boc-2-benzylpiperazine (20 mg, 0.072 mmol) (1) in dry DMF (0.6 mL) was treated with isobutyric acid (7.3 μL, 0.079 mmol), iPr$_2$NEt (19.6 μL, 0.14 mmol) and PyBOP (49 mg, 0.094 mmol), and the reaction mixture was stirred for 2 h at room temp. The mixture was poured into Sat. NaHCO$_3$ and extracted with DCM. The organic layer was washed with brine, dried over Na$_2$SO$_4$ and concentrated under reduced pressure. The residue was purified by flash column chromatography (ethyl acetate:hexane=1:5) to afford intermediate 24 (25 mg, 100%).

To intermediate 24 in DCM (0.6 mL) was added 4N HCl in dioxane (0.34 mL, 1.36 mmol) in a dropwise fashion and stirred for 4 h at room temp. The mixture was concentrated under the stream of nitrogen to give intermediate 25.HCl, which was used in the next step without further purification.

A solution of intermediate 25-HCl (10.4 mg, 0.037 mmol) in dry THF (0.3 mL) was treated with iPr$_2$NEt (30 μL, 0.15 mmol) and triphosgene (5.6 mg, 0.019 mmol), and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The residue was dissolved in THF (0.42 mL), and iPr$_2$NEt (23 μL, 0.12 mmol), DMAP (4.6 mg, 0.037 mmol) and 4-(4-trifluoromethoxyphenyl)-1H-1,2,3-triazole (16) (8.6 mg, 0.037 mmol) were added to the solution. The mixture was stirred for 1.5 h at 50° C. and poured into saturated aqueous NH$_4$Cl solution. The mixture was extracted with ethyl acetate. The organic layer was washed with H$_2$O and brine, dried over Na$_2$SO$_4$ and concentrated under reduced pressure. The residue was purified by preparative TLC (ethyl acetate:hexane=2:5) to afford 1-(3-benzyl-4-(4-(4-(trifluoromethoxy)phenyl)-1H-1,2,3-triazole-1-carbonyl)piperazin-1-yl)-2-methylpropan-1-one (26) (2.9 mg, 16%) and 1-(3-benzyl-4-(4-(4-(trifluoromethoxy)phenyl)-2H-1,2,3-triazole-2-carbonyl)piperazin-1-yl)-2-methylpropan-1-one (27) (4.1 mg, 22%). Compound 26: $^1$H NMR (CDCl$_3$, 600 MHz) δ 7.82 (brs, 2H), 7.54-6.97 (m, 7H), 5.20-2.76 (m, 10H), 3.80 (s, 3H), 1.28-1.11 (m, 6H). ESI-MS [M+Na]$^+$ 524.1. Compound 27: ESI-MS [M+Na]$^+$524.1.

Example 7: 1-(3-Benzyl-4-(4-(4-(trifluoromethoxy)
phenyl)-1H-1,2,3-triazole-1-carbonyl)piperazin-1-
yl)-2-methylpropan-1-one (30) and 1-(3-Benzyl-4-
(4-(4-(trifluoromethoxy)phenyl)-2H-1,2,3-triazole-
2-carbonyl)piperazin-1-yl)-2-methylpropan-1-one
(31)

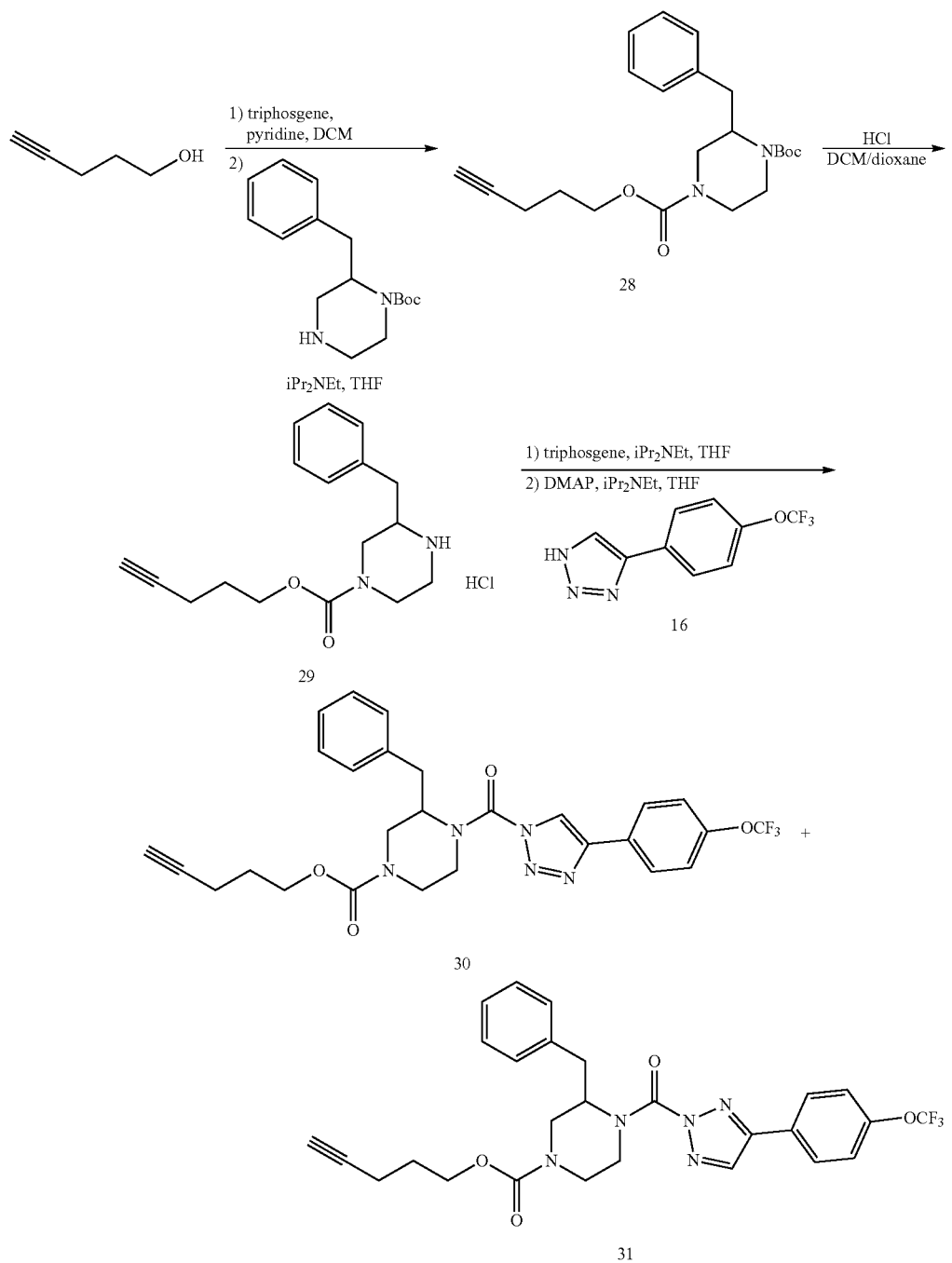

A solution of 4-pentyne-1-ol (22 mg, 0.25 mmol) in dry DCM (2.5 mL) was treated with pyridine (21 μL, 0.25 mmol) and triphosgene (75.6 mg, 0.25 mmol), and the reaction mixture was stirred for 30 min at 0° C. The mixture was poured into H₂O and extracted with ethyl acetate. The organic layer was washed with H₂O and brine, dried over Na2SO4 and concentrated under reduced pressure. The residue was dissolved in THF (2 mL), and iPr₂NEt (21 μL, 0.11 mmol), and 1-Boc-2-benzylpiperazine (10 mg, 0.036 mmol) were added to the solution. The mixture was stirred for 2 h at room temp and poured into saturated aqueous NH₄Cl solution. The mixture was extracted with ethyl acetate. The organic layer was washed with H₂O and brine, dried over Na₂SO₄ and concentrated under reduced pressure. The residue was purified by flash column chromatography (ethyl acetate:hexane=1:4) to afford intermediate 28 (14 mg, 100%).

To intermediate 28 in DCM (0.8 mL) was added 4N HCl in dioxane (0.8 mL, 3.2 mmol) in a dropwise fashion and stirred for 4 h at room temp. The mixture was concentrated under the stream of nitrogen to give intermediate 29.HCl, which was used in the next step without further purification.

A solution of intermediate 29.HCl (11 mg, 0.036 mmol) in dry THF (0.3 mL) was treated with iPr₂NEt (30 μL, 0.15 mmol) and triphosgene (5.3 mg, 0.018 mmol), and the reaction mixture was stirred for 30 min at 4° C. The mixture was poured into H₂O and extracted with ethyl acetate. The organic layer was washed with H₂O and brine, dried over Na₂SO₄ and concentrated under reduced pressure. The residue was dissolved in THF (1.0 mL), and iPr₂NEt (21 μL, 0.11 mmol), DMAP (4.4 mg, 0.035 mmol) and 4-(4-trifluoromethoxyphenyl)-1H-1,2,3-triazole (16) (8.1 mg, 0.035 mmol) were added to the solution. The mixture was stirred for 1.5 h at 50° C. and poured into saturated aqueous NH₄Cl solution. The mixture was extracted with ethyl acetate. The organic layer was washed with H₂O and brine, dried over Na₂SO₄ and concentrated under reduced pressure. The residue was purified by preparative TLC (ethyl acetate:hexane=1:3) to afford 1-(3-benzyl-4-(4-(4-(trifluoromethoxy)phenyl)-1H-1,2,3-triazole-1-carbonyl)piperazin-1-yl)-2-methylpropan-1-one (30) (6.2 mg, 32%) and 1-(3-benzyl-4-(4-(4-(trifluoromethoxy)phenyl)-2H-1,2,3-triazole-2-carbonyl)piperazin-1-yl)-2-methylpropan-1-one (31) (7.3 mg, 38%). Compound 30: ¹H NMR (CDCl₃, 600 MHz) δ 7.88-7.80 (m, 2H), 7.55 (s, 1H), 7.34-7.00 (m, 6H), 5.02 (brs, 1H), 4.72-4.10 (m, 5H), 3.60-2.79 (m, 5H), 2.30 (brs, 2H), 1.99 (s, 1H), 1.92 (brs, 2H). ESI-MS [M+Na]⁺ 564.2. Compound 31: ¹H NMR (CDCl₃, 600 MHz) δ 8.06 (s, 1H), 7.84 (d, 2H, J=8.8 Hz), 7.34-7.23 (m, 7H), 4.65 (brs, 1H), 4.30-4.04 (m, 5H), 3.51 (brs, 1H), 3.13-3.01 (m, 4H), 2.30 (brs, 2H), 2.00 (s, 1H), 1.91 (brs, 2H). ESI-MS [M+Na]⁺564.1.

Example 8: 1-(3-Benzyl-4-(4-(4-(trifluoromethoxy)phenyl)-1H-1,2,3-triazole-1-carbonyl)piperazin-1-yl)hex-5-yn-1-one (34) and 1-(3-Benzyl-4-(4-(4-(trifluoromethoxy)phenyl)-2H-1,2,3-triazole-2-carbonyl)piperazin-1-yl)hex-5-yn-1-one (35)

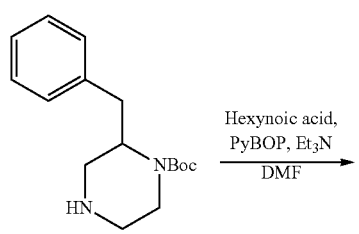

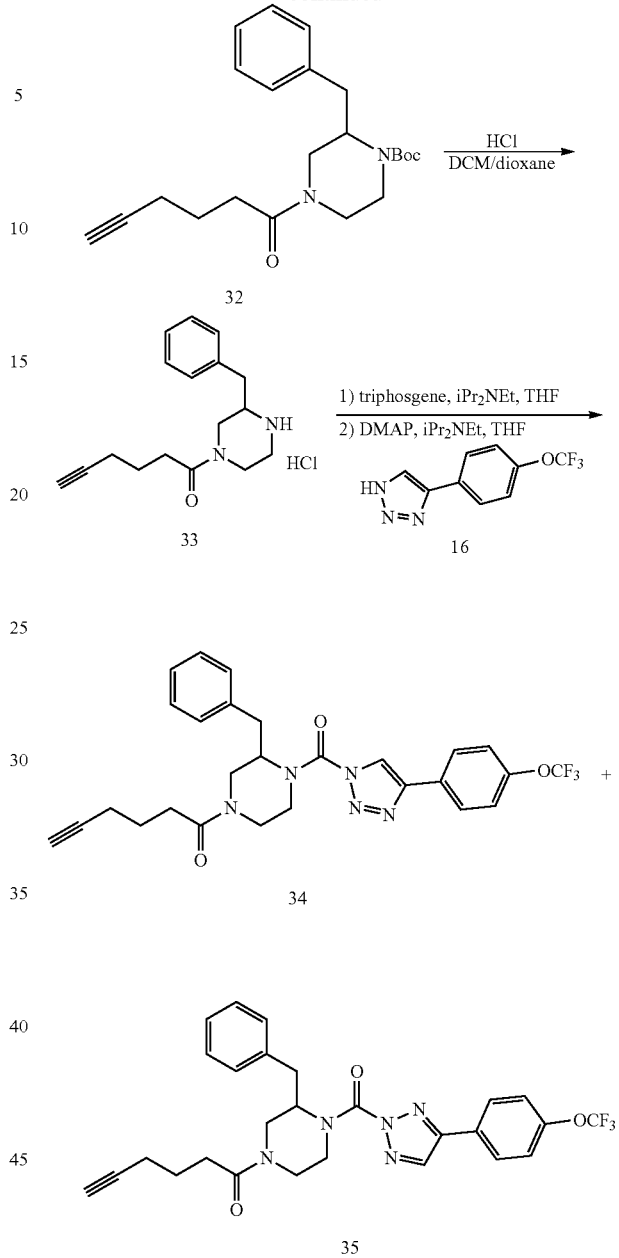

A solution of 1-Boc-2-benzylpiperazine (10 mg, 0.036 mmol) in dry DMF (0.3 mL) was treated with hexynoic acid (4.5 μL, 0.040 mmol), Et₃N (10 μL, 0.07 mmol) and PyBOP (24 mg, 0.049 mmol), and the reaction mixture was stirred for 3 h at room temp. The mixture was poured into Sat. NaHCO₃ and extracted with EtOAc. The organic layer was washed with brine, dried over Na₂SO₄ and concentrated under reduced pressure. The residue was purified by flash column chromatography (ethyl acetate:hexane=1:3) to afford intermediate 32 (13 mg, 100%).

To intermediate 32 in DCM (0.8 mL) was added 4N HCl in dioxane (0.8 mL, 3.2 mmol) in a dropwise fashion and stirred for 3 h at room temp. The mixture was concentrated under the stream of nitrogen to give intermediate 33.HCl, which was used in the next step without further purification.

A solution of intermediate 33.HCl (11 mg, 0.036 mmol) in dry THF (0.3 mL) was treated with iPr₂NEt (30 μL, 0.15 mmol) and triphosgene (5.3 mg, 0.018 mmol), and the reaction mixture was stirred for 30 min at 4° C. The mixture was poured into H₂O and extracted with ethyl acetate. The organic layer was washed with H₂O and brine, dried over Na₂SO₄ and concentrated under reduced pressure. The residue was dissolved in THF (1.0 mL), and iPr₂NEt (21 µL, 0.11 mmol), DMAP (4.4 mg, 0.035 mmol) and 4-(4-trifluoromethoxyphenyl)-1H-1,2,3-triazole (16) (8.1 mg, 0.035 mmol) were added to the solution. The mixture was stirred for 1.5 h at 50° C. and poured into saturated aqueous NH₄Cl solution. The mixture was extracted with ethyl acetate. The organic layer was washed with H₂O and brine, dried over Na₂SO₄ and concentrated under reduced pressure. The residue was purified by preparative TLC (ethyl acetate:hexane=2:5) to afford 1-(3-benzyl-4-(4-(4-(trifluoromethoxy)phenyl)-1H-1,2,3-triazole-1-carbonyl)piperazin-1-yl)hex-5-yn-1-one (34) (6.1 mg, 32%) and 1-(3-benzyl-4-(4-(4-(trifluoromethoxy)phenyl)-2H-1,2,3-triazole-2-carbonyl)piperazin-1-yl)hex-5-yn-1-one (35) (6.0 mg, 31%). Compound 34: ¹H NMR (CDCl₃, 600 MHz) δ 7.82 (brs, 2H), 7.47-6.98 (m, 7H), 5.21-2.31 (m, 13H), 2.04-1.91 (s, 2H), 1.95 (s, 1H). ESI-MS [M+Na]⁺548.2. Compound 35: ¹H NMR (CDCl₃, 600 MHz) δ 8.06 (s, 1H), 7.89 (d, 2H, J=8.8 Hz), 7.34-7.21 (m, 7H), 4.84-4.58 (m, 2H), 4.29-4.01 (m, 2H), 3.51-2.97 (m, 5H), 2.68-2.18 (m, 4H), 2.04-1.87 (m, 3H). ESI-MS [M+Na]⁺548.2.

Example 9: ((2R,5S)-2-Benzyl-5-(cyclopropylmethoxy)piperidin-1-yl)(4-(4-(trifluoromethoxy)phenyl)-1H-1,2,3-triazol-1-yl)methanone (44) and ((2R,5S)-2-Benzyl-5-(cyclopropylmethoxy)piperidin-1-yl)(4-(4-(trifluoromethoxy)phenyl)-2H-1,2,3-triazol-2-yl)methanone (45)

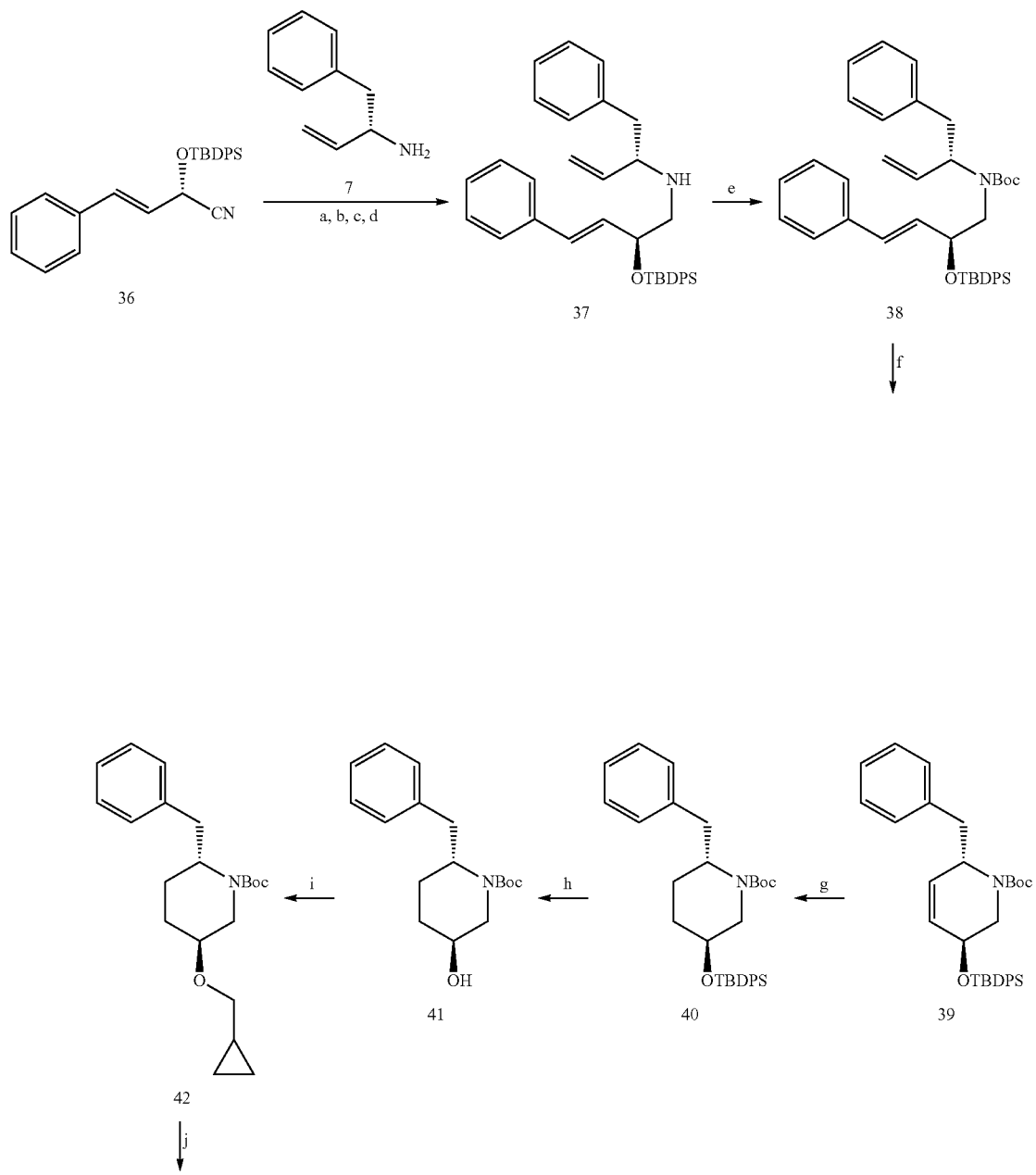

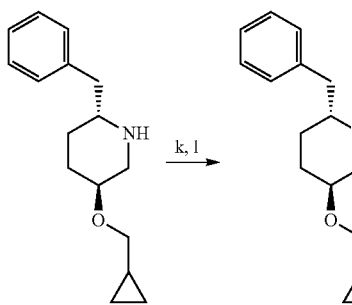

43

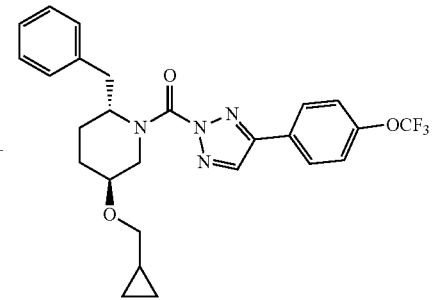

44    45

Reagents and conditions: (a) diethyl ether, DIBAL-H, -80° C. to 0° C.; (b) MeOH, -90° C.; (c) (S)-amine (7) (3 equiv), r.t., 20 h (d) NaBH₄; (e) Boc₂O, TEA, THF, 50° C., 20 h; (f) Grubbs I cat. 4 mol %, DCM, reflux, 48 h; (g) Hydrazine, CuSO₄, EtOH, 0° to 70° C.; (h) TBAF, THF, r.t.; (i) NaH, (bromomethyl)cyclopropane; (j) 25% TFA, DCM, r.t.; (k) DIPEA, Triphosgene, THF, 0° C.; (l) DIPEA, DMAP, traizole, THF, 60° C.

Under an argon atmosphere cyanohydrin 36 (2.80 g, 7.05 mmol) was dissolved in dry diethyl ether (40 mL) and at −78° C. a 1.0 M solution of DIBAL-H in toluene (11.0 mL, 11.0 mmol) was added dropwise in 15 min. The mixture was slowly warmed on the cooling bath to 5° C. After re-cooling to −90° C., methanol (10 mL) was added at once, followed by a solution of (S)-1-phenylbut-3-en-2-amine 7 (3.00 g, 20.4 mmol) in methanol (10 mL). The cooling bath was removed and the remaining mixture stirred at room temperature, under a light flow of argon, for 28 h. The remaining mixture was cooled on an ice-bath and NaBH₄ (880 mg, 23.0 mmol) was added in three portions with five minute intervals. The mixture was stirred overnight while slowly warming to room temperature. The reaction was quenched with a 0.8 M NaOH solution (150 mL) and the resulting mixture extracted with diethyl ether (3×60 mL). The combined organic layers were washed subsequently with 1.0 M HCl solution (2×30 mL) and 0.8 M NaOH solution, dried (MgSO₄), filtered and concentrated in vacuo to afford the crude product that was purified by silica gel column chromatography (pentane/EtOAc=97:3→9:1) to give the target amine 37 as a colorless oil (3.50 g, 93%). $[\alpha]_D^{23}$=+116 (c=1.0, CHCl₃). HRMS calculated for C₃₆H₄₁NOSi [M+H]⁺: 532.3030 found: 532.3021. IR: 3071, 3026, 2930, 2893, 2857, 1495, 1454, 1427, 1362, 1109, 1059, 962, 918. ¹H NMR (400 MHz, CDCl₃) δ 7.66 (dd, J=8.0, 1.4 Hz, 2H), 7.61 (dd, J=8.0, 1.4 Hz, 2H), 7.42-7.05 (m, 16H), 6.09-5.91 (m, 2H), 5.59 (ddd, J=17.0, 10.3, 8.0 Hz, 1H), 5.07-4.92 (m, 2H), 4.37 (app. q, J=6.1 Hz, 1H), 3.23 (app q, J=7.7 Hz, 1H), 2.76-2.61 (m, 4H), 1.59 (br s, 1H), 1.00 (s, 9H). ¹³C NMR (101 MHz, CDCl₃) δ 140.67, 138.36, 136.66, 135.89, 135.88, 134.05, 133.95, 131.00, 130.58, 129.54, 129.41, 129.28, 128.30, 128.22, 127.47, 127.34, 127.30, 126.38, 126.21, 116.00, 74.22, 62.69, 53.55, 42.40, 26.99, 19.25.

To a solution of intermediate 37 (3.30 g, 6.21 mmol) in THF (50 mL) was added Boc₂O (2.80 g, 12.8 mmol) and Et₃N (2 mL). The mixture was heated at reflux overnight. Concentration in vacuo and purification by silica gel column chromatography (pentane/EtOAc=99:1→97:3) afforded intermediate 38 (5.10 g). $[\alpha]_D^{21}$=−4.6 (c=1.0, CHCl₃). HRMS calculated for C₄₁H₄₉NO₃Si [M+H]⁺: 632.3555; found: 632.3555. IR 3069, 3028, 2963, 2930, 2859, 1694, 1454, 1427, 1410, 1366, 1250, 1167, 1113, 964. ¹H NMR (400 MHz, CDCl₃) mixture of rotamers (2:1 ratio): δ 7.75 (d, J=6.8 Hz, 2H), 7.68 (d, J=6.8 Hz, 2H), 7.47-7.29 (m, 6H), 7.29-7.11 (m, 8H), 7.08-6.95 (m, 2H), 6.10 (s, 0.35H), 6.06 (s, 0.65H), 5.92-5.63 (m, 2H), 4.93 (d, J=10.5 Hz, 1H), 4.88 (d, J=17.4 Hz, 1H), 4.33 (br s, 0.4H), 4.12 (br s, 1H), 3.91 (br s, 0.6H), 3.53-3.15 (m, 1H), 3.13-2.64 (m, 3H), 1.23 (s, 3H), 1.19 (s, 6H), 1.07 (s, 9H). ¹³C NMR (101 MHz, CDCl₃) mixture of rotamers (2:1 ratio): δ 154.77, 138.63, 137.93, 137.23, 137.01, 135.98, 135.88, 134.16, 133.59, 130.73, 130.41, 129.66, 129.30, 128.22, 128.16, 127.59, 127.47, 127.11, 126.35, 126.17, 115.87, 79.34, 73.59 (minor CHO), 72.58 (major CHO), 62.70 (major CHN), 61.71 (minor CHN), 53.02 (major CH₂N), 50.99 (minor CH₂N), 38.64 (minor CH₂Ph), 38.12 (major CH₂Ph), 28.13, 27.03, 19.27.

Intermediate 38 (5.10 g) was dissolved in DCM under argon. Grubbs I catalyst (309 mg, 0.375 mmol) was added and the mixture was heated at reflux overnight. The solvent was evaporated and the crude product purified by silica gel column chromatography (pentane/EtOAc=99:1→96:4) to intermediate 39 as a colorless oil (2.84 g, 5.39 mmol, 76% over two steps). $[\alpha]_D^{21}$=+159 (c=1.0, CHCl₃). HRMS calculated for C₃₃H₄₁NO₃Si [M+H]⁺: 528.2929; found: 528.2922. IR 3028, 2971, 2931, 2858, 1810, 1756, 1692, 1454, 1448, 1417, 1364, 1112, 1072. ¹H NMR (400 MHz, CDCl₃, 60° C.) δ 7.70 (d, J=7.4 Hz, 2H), 7.64 (d, J=7.7 Hz, 2H), 7.41-7.27 (m, 6H), 7.24-7.09 (m, 5H), 5.62 (dd, J=10.1, 3.7 Hz, 1H), 5.59-5.52 (m, 1H), 4.69 (br s, 1H), 4.23 (br s, 1H), 4.07-3.98 (m, 1H), 2.82 (dd, J=12.9, 5.9 Hz, 1H), 2.77-2.67 (m, 2H), 1.44 (s, 9H), 1.04 (s, 9H). ¹³C NMR (101 MHz, CDCl₃, 60° C.) δ 154.73, 138.04, 135.80, 134.65, 134.22, 131.16, 129.60, 129.46, 128.22, 127.61, 127.42, 126.53, 126.25, 79.35, 64.08, 38.95, 28.44, 26.95, 19.20.

A suspension of intermediate 39 (500 mg, 0.947 mmol) and copper (II) sulfate (1.50 g, 9.47 mmol) in ethanol (2 mL) was cooled on an ice bath. Hydrazine (3.01 mL, 96.0 mmol) was added drop wise and the reaction was subsequently stirred for 15 min. After that, the reaction mixture was stirred at 70° C. for 24 h until TLC showed the reaction was completed. The mixture was filtered over celite and concentrated in vacuo. The residue was diluted with ethyl acetate and washed with water, brine and dried over MgSO₄, and concentrated in vacuo. The residue was purified by flash chromatography (pentane/EtOAc=99:1→90:10) to furnish intermediate 40 (400 mg, 0.756 mmol, 80% yield) as a colorless oil. LC-MS m/z: calculated for C₃₃H₄₃NO₃Si [M+H]⁺ 530.30, found 530.81. ¹H NMR (400 MHz, CDCl₃) δ 7.72-7.65 (m, 4H), 7.42-7.33 (m, 6H), 7.27-7.20 (m, 2H), 7.18-7.14 (m, 3H), 4.56 (br s, 1H), 4.09 (br d, J=7.0 Hz, 1H), 3.91 (br s, 1H), 2.94-2.78 (m, 2H), 2.72-2.61 (m, 1H), 2.19

(br, 1H), 1.72-1.47 (m, 3H), 1.35 (s, 9H), 1.06 (s, 9H). $^{13}$C NMR (101 MHz, CDCl$_3$) δ 155.20, 139.35, 135.97, 135.79, 134.52, 133.99, 129.72, 129.66, 129.27, 128.36, 127.69, 127.64, 126.16, 79.04, 65.79, 50.37, 44.02, 35.99, 28.41, 27.04, 26.24, 20.28, 19.38.

A solution of TBAF (2.83 mL, 2.83 mmol) was added to a solution of intermediate 40 (1.00 g, 1.89 mmol) in THF (15 mL) with ice cooling and the mixture was stirred at r.t. for 2.5 h, After being diluted with water, the mixture was extracted with ethyl acetate (3 times), the organic layer was washed with water and brine, dried over MgSO$_4$ and concentrated under in vacuo. The residue was purified by flash chromatography (pentane/EtOAc=99:1→80:20) to furnish intermediate 41 (440 mg, 1.51 mmol, 80% yield) as a colorless oil. [α]$_D^{22}$=−33 (c=1.0, CHCl$_3$). LC-MS m/z: calculated for C$_{17}$H$_{25}$NO$_3$ [M+H]$^+$ 292.18, found: 292.71. $^1$H NMR (400 MHz, CDCl$_3$) δ 7.30-7.25 (m, 2H), 7.21-7.15 (m, 3H), 4.35 (br s, 1H), 4.25 (br s, 1H), 3.64-3.57 (m, 1H), 2.91 (dd, J=13.1, 8.1 Hz, 1H), 2.75 (dd, J=12.8, 10.8 Hz, 2H), 1.90 (br s, 1H), 1.66-1.59 (m, 3H), 1.30 (s, 9H). $^{13}$C NMR (101 MHz, CDCl$_3$) δ 154.78, 138.98, 129.20, 128.44, 126.26, 79.72, 67.03, 53.90, 45.69, 35.81, 28.26, 28.12, 26.28.

To a solution of intermediate 41 (100 mg, 0.344 mmol) and NaH (60%, 24.7 mg, 1.03 mmol) in DMF (3 mL) at 0° C., (bromomethyl)cyclopropane (139 mg, 1.03 mmol) was added dropwise with continuous stirring, and the mixture was allowed to stand at room temperature for 24 h. The mixture was diluted with water (10 mL), and extracted with ethyl acetate (3×20 mL). The organic layer was washed with water, brine, dried over MgSO$_4$, filtered, and concentrated. The residue was purified by flash chromatography (pentane/EtOAc=99:1→90:10) to furnish intermediate 42 (110 mg, 0.318 mmol, 89% yield). [α]$_D^{22}$=−38 (c=1.0, CHCl$_3$). LC-MS m/z: calculated for C$_{21}$H$_{31}$NO$_3$ [M+H]$^+$ 346.18, found 346.40. $^1$H NMR (400 MHz, CDCl$_3$) δ 7.29-7.25 (m, 2H), 7.22-7.15 (m, 3H), 4.44 (br s, 1H), 4.28 (d, J=13.9 Hz, 1H), 3.54 (s, 1H), 3.40-3.20 (m, 2H), 2.96-2.84 (m, 2H), 2.74 (dd, J=13.2, 8.1 Hz, 1H), 2.02-1.93 (m, 1H), 1.89-1.67 (m, 2H), 1.34 (s, 9H), 1.29-1.24 (m, 1H), 1.08-0.98 (m, 1H), 0.50-0.47 (m, 2H), 0.30-0.10 (m, 2H). $^{13}$C NMR (101 MHz, CDCl$_3$) δ 155.17, 139.27, 129.27, 128.33, 126.23, 79.20, 72.66, 71.08, 51.90, 40.42, 36.08, 28.40, 24.50, 21.74, 10.83, 3.18, 2.92.

To a solution of solution of intermediate 42 (50.0 mg, 0.145 mmol) in DCM was added 20% TFA, the reaction mixture was stirred at r.t. for 2.5 h. The mixture was co-evaporated with toluene (3 times), the residue was diluted with ethyl acetate and washed with 10% Na$_2$CO$_3$, water, brine, dried over MgSO$_4$, filtered and concentrated under reduced pressure afforded intermediate 43 which was used without further purification. $^1$H NMR (400 MHz, CDCl$_3$) δ 7.31-7.23 (m, 3H), 7.20-7.10 (m, 2H), 3.70 (s, 1H), 3.51 (s, 1H), 3.31 (p, J=9.9 Hz, 2H), 3.16 (s, 2H), 2.74 (br s, 2H), 2.17 (br d, J=11.6 Hz, 1H), 1.87 (br d, J=13.4 Hz, 1H), 1.62 (br d, J=11.5 Hz, 1H), 1.32 (br d, J=11.7 Hz, 1H), 0.99 (br s, 1H), 0.51 (d, J=7.7 Hz, 2H), 0.16 (d, J=4.5 Hz, 2H). $^{13}$C NMR (101 MHz, CDCl$_3$) δ 135.38, 129.33, 128.98, 127.46, 74.17, 71.12, 57.86, 47.58, 39.23, 29.26, 26.09, 10.82, 3.12, 3.07.

A solution of the intermediate 43 (15 mg, 0.061 mmol) in dry THF (0.6 mL) was treated with iPr$_2$NEt (31 μL, 0.18 mmol) and triphosgene (9.4 mg, 0.032 mmol), and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The residue was dissolved in THF (0.8 mL), and iPr$_2$NEt (31 μL, 0.18 mmol), DMAP (7.1 mg, 0.058 mmol) and 4-(4-trifluoromethoxyphenyl)-1H-1,2,3-triazole (16) (14 mg, 0.061 mmol) were added to the solution. The mixture was stirred for 1.5 h at 50° C. and poured into saturated aqueous NH$_4$Cl solution. The mixture was extracted with ethyl acetate. The organic layer was washed with H$_2$O and brine, dried over Na$_2$SO$_4$ and concentrated under reduced pressure. The residue was purified by flash column chromatography (ethyl acetate:hexane=1:2) then purified again by preparative TLC (ethyl acetate:hexane=1:3) to afford ((2R,5S)-2-benzyl-5-(cyclopropylmethoxy)piperidin-1-yl)(4-(4-(trifluoromethoxy)phenyl)-1H-1,2,3-triazol-1-yl)methanone (44) (10 mg, 34%) and ((2R,5S)-2-benzyl-5-(cyclopropylmethoxy)piperidin-1-yl)(4-(4-(trifluoromethoxy)phenyl)-2H-1,2,3-triazol-2-yl)methanone (45) (10.3 mg, 34%). Compound 44: $^1$H NMR (CDCl$_3$, 600 MHz) δ 7.93-7.86 (m, 2H), 7.68-7.09 (m, 7H), 4.92-4.61 (m, 1H), 3.81-2.82 (m, 5H), 2.39-1.51 (m, 4H), 1.04-0.89 (m, 1H), 0.53 (brs, 2H), 0.21-0.10 (m, 2H). ESI-MS [M+Na]$^+$523.1. Compound 45: $^1$H NMR (CDCl$_3$, 600 MHz) δ 8.04-8.02 (m, 1H), 7.91-7.88 (m, 2H), 7.40-7.16 (m, 7H), 4.67 (brs, 1H), 3.65-2.97 (m, 5H), 2.22-2.15 (m, 1H), 1.96-1.91 (m, 2H), 1.44-1.42 (m, 1H) 1.00 (brs, 1H) 0.47-0.14 (m, 4H). ESI-MS [M+Na]$^+$ 523.1.

Example 10: ((3R,6R)-6-((Benzyloxy)methyl)-3-hydroxy-3,6-dihydropyridin-1(2H)-yl)(4-(4-(trifluoromethoxy)phenyl)-1H-1,2,3-triazol-1-yl)methanone (50)

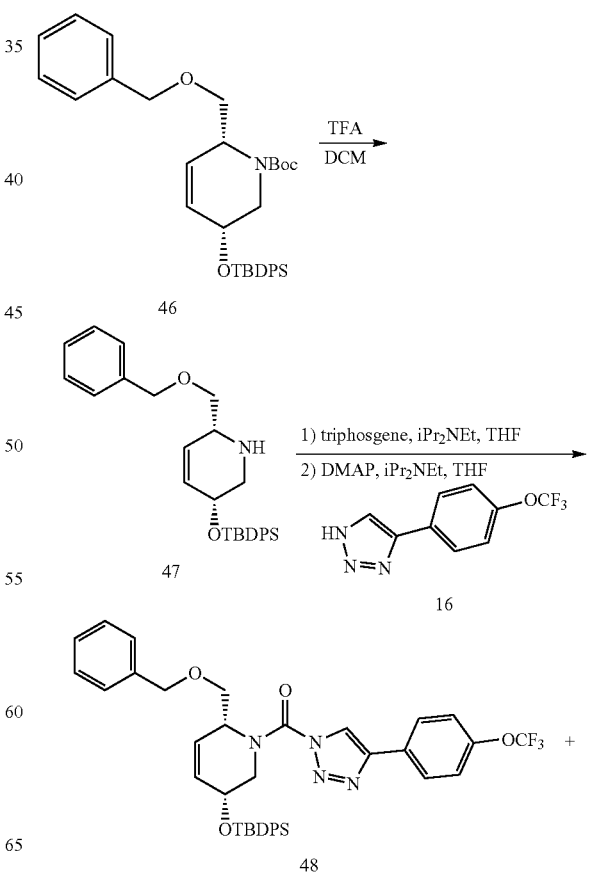

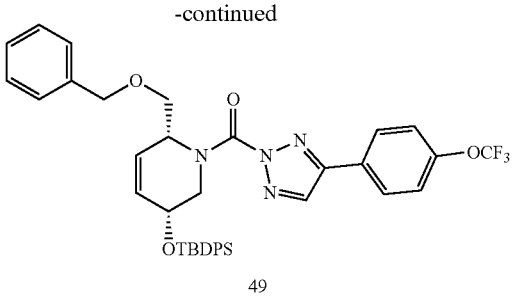

49

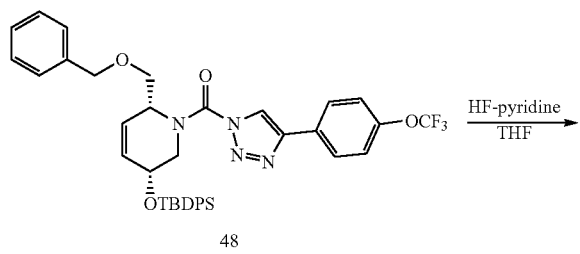

48

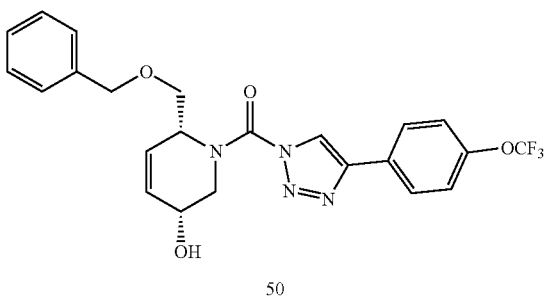

50

Compound 46 (European Journal of Organic Chemistry 2012, 3437-3446; Org Lett 2010, 12, 3957-9) (500 mg, 0.896 mmol) was dissolved in a mixture of 25% TFA in DCM (5 mL). The reaction mixture was stirred at r.t. for 2.5 h. The mixture was co-evaporated with toluene (3×20 mL), the residue diluted with ethyl acetate and washed with 10% $Na_2CO_3$, water, brine and dried over $MgSO_4$, and concentrated under reduced pressure to afford intermediate 47 (347 mg, 0.758 mmol, 85% yield) as a light yellow oil which was used without further purification. $^1H$ NMR (400 MHz, $CDCl_3$) δ 7.70-7.65 (m, 4H), 7.39-7.22 (m, 11H), 5.71 (s, 2H), 4.54 (s, 2H), 4.0-4.06 (m, 1H), 3.55-3.51 (m, 1H), 3.49-3.45 (m, 1H), 3.39-3.35 (m, 1H), 2.98 (dd, J=13.8, 4.2 Hz, 1H), 2.77 (dd, J=12.2, 4.0 Hz, 1H), 2.56 (br s, 1H), 1.07 (s, 9H). $^{13}C$ NMR (101 MHz, $CDCl_3$) δ 138.19, 135.80, 135.69, 134.15, 134.01, 130.67, 130.39, 129.65, 129.58, 128.33, 127.62, 127.54, 127.52, 127.51, 73.18, 71.82, 64.24, 53.71, 48.88, 26.96, 19.15.

A solution of the intermediate 47 (25 mg, 0.057 mmol) in dry THF (0.5 mL) was treated with $iPr_2NEt$ (29 μL, 0.17 mmol) and triphosgene (8.8 mg, 0.030 mmol), and the reaction mixture was stirred for 30 min at 4° C. The mixture was poured into $H_2O$ and extracted with ethyl acetate. The organic layer was washed with $H_2O$ and brine, dried over $Na_2SO_4$ and concentrated under reduced pressure. The residue was dissolved in THF (0.6 mL), and $iPr_2NEt$ (29 μL, 0.17 mmol), DMAP (6.6 mg, 0.054 mmol) and 4-(4-trifluoromethoxyphenyl)-1H-1,2,3-triazole (16) (13 mg, 0.057 mmol) were added to the solution. The mixture was stirred for 1.5 h at 50° C. and poured into saturated aqueous $NH_4Cl$ solution. The mixture was extracted with ethyl acetate. The organic layer was washed with $H_2O$ and brine, dried over $Na_2SO_4$ and concentrated under reduced pressure. The residue was purified by flash column chromatography (ethyl acetate:hexane=1:2) then purified again by preparative TLC (ethyl acetate:hexane=1:4) to afford intermediate 48 (8.3 mg, 21%) and intermediate 49 (9.9 mg, 25%).

A solution of the intermediate 48 (4.1 mg, 0.0058 mmol) in THF (0.2 mL) was treated with 70% hydrogene fluoride-pyridine (2.3 μL, 0.085 mmol) at 0° C. and stirred overnight. The mixture was poured into saturated aqueous $NH_4Cl$ solution and extracted with ethyl acetate. The organic layer was washed with $H_2O$ and brine, dried over $Na_2SO_4$ and concentrated under reduced pressure. The residue was purified by flash column chromatography (ethyl acetate:hexane=1:1) to afford ((3R,6R)-6-((benzyloxy)methyl)-3-hydroxy-3,6-dihydropyridin-1(2H)-yl)(4-(4-(trifluoromethoxy)phenyl)-1H-1,2,3-triazol-1-yl)methanone (50) (0.7 mg, 25%). ESI-MS [M+Na]$^+$497.1.

Example 11: ((3R,6R)-6-((Benzyloxy)methyl)-3-hydroxy-3,6-dihydropyridin-1(2H)-yl)(4-(4-(trifluoromethoxy)phenyl)-2H-1,2,3-triazol-2-yl)methanone (51)

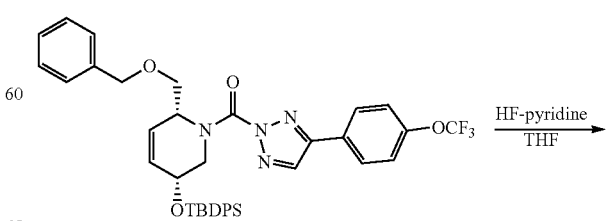

49

-continued

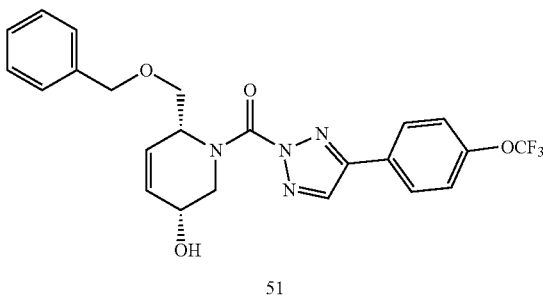

51

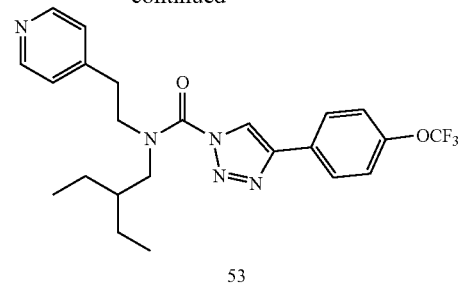

53

+

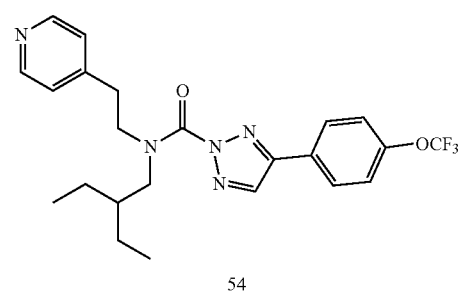

54

Using the procedure described in Example 10, compound 49 was deprotected to afford ((3R,6R)-6-((benzyloxy)methyl)-3-hydroxy-3,6-dihydropyridin-1(2H)-yl)(4-(4-(trifluoromethoxy)phenyl)-2H-1,2,3-triazol-2-yl)methanone (51) (0.4 mg, 14%). ESI-MS [M+Na]$^+$497.1.

Example 12: N-(2-Ethylbutyl)-N-(2-(pyridin-4-yl)ethyl)-4-(4-(trifluoromethoxy)phenyl)-1H-1,2,3-triazole-1-carboxamide (53) and N-(2-Ethylbutyl)-N-(2-(pyridin-4-yl)ethyl)-4-(4-(trifluoromethoxy)phenyl)-2H-1,2,3-triazole-2-carboxamide (54)

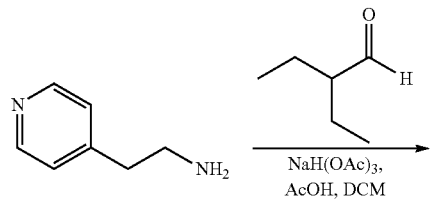

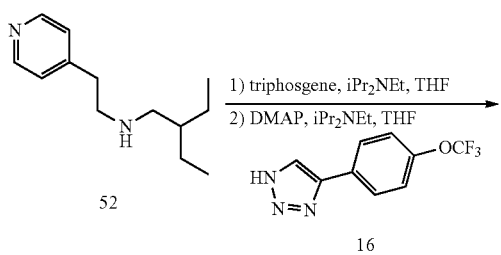

A solution of 2-(4-pyridyl)ethylamine (250 mg, 2.05 mmol) in DCM (5 mL) was treated with 2-ethylbutanal (307 mg, 3.07 mmol), NaH(OAc)$_3$ (540 mg, 2.86 mmol) and acetic acid (123 mg, 2.05 mmol), and the reaction mixture was stirred overnight at room temp. The mixture was poured into sat. NaHCO$_3$ and extracted with DCM and the organic layer was concentrated under reduced pressure. The residue was purified by flash column chromatography (DCM:MeOH=10:1) to afford intermediate 52 (156 mg, 37%) as a colorless oil.

A solution of the intermediate 52 (30 mg, 0.15 mmol) in dry THF (2.4 mL) was treated with iPr$_2$NEt (76 μL, 0.44 mmol) and triphosgene (16 mg, 0.055 mmol), and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The residue was dissolved in THF (3 mL), and iPr$_2$NEt (51 μL, 0.29 mmol), DMAP (27 mg, 0.22 mmol) and 4-(4-trifluoromethoxyphenyl)-1H-1,2,3-triazole (16) (33 mg, 0.15 mmol) were added to the solution. The mixture was stirred for 1.5 h at 50° C. and poured into saturated aqueous NH$_4$Cl solution. The mixture was extracted with ethyl acetate. The organic layer was washed with H$_2$O and brine, dried over Na$_2$SO$_4$ and concentrated under reduced pressure. The residue was purified by flash column chromatography (ethyl acetate:hexane=1:2) then purified again by preparative TLC (ethyl acetate:hexane=2:3) to afford N-(2-ethylbutyl)-N-(2-(pyridin-4-yl)ethyl)-4-(4-(trifluoromethoxy)phenyl)-1H-1,2,3-triazole-1-carboxamide (53) (7.3 mg, 11%) and N-(2-ethylbutyl)-N-(2-(pyridin-4-yl)ethyl)-4-(4-(trifluoromethoxy)phenyl)-2H-1,2,3-triazole-2-carboxamide (54) (8.8 mg, 13%). Compound 53: ESI-MS [M+Na]$^+$462.2. Compound 54: ESI-MS [M+Na]$^+$462.2.

Example 13: Probe Compound (55)

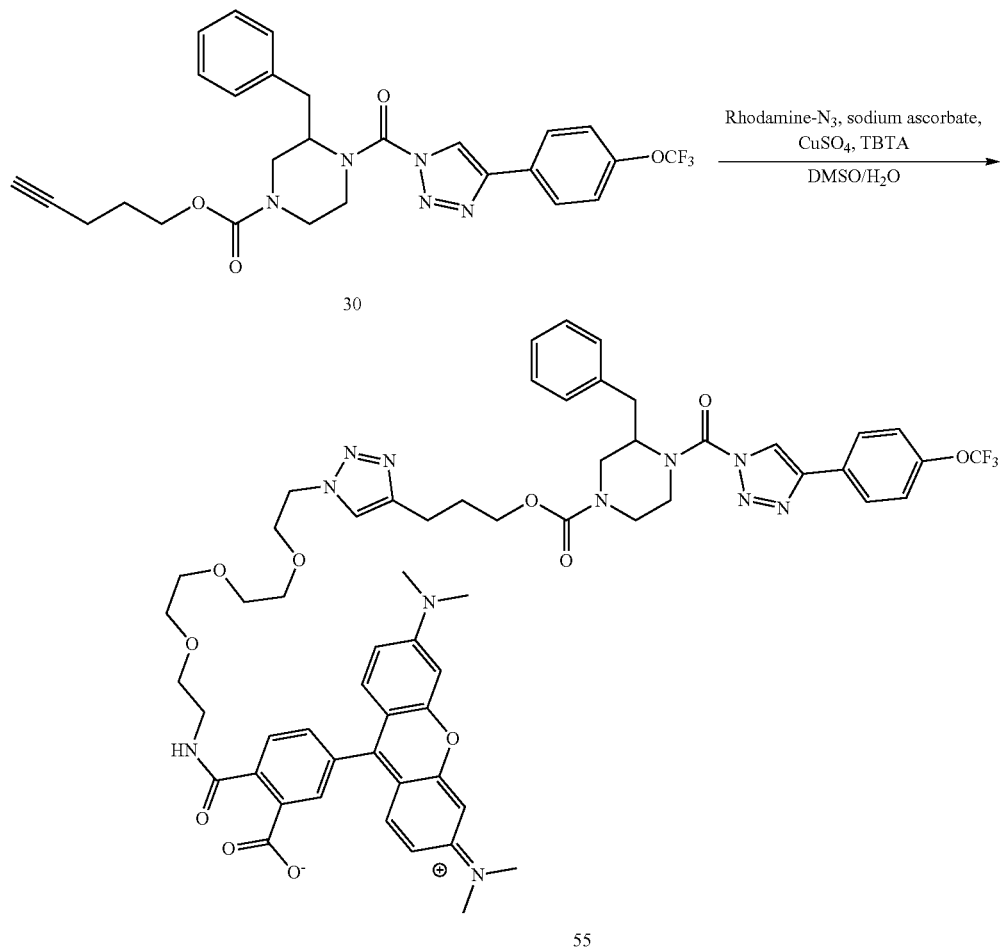

A 100 mM solution of compound 30 (25 μL, 2.5 mop in DMSO was treated with 12.5 mM solution of rhodamine-$N_3$ (200 μL, 2.5 mop in DMSO, 50 mM solution of TBTA (5.6 μL, 0.28 μmol) in DMSO, 100 mM solution of sodium ascorbate (8.9 μL, 0.89 μmol) in $H_2O$ and 10 mM solution of $CuSO_4$ (22 μL, 0.22 μmol) in $H_2O$. The reaction mixture was stirred for 2 days at room temp. The mixture was concentrated under a stream of nitrogen and the residue was purified by RP-HPLC to give compound 55 (1.1 mg, 38%). ESI-MS [M+H]$^+$ 1172.5.

Example 14: Probe Compound (56)

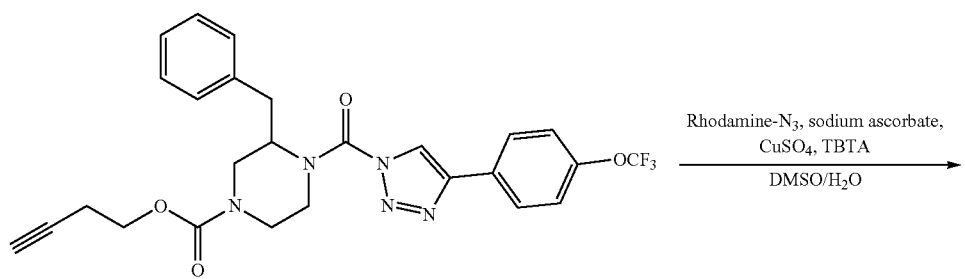

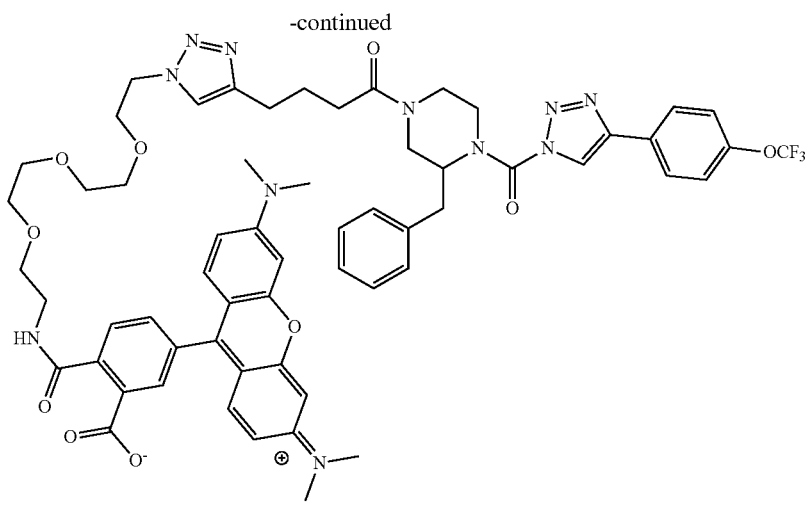

56

Compound 56 was prepared in a similar matter as described in Example 13. ESI-MS [M+H]+ 1156.4.

Example 15: Probe Compound (58)

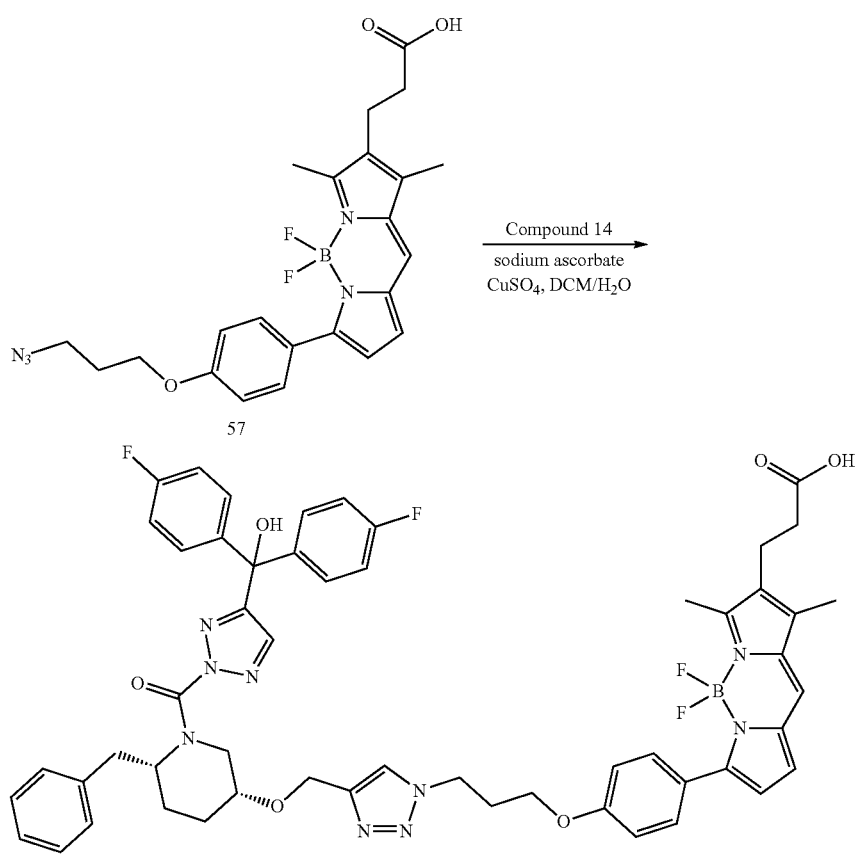

Bodipy-Azide 57 (Chembiochem 9(11):1735-1738) (14.2 mg, 0.030 mmol) and compound 14 (15.0 mg, 0.028 mmol) were dissolved in degassed DCM/H$_2$O (1:1, 2 mL) and sodium ascorbate (6.57 mg, 0.033 mmol) and CuSO$_4$ (3.45 mg, 0.014 mmol) were added. The resulting mixture was stirred vigorously for two hours, after which TLC indicated completed conversion of the reaction. The solvents were evaporated in vacuo and the residue was taken up in DCM and purified by silica gel column chromatography (ethyl acetate with 1% AcOH) yielding probe 58 (9.0 mg, 0.009 mmol, 32%) as a purple solid. $^1$H NMR (600 MHz, CDCl$_3$) δ 7.85 (br s, 2H), 7.43 (br s, 11H), 7.09-6.91 (m, 8H), 6.51 (br s, 1H), 4.73 (br s, 2H), 3.94 (br s, 2H), 3.67 (br s, 1H), 3.53 (br s, 1H), 3.04 (br s, 2H), 2.74 (br s, 3H), 2.51 (br s, 5H), 2.21 (br s, 3H), 1.72 (br s, 3H), 1.25 (br s, 5H), 0.92-0.84 (m, 2H); $^{13}$C NMR (151 MHz, CDCl$_3$) δ 176.20, 162.81 (d, J=242 Hz), 159.61, 159.12, 155.38, 148.95, 141.55, 141.14, 140.72, 140.16, 137.78, 135.10, 134.51, 130.94, 130.05, 129.56, 129.24, 128.76, 128.14, 126.84, 126.22, 123.23, 118.45, 115.19 (d, J=18 Hz), 114.25, 76.24, 73.67, 64.09, 54.22, 51.04, 48.95, 46.61, 35.69, 29.84, 26.55, 24.64, 22.83, 14.27, 13.34, 9.83; HRMS (m/z): [M+H]$^+$ calcd. for C$_{54}$H$_{52}$BF$_4$N$_9$O$_6$, 1010.41515; found 1010.41550.

Compounds 59-137 (Table 2) were synthesized using similar procedures as described in previous Examples using the appropriate starting materials.

TABLE 2

| Compound | Structure | Name | MS |
|---|---|---|---|
| 59 | 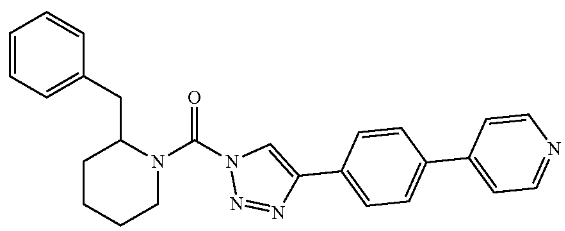 [SMILES: O=C(N1CCCCC1Cc1ccccc1)n1cc(-c2ccc(-c3ccncc3)cc2)nn1] | (2-benzylpiperidin-1-yl)(4-(4-(pyridin-4-yl)phenyl)-1H-1,2,3-triazol-1-yl)methanone | 424.2 [M + H]$^+$ |
| 60 | 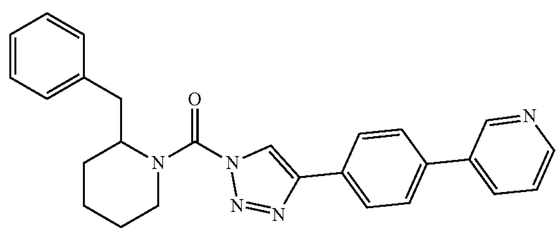 [SMILES: O=C(N1CCCCC1Cc1ccccc1)n1cc(-c2ccc(-c3cccnc3)cc2)nn1] | (2-benzylpiperidin-1-yl)(4-(4-(pyridin-3-yl)phenyl)-1H-1,2,3-triazol-1-yl)methanone | 424.2 [M + H]$^+$ |
| 61 | 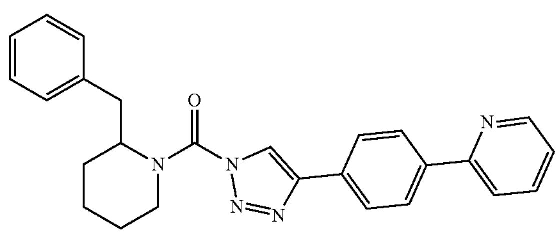 [SMILES: O=C(N1CCCCC1Cc1ccccc1)n1cc(-c2ccc(-c3ccccn3)cc2)nn1] | (2-benzylpiperidin-1-yl)(4-(4-(pyridin-2-yl)phenyl)-1H-1,2,3-triazol-1-yl)methanone | 424.2 [M + H]$^+$ |
| 62 | 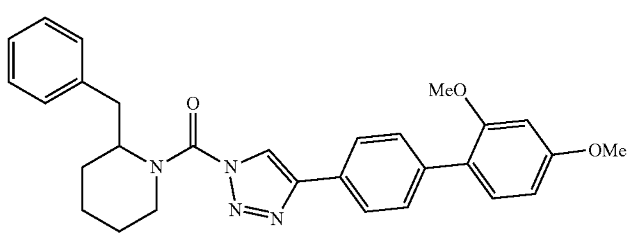 [SMILES: COc1ccc(-c2ccc(-c3cn(C(=O)N4CCCCC4Cc4ccccc4)nn3)cc2)c(OC)c1] | (2-benzylpiperidin-1-yl)(4-(2',4'-dimethoxy-[1,1'-biphenyl]-4-yl)-1H-1,2,3-triazol-1-yl)methanone | 505.0 [M + Na]$^+$ |
| 63 | 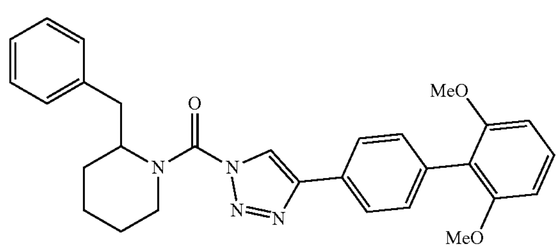 [SMILES: COc1cccc(OC)c1-c1ccc(-c2cn(C(=O)N3CCCCC3Cc3ccccc3)nn2)cc1] | (2-benzylpiperidin-1-yl)(4-(2',6'-dimethoxy-[1,1'-biphenyl]-4-yl)-1H-1,2,3-triazol-1-yl)methanone | 505.1 [M + Na]$^+$ |

TABLE 2-continued

| Compound | Structure | Name | MS |
|---|---|---|---|
| 64 | 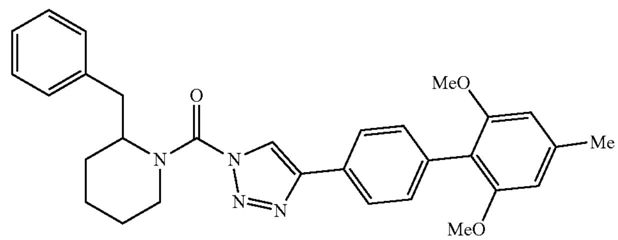 [SMILES: COc1cc(C)cc(OC)c1-c1ccc(-c2cn(C(=O)N3CCCCC3Cc3ccccc3)nn2)cc1] | (2-benzylpiperidin-1-yl)(4-(2',6'-dimethoxy-4'-methyl-[1,1'-biphenyl]-4-yl)-1H-1,2,3-triazol-1-yl)methanone | 519.2 [M + Na]+ |
| 65 | 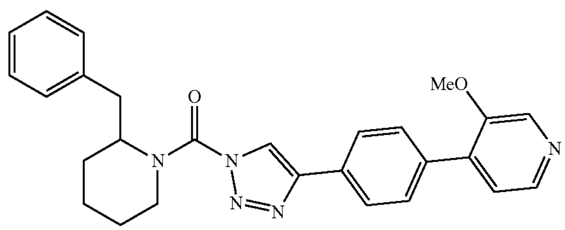 [SMILES: COc1cnccc1-c1ccc(-c2cn(C(=O)N3CCCCC3Cc3ccccc3)nn2)cc1] | (2-benzylpiperidin-1-yl)(4-(4-(3-methoxypyridin-4-yl)phenyl)-1H-1,2,3-triazol-1-yl)methanone | 454.2 [M + H]+ |
| 66 | 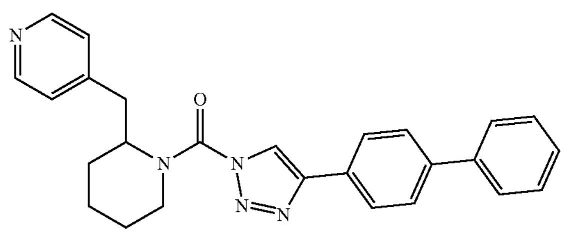 [SMILES: O=C(N1CCCCC1Cc1ccncc1)n1cc(-c2ccc(-c3ccccc3)cc2)nn1] | (4-([1,1'-biphenyl]-4-yl)-1H-1,2,3-triazol-1-yl)(2-(pyridin-4-ylmethyl)piperidin-1-yl)methanone | 424.2 [M + H]+ |
| 67 | 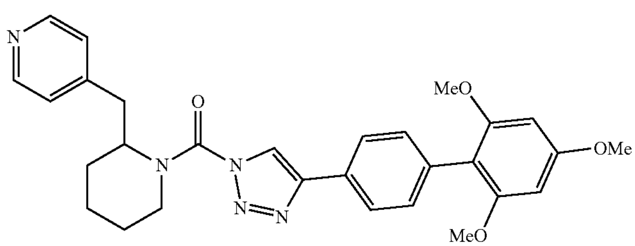 [SMILES: COc1cc(OC)c(-c2ccc(-c3cn(C(=O)N4CCCCC4Cc4ccncc4)nn3)cc2)c(OC)c1] | (2-(pyridin-4-ylmethyl)piperidin-1-yl)(4-(2',4',6'-trimethoxy-[1,1'-biphenyl]-4-yl)-1H-1,2,3-triazol-1-yl)methanone | 514.2 [M + H]+ |
| 68 | 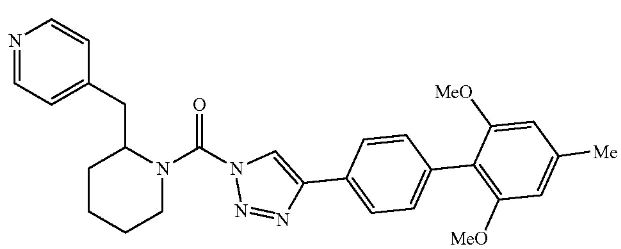 [SMILES: COc1cc(C)cc(OC)c1-c1ccc(-c2cn(C(=O)N3CCCCC3Cc3ccncc3)nn2)cc1] | (4-(2',6'-dimethoxy-4'-methyl-[1,1'-biphenyl]-4-yl)-1H-1,2,3-triazol-1-yl)(2-(pyridin-4-ylmethyl)piperidin-1-yl)methanone | 498.3 [M + H]+ |
| 69 | 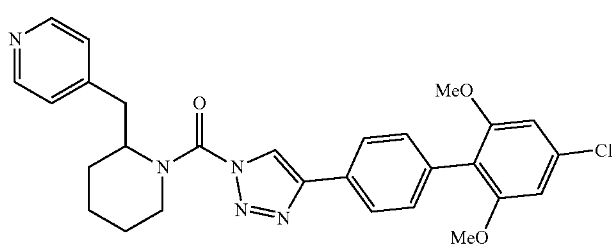 [SMILES: COc1cc(Cl)cc(OC)c1-c1ccc(-c2cn(C(=O)N3CCCCC3Cc3ccncc3)nn2)cc1] | (4-(4'-chloro-2',6'-dimethoxy-[1,1'-biphenyl]-4-yl)-1H-1,2,3-triazol-1-yl)(2-(pyridin-4-ylmethyl)piperidin-1-yl)methanone | 518.2 [M + H]+ |

TABLE 2-continued

| Compound | Structure | Name | MS |
|---|---|---|---|
| 70 | 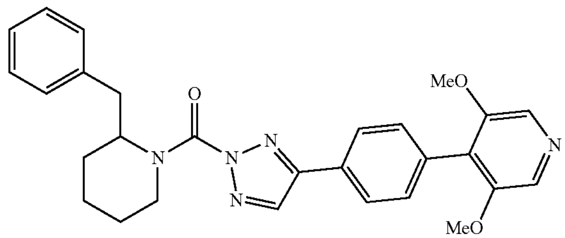 [SMILES: COc1cncc(OC)c1-c1ccc(-c2cnn(C(=O)N3CCCCC3Cc3ccccc3)n2)cc1] | (2-benzylpiperidin-1-yl)(4-(4-(3,5-dimethoxypyridin-4-yl)phenyl)-2H-1,2,3-triazol-2-yl)methanone | 484.2 [M + H]+ |
| 71 | 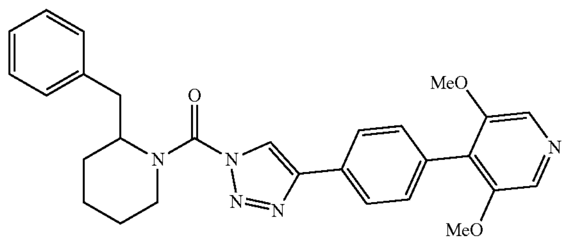 [SMILES: COc1cncc(OC)c1-c1ccc(-c2cn(C(=O)N3CCCCC3Cc3ccccc3)nn2)cc1] | (2-benzylpiperidin-1-yl)(4-(4-(3,5-dimethylpyridin-4-yl)phenyl)-1H-1,2,3-triazol-1-yl)methanone | 452.2 [M + H]+ |
| 72 | 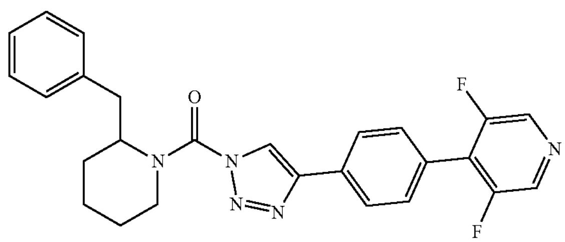 [SMILES: O=C(N1CCCCC1Cc1ccccc1)n1cc(-c2ccc(-c3c(F)cncc3F)cc2)nn1] | (2-benzylpiperidin-1-yl)(4-(4-(3,5-difluoropyridin-4-yl)phenyl)-1H-1,2,3-triazol-1-yl)methanone | 482.2 [M + Na]+ |
| 73 | 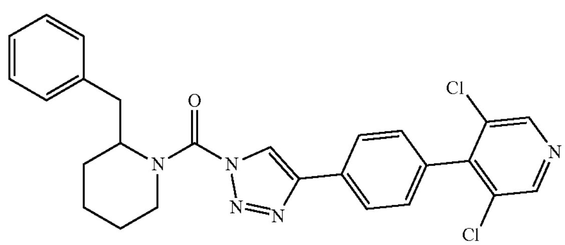 [SMILES: O=C(N1CCCCC1Cc1ccccc1)n1cc(-c2ccc(-c3c(Cl)cncc3Cl)cc2)nn1] | (2-benzylpiperidin-1-yl)(4-(4-(3,5-dichloropyridin-4-yl)phenyl)-1H-1,2,3-triazol-1-yl)methanone | 514.1 [M + Na]+ |
| 74 | 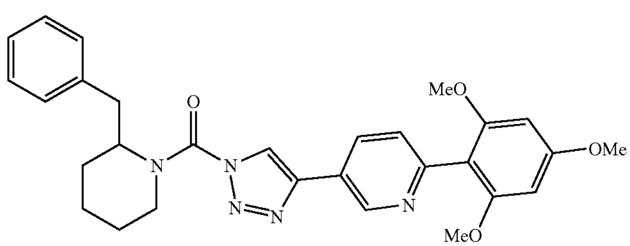 [SMILES: COc1cc(OC)c(-c2ccc(-c3cn(C(=O)N4CCCCC4Cc4ccccc4)nn3)cn2)c(OC)c1] | (2-benzylpiperidin-1-yl)(4-(6-(2,4,6-trimethoxyphenyl)pyridin-3-yl)-1H-1,2,3-triazol-1-yl)methanone | 514.2 [M + H]+ |
| 75 | 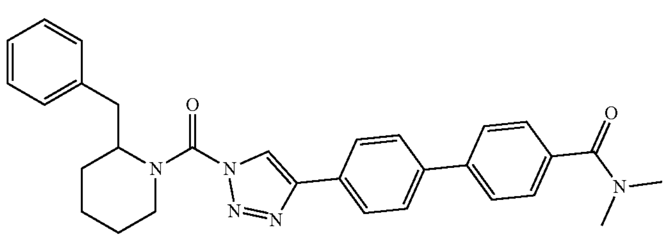 [SMILES: CN(C)C(=O)c1ccc(-c2ccc(-c3cn(C(=O)N4CCCCC4Cc4ccccc4)nn3)cc2)cc1] | 4'-(1-(2-benzylpiperidine-1-carbonyl)-1H-1,2,3-triazol-4-yl)-N,N-dimethyl-[1,1'-biphenyl]-4-carboxamide | 516.3 [M + Na]+ |

TABLE 2-continued

| Compound | Structure | Name | MS |
|---|---|---|---|
| 76 | 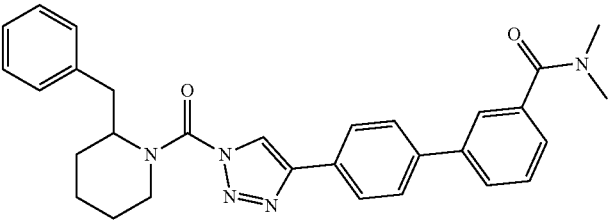 [SMILES: CN(C)C(=O)c1cccc(-c2ccc(-c3cn(C(=O)N4CCCCC4Cc4ccccc4)nn3)cc2)c1] | 4'-(1-(2-benzylpiperidine-1-carbonyl)-1H-1,2,3-triazol-4-yl)-N,N-dimethyl-[1,1'-biphenyl]-3-carboxamide | 516.2 [M + Na]+ |
| 77 | 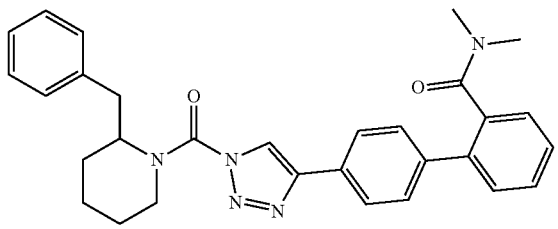 [SMILES: CN(C)C(=O)c1ccccc1-c1ccc(-c2cn(C(=O)N3CCCCC3Cc3ccccc3)nn2)cc1] | 4'-(1-(2-benzylpiperidine-1-carbonyl)-1H-1,2,3-triazol-4-yl)-N,N-dimethyl-[1,1'-biphenyl]-2-carboxamide | 516.3 [M + Na]+ |
| 78 | 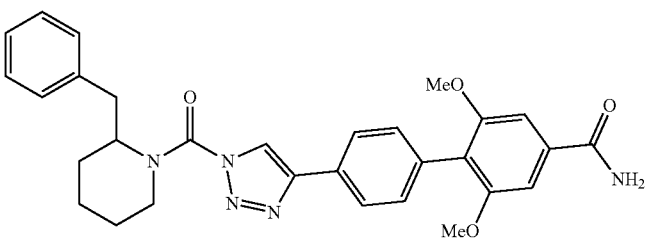 [SMILES: COc1cc(C(N)=O)cc(OC)c1-c1ccc(-c2cn(C(=O)N3CCCCC3Cc3ccccc3)nn2)cc1] | 4'-(1-(2-benzylpiperidine-1-carbonyl)-1H-1,2,3-triazol-4-yl)-2,6-dimethoxy-[1,1'-biphenyl]-4-carboxamide | 548.2 [M + Na]+ |
| 79 | 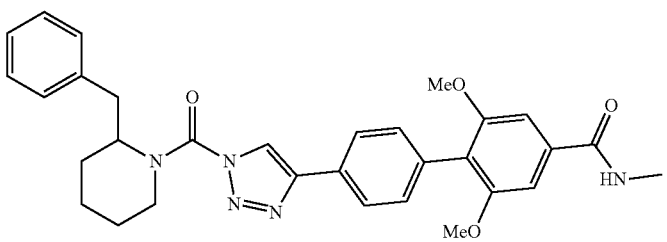 [SMILES: CNC(=O)c1cc(OC)c(-c2ccc(-c3cn(C(=O)N4CCCCC4Cc4ccccc4)nn3)cc2)c(OC)c1] | 4'-(1-(2-benzylpiperidine-1-carbonyl)-1H-1,2,3-triazol-4-yl)-2,6-dimethoxy-N-methyl-[1,1'-biphenyl]-4-carboxamide | 562.1 [M + Na]+ |
| 80 | 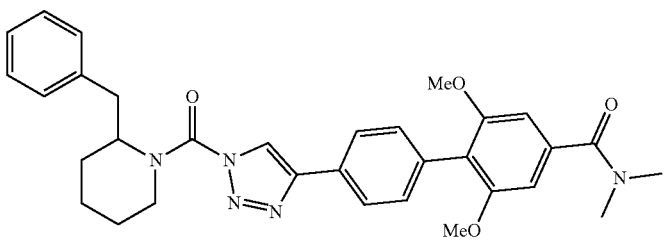 [SMILES: COc1cc(C(=O)N(C)C)cc(OC)c1-c1ccc(-c2cn(C(=O)N3CCCCC3Cc3ccccc3)nn2)cc1] | 4'-(1-(2-benzylpiperidine-1-carbonyl)-1H-1,2,3-triazol-4-yl)-2,6-dimethoxy-N,N-dimethyl-[1,1'-biphenyl]-4-carboxamide | 576.3 [M + Na]+ |
| 81 | 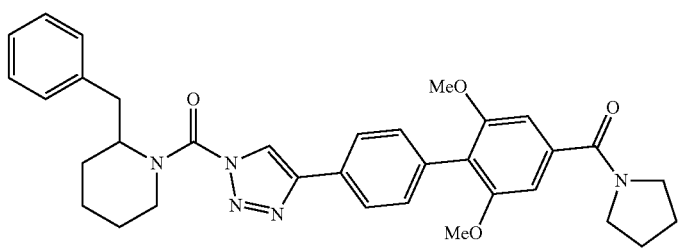 [SMILES: COc1cc(C(=O)N2CCCC2)cc(OC)c1-c1ccc(-c2cn(C(=O)N3CCCCC3Cc3ccccc3)nn2)cc1] | (2-benzylpiperidin-1-yl)(4-(2',6'-dimethoxy-4'-(pyrrolidine-1-carbonyl)-[1,1'-biphenyl]-4-yl)-1H-1,2,3-triazol-1-yl)methanone | 580.2 [M + H]+ |

TABLE 2-continued

| Compound | Structure | Name | MS |
|---|---|---|---|
| 82 | 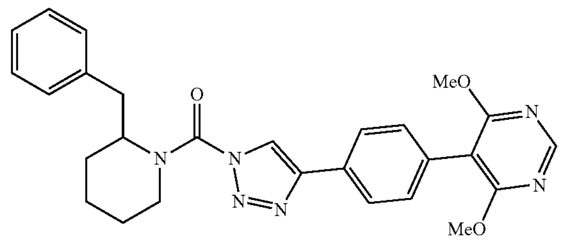 [SMILES: COc1ncnc(OC)c1-c1ccc(-c2cn(C(=O)N3CCCCC3Cc3ccccc3)nn2)cc1] | (2-benzylpiperidin-1-yl)(4-(4-(4,6-dimethoxypyrimidin-5-yl)phenyl)-1H-1,2,3-triazol-1-yl)methanone | 507.3 [M + Na]+ |
| 83 | 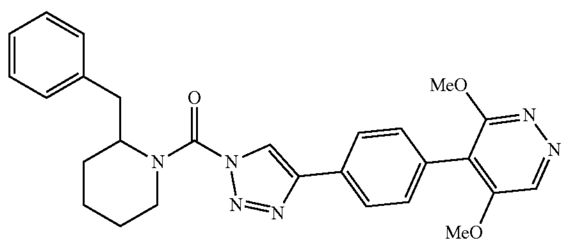 [SMILES: COc1cnnc(OC)c1-c1ccc(-c2cn(C(=O)N3CCCCC3Cc3ccccc3)nn2)cc1] | (2-benzylpiperidin-1-yl)(4-(4-(3,5-dimethoxypyridazin-4-yl)phenyl)-1H-1,2,3-triazol-1-yl)methanone | 485.2 [M + H]+ |
| 84 | 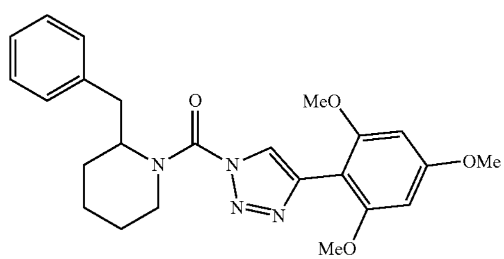 [SMILES: COc1cc(OC)c(-c2cn(C(=O)N3CCCCC3Cc3ccccc3)nn2)c(OC)c1] | (2-benzylpiperidin-1-yl)(4-(2,4,6-trimethoxyphenyl)-1H-1,2,3-triazol-1-yl)methanone | 437.2 [M + H]+ |
| 85 | 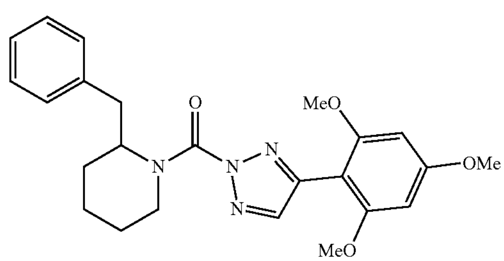 [SMILES: COc1cc(OC)c(-c2cnn(C(=O)N3CCCCC3Cc3ccccc3)n2)c(OC)c1] | (2-benzylpiperidin-1-yl)(4-(2,4,6-trimethoxyphenyl)-1H-1,2,3-triazol-2-yl)methanone | 437.3 [M + H]+ |
| 86 | 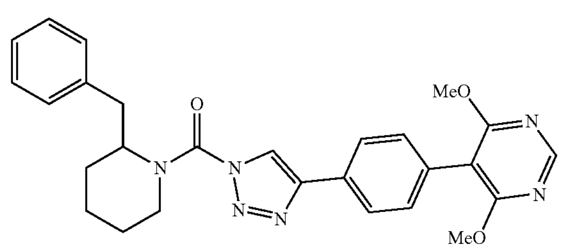 [SMILES: COc1ncnc(OC)c1-c1ccc(-c2cn(C(=O)N3CCCCC3Cc3ccccc3)nn2)cc1] | (2-benzylpiperidin-1-yl)(4-(4-(4-methoxy-6-methylpyrimidin-5-yl)phenyl)-1H-1,2,3-triazol-1-yl)methanone | 469.1 [M + H]+ |
| 87 | 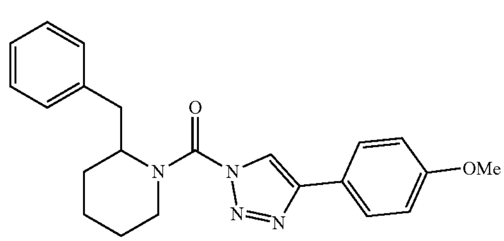 [SMILES: COc1ccc(-c2cn(C(=O)N3CCCCC3Cc3ccccc3)nn2)cc1] | (2-benzylpiperidin-1-yl)(4-(4-methoxyphenyl)-1H-1,2,3-triazol-1-yl)methanone | 399.0 [M + Na]+ |

TABLE 2-continued

| Compound | Structure | Name | MS |
|---|---|---|---|
| 88 | 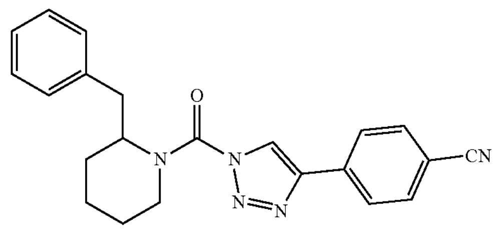 [SMILES: N#Cc1ccc(-c2cn(C(=O)N3CCCCC3Cc3ccccc3)nn2)cc1] | 4-(1-(2-benzylpiperidine-1-carbonyl)-1H-1,2,3-triazol-4-yl)benzonitrile | 394.1 [M + Na]+ |
| 89 | 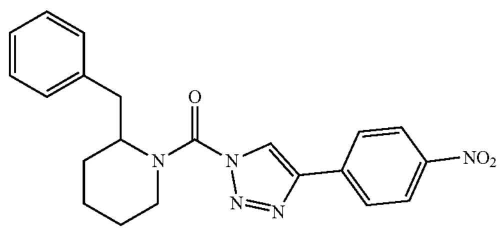 [SMILES: O=C(N1CCCCC1Cc1ccccc1)n1cc(-c2ccc([N+](=O)[O-])cc2)nn1] | (2-benzylpiperidin-1-yl)(4-(4-nitrophenyl)-1H-1,2,3-triazol-1-yl)methanone | 414.1 [M + Na]+ |
| 90 | 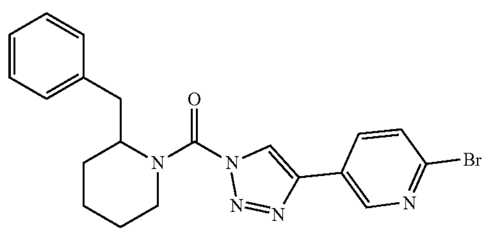 [SMILES: O=C(N1CCCCC1Cc1ccccc1)n1cc(-c2ccc(Br)nc2)nn1] | (2-benzylpiperidin-1-yl)(4-(6-bromopyridin-3-yl)-1H-1,2,3-triazol-1-yl)methanone | 448.1 [M + Na]+ |
| 91 | 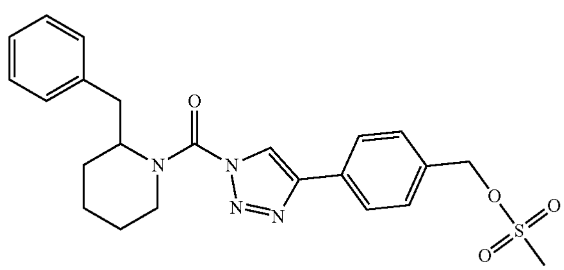 [SMILES: CS(=O)(=O)OCc1ccc(-c2cn(C(=O)N3CCCCC3Cc3ccccc3)nn2)cc1] | 4-(1-(2-benzylpiperidine-1-carbonyl)-1H-1,2,3-triazol-4-yl)benzyl methanesulfonate | 455.1 [M + H]+ |
| 92 | 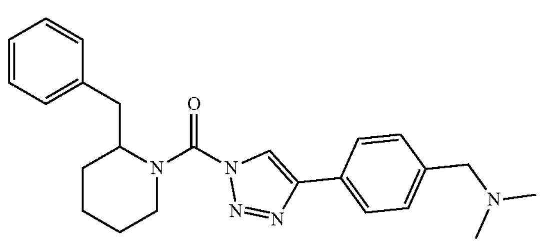 [SMILES: CN(C)Cc1ccc(-c2cn(C(=O)N3CCCCC3Cc3ccccc3)nn2)cc1] | (2-benzylpiperidin-1-yl)(4-(4-((dimethylamino)methyl)phenyl)-1H-1,2,3-triazol-1-yl)methanone | 404.2 [M + H]+ |
| 93 | 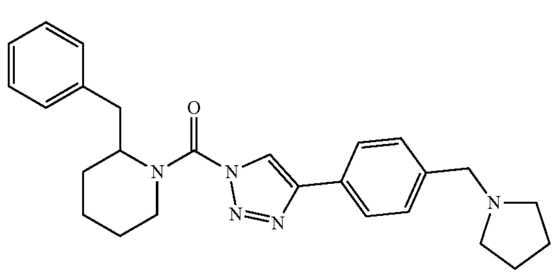 [SMILES: O=C(N1CCCCC1Cc1ccccc1)n1cc(-c2ccc(CN3CCCC3)cc2)nn1] | (2-benzylpiperidin-1-yl)(4-(4-(pyrrolidin-1-ylmethyl)phenyl)-1H-1,2,3-triazol-1-yl)methanone | 430.2 [M + H]+ |

TABLE 2-continued

| Compound | Structure | Name | MS |
|---|---|---|---|
| 94 | 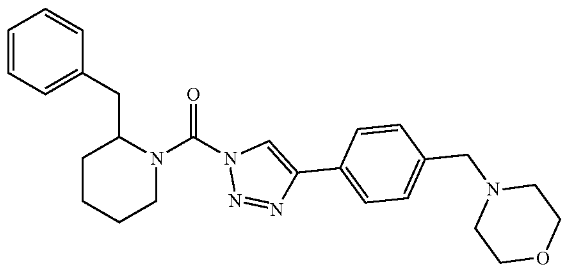 [SMILES: O=C(N1CCCCC1Cc1ccccc1)n1cc(-c2ccc(CN3CCOCC3)cc2)nn1] | (2-benzylpiperidin-1-yl)(4-(4-(morpholinomethyl)phenyl)-1H-1,2,3-triazol-1-yl)methanone | 446.2 [M + H]+ |
| 95 | 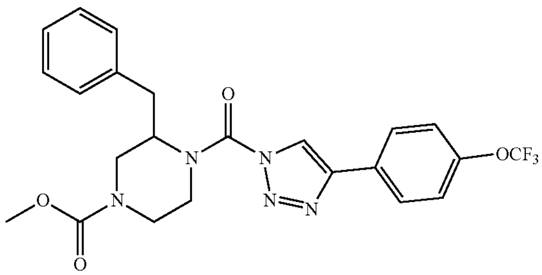 [SMILES: COC(=O)N1CCN(C(=O)n2cc(-c3ccc(OC(F)(F)F)cc3)nn2)C(Cc2ccccc2)C1] | methyl 3-benzyl-4-(4-(4-(trifluoromethoxy)phenyl)-1H-1,2,3-triazole-1-carbonyl)piperazine-1-carboxylate | 512.2 [M + Na]+ |
| 96 | 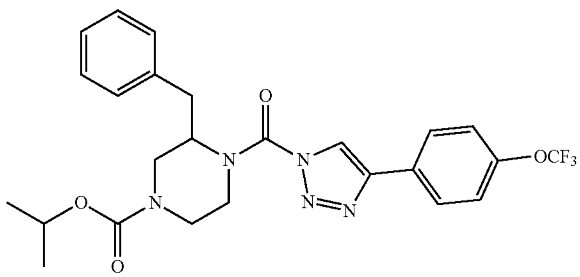 [SMILES: CC(C)OC(=O)N1CCN(C(=O)n2cc(-c3ccc(OC(F)(F)F)cc3)nn2)C(Cc2ccccc2)C1] | isopropyl 3-benzyl-4-(4-(4-(trifluoromethoxy)phenyl)-1H-1,2,3-triazole-1-carbonyl)piperazine-1-carboxylate | 540.2 [M + Na]+ |
| 97 | 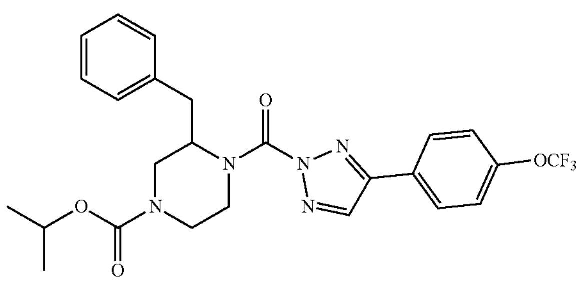 [SMILES: CC(C)OC(=O)N1CCN(C(=O)n2ncc(-c3ccc(OC(F)(F)F)cc3)n2)C(Cc2ccccc2)C1] | isopropyl 3-benzyl-4-(4-(4-(trifluoromethoxy)phenyl)-2H-1,2,3-triazole-2-carbonyl)piperazine-1-carboxylate | 540.2 [M + Na]+ |
| 98 | 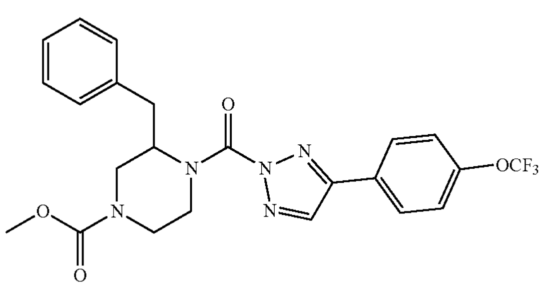 [SMILES: COC(=O)N1CCN(C(=O)n2ncc(-c3ccc(OC(F)(F)F)cc3)n2)C(Cc2ccccc2)C1] | methyl 3-benzyl-4-(4-(4-(trifluoromethoxy)phenyl)-2H-1,2,3-triazole-2-carbonyl)piperazine-1-carboxylate | 512.2 [M + Na]+ |

TABLE 2-continued

| Compound | Structure | Name | MS |
|---|---|---|---|
| 99 | 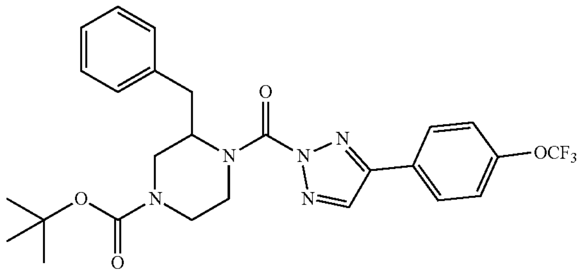 [SMILES: CC(C)(C)OC(=O)N1CCN(C(=O)n2ncc(-c3ccc(OC(F)(F)F)cc3)n2)C(Cc2ccccc2)C1] | tert-butyl 3-benzyl-4-(4-(4-(trifluoromethoxy)phenyl)-2H-1,2,3-triazole-2-carbonyl)piperazine-1-carboxylate | 554.2 [M + Na]+ |
| 100 | 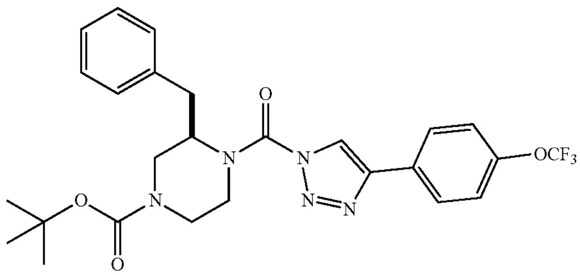 | tert-butyl (R)-3-benzyl-4-(4-(4-(trifluoromethoxy)phenyl)-1H-1,2,3-triazole-1-carbonyl)piperazine-1-carboxylate | 554.2 [M + Na]+ |
| 101 | 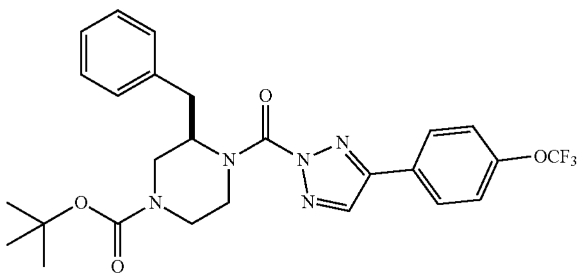 | tert-butyl (R)-3-benzyl-4-(4-(4-(trifluoromethoxy)phenyl)-2H-1,2,3-triazole-2-carbonyl)piperazine-1-carboxylate | 554.2 [M + Na]+ |
| 102 | 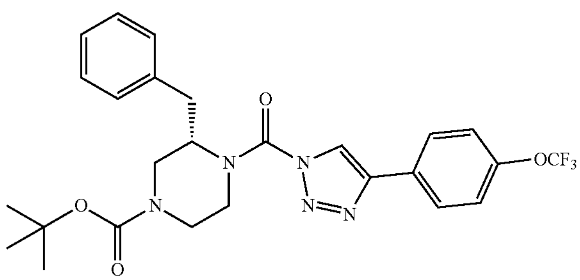 [SMILES: CC(C)(C)OC(=O)N1CCN(C(=O)n2cc(-c3ccc(OC(F)(F)F)cc3)nn2)[C@@H](Cc2ccccc2)C1] | tert-butyl (S)-3-benzyl-4-(4-(4-(trifluoromethoxy)phenyl)-1H-1,2,3-triazole-1-carbonyl)piperazine-1-carboxylate | 554.2 [M + Na]+ |
| 103 | 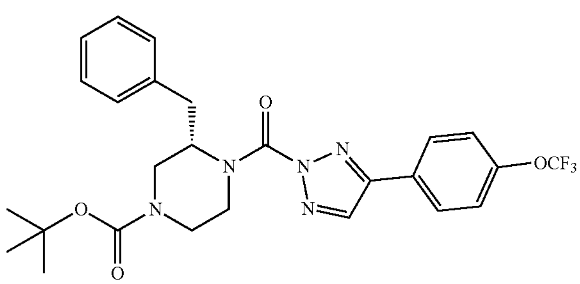 [SMILES: CC(C)(C)OC(=O)N1CCN(C(=O)n2ncc(-c3ccc(OC(F)(F)F)cc3)n2)[C@@H](Cc2ccccc2)C1] | tert-butyl (S)-3-benzyl-4-(4-(4-(trifluoromethoxy)phenyl)-2H-1,2,3-triazole-2-carbonyl)piperazine-1-carboxylate | 554.2 [M + Na]+ |

TABLE 2-continued

| Compound | Structure | Name | MS |
|---|---|---|---|
| 104 | 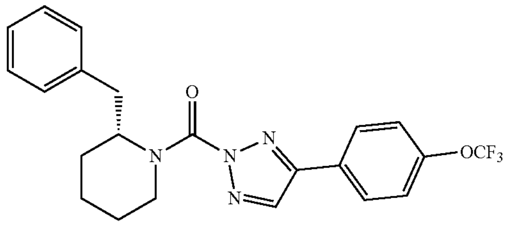 [SMILES: O=C(N1CCCC[C@@H]1Cc1ccccc1)n1ncc(-c2ccc(OC(F)(F)F)cc2)n1] | (R)-(2-benzylpiperidin-1-yl)(4-(4-(trifluoromethoxy)phenyl)-2H-1,2,3-triazol-2-yl)methanone | 453.1 [M + Na]+ |
| 105 | 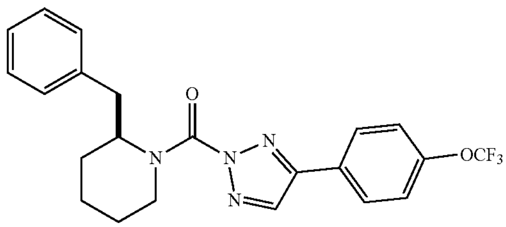 | (S)-(2-benzylpiperidin-1-yl)(4-(4-(trifluoromethoxy)phenyl)-2H-1,2,3-triazol-2-yl)methanone | 453.1 [M + Na]+ |
| 106 | 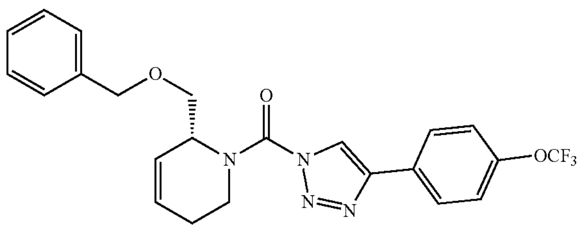 [SMILES: O=C(N1CCC=C[C@@H]1COCc1ccccc1)n1cc(-c2ccc(OC(F)(F)F)cc2)nn1] | (R)-(6-((benzyloxy)methyl)-3,6-dihydropyridin-1(2H)-yl)(4-(4-(trifluoromethoxy)phenyl)-1H-1,2,3-triazol-1-yl)methanone | 481.1 [M + Na]+ |
| 107 | 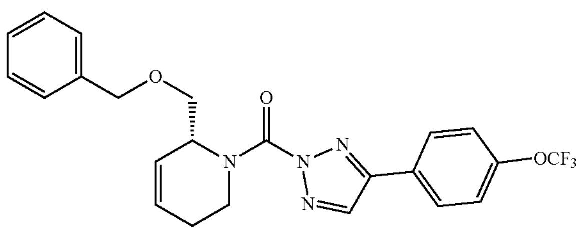 [SMILES: O=C(N1CCC=C[C@@H]1COCc1ccccc1)n1ncc(-c2ccc(OC(F)(F)F)cc2)n1] | (R)-(6-((benzyloxy)methyl)-3,6-dihydropyridin-1(2H)-yl)(4-(4-(trifluoromethoxy)phenyl)-2H-1,2,3-triazol-2-yl)methanone | 481.1 [M + Na]+ |
| 108 | 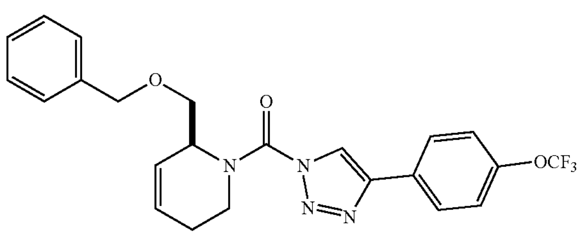 | (S)-(6-((benzyloxy)methyl)-3,6-dihydropyridin-1(2H)-yl)(4-(4-(trifluoromethoxy)phenyl)-1H-1,2,3-triazol-1-yl)methanone | 481.1 [M + Na]+ |
| 109 | 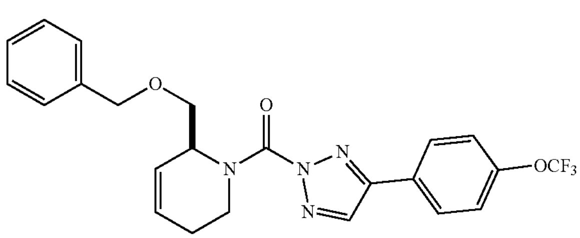 | (S)-(6-((benzyloxy)methyl)-3,6-dihydropyridin-1(2H)-yl)(4-(4-(trifluoromethoxy)phenyl)-2H-1,2,3-triazol-2-yl)methanone | 481.1 [M + Na]+ |
| 110 | 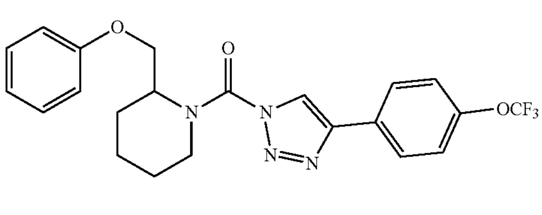 [SMILES: O=C(N1CCCCC1COc1ccccc1)n1cc(-c2ccc(OC(F)(F)F)cc2)nn1] | (2-(phenoxymethyl)piperidin-1-yl)(4-(4-(trifluoromethoxy)phenyl)-1H-1,2,3-triazol-1-yl)methanone | 469.1 [M + Na]+ |

TABLE 2-continued

| Compound | Name | MS |
|---|---|---|
| 111 | (2-(phenoxymethyl)piperidin-1-yl)(4-(4-(trifluoromethoxy)phenyl)-2H-1,2,3-triazol-2-yl)methanone | 469.1 [M + Na]+ |
| 112 | ((3R,6S)-6-benzyl-3-hydroxy-3,6-dihydropyridin-1(2H)-yl)(4-(4-(trifluoromethoxy)phenyl)-1H-1,2,3-triazol-1-yl)methanone | 445.0 [M + H]+ |
| 113 | ((3R,6S)-6-benzyl-3-hydroxy-3,6-dihydropyridin-1(2H)-yl)(4-(4-(trifluoromethoxy)phenyl)-2H-1,2,3-triazol-2-yl)methanone | 445.0 [M + H]+ |
| 114 | ((3S,6S)-6-benzyl-3-hydroxy-3,6-dihydropyridin-1(2H)-yl)(4-(4-(trifluoromethoxy)phenyl)-1H-1,2,3-triazol-1-yl)methanone | 467.0 [M + Na]+ |
| 115 | ((3S,6S)-6-benzyl-3-hydroxy-3,6-dihydropyridin-1(2H)-yl)(4-(4-(trifluoromethoxy)phenyl)-2H-1,2,3-triazol-1-yl)methanone | 445.2 [M + H]+ |
| 116 | ((2R,5R)-2-benzyl-5-methoxypiperidin-1-yl)(4-(4-(trifluoromethoxy)phenyl)-1H-1,2,3-triazol-1-yl)methanone | 483.1 [M + Na]+ |

TABLE 2-continued

| Compound | Structure | Name | MS |
|---|---|---|---|
| 117 | 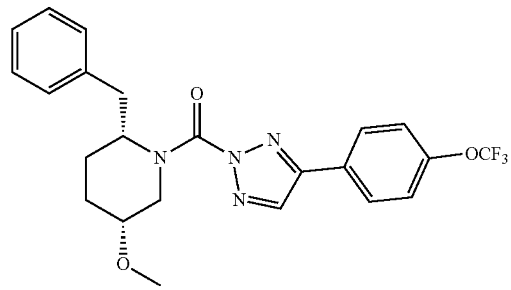 [SMILES: CO[C@@H]1CC[C@H](Cc2ccccc2)N(C(=O)n2ncc(-c3ccc(OC(F)(F)F)cc3)n2)C1] | ((2R,5R)-2-benzyl-5-methoxypiperidin-1-yl)(4-(4-(trifluoromethoxy)phenyl)-2H-1,2,3-triazol-1-yl)methanone | 483.1 [M + Na]+ |
| 118 | 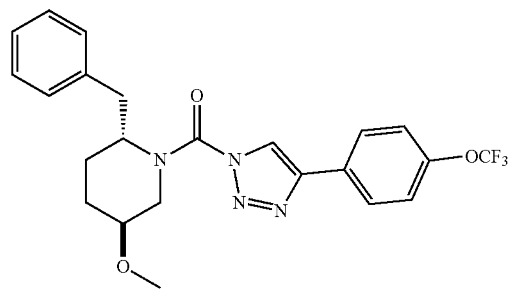 [SMILES: CO[C@H]1CC[C@H](Cc2ccccc2)N(C(=O)n2cc(-c3ccc(OC(F)(F)F)cc3)nn2)C1] | ((2R,5S)-2-benzyl-5-methoxypiperidin-1-yl)(4-(4-(trifluoromethoxy)phenyl)-1H-1,2,3-triazol-1-yl)methanone | 483.1 [M + Na]+ |
| 119 | 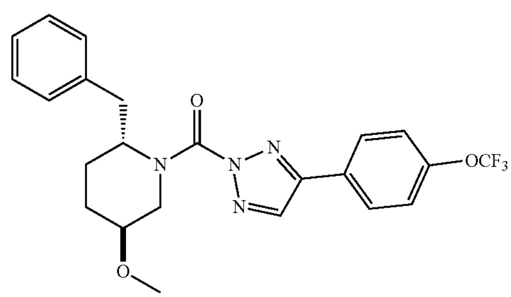 [SMILES: CO[C@H]1CC[C@H](Cc2ccccc2)N(C(=O)n2ncc(-c3ccc(OC(F)(F)F)cc3)n2)C1] | ((2R,5S)-2-benzyl-5-methoxypiperidin-1-yl)(4-(4-(trifluoromethoxy)phenyl)-2H-1,2,3-triazol-1-yl)methanone | 483.1 [M + Na]+ |
| 120 | 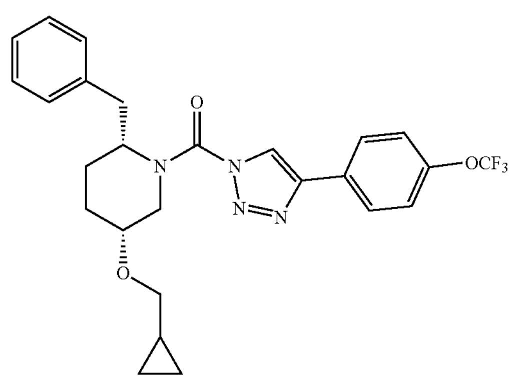 [SMILES: O=C(N1C[C@H](OCC2CC2)CC[C@@H]1Cc1ccccc1)n1cc(-c2ccc(OC(F)(F)F)cc2)nn1] | ((2R,5R)-2-benzyl-5-(cyclopropylmethoxy)piperidin-1-yl)(4-(4-(trifluoromethoxy)phenyl)-1H-1,2,3-triazol-1-yl)methanone | 523.1 [M + Na]+ |

TABLE 2-continued

| Compound | Structure | Name | MS |
|---|---|---|---|
| 121 | 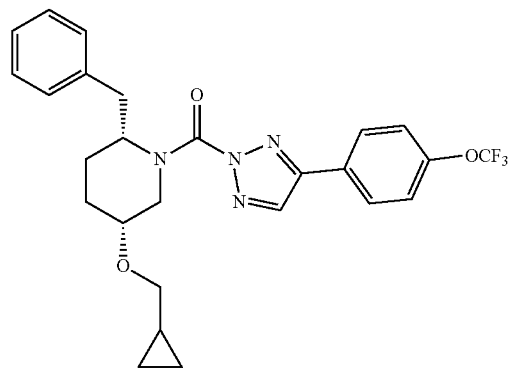 [SMILES: O=C(N1C[C@H](OCC2CC2)CC[C@@H]1Cc1ccccc1)n1ncc(-c2ccc(OC(F)(F)F)cc2)n1] | ((2R,5R)-2-benzyl-5-(cyclopropylmethoxy)piperidin-1-yl)(4-(4-(trifluoromethoxy)phenyl)-2H-1,2,3-triazol-1-yl)methanone | 523.1 [M + Na]+ |
| 122 | 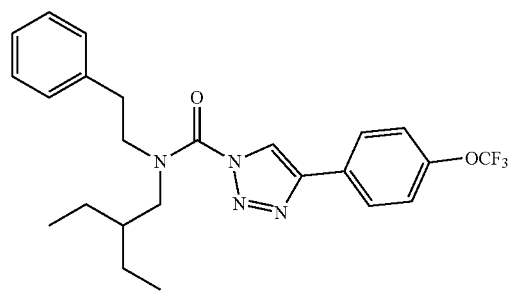 [SMILES: CCC(CC)CN(CCc1ccccc1)C(=O)n1cc(-c2ccc(OC(F)(F)F)cc2)nn1] | N-(2-ethylbutyl)-N-phenethyl-4-(4-(trifluoromethoxy)phenyl)-1H-1,2,3-triazole-1-carboxamide | 583.1 [M + Na]+ |
| 123 | 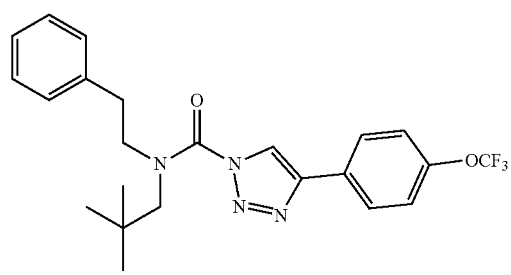 [SMILES: CC(C)(C)CN(CCc1ccccc1)C(=O)n1cc(-c2ccc(OC(F)(F)F)cc2)nn1] | N-neopentyl-N-phenethyl-4-(4-(trifluoromethoxy)phenyl)-1H-1,2,3-triazole-1-carboxamide | 469.1 [M + Na]+ |
| 124 | 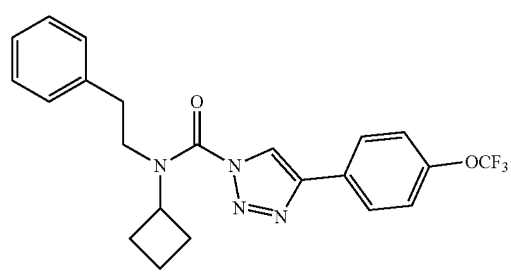 [SMILES: O=C(N(CCc1ccccc1)C1CCC1)n1cc(-c2ccc(OC(F)(F)F)cc2)nn1] | N-cyclobutyl-N-phenethyl-4-(4-(trifluoromethoxy)phenyl)-1H-1,2,3-triazole-1-carboxamide | 453.1 [M + Na]+ |
| 125 | 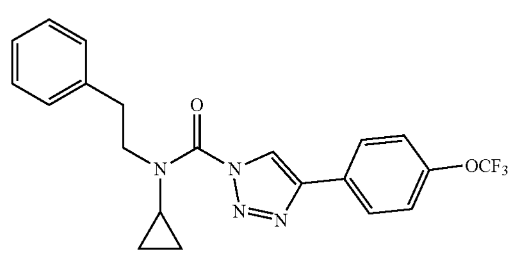 [SMILES: O=C(N(CCc1ccccc1)C1CC1)n1cc(-c2ccc(OC(F)(F)F)cc2)nn1] | N-cyclopropyl-N-phenethyl-4-(4-(trifluoromethoxy)phenyl)-1H-1,2,3-triazole-1-carboxamide | 439.0 [M + Na]+ |

TABLE 2-continued

| Compound | Structure | Name | MS |
|---|---|---|---|
| 126 | 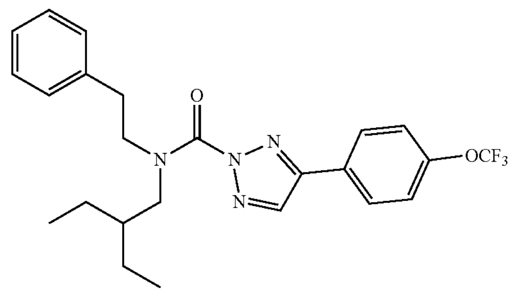 [SMILES: CCC(CC)CN(CCc1ccccc1)C(=O)n1ncc(-c2ccc(OC(F)(F)F)cc2)n1] | N-(2-ethylbutyl)-N-phenethyl-4-(4-(trifluoromethoxy)phenyl)-2H-1,2,3-triazole-2-carboxamide | 460.1 [M + H]+ |
| 127 | 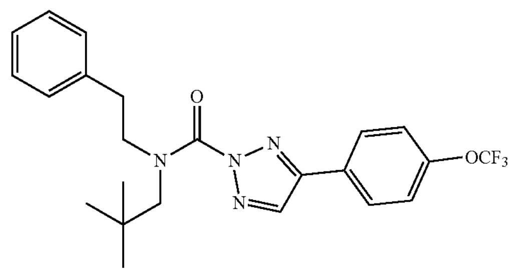 [SMILES: CC(C)(C)CN(CCc1ccccc1)C(=O)n1ncc(-c2ccc(OC(F)(F)F)cc2)n1] | N-neopentyl-N-phenethyl-4-(4-(trifluoromethoxy)phenyl)-2H-1,2,3-triazole-2-carboxamide | 469.1 [M + Na]+ |
| 128 | 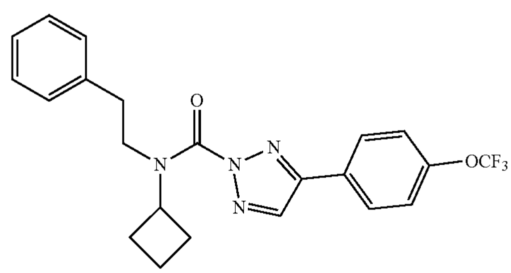 [SMILES: O=C(N(CCc1ccccc1)C1CCC1)n1ncc(-c2ccc(OC(F)(F)F)cc2)n1] | N-cyclobutyl-N-phenethyl-4-(4-(trifluoromethoxy)phenyl)-2H-1,2,3-triazole-2-carboxamide | 453.1 [M + Na]+ |
| 129 | 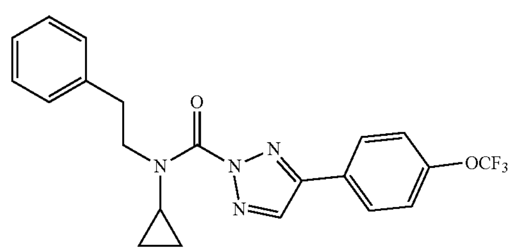 [SMILES: O=C(N(CCc1ccccc1)C1CC1)n1ncc(-c2ccc(OC(F)(F)F)cc2)n1] | N-cyclopropyl-N-phenethyl-4-(4-(trifluoromethoxy)phenyl)-2H-1,2,3-triazole-2-carboxamide | 439.1 [M + Na]+ |
| 130 | 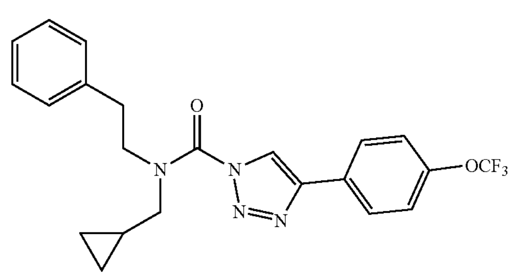 [SMILES: O=C(N(CCc1ccccc1)CC1CC1)n1cc(-c2ccc(OC(F)(F)F)cc2)nn1] | N-(cyclopropylmethyl)-N-phenethyl-4-(4-(trifluoromethoxy)phenyl)-1H-1,2,3-triazole-1-carboxamide | 453.1 [M + Na]+ |

TABLE 2-continued

| Compound | Structure | Name | MS |
|---|---|---|---|
| 131 | 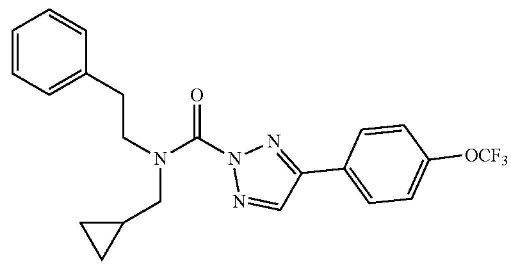 [SMILES: O=C(N(CCc1ccccc1)CC1CC1)n1ncc(-c2ccc(OC(F)(F)F)cc2)n1] | N-(cyclopropylmethyl)-N-phenethyl-4-(4-(trifluoromethoxy)phenyl)-2H-1,2,3-triazole-1-carboxamide | 453.1 [M + Na]+ |
| 132 | 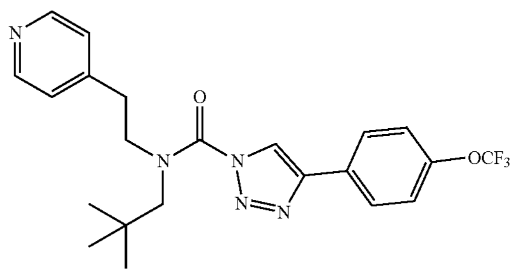 [SMILES: CC(C)(C)CN(CCc1ccncc1)C(=O)n1cc(-c2ccc(OC(F)(F)F)cc2)nn1] | N-neopentyl-N-(2-(pyridin-4-yl)ethyl)-4-(4-(trifluoromethoxy)phenyl)-1H-1,2,3-triazole-1-carboxamide | 448.2 [M + H]+ |
| 133 | 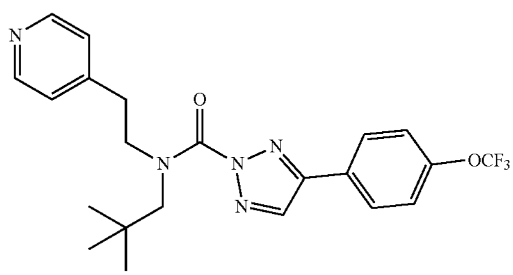 [SMILES: CC(C)(C)CN(CCc1ccncc1)C(=O)n1ncc(-c2ccc(OC(F)(F)F)cc2)n1] | N-neopentyl-N-(2-(pyridin-4-yl)ethyl)-4-(4-(trifluoromethoxy)phenyl)-2H-1,2,3-triazole-1-carboxamide | 448.2 [M + H]+ |
| 134 | 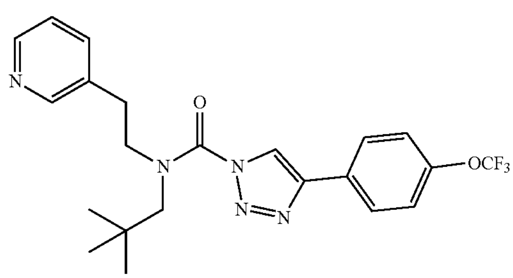 [SMILES: CC(C)(C)CN(CCc1cccnc1)C(=O)n1cc(-c2ccc(OC(F)(F)F)cc2)nn1] | N-neopentyl-N-(2-(pyridin-3-yl)ethyl)-4-(4-(trifluoromethoxy)phenyl)-1H-1,2,3-triazole-1-carboxamide | 448.2 [M + H]+ |
| 135 | 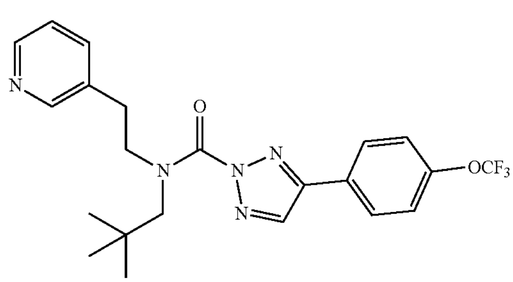 [SMILES: CC(C)(C)CN(CCc1cccnc1)C(=O)n1ncc(-c2ccc(OC(F)(F)F)cc2)n1] | N-neopentyl-N-(2-(pyridin-3-yl)ethyl)-4-(4-(trifluoromethoxy)phenyl)-2H-1,2,3-triazole-1-carboxamide | 448.2 [M + H]+ |

TABLE 2-continued

| Compound | Structure | Name | MS |
|---|---|---|---|
| 136 | 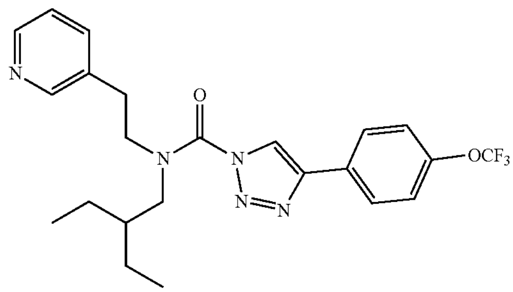 [SMILES: CCC(CC)CN(CCc1cccnc1)C(=O)n1cc(-c2ccc(OC(F)(F)F)cc2)nn1] | N-(2-ethylbutyl)-N-(2-(pyridin-3-yl)ethyl)-4-(4-(trifluoromethoxy)phenyl)-1H-1,2,3-triazole-1-carboxamide | 462.2 [M + H]+ |
| 137 | 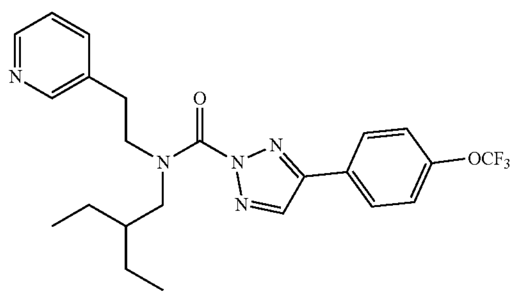 [SMILES: CCC(CC)CN(CCc1cccnc1)C(=O)n1ncc(-c2ccc(OC(F)(F)F)cc2)n1] | N-(2-ethylbutyl)-N-(2-(pyridin-3-yl)ethyl)-4-(4-(trifluoromethoxy)phenyl)-2H-1,2,3-triazole-1-carboxamide | 462.2 [M + H]+ |

II. Biological Evaluation

Compounds were tested to assess their DAGL activity using the following in vitro and in vivo assays.

Example 16: In Vitro Inhibition of 2-AG Biosynthesis

DAGL modulators were tested for in vitro inhibition of 2-AG biosynthesis using a 1-stearoyl-2-arachidonoyl-sn-glycerol (SAG) substrate assay in DAGL-transfected HEK293 cells.

The SAG substrate assay, as described in *Journal of lipid research* 56(4):927-935, was performed using the following assay conditions: 0.2 U/mL glycerol kinase (GK), glycerol-3-phosphate oxidase (GPO) and horseradish peroxidase (HRP), 0.125 mM ATP, 10 µM Amplifu™Red, 5% DMSO in a total volume of 200 µL. The assay additionally contained SAG, a DAGL modulator, and membrane lysates from HEK293T cells expressing recombinant human DAGLα or DAGLβ.

Membranes were prepared from HEK293T cells transiently transfected with DAGLα or DAGLβ plasmids encoding for full length DAGLα or DAGLβ, respectively (*Angewandte Chemie* 52(46):12081-12085; *Journal of Medicinal Chemistry* 57(15):6610-6622). Briefly, one day prior to transfection, $10^7$ cells were seeded in a 15 cm petri dish. The seeded cells were transfected by the addition of a 3:1 mixture of polyethyleneimine (60 µg) and plasmid DNA (20 µg) in 2 mL serum free medium. The medium was refreshed after 24 hr, and after 72 hr the cells were harvested by suspending them in 20 mL medium. The suspension was centrifuged for 10 min at 1000 rpm, and the supernatant was removed. The cell pellet was stored at −80° C. until use. Cell pellets were thawed on ice and suspended in lysis buffer A (20 mM HEPES, 2 mM DTT, 0.25 M sucrose, 1 mM MgCl$_2$, 1x protease inhibitor cocktail (Roche cOmplete EDTA free), 25 U/µL Benzonase). The suspension was homogenized by polytrone (3×7 sec) and incubated for 30 min on ice. The suspension was subjected to ultracentrifugation (100,000×g, 30 min, 4° C., Beckman Coulter, Type Ti70 rotor) to yield the cytosolic fraction in the supernatant and the membrane fraction as a pellet. The pellet was resuspended in lysis buffer B (20 mM HEPES, 2 mM DTT, 1x protease inhibitor cocktail (Roche cOmplete EDTA free)) and the protein concentration determined with Quick Start Bradford assay (Biorad). The protein fractions were diluted to a total protein concentration of 1 mg/mL and stored in small aliquots at −80° C. until use.

FIG. 1 shows concentration-dependent inhibition curves for compounds 14, 17 and 22 against DAGLα and DAGLβ as determined using the SAG substrate assay. Compounds 14 and 17 blocked the DAGLα conversion of SAG to 2-AG with IC$_{50}$ values of 6 nM [5-9 nM; 95% confidence interval (CI), n=4] and 6 nM (3-11 nM 95% CI, n=4), respectively. Compound 22 did not substantially inhibit DAGLα at any dose tested. Compounds 14 and 17 inhibited DAGLβ with IC$_{50}$ values of 3-8 nM.

Example 17: In Vitro Inhibition of DAGL

Compounds 19 and 20 were tested for in vitro inhibition of DAGLα and DAGLβ as measured by competitive activity-based protein profiling (ABPP) of mouse brain proteome using a HT-01 probe (targets DAGLα and DAGLβ) and a FP-Rh probe (targets serine hydrolases).

Briefly, membrane proteome (1 mg/ml, 20 µL) was prepared from HEK293T cells (transiently transfected with hDAGLα-FLAG or hDAGLα-S472A-FLAG, hDAGLβ-FLAG or hDAGLβ-S443A-FLAG) as described in Example 16. The proteome was incubated at room temperature with vehicle (DMSO) or compound in 0.5 µL DMSO for 30 min. The membrane proteome sample was subsequently treated for 30 min with HT-01 probe (1 µM) or FP-Rh probe (1 µM). The reactions were quenched with 10 µL 3× Laemmli sample buffer (final concentrations: 60 mM Tris-Cl pH 6.8, 2% (w/v) SDS, 10% (v/v) glycerol, 5% (v/v) (β-mercaptoethanol, 0.01% (v/v) bromophenol blue). The samples were directly loaded and resolved on SDS page gel (10% acrylamide). The gels were scanned using a ChemiDoc MP system (Cy3 settings, 605/50 filter).

The resolved proteins were transferred from the gels to a polyvinyldifluoride membrane for Western Blotting using a Trans-Blot® Turbo (BioRad). FLAG-tagged enzymes were stained using rabbit anti-FLAG as primary antibody, and goat-anti-rabbit HRP as secondary antibody. The blot was developed in the dark using a 10 mL luminal solution, 100 µL ECL enhancer and 3 µL $H_2O_2$. Chemiluminescence was visualized using a ChemiDoc XRS (BioRad).

The percentage of DAGL activity remaining in the assayed samples was determined by measuring the integrated optical intensity of the fluorescent protein bands of the Western Blot using image lab 4.1. The relative intensity was compared to the vehicle (DMSO) treated proteins, which were set to 100%. $IC_{50}$ values were determined by plotting a log(inhibitor) vs. normalized response (Variable slope) dose-response curve generated using Prism software (GraphPad).

Figure 2:
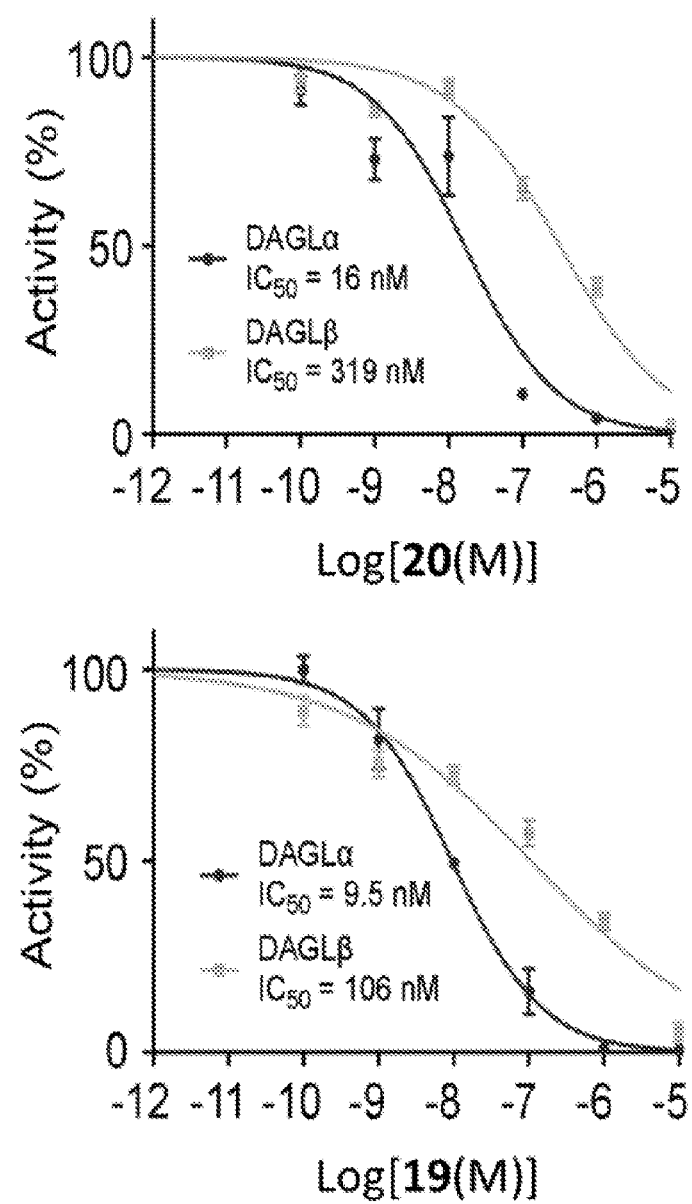
FIG. 2 provides concentration-dependent inhibition curves for compounds 20 and 19 against DAGLα and DAGLβ as determined using an ABPP assay. Data represent average values±SD; n=3 per group.

FIG. 2 shows concentration-dependent inhibition curves for compounds 20 and 19 against DAGLα and DAGLβ as determined using the ABPP method (corresponding Western Blot data not shown). Data represent average values, n=3. Compound 20 inhibited DAGLα with an $IC_{50}$ value of 16 nM and DAGLβ with an $IC_{50}$ value of 319 nM. Compound 19 inhibited DAGLα with an $IC_{50}$ value of 9.5 nM and DAGLβ with an $IC_{50}$ value of 106 nM. $IC_{50}$ values or % inhibition data for compounds described herein are shown in Table 3.

TABLE 3

| Compound | DAGLα $IC_{50}$ | DAGLβ $IC_{50}$ | DAGLα % inh. 0.4 µM | DAGLβ % inh. 0.4 µM | DAGLα % inh. 3.2 nM | DAGLβ % inh. 3.2 nM |
|---|---|---|---|---|---|---|
| 14 | A | A | | | | |
| 17 | A | A | | | | |
| 19 | A | A | | | | |
| 20 | A | A | | | | |
| 22 | | | * % inh. 0.8 µM | * % inh. 0.8 µM | | |
| 23 | | | * % inh. 0.8 µM | * % inh. 0.8 µM | | |
| 26 | | | * % inh. 0.8 µM | * % inh. 0.8 µM | | |
| 27 | | | * % inh. 0.8 µM | * % inh. 0.8 µM | | |
| 30 | | | *** % inh. 0.8 µM | * % inh. 0.8 µM | | |
| 31 | | | * % inh. 0.8 µM | * % inh. 0.8 µM | | |
| 34 | | | ** % inh. 0.8 µM | * % inh. 0.8 µM | | |
| 35 | | | * % inh. 0.8 µM | * % inh. 0.8 µM | | |
| 44 | | | | | ** | * |
| 45 | | | | | ** | * |
| 50 | | | | | * | * |
| 51 | | | | | * | * |
| 53 | B | A | | | | |
| 54 | D | C | | | | |
| 59 | B | C | | | | |
| 60 | A | C | | | | |
| 61 | B | C | | | | |
| 62 | A | C | | | | |
| 63 | A | C | | | | |
| 64 | A | C | | | | |
| 65 | B | C | | | | |
| 66 | A | A | | | | |
| 67 | A | C | | | | |
| 68 | A | C | | | | |
| 69 | A | C | | | | |
| 70 | C | D | | | | |
| 71 | A | B | | | | |
| 72 | B | B | | | | |
| 73 | A | A | | | | |
| 74 | A | C | | | | |
| 75 | C | D | | | | |
| 76 | B | D | | | | |
| 77 | A | B | | | | |
| 78 | B | D | | | | |
| 79 | B | D | | | | |
| 80 | B | D | | | | |
| 81 | B | D | | | | |
| 82 | A | A | | | | |
| 83 | A | C | | | | |
| 84 | D | C | | | | |
| 85 | D | C | | | | |
| 86 | A | A | | | | |
| 87 | A | A | | | | |
| 88 | A | A | | | | |
| 89 | A | A | | | | |
| 90 | A | A | | | | |
| 91 | A | C | | | | |
| 92 | C | C | | | | |
| 93 | C | D | | | | |
| 94 | A | B | | | | |
| 95 | | | **** | ** | | |
| 96 | | | **** | *** | | |
| 97 | | | ** | * | | |
| 98 | | | * | * | | |
| 99 | | | * | * | | |
| 100 | | | **** | **** | | |
| 101 | | | NT | NT | | |
| 102 | | | **** | **** | | |
| 103 | | | NT | NT | | |
| 104 | | | | | * | * |
| 105 | | | | | * | * |
| 106 | | | | | * | * |
| 107 | | | | | * | * |
| 108 | | | | | * | * |
| 109 | | | | | * | * |
| 110 | | | | | * | * |
| 111 | | | | | * | * |
| 112 | | | | | * | * |
| 113 | | | | | * | * |
| 114 | | | | | * | * |
| 115 | | | | | * | * |
| 116 | | | | | ** | * |
| 117 | | | | | * | * |
| 118 | | | | | ** | * |
| 119 | | | | | * | * |
| 120 | | | | | **** | ** |
| 121 | | | | | * | * |
| 122 | A | A | | | | |
| 123 | A | A | | | | |
| 124 | A | A | | | | |
| 125 | A | A | | | | |
| 126 | C | A | | | | |
| 127 | C | A | | | | |
| 128 | C | B | | | | |
| 129 | C | B | | | | |
| 130 | A | A | | | | |
| 131 | C | B | | | | |
| 132 | A | A | | | | |
| 133 | C | B | | | | |
| 134 | A | A | | | | |
| 135 | B | C | | | | |

TABLE 3-continued

| Compound | DAGLα $IC_{50}$ | DAGLβ $IC_{50}$ | DAGLα % inh. 0.4 µM | DAGLβ % inh. 0.4 µM | DAGLα % inh. 3.2 nM | DAGLβ % inh. 3.2 nM |
|---|---|---|---|---|---|---|
| 136 | A | A | | | | |
| 137 | B | B | | | | |

A = $IC_{50}$ less than or equal to 400 nM; B = $IC_{50}$ is greater than 400 nM and less than or equal to 2 µM; C = $IC_{50}$ is greater than 2 µM and less than or equal to 10 µM; ; D = $IC_{50}$ is greater than 10 µM.
** % inhibition greater than or equal to 75%;; * % inhibition greater than or equal to 50% and less than 75%; ** % inhibition greater than or equal to 25% and less than 50%; * % inhibition greater than or equal to 0% and less than 25%; NT = not tested.

Example 18: Activity and Selectivity of DAHL Modulators Against Endogenous DAGLs Compounds 14 and 17 were evaluated for activity and selectivity against endogenous DAGLs and other serine hydrolases in the mouse brain proteome using a ABPP of mouse brain proteome assay as described in Example 16. These experiments were performed using three different activity-based probesprobe compound 58 (targets DAGLα and DAGLβ), HT-01 (targets DAGLα and DAGLβ), and FP-Rh (broad-spectrum serine hydrolase-directed probe fluorophosphonate-rhodamine).

Figure 3:
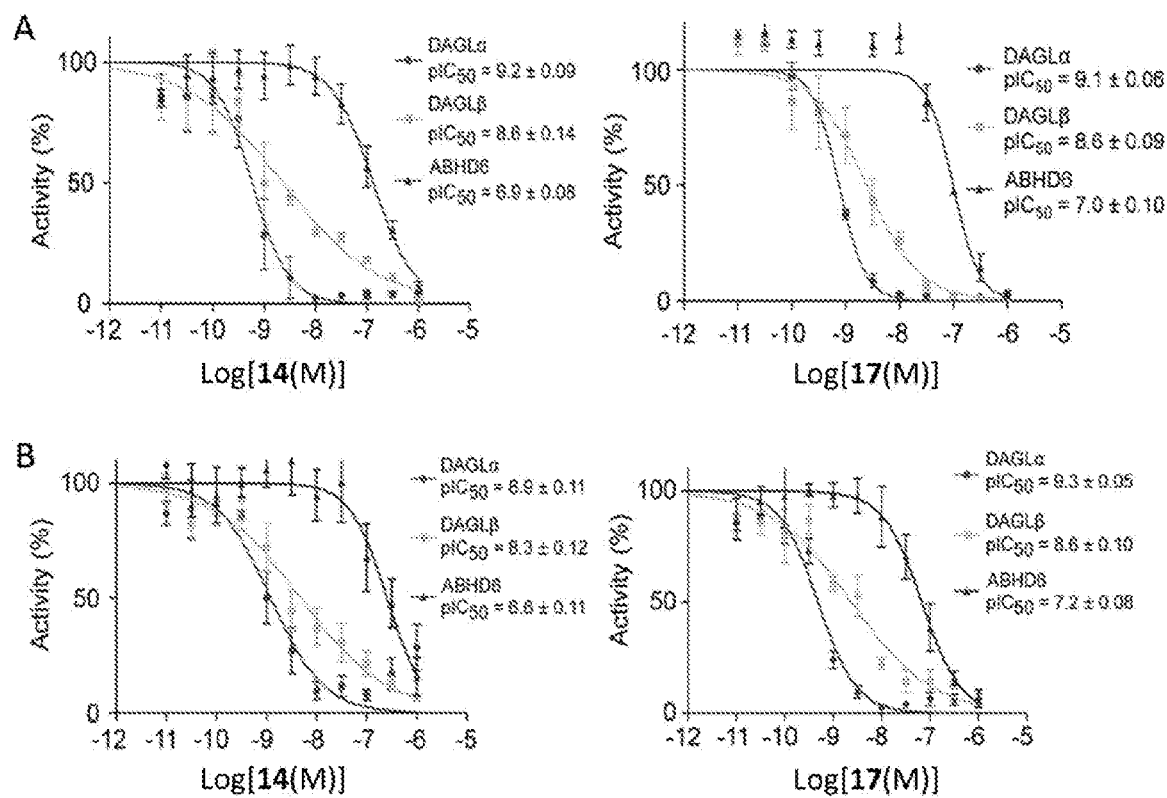
FIG. 3 provides concentration-dependent inhibition curves for compounds 14 and 17 against DAGLα and DAGLβ as measured using a gel-based ABPP assay with probe compound 58 (A) and HT-01 probe (B). Data represent average values±SEM; n=3 per group.

FIG. 3 shows concentration-dependent inhibition curves for compounds 14 and 17 against DAGLα and DAGLβ as measured using the ABPP assay with probe compound 58 (1 µM, 30 min; shown in panel A) and HT-01 probe (1 µM, 30 min; shown in panel B). Data represent average values±SEM; n=3 per group. Compounds 14 and 17 inhibited DAGLα and DAGLβ labeling by compound 58 and HT-01 with $IC_{50}$ values in the range of 0.5-1.2 (DAGLα) and 2.3-4.8 (DAGLβ) nM, respectively. Compounds 14 and 17 were selective for DAGLs, with the only detectable serine hydrolase off-targets being ABHD6 and PLA2G7 (data not shown). Compounds 14 and 17 had minimal and negligible binding, respectively, to cannabinoid CB1 (CB1R) and CB2 (CB2R) receptors as measured with a radioligand binding assay ($IC_{50}$ values>1 µM) (data not shown).

The selectivity of compounds 14 and 17 for additional serine hydrolases was assessed using probe FP-Rh (0.5 µM, 20 min; data not shown). Representative mouse brain serine hydrolases detected by FP-Rh were FAAH, MAGL, and ABHD6.

Example 19: Inhibition of DAGLα In Vivo

Mice were administered DAGL test compounds and the activity and selectivity of compounds 14 and 17 in vivo was assessed.

Compound 14, 17 or vehicle was administered intraperitoneally to male C57BL/6 mice across a dose range of 3-50 mg/kg. After 4 hr, the mice were sacrificed and brain tissue analyzed by ABPP, generally as described in Example 16, with compound probe 58, HT-01 probe, and FP-Rh probe.

Figure 4:
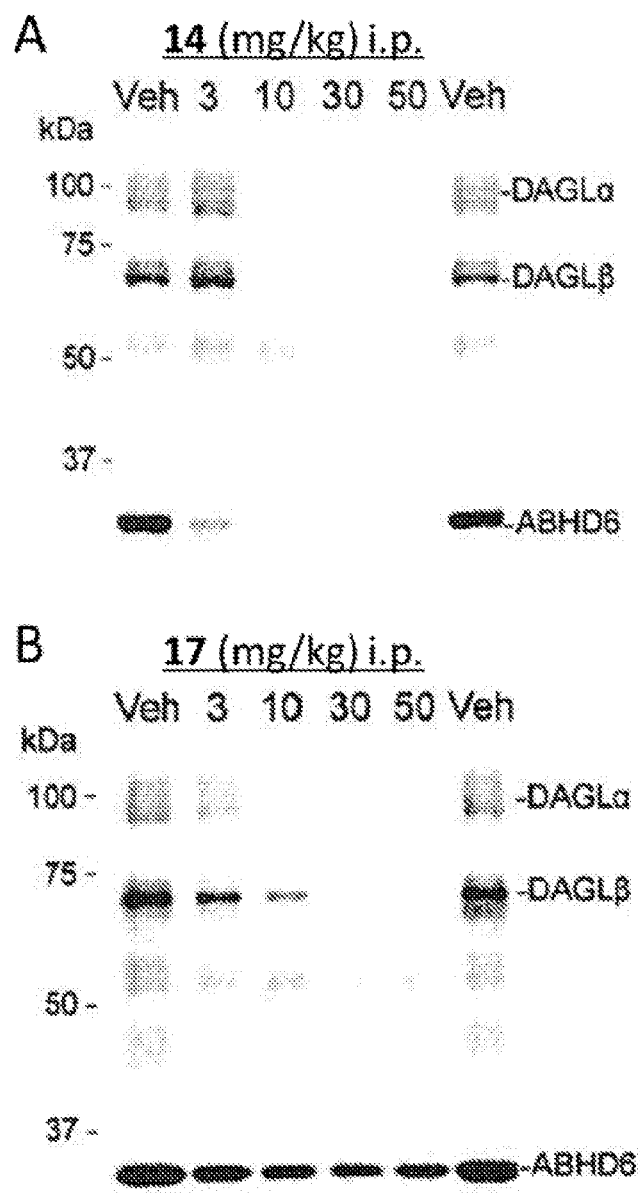
FIG. 4 provides images of Western blots obtained during an ABPP in vivo activity assay for measuring concentration-dependent inhibition of DAGL in mice after administration of compounds 14 (A) and 17 (B).

Both compounds 14 and 17 inhibited DAGLα activity with $ED_{50}$ values of 5-10 mg/kg, with full inhibition of DAGLα observed at 30-50 mg/kg of inhibitor. FIG. 4 shows images of the Western blots obtained using the HT-01 probe for administered compounds 14 (A) and 17 (B). DAGLβ (and ABHD6) were also inhibited by compounds 14 and 17.

Brain proteomes from compound 14-treated mice were conjugated to a Cy5 fluorophore by CuAAC, which confirmed direct, dose-dependent labeling of DAGL enzymes (data not shown).

The extent of these target profiles were confirmed by performing ABPP coupled to high-resolution, quantitative mass spectrometry (MS). Briefly, brain proteomes from compound and vehicle-treated mice were incubated with the serine hydrolase directed activity-based probe FP-biotin, and probe-labeled enzymes were enriched by streptavidin chromatography, digested on bead with trypsin, and the resulting tryptic peptides modified by reductive dimethylation (ReDiMe) of lysine residues using isotopically heavy and light formaldehyde, respectively. In these experiments, inhibited serine hydrolases are identified as enzymes showing low heavy/light ReDiMe ratios. Quantitative MS confirmed complete inhibition of DAGLα by compounds 14 and 17, with DAGLβ also being strongly and partially inhibited by these compounds, respectively, and revealed the following off-targets (defined as serine hydrolases with heavy/light ratios <0.5): ABHD6 (compounds 14, 17), CES1C (compounds 14, 17), ABHD2 (compound 17), BCHE (compound 14), LIPE (compound 14), PAFAH2 (compound 17), and PLA2G7 (compound 17).

These competitive ABPP studies designated compounds 14 and 17 as in vivo active inhibitors with complementary selectivity profiles that, when used in combination with the control compound 22, are useful for reporting on the function of DAGLs in the central nervous system.

Example 20: Time-Course Analysis of DAGL Inhibition and Recovery

Inhibition of DAGL in mice with DAGL compounds 14 and 17 was investigated as a function of time as determined by competitive ABPP using the compound 58 probe (1 µM, 30 min).

Figure 5:
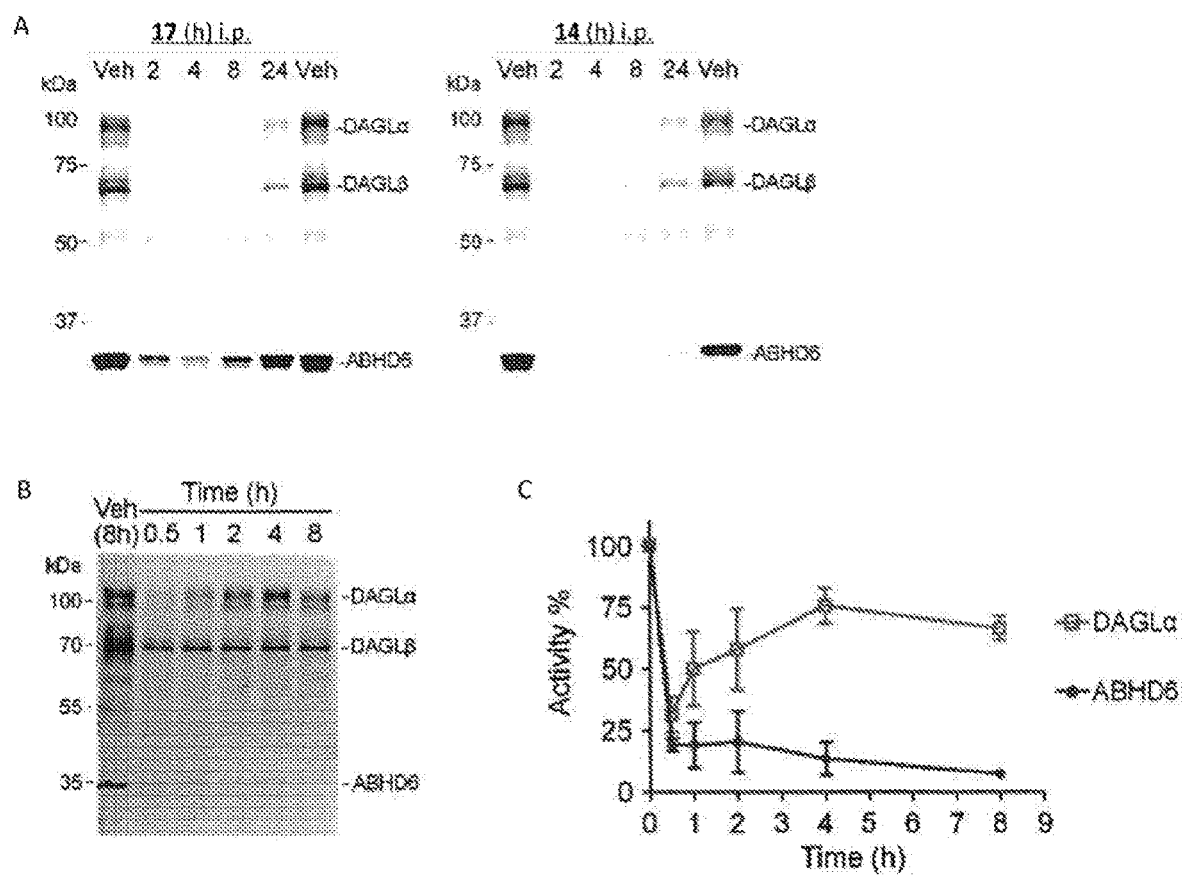
FIGS. 5A-B provide images of Western blots obtained during an ABPP in vivo activity assay showing time course of inhibition of DAGL in brain tissue from mice treated with a high dose (A) or a low dose (B) of compounds 14 or 17.
FIG. 5C shows quantification of the Western blot data from FIG. 5B. Data represent average values±SEM; n=3 mice per group.

At a high dose (50 mg/kg), compounds 14 and 17 demonstrated sustained inhibition of DAGLs for up to 8 hr, with partial recovery at 24-hr post dosing (FIG. 5A). At a lower dose (3 mg/kg), compound 17 produced substantial inhibition of DAGLα within 30 min after administration, but enzyme activity quickly recovered by 4 hr (FIGS. 5B and 5C). DAGLβ was also inhibited at 3 mg/kg (FIG. 5B).

Example 21: Brain Lipid Profiles of Mice Treated with DAGL Modulators

Brain lipid profiles of mice treated with compounds 14, 17 and control compound 22.

Figure 6:
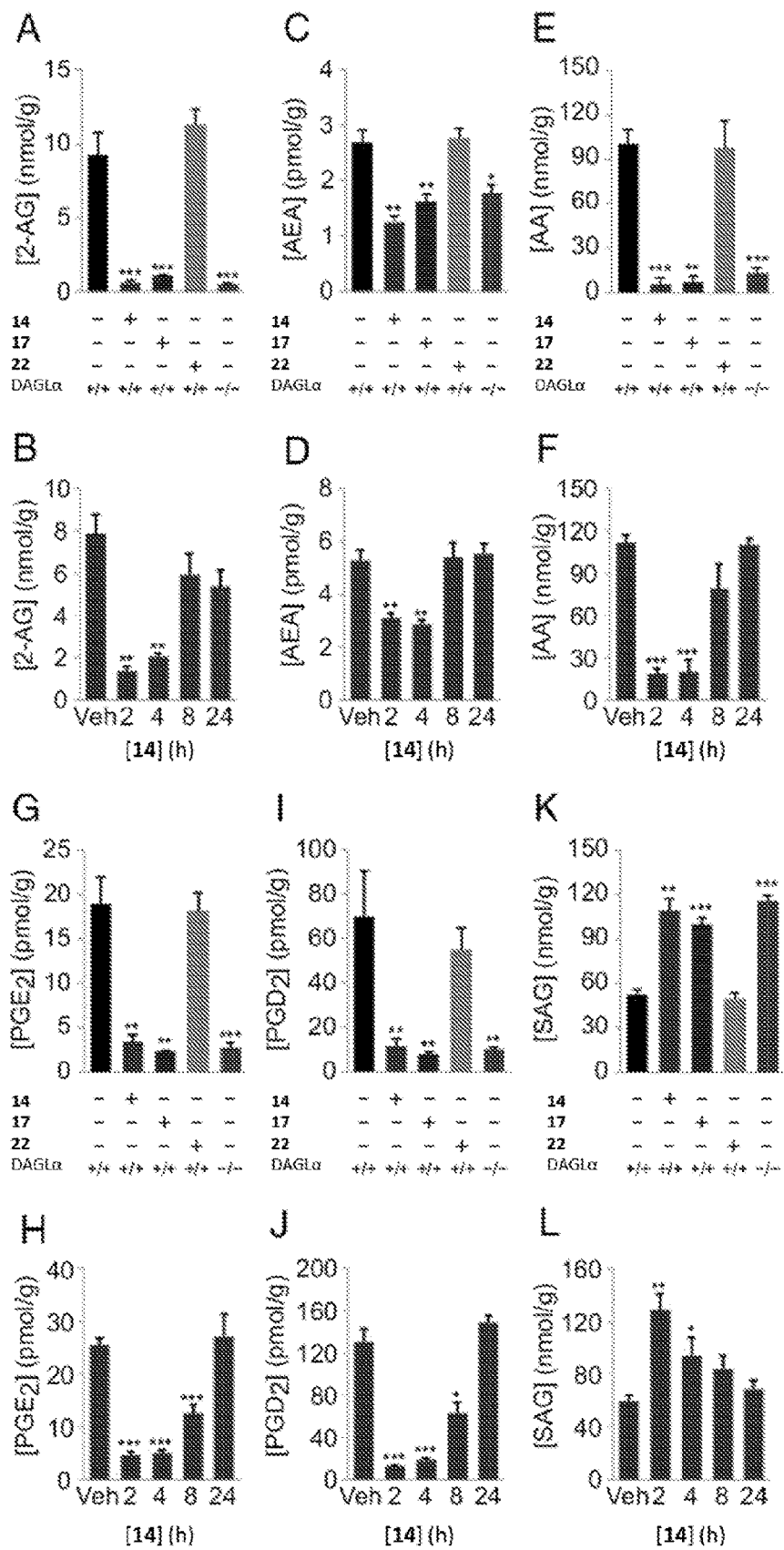
FIG. 6 shows the quantification of lipid pathway molecules in the brain of mice after treatment with DAGL modulators provided herein.

Mice were treated with 50 mg/kg compound (i.p.), followed by lipid profiling using LC-MS at a 4 hr post-dosing. As shown in FIG. 6A, 2-AG levels were reduced in compound 14 and 17 treated mice, but not in compound 22 treated mice. This depletion of brain 2-AG in compound 14 and 17-treated mice was dose-dependent (data not shown) and was observed within 2 h after injection. Compounds 14 and 17 also caused dose-dependent changes in other DAGL-regulated lipids, including reductions in AEA (FIGS. 6C and D), AA (FIGS. 6E and F), and the prostaglandins PGD2 and PGE2 (FIGS. 6G-J), as well as elevations in SAG (FIGS. 6K and L) and C18:1/C20:4 DAG (not shown). The changes in each lipid species were dose-dependent and were absent in compound 22 treated mice (FIGS. 6C, E, G, I, and K).

These studies demonstrate that acute pharmacological blockade of DAGLs produces a reorganization of lipid signaling networks in the mammalian brain.

Example 22: Inhibition of Endocannabinoid-Dependent Synaptic Plasticity

The effects of compounds 14 and 17 in models of endocannabinoid-dependent synaptic plasticity were examined.

Figure 7:
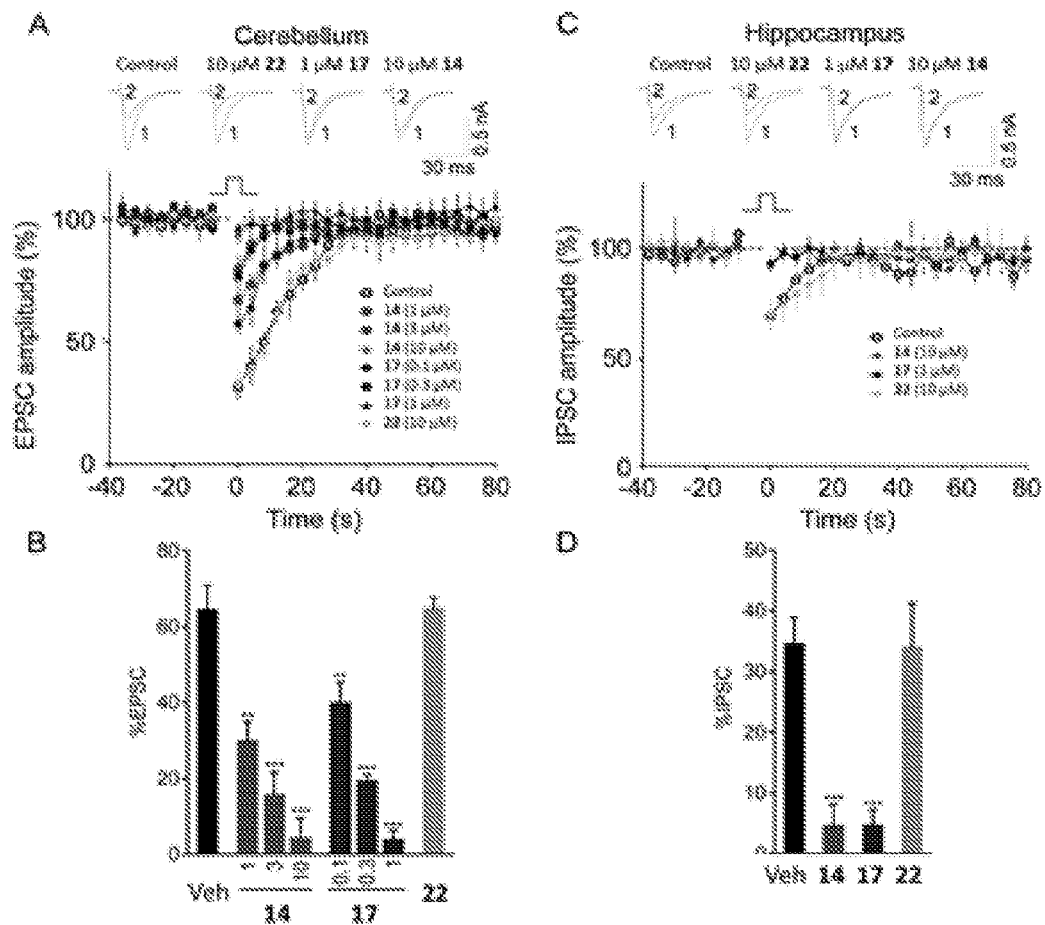
FIGS. 7A-B show sample traces and average time course (A) and magnitude (B) of parallel fiber-excitatory postsynaptic currents (PF-EPSCs) in response to depolarization in cerebellar slices following treatment with DAGL modulators provided herein.
FIGS. 7C-D show sample traces and average time course (C) and magnitude (D) of inhibitory postsynaptic currents (IPSCs) in CA1 pyramidal neurons in response to a brief depolarization in hippocampal slices following treatment with DAGL modulators. Data represent average values±SEM; n=7-8 samples per group. *P<0.05; P<0.01; *P<0.001 for modulator vs. vehicle treated samples.

Various forms of synaptic plasticity are regulated by 2-AG signaling, included depolarization-induced suppression of excitation (DSE) and inhibition (DSI). DSE was examined at parallel fiber (PF) to Purkinje cell (PC) synapses in acute cerebellar slices. A brief depolarization of PCs induced robust transient DSE at PF-PC synapses in vehicle treated cerebellar slices (FIG. 7A). Bath application of compound 14 (1-10 µM) or compound 17 (0.1-1 µM) to cerebellar slices 30 min before starting electrophysiological recordings blocked DSE in a concentration-dependent manner with a half-maximal inhibition of 1.1 µM and 0.18 µM, respectively (FIGS. 7A and B). The control compound 22 did not alter cerebellar DSE (10 µM) (FIGS. 7A and B).

DSI was evaluated at CA1 pyramidal neuron synapses in hippocampal slices. DSI was induced in vehicle-treated hippocampal slices by applying a brief depolarization while evoking induced pluripotent stem cells through stimulation of synaptic inhibitory inputs (FIG. 7C). Bath application of compound 14 (10 µM) and compound 17 (1 µM), but not compound 22 (10 µM), for 30 min before starting electrophysiological recordings blocked hippocampal DSI (FIGS. 7C and D).

These results indicate that DAGL inhibition blocks endocannabinoid-mediated forms of synaptic plasticity.

Example 23: Effect of DAGL Modulators on Neuroinflammatory Responses In Vivo The effects of pharmacological and genetic inactivation of DAGL activity on neuroinflammatory responses (brain prostaglandin and cytokine production) induced by high-dose lipopolysaccharide treatment was examined.

Figure 8:
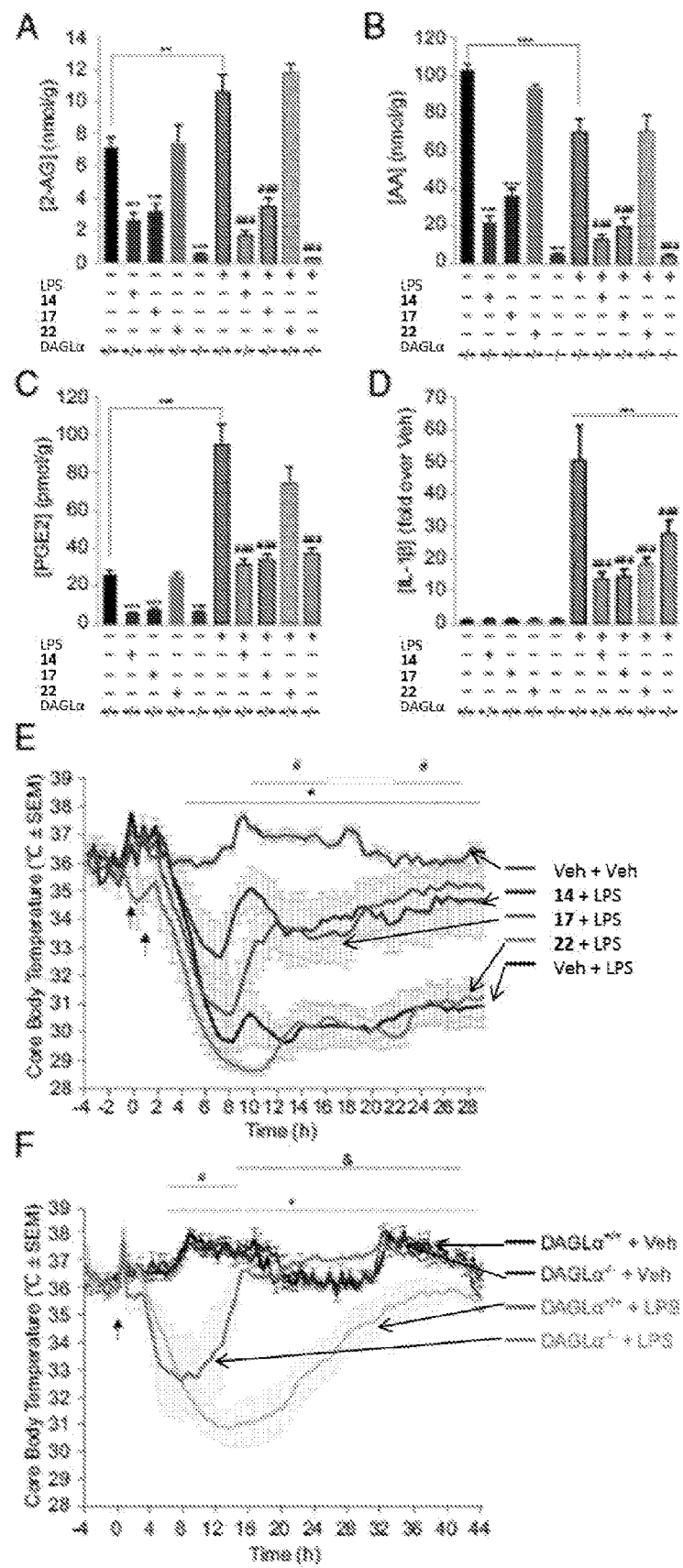
FIG. 8 shows that inhibition of DAGL by DAGL modulators provided herein suppresses LPS-induced neuroinflammatory responses in mouse brain.

Mice were treated with compounds 14, 17, control compound 22 or vehicle (50 mg/kg, i.p) for 60-90 min, followed by LPS (20 mg/kg, i.p., 6 hr) or vehicle. The mice were subsequently sacrificed and their brain lipid and cytokine profiles analyzed. Mice treated with compounds 14, 17, as well as DAGLα-/- mice, but not compound 22 treated mice, exhibited severely depleted brain 2-AG (FIG. 8A), AA (FIG. 8B), and PGE2 (FIG. 8C) under basal control conditions. LPS treatment caused an increase in 2-AG (FIG. 8A), a reduction in AA (FIG. 8B), and an increase in PGE2 (FIG. 8C). The LPS-induced elevations in both 2-AG and PGE2 were suppressed in compound 14 and compound 17 treated mice and DAGLα/mice, but not compound 22 treated mice. LPS treatment also increased brain cytokines, and this effect was attenuated in DAGLα-/- mice (FIG. 8D). Compound 14 and 17 treated mice also showed reductions in LPS-stimulated brain cytokines. LPS-induced anapyrexia was blunted in compound 14 and 17 treated mice (FIG. 8E) and DAGLα-/- mice (FIG. 8F), but not compound 22 treated mice (FIG. 8E). These results indicate that inhibition of DAGL suppresses LPS-induced neuroinflammatory responses in mouse brain.

We claim:

1. A compound of Formula (XI):

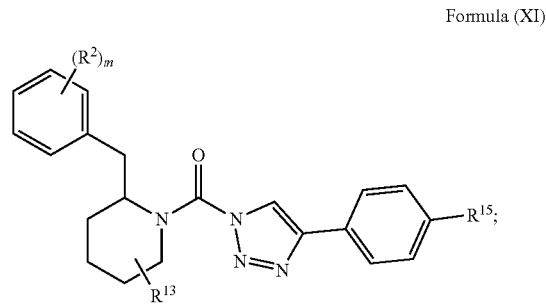

Formula (XI)

wherein:
each $R^2$ is independently halogen, —CN, —NH$_2$, —NH(CH$_3$), —N(CH$_3$)$_2$, —OH, —C(=O)OH, —C(=O)O(C$_{1-6}$alkyl), —C(=O)NH$_2$, —C(=O)NH(C$_{1-6}$alkyl), —C(=O)N(C$_{1-6}$alkyl)$_2$, —S(=O)$_2$NH$_2$, —S(=O)$_2$NH(C$_{1-6}$alkyl), —S(=O)$_2$N(C$_{1-6}$alkyl)$_2$, C$_{1-6}$alkyl, C$_{3-6}$cycloalkyl, C$_{1-6}$haloalkyl, C$_{1-6}$alkoxy, —O—C$_{2-6}$alkenyl, —O—C$_{2-6}$alkynyl, C$_{1-6}$haloalkoxy, C$_{2-9}$heterocycloalkyl, C$_{6-10}$aryl, or C$_{2-9}$heteroaryl;

$R^{13}$ is hydrogen, C$_{1-6}$alkyl, C$_{1-6}$alkoxy, —O—C$_{2-6}$alkenyl, —O—C$_{2-6}$alkynyl, or —O—CH$_2$C$_{3-6}$cycloalkyl;

$R^{15}$ is a monocyclic C$_{2-5}$heteroaryl optionally substituted with one, two, or three groups selected from halogen, C$_{1-6}$alkyl, C$_{1-6}$haloalkyl, C$_{1-6}$alkoxy, and C$_{1-6}$haloalkoxy; and m is 0, 1, 2, or 3;

or a solvate, hydrate, tautomer, N-oxide, or pharmaceutically acceptable salt thereof.

2. The compound of claim 1, or a solvate, hydrate, tautomer, N-oxide, or pharmaceutically acceptable salt thereof, wherein $R^{13}$ is hydrogen.

3. The compound of claim 2, or a solvate, hydrate, tautomer, N-oxide, or pharmaceutically acceptable salt thereof, wherein $R^{15}$ is pyridine optionally substituted with one or two groups selected from halogen, C$_{1-6}$alkyl, C$_{1-6}$alkoxy, and C$_{1-6}$haloalkoxy.

4. The compound of claim 2, or a solvate, hydrate, tautomer, N-oxide, or pharmaceutically acceptable salt thereof, wherein $R^{15}$ is pyrimidine optionally substituted with one or two groups selected from halogen, C$_{1-6}$alkyl, C$_{1-6}$alkoxy, and C$_{1-6}$haloalkoxy.

5. The compound of claim 2, or a solvate, hydrate, tautomer, N-oxide, or pharmaceutically acceptable salt thereof, wherein $R^{15}$ is pyridazine optionally substituted with one or two groups selected from halogen, C$_{1-6}$alkyl, C$_{1-6}$haloalkyl, C$_{1-6}$alkoxy, and C$_{1-6}$haloalkoxy.

6. The compound of claim 2, or a solvate, hydrate, tautomer, N-oxide, or pharmaceutically acceptable salt thereof, wherein each $R^2$ is independently halogen, C$_{1-6}$alkyl, C$_{1-6}$haloalkyl, C$_{1-6}$alkoxy, —O—C$_{2-6}$alkenyl, —O—C$_{2-6}$alkynyl, or C$_{1-6}$haloalkoxy.

7. The compound of claim 2, or a solvate, hydrate, tautomer, N-oxide, or pharmaceutically acceptable salt thereof, wherein each $R^2$ is independently halogen, C$_{1-6}$alkyl, C$_{1-6}$haloalkyl, C$_{1-6}$alkoxy, or C$_{1-6}$haloalkoxy.

8. The compound of claim 2, or a solvate, hydrate, tautomer, N-oxide, or pharmaceutically acceptable salt thereof, wherein m is 0.

9. The compound of claim 2, or a solvate, hydrate, tautomer, N-oxide, or pharmaceutically acceptable salt thereof, wherein m is 1.

10. The compound of claim 2, or a solvate, hydrate, tautomer, N-oxide, or pharmaceutically acceptable salt thereof, wherein m is 2.

11. A compound having the structure:

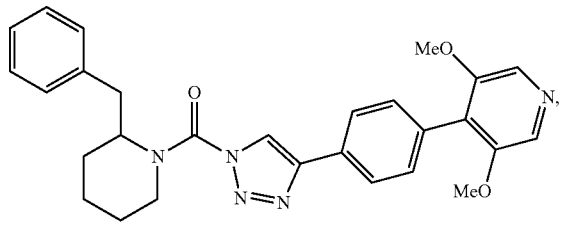

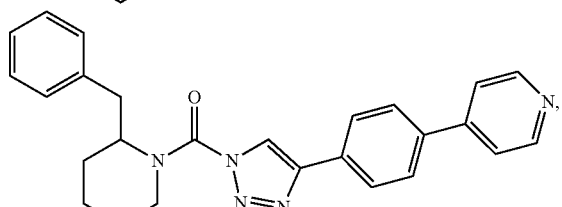

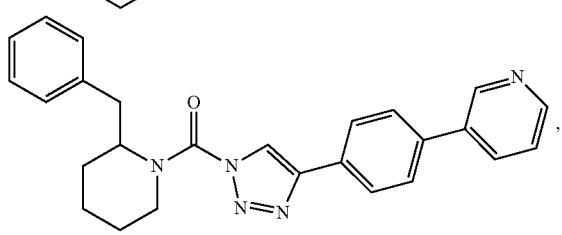

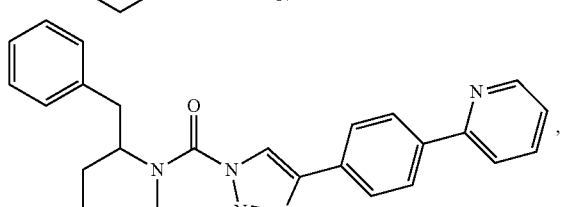

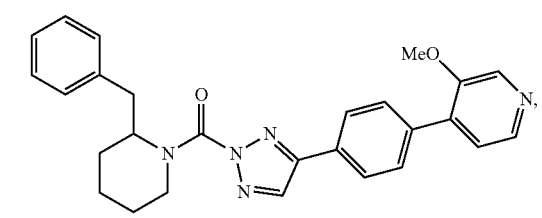

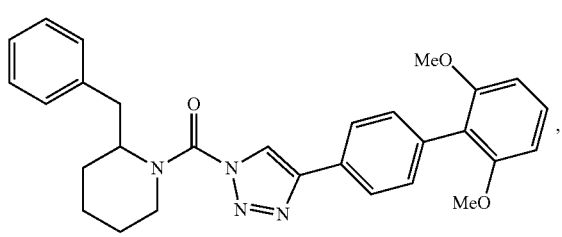

-continued

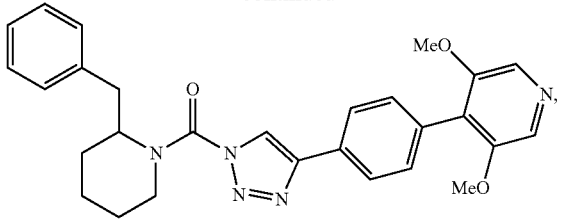

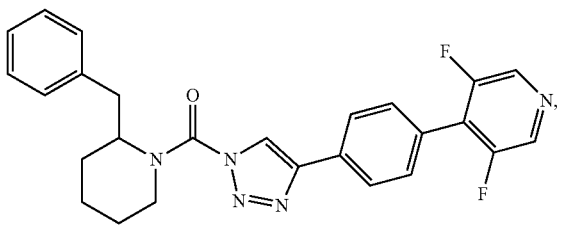

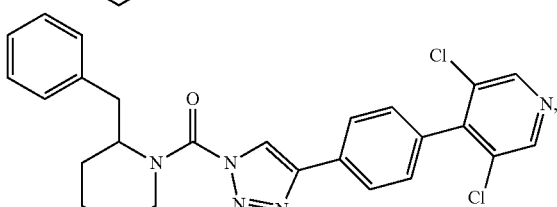

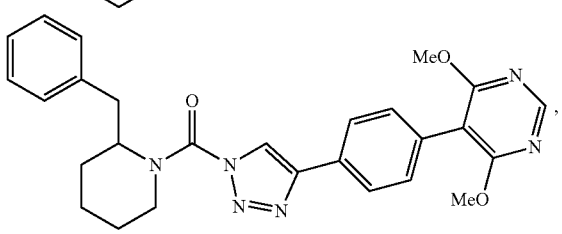

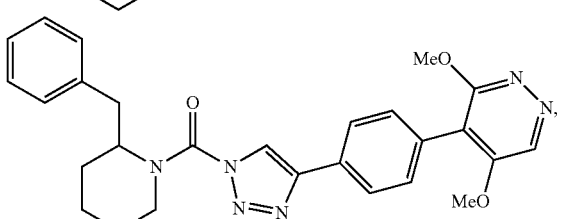

or

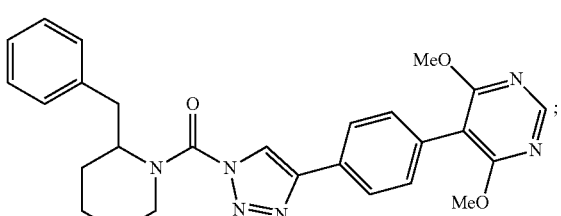

or a solvate, hydrate, N-oxide, or a pharmaceutically acceptable salt thereof.

12. A pharmaceutical composition comprising a compound of claim 1, or a solvate, hydrate, tautomer, N-oxide, or a pharmaceutically acceptable salt thereof, and at least one pharmaceutically acceptable excipient.

13. A method of treating a neurodegenerative disease, or neuroinflammatory disease in a patient in need thereof, comprising administering to the patient a therapeutically effective amount of a compound of claim 1, or a solvate, hydrate, tautomer, N-oxide, or a pharmaceutically acceptable salt thereof.

14. The method of claim 13 wherein the neurodegenerative disease or neuroinflammatory disease is Parkinson's Disease, Alzheimer's Disease, Huntington's Disease, or Amyotrophic Lateral Sclerosis (ALS).

* * * * *

UNITED STATES PATENT AND TRADEMARK OFFICE
CERTIFICATE OF CORRECTION

PATENT NO. : 10,583,137 B2
APPLICATION NO. : 15/778207
DATED : March 10, 2020
INVENTOR(S) : Cravatt et al.

Page 1 of 1

It is certified that error appears in the above-identified patent and that said Letters Patent is hereby corrected as shown below:

In the Claims

In Claim 3, Column 264, Lines 43-44, the portion of the formula reading:
"$C_{1-6}$alkyl, $C_{1-6}$alkoxy, and $C_{1-6}$haloalkoxy."
Should read:
--$C_{1-6}$alkyl, $C_{1-6}$haloalkyl, $C_{1-6}$alkoxy, and $C_{1-6}$haloalkoxy.--.

In Claim 4, Column 264, Lines 53-54, the portion of the formula reading:
"$C_{1-6}$alkyl, $C_{1-6}$alkoxy, and $C_{1-6}$haloalkoxy."
Should read:
--$C_{1-6}$alkyl, $C_{1-6}$haloalkyl, $C_{1-6}$alkoxy, and $C_{1-6}$haloalkoxy.--.

Signed and Sealed this
Sixteenth Day of June, 2020

Andrei Iancu
*Director of the United States Patent and Trademark Office*